(12) United States Patent
Schupp et al.

(10) Patent No.: US 6,383,787 B1
(45) Date of Patent: May 7, 2002

(54) GENES FOR THE BIOSYNTHESIS OF EPOTHILONES

(75) Inventors: Thomas Schupp, Mohlin (CH); James Madison Ligon, Apex, NC (US); Istvan Molnar, Durham, NC (US); Ross Zirkle, Raleigh, NC (US); Devon Dawn Cyr, Fuquay-Varina, NC (US); Jörn Görlach, Durham, NC (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/567,899

(22) Filed: May 10, 2000

Related U.S. Application Data

(62) Division of application No. 09/335,409, filed on Jun. 17, 1999, now Pat. No. 6,121,029.
(60) Provisional application No. 60/155,183, filed on Jun. 18, 1998, provisional application No. 60/101,631, filed on Sep. 24, 1998, and provisional application No. 60/118,906, filed on Feb. 5, 1999.

(51) Int. Cl.[7] .............................. C12N 9/00; C12N 9/10; C07H 21/04
(52) U.S. Cl. ................. 435/183; 435/193; 435/252.3; 435/252.35; 435/320.1; 536/23.2; 536/23.7; 536/23.1
(58) Field of Search ................. 435/183, 189, 435/193, 232, 252.3, 252.35, 320.1; 536/23.2, 23.7, 23.1

(56) References Cited

U.S. PATENT DOCUMENTS

| | | | |
|---|---|---|---|
| 5,496,804 A | 3/1996 | Reed et al. | 514/12 |
| 5,521,077 A | 5/1996 | Khosla et al. | 435/172.3 |
| 5,565,478 A | 10/1996 | Kohn et al. | 514/359 |
| 5,641,803 A | 6/1997 | Caretta et al. | 514/449 |
| 5,672,491 A | 9/1997 | Khosla et al. | 435/148 |
| 5,686,295 A | 11/1997 | Jaoua et al. | 435/252.3 |
| 5,712,146 A | 1/1998 | Khosla et al. | 435/252.35 |
| 5,716,849 A | 2/1998 | Ligon et al. | 435/419 |
| 5,876,991 A | 3/1999 | DeHoff et al. | 435/183 |
| 6,303,342 B1 | 10/2001 | Julien et al. | 435/76 |

FOREIGN PATENT DOCUMENTS

| | | |
|---|---|---|
| DE | 19846493 * | 4/2000 |
| WO | 93/10121 | 5/1993 |
| WO | 98/07868 | 2/1998 |
| WO | 98/25929 | 6/1998 |

OTHER PUBLICATIONS

Bollag, et al., Epothilones, A New Class of Micro–Tubule–stabilizing Agents with a Taxol–like Mechanism of Action, Cancer Research, 55, 2325–2333, Jun. 1995.
Gerth et al., Epothilons A and B: Antifungal and Cytotoxic Compounds from Sorangium cellulosum (Myxobacteria), The Journal of Antibiotics, 49:6, 560–563, Jun. 1996.
Nicolaou, et al., Chemical Biology of Epothilones, Angew. Chem. Int. Ed., 1998, 37, 2014–2045.
Schupp, et al., Cloning and sequence analysis of the putative rifamycin polyketide synthase gene cluster from Amycolatopsis mediterranei, FEMS Microbiology Letters, 159, 1998, 201–207.
Kealey et al., PNAS USA 95:505–509 (1998).
Caffrey et al., Eur. J. Biochem. 195:823–830 (1991).
Marsden et al., Science 279:199–202 (1998).
Kao et al., Science 265:509–512 (1994).
McDaniel et al., Science 262:1546–1550 (1993).
Beyer et al., Biochimica et Biophysica Acta 1445(2):185–195 (1999).
Molnar et al., Gene 169(1):1–7 (1996).
Aparicio et al., Gene 169(1)9–16 (1996).
Swan et al., Mol. Gen. Genet. 242(3):358–362 (1994).
Kakavas et al., J. Bacteriol. 179(23):7515–7522 (1997).
Schwecke et al., PNAS USA 92(17):7839–7843 (1995).
Molnar et al., Chemistry & Biology, 7:97–109 (2000).
Tang et al., Science, 287:640–642 (2000).

* cited by examiner

*Primary Examiner*—Nashaat T. Nashed
(74) *Attorney, Agent, or Firm*—J. Timothy Meigs; George R. Dohmann

(57) ABSTRACT

Nucleic acid molecules are isolated from *Sorangium cellulosum* that encode polypeptides necessary for the biosynthesis of epothilone. Disclosed are methods for the production of epothilone in recombinant hosts transformed with the genes of the invention. In this manner, epothilone can be produced in quantities large enough to enable their purification and use in pharmaceutical formulations such as those for the treatment of cancer.

25 Claims, No Drawings

GENES FOR THE BIOSYNTHESIS OF EPOTHILONES

CROSS REFERENCE TO RELATED APPLICATIONS

This application is a division of U.S. application Ser. No. 09/335,409, filed Jun. 17, 1999, now U.S. Pat. No. 6,121,029 which claims the benefit of U.S. Provisional Application No. 60/155,183, filed Jun. 18, 1998; U.S. Provisional Application No. 60/101,631, filed Sep. 24, 1998; and U.S. Provisional Application No. 60/118,906, filed Feb. 5, 1999. The full disclosure of each of these provisional applications is incorporated herein by reference.

FIELD OF THE INVENTION

The present invention relates generally to polyketides and genes for their synthesis. In particular, the present invention relates to the isolation and characterization of novel polyketide synthase and nonribosomal peptide synthetase genes from *Sorangium cellulosum* that are necessary for the biosynthesis of epothilones A and B.

BACKGROUND OF THE INVENTION

Polyketides are compounds synthesized from two-carbon building blocks, the β-carbon of which always carries a keto group, thus the name polyketide. These compounds include many important antibiotics, immunosuppressants, cancer chemotherapeutic agents, and other compounds possessing a broad range of biological properties. The tremendous structural diversity derives from the different lengths of the polyketide chain, the different side-chains introduced (either as part of the two-carbon building blocks or after the polyketide backbone is formed), and the stereochemistry of such groups. The keto groups may also be reduced to hydroxyls, enoyls, or removed altogether. Each round of two-carbon addition is carried out by a complex of enzymes called the polyketide synthase (PKS) in a manner similar to fatty acid biosynthesis.

The biosynthetic genes for an increasing number of polyketides have been isolated and sequenced. For example, see U.S. Pat. Nos. 5,639,949, 5,693,774, and 5,716,849, all of which are incorporated herein by reference, which describe genes for the biosynthesis of soraphen. See also, Schupp et al., *FEMS Microbiology Letters* 159: 201–207 (1998) and WO 98/07868, which describe genes for the biosynthesis of rifamycin, and U.S. Pat. No. 5,876,991, which describes genes for the biosynthesis of tylactone, all of which are incorporated herein by reference. The encoded proteins generally fall into tow types: type I and type II. Type I proteins are polyfunctional, with several catalytic domains carrying out different enzymatic steps covalently linked together (e.g. PKS for erythromycin, soraphen, rifamycin, and avermectin (MacNeil et al., in *Industrial Microorganisms: Basic and Applied Molecular Genetics*, (ed.: Baltz et al.), American Society for Microbiology, Washington D.C. pp. 245–256 (1993)); whereas type II proteins are monofunctional (Hutchinson et al., in *Industrial Microorganisms: Basic and Applied Molecular Genetics*, (ed.: Baltz et al.), American Society for Microbiology, Washington D.C. pp. 203–216 (1993)).

For the simpler polyketides such as actinorhodin (produced by *Streptomyces coelicolor*), the several rounds of two-carbon additions are carried out iteratively on PKS enzymes encoded by one set of PKS genes. In contrast, synthesis of the more complicated compounds such as erythromycin and soraphen involves PKS enzymes that are organized into modules, whereby each module carries out one round of two-carbon addition (for review, see Hopwood et al., in *Industrial Microorganisms: Basic and Applied Molecular Genetics*, (ed.: Baltz et al.), American Society for Microbiology, Washington D.C., pp. 267–275 (1993)).

Complex polyketides and secondary metabolites in general may contain substructures that are derived from amino acids instead of simple carboxylic acids. Incorporations of these building blocks are accomplished by non-ribosomal polypeptide synthetases (NRPSs). NRPSs are multienzymes that are organized in modules. Each module is responsible for the addition (and the additional processing, if required) of one amino acid building block. NRPSs activate amino acids by forming aminoacyl-adenylates, and capture the activated amino acids on thiol groups of phophopantheteinyl prosthetic groups on peptidyl carrier protein domains. Further, NRPSs modify the amino acids by epimerization, N-methylation, or cyclization if necessary, and catalyse the formation of peptide bonds between the enzyme-bound amino acids. NRPSs are responsible for the biosynthesis of peptide secondary metabolites like cyclosporin, could provide polyketide chain terminator units as in rapamycin, or form mixed systems with PKSs as in yersiniabactin biosynthesis.

Epothilones A and B are 16-membered macrocyclic polyketides with an acylcysteine-derived starter unit that are produced by the bacterium *Sorangium cellulosum* strain So ce90 (Gerth et al., *J. Antibiotics* 49: 560–563 (1996), incorporated herein by reference). The structure of epothilone A and B wherein R signifies hydrogen (epothilone A) or methyl (epothilone B) is:

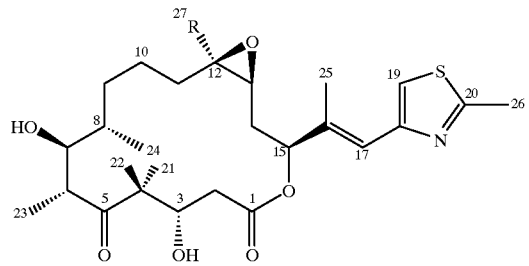

The epothilones have a narrow antifungal spectrum and especially show a high cytotoxicity in animal cell cultures (see, Höfle et al, Patent DE 4138042 (1993), incorporated herein by reference). Of significant importance, epothilones mimic the biological effects of taxol, both in vivo and in cultured cells (Bollag et al., *Cancer Research* 55: 2325–2333 (1995), incorporated herein by reference). Taxol and taxotere, which stabilize cellular microtubules, are cancer chemotherapeutic agents with significant activity against various human solid tumors (Rowinsky et al., *J. Natl. Cancer Inst.* 83: 1778–1781 (1991)). Competition studies have revealed that epothilones act as competitive inhibitors of taxol binding to microtubules, consistent with the interpretation that they share the same microtubule-binding site and possess a similar microtubule affinity as taxol. However, epothilones enjoy a significant advantage over taxol in that epothilones exhibit a much lower drop in potency compared to taxol against a multiple drug-resistant cell line (Bollag et al. (1995)). Furthermore, epothilones are considerably less efficiently exported from the cells by P-glycoprotein than is taxol (Gerth et al. (1996)). In addition, several epothilone analogs have been synthesized that have a superior cytotoxic activity as compared to epothilone A or epothilone B as demonstrated by their enhanced ability to induce the polymerization and stabilization of microtubules (WO 98/25929, incorporated herein by reference).

Despite the promise shown by the epothilones as anticancer agents, problems pertaining to the production of these compounds presently limit their commercial potential. The compounds are too complex for industrial-scale chemical synthesis and so must be produced by fermentation. Techniques for the genetic manipulation of myxobacteria such as *Sorangium cellulosum* are described in U.S. Pat. No. 5,686, 295, incorporated herein by reference. However, *Sorangium cellulosum* is notoriously difficult to ferment and production levels of epothilones are therefore low. Recombinant production of epothilones in heterologous hosts that are more amenable to fermentation could solve current production problems. However, the genes that encode the polypeptides responsible for epothilone biosynthesis have heretofore not been isolated. Furthermore, the strain that produces epothilones, i.e. So ce90, also produces at least one additional polyketide, spirangien, which would be expected to greatly complicate the isolation of the genes particularly responsible for epothilone biosynthesis.

Therefore, in view of the foregoing, one object of the present invention is to isolate the genes that are involved in the synthesis of epothilones, particularly the genes that are involved in the synthesis of epothilones A and B in myxobacteria of the Sorangium/Polyangium group, i.e., *Sorangium cellulosum* strain So ce90. A further object of the invention is to provide a method for the recombinant production of epothilones for application in anticancer formulations.

SUMMARY OF THE INVENTION

In furtherance of the aforementioned and other objects, the present invention unexpectedly overcomes the difficulties set forth above to provide for the first time a nucleic acid molecule comprising a nucleotide sequence that encodes at least one polypeptide involved in the biosynthesis of epothilone. In a preferred embodiment, the nucleotide sequence is isolated from a species belonging to Myxobacteria, most preferably *Sorangium cellulosum*.

In another preferred embodiment, the present invention provides an isolated nucleic acid molecule comprising a nucleotide sequence that encodes at least one polypeptide involved in the biosynthesis of an epothilone, wherein said polypeptide comprises an amino acid sequence substantially similar to an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, amino acids 1314–1385 of SEQ ID NO:2, SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, amino acids 1344–1351 of SEQ ID NO:3, SEQ ID NO:4, amino acids 7–432 of SEQ ID NO:4, amino acids 539–859 of SEQ ID NO:4, amino acids 869–1037 of SEQ ID NO:4, amino acids 1439–1684 of SEQ ID NO:4, amino acids 1722–1792 of SEQ ID NO:4, SEQ ID NO:5, amino acids 39–457 of SEQ ID NO:5, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, amino acids 7140–7211 of SEQ ID NO:5, SEQ ID NO:6, amino acids 35–454 of SEQ ID NO:6, amino acids 561–881 of SEQ ID NO:6, amino acids 1143–1393 of SEQ ID NO:6, amino acids 1430–1503 of SEQ ID NO:6, amino acids 1522–1946 of SEQ ID NO: 6, amino acids 2053–2373 of SEQ ID NO:6, amino acids 2383–2551 of SEQ ID NO:6, amino acids 2671–3045 of SEQ ID NO:6, amino acids 3392–3636 of SEQ ID NO:6, amino acids 3673–3745 of SEQ ID NO:6, SEQ ID NO:7, amino acids 32–450 of SEQ ID NO:7, amino acids 556–877 of SEQ ID NO:7, amino acids 887–1051 of SEQ ID NO:7, amino acids 1478–1790 of SEQ ID NO:7, amino acids 1810–2055 of SEQ ID NO:7, amino acids 2093–2164 of SEQ ID NO:7, amino acids 2165–2439 of SEQ ID NO:7, SEQ ID NO:8, SEQ ID NO:10, SEQ ID NO:11, and SEQ ID NO:22.

In a more preferred embodiment, the present invention provides an isolated nucleic acid molecule comprising a nucleotide sequence that encodes at least one polypeptide involved in the biosynthesis of an epothilone, wherein said polypeptide comprises an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, amino acids 1314–1385 of SEQ ID NO:2, SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, amino acids 1344–1351 of SEQ ID NO:3, SEQ ID NO:4, amino acids 7–432 of SEQ ID NO:4, amino acids 539–859 of SEQ ID NO:4, amino acids 869–1037 of SEQ ID NO:4, amino acids 1439–1684 of SEQ ID NO:4, amino acids 1722–1792 of SEQ ID NO:4, SEQ ID NO:5, amino acids 39–457 of SEQ ID NO:S, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, amino acids 7140–7211 of SEQ ID NO:5, SEQ ID NO:6, amino acids 35–454 of SEQ ID NO:6, amino acids 561–881 of SEQ ID NO:6, amino acids 1143–1393 of SEQ ID NO:6, amino acids 1430–1503 of SEQ ID NO: 6, amino acids 1522–1946 of SEQ ID NO: 6, amino acids 2053–2373 of SEQ ID NO:6, amino acids 2383–2551 of SEQ ID NO:6, amino acids 2671–3045 of SEQ ID NO:6, amino acids 3392–3636 of SEQ ID NO:6, amino acids 3673–3745 of SEQ ID NO:6, SEQ ID NO:7, amino acids 32–450 of SEQ ID NO:7, amino acids 556–877 of SEQ ID NO:7, amino acids 887–1051 of SEQ ID NO:7, amino acids 1478–1790 of SEQ ID NO:7, amino acids 1810–2055 of SEQ ID NO:7, amino acids 2093–2164 of SEQ ID NO:7, amino acids 2165–2439 of SEQ ID NO:7, SEQ ID NO:8, SEQ ID NO:10, SEQ ID NO:11, and SEQ ID NO:22.

In yet another preferred embodiment, the present invention provides an isolated nucleic acid molecule comprising a nucleotide sequence that encodes at least one polypeptide involved in the biosynthesis of an epothilone, wherein said nucleotide sequence is substantially similar to a nucleotide sequence selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1 nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ, ID NO:1, nucleotides 67334–68251 of SEQ ID NO:1, and nucleotides 1–68750 SEQ ID NO:1.

In an especially preferred embodiment, the present invention provides a nucleic acid molecule comprising a nucleotide sequence that encodes at least one polypeptide involved in the biosynthesis of an epothilone, wherein said nucleotide sequence is selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

In yet another preferred embodiment, the present invention provides an isolated nucleic acid molecule comprising a nucleotide sequence that encodes at least one polypeptide involved in the biosynthesis of an epothilone, wherein said nucleotide sequence comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30816–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides,38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

The present invention also provides a chimeric gene comprising a heterologous promoter sequence operatively linked to a nucleic acid molecule of the invention. Further, the present invention provides a recombinant vector comprising such a chimeric gene, wherein the vector is capable of being stably transformed into a host cell. Still further, the present invention provides a recombinant host cell comprising such a chimeric gene, wherein the host cell is capable of expressing the nucleotide sequence that encodes at least one polypeptide necessary for the biosynthesis of an epothilone. In a preferred embodiment, the recombinant host cell is a bacterium belonging to the order Actinomycetales, and in a more preferred embodiment the recombinant host cell is a strain of Streptomyces. In other embodiments, the recombinant host cell is any other bacterium amenable to fermentation, such as a pseudomonad or E. coli. Even further, the present invention provides a Bac clone comprising a nucleic acid molecule of the invention, preferably Bac clone pEPO15.

In another aspect, the present invention provides an isolated nucleic acid molecule comprising a nucleotide sequence that encodes an epothilone synthase domain.

According to one embodiment, the epothilone synthase domain is a β-ketoacyl-synthase (KS) domain comprising an amino acid sequence substantially similar to an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7. According to this embodiment, said KS domain preferably comprises an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7. Also, according to this embodiment, said nucleotide sequence preferably is substantially similar to a nucleotide sequence selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1. In addition, according to this embodiment, said nucleotide sequence most preferably is selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1.

According to another embodiment, the epothilone synthase domain is an acyltransferase (AT) domain comprising an amino acid sequence substantially similar to an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. According to this embodiment, said AT domain preferably comprises an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. Also, according to this embodiment, said nucleotide sequence preferably is substantially similar to a nucleotide sequence selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1. In addition, according to this embodiment, said nucleotide sequence most preferably is selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1.

According to still another embodiment, the epothilone synthase domain is an enoyl reductase (ER) domain comprising an amino acid sequence substantially similar to an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. According to this embodiment, said ER domain preferably comprises an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. Also, according to this embodiment, said nucleotide sequence preferably is substantially similar to a nucleotide sequence selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1. In addition, according to this embodiment, said nucleotide sequence most preferably is selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1.

According to another embodiment, the epothilone synthase domain is an acyl carrier protein (ACP) domain, wherein said polypeptide comprises an amino acid sequence substantially similar to an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. According to this embodiment, said ACP domain preferably comprises an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. Also, according to this embodiment, said nucleotide sequence preferably is substantially similar to a nucleotide sequence selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1. In addition, according to this embodiment, said nucleotide sequence most preferably is selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1.

According to another embodiment, the epothilone synthase domain is a dehydratase (DH) domain comprising an amino acid sequence substantially similar to an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. According to this embodiment, said DH domain preferably comprises an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. Also, according to this embodiment, said nucleotide sequence preferably is substantially similar to a nucleotide sequence selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1. In addition, according to this embodiment, said nucleotide sequence most preferably is selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1.

According to yet another embodiment, the epothilone synthase domain is a β-keto-reductase (KR) domain comprising an amino acid sequence substantially similar to an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. According to this embodiment, said KR domain preferably comprises an amino acid sequence selected from the group consisting of: amino acids 1439– 1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. Also, according to this embodiment, said nucleotide sequence preferably is substantially similar to a nucleotide sequence selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1. In addition, according to this embodiment, said nucleotide sequence most preferably is selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1.

According to an additional embodiment, the epothilone synthase domain is a methyltransferase (MT) domain comprising an amino acid sequence substantially similar to amino acids 2671–3045 of SEQ ID NO:6. According to this embodiment, said MT domain preferably comprises amino acids 2671–3045 of SEQ ID NO:6. Also, according to this embodiment, said nucleotide sequence preferably is substantially similar to nucleotides 51534–52657 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of nucleotides 51534–52657 of SEQ ID NO:1. In addition, according to this embodiment, said nucleotide sequence most preferably is nucleotides 51534–52657 of SEQ ID NO:1.

According to another embodiment, the epothilone synthase domain is a thioesterase (TE) domain comprising an amino acid sequence substantially similar to amino acids 2165–2439 of SEQ ID NO:7. According to this embodiment, said TE domain preferably comprises amino acids 2165–2439 of SEQ ID NO:7. Also, according to this embodiment, said nucleotide sequence preferably is substantially similar to nucleotides 61427–62254 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of nucleotides 61427–62254 of SEQ ID NO:1. In addition, according to this embodiment, said nucleotide sequence most preferably is nucleotides 61427–62254 of SEQ ID NO:1.

In still another aspect, the present invention provides an isolated nucleic acid molecule comprising a nucleotide sequence that encodes a non-ribosomal peptide synthetase, wherein said non-ribosomal peptide synthetase comprises an amino acid sequence substantially similar to an amino acid sequence selected from the group consisting of: SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, and amino acids 1344–1351 of SEQ ID NO:3. According to this embodiment, said non-ribosomal peptide synthetase preferably comprises an amino acid sequence selected from the group consisting of: SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, and amino acids 1344–1351 of SEQ ID NO:3. Also, according to this embodiment, said nucleotide sequence preferably is substantially similar to a nucleotide sequence selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ Ib NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1. In addition, according to this embodiment, said nucleotide sequence most preferably is selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1.

The present invention further provides an isolated nucleic acid molecule comprising a nucleotide sequence that encodes a polypeptide comprising an amino acid sequence selected from the group consisting of SEQ ID NOs:2–23.

In accordance with another aspect, the present invention also provides methods for the recombinant production of polyketides such as epothilones in quantities large enough to enable their purification and use in pharmaceutical formulations such as those for the treatment of cancer. A specific advantage of these production methods is the chirality of the molecules produced; production in transgenic organisms avoids the generation of populations of racemic mixtures, within which some enantiomers may have reduced activity. In particular, the present invention provides a method for heterologous expression of epothilone in a recombinant host, comprising: (a) introducing into a host a chimeric gene comprising a heterologous promoter sequence operatively linked to a nucleic acid molecule of the invention that comprises a nucleotide sequence that encodes at least one polypeptide involved in the biosynthesis of epothilone; and (b) growing the host in conditions that allow biosynthesis of epothilone in the host. The present invention also provides a method for producing epothilone, comprising: (a) expressing epothilone in a recombinant host by the aforementioned method; and (b) extracting epothilone from the recombinant host.

According to still another aspect, the present invention provides an isolated polypeptide comprising an amino acid sequence that consists of an epothilone synthase domain.

According to one embodiment, the epothilone synthase domain is a β-ketoacyl-synthase (KS) domain comprising an amino acid sequence substantially similar to an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7. According to this embodiment, said KS domain preferably comprises an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7.

According to another embodiment, the epothilone synthase domain is an acyltransferase (AT) domain comprising an amino acid sequence substantially similar to an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. According to this embodiment, said AT domain preferably comprises an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7.

According to still another embodiment, the epothilone synthase domain is an enoyl reductase (ER) domain comprising an amino acid sequence substantially similar to an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. According to this embodiment, said ER domain preferably comprises an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7.

According to another embodiment, the epothilone synthase domain is an acyl carrier protein (ACP) domain, wherein said polypeptide comprises an amino acid sequence substantially similar to an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. According to this embodiment, said ACP domain preferably comprises an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7.

According to another embodiment, the epothilone synthase domain is a dehydratase (DH) domain comprising an amino acid sequence substantially similar to an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. According to this embodiment, said DH domain preferably comprises an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7.

According to yet another embodiment, the epothilone synthase domain is a β-keto-reductase (KR) domain comprising an amino acid sequence substantially similar to an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. According to this embodiment, said KR domain preferably comprises an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7.

According to an additional embodiment, the epothilone synthase domain is a methyl-transferase (MT) domain comprising an amino acid sequence substantially similar to amino acids 2671–3045 of SEQ ID NO:6. According to this embodiment, said MT domain preferably comprises amino acids 2671–3045 of SEQ ID NO:6.

According to another embodiment, the epothilone synthase domain is a thioesterase (TE) domain comprising an amino acid sequence substantially similar to amino acids 2165–2439 of SEQ ID NO:7. According to this embodiment, said TE domain preferably comprises amino acids 2165–2439 of SEQ ID NO:7.

Other aspects and advantages of the present invention will become apparent to those skilled in the art from a study of the following description of the invention and non-limiting examples.

DEFINITIONS

In describing the present invention, the following terms will be employed, and are intended to be defined as indicated below.

Associated With/Operatively Linked: Refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene: A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene is not normally operatively linked to the associated DNA sequence as found in nature.

Coding DNA Sequence: A DNA sequence that is translated in an organism to produce a protein.

Domain: That part of a polyketide synthase necessary for a given distinct activity. Examples include acyl carrier protein (ACP), β-ketosynthase (KS), acyltransferase (AT), β-ketoreductase (KR), dehydratase (DH), enoylreductase (ER), and thioesterase (TE) domains.

Epothilones: 16-membered macrocyclic polyketides naturally produced by the bacterium *Sorangium cellulosum* strain So ce90, which mimic the biological effects of taxol. In this application, "epothilone" refers to the class of polyketides that includes epothilone A and epothilone B, as well as analogs thereof such as those described in WO 98/25929.

Epothilone Synthase: A polyketide synthase responsible for the biosynthesis of epothilone.

Gene: A defined region that is located within a genome and that, besides the aforementioned coding DNA sequence, comprises other, primarily regulatory, DNA sequences responsible for the control of the expression, that is to say the transcription and translation, of the coding portion.

Heterologous DNA Sequence: A DNA sequence not naturally associated with a host cell into which it is introduced, including non-naturally occurring multiple copies of a naturally occurring DNA sequence.

Homologous DNA Sequence: A DNA sequence naturally associated with a host cell into which it is introduced.

Homologous Recombination: Reciprocal exchange of DNA fragments between homologous DNA molecules.

Isolated: In the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

Module: A genetic element encoding all of the distinct activities required in a single round of polyketide biosynthesis, i.e., one condensation step and all the β-carbonyl processing steps associated therewith. Each module encodes an ACP, a KS, and an AT activity to accomplish the condensation portion of the biosynthesis, and selected post-condensation activities to effect the β-carbonyl processing.

NRPS: A non-ribosomal polypeptide synthetase, which is a complex of enzymatic activities responsible for the incorporation of amino acids into secondary metabolites including, for example, amino acid adenylation, epimerization, N-methylation, cyclization, peptidyl carrier protein, and condensation domains. A functional NRPS is one that catalyzes the incorporation of an amino acid into a secondary metabolite.

NRPS gene: One or more genes encoding NRPSs for producing functional secondary metabolites, e.g., epothilones A and B, when under the direction of one or more compatible control elements.

Nucleic Acid Molecule: A linear segment of single- or double-stranded DNA or RNA that can be isolated from any source. In the context of the present invention, the nucleic acid molecule is preferably a segment of DNA.

ORF: Open Reading Frame.

PKS: A polyketide synthase, which is a complex of enzymatic activities (domains) responsible for the biosynthesis of polyketides including, for example, ketoreductase, dehydratase, acyl carrier protein, enoylreductase, ketoacyl ACP synthase, and acyltransferase. A functional PKS is one that catalyzes the synthesis of a polyketide.

PKS Genes: One or more genes encoding various polypeptides required for producing functional polyketides, e.g., epothilones A and B, when under the direction of one or more compatible control elements.

Substantially Similar: With respect to nucleic acids, a nucleic acid molecule that has at least 60 percent sequence identity with a reference nucleic acid molecule. In a preferred embodiment, a substantially similar DNA sequence is at least 80% identical to a reference DNA sequence; in a more preferred embodiment, a substantially similar DNA sequence is at least 90% identical to a reference DNA sequence; and in a most preferred embodiment, a substantially similar DNA sequence is at least 95% identical to a reference DNA sequence. A substantially similar DNA sequence preferably encodes a protein or peptide having substantially the same activity as the protein or peptide encoded by the reference DNA sequence. A substantially similar nucleotide sequence typically hybridizes to a reference nucleic acid molecule, or fragments thereof, under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C. With respect to proteins or peptides, a substantially similar amino acid sequence is an amino acid sequence that is at least 90% identical to the amino acid sequence of a reference protein or peptide and has substantially the same activity as the reference protein or peptide.

Transformation: A process for introducing heterologous nucleic acid into a host cell or organism.

Transformed/Transgenic/Recombinant: Refers to a host organism such as a bacterium into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, i.e., a bacterium, which does not contain the heterologous nucleic acid molecule.

Nucleotides are indicated by their bases by the following standard abbreviations:

adenine (A), cytosine (C), thymine (T), and guanine (G). Amino acids are likewise indicated by the following standard abbreviations: alanine (ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DESCRIPTION OF THE SEQUENCES IN THE SEQUENCE LISTING

SEQ ID NO:1 is the nucleotide sequence of a 68750 bp contig containing 22 open reading frames (ORFs), which comprises the epothilone biosynthesis genes.

SEQ ID NO:2 is the protein sequence of a type I polyketide synthase (EPOS A) encoded by epoA (nucleotides 7610–11875 of SEQ ID NO:1).

SEQ ID NO:3 is the protein sequence of a non-ribosomal peptide synthetase (EPOS P) encoded by epoP (nucleotides 11872–16104 of SEQ ID NO:1).

SEQ ID NO:4 is the protein sequence of a type I polyketide synthase (EPOS B) encoded by epoB (nucleotides 16251–21749 of SEQ ID NO:1).

SEQ ID NO:5 is the protein sequence of a type I polyketide synthase (EPOS C) encoded by epoC (nucleotides 21746–43519 of SEQ ID NO:1).

SEQ ID NO:6 is the protein sequence of a type I polyketide synthase (EPOS D) encoded by epoD (nucleotides 43524–54920 of SEQ ID NO:1).

SEQ ID NO:7 is the protein sequence of a type I polyketide synthase (EPOS E) encoded by epoE (nucleotides 54935–62254 of SEQ ID NO:1).

SEQ ID NO:8 is the protein sequence of a cytochrome P450 oxygenase homologue (EPOS F) encoded by epoF (nucleotides 62369–63628 of SEQ ID NO:1).

SEQ ID NO:9 is a partial protein sequence (partial Orf 1) encoded by orf1 (nucleotides 1–1826 of SEQ ID NO:1).

SEQ ID NO:10 is a protein sequence (Orf 2) encoded by orf2 (nucleotides 3171–1900 on the reverse complement strand of SEQ ID NO:1).

SEQ ID NO:11 is a protein sequence (Orf 3) encoded by orf3 (nucleotides 3415–5556 of SEQ ID NO:1).

SEQ ID NO:12 is a protein sequence (Orf 4) encoded by orf4 (nucleotides 5992–5612 on the reverse complement strand of SEQ ID NO:1).

SEQ ID NO:13 is a protein sequence (Orf 5) encoded by orf5 (nucleotides 6226–6675 of SEQ ID NO:1).

SEQ ID NO:14 is a protein sequence (Orf 6) encoded by orf6 (nucleotides 63779–64333 of SEQ ID NO:1).

SEQ ID NO:15 is a protein sequence (Orf 7) encoded by orf7 (nucleotides 64290–63853 on the reverse complement strand of SEQ ID NO:1).

SEQ ID NO:16 is a protein sequence (Orf 8) encoded by orf8 (nucleotides 64363–64920 of SEQ ID NO:1).

SEQ ID NO:17 is a protein sequence (Orf 9) encoded by orf9 (nucleotides 64727–64287 on the reverse complement strand of SEQ ID NO:1).

SEQ ID NO:18 is a protein sequence (Orf 10) encoded by orf10 (nucleotides 65063–65767 of SEQ ID NO:1).

SEQ ID NO:19 is a protein sequence (Orf 11) encoded by orf11 (nucleotides 65874–65008 on the reverse complement strand of SEQ ID NO:1).

SEQ ID NO:20 is a protein sequence (Orf 12) encoded by orf12 (nucleotides 66338–65871 on the reverse complement strand of SEQ ID NO:1).

SEQ ID NO:21 is a protein sequence (Orf 13) encoded by orf13 (nucleotides 66667–67137 of SEQ ID NO:1).

SEQ ID NO:22 is a protein sequence (Orf 14) encoded by orf14 (nucleotides 67334–68251 of SEQ ID NO:1).

SEQ ID NO:23 is a partial protein sequence (partial Orf 15) encoded by orf15 (nucleotides 68346–68750 of SEQ ID NO:1).

SEQ ID NO:24 is the universal reverse PCR primer sequence.

SEQ ID NO:25 is the universal forward PCR primer sequence.

SEQ ID NO:26 is the NH24 end "B" PCR primer sequence.

SEQ ID NO:27 is the NH2 end "A" PCR primer sequence.

SEQ ID NO:28 is the NH2 end "B" PCR primer sequence.

SEQ ID NO:29 is the pEPO15-NH6 end "B" PCR primer sequence.

SEQ ID NO:30 is the pEPO15-H2.7 end "A" PCR primer sequence.

DEPOSIT INFORMATION

The following material has been deposited with the Agricultural Research Service, Patent Culture Collection (NRRL), 1815 North University Street, Peoria, Ill. 61604, under the Budapest Treaty on the International Recognition of the Deposit of Microorganisms for the Purposes of Patent Procedure. All restrictions on the availability of the deposited material will be irrevocably removed upon the granting of a patent.

| Deposited Material | Accession Number | Deposit Date |
| --- | --- | --- |
| pEPO15 | NRRL B-30033 | June 11, 1998 |
| pEPO32 | NRRL B-30119 | April 16, 1999 |

DETAILED DESCRIPTION OF THE INVENTION

The genes involved in the biosynthesis of epothilones can be isolated using the techniques according to the present invention. The preferable procedure for the isolation of epothilone biosynthesis genes requires the isolation of genomic DNA from an organism identified as producing epothilones A and B, and the transfer of the isolated DNA on a suitable plasmid or vector to a host organism that does not normally produce the polyketide, followed by the identification of transformed host colonies to which the epothilone-producing ability has been conferred. Using a technique such as λ::Tn5 transposon mutagenesis (de Bruijn & Lupski, Gene 27: 131–149 (1984)), the exact region of the transforming epothilone-conferring DNA can be more precisely defined. Alternatively or additionally, the transforming epothilone-conferring DNA can be cleaved into smaller fragments and the smallest that maintains the epothilone-conferring ability further characterized. Whereas the host organism lacking the ability to produce epothilone may be a different species from the organism from which the polyketide derives, a variation of this technique involves the transformation of host DNA into the same host that has had its epothilone-producing ability disrupted by mutagenesis. In this method, an epothilone-producing organism is mutated and non-epothiline-producing mutants are isolated. These are then complemented by genomic DNA isolated from the epothilone-producing parent strain.

A further example of a technique that can be used to isolate genes required for epothilone biosynthesis is the use of transposon mutagenesis to generate mutants of an epothilone-producing organism that, after mutagenesis, fails to produce the polyketide. Thus, the region of the host genome responsible for epothilone production is tagged by the transposon and can be recovered and used as a probe to isolate the native genes from the parent strain. PKS genes that are required for the synthesis of polyketides and that are similar to known PKS genes may be isolated by virtue of their sequence homology to the biosynthetic genes for which the sequence is known, such as those for the biosynthesis of rifamycin or soraphen. Techniques suitable for isolation by homology include standard library screening by DNA hybridization.

Preferred for use as a probe molecule is a DNA fragment that is obtainable from a gene or another DNA sequence that plays a part in the synthesis of a known polyketide. A preferred probe molecule comprises a 1.2 kb SmaI DNA fragment encoding the ketosynthase domain of the fourth module of the soraphen PKS (U.S. Pat. No. 5,716,849), and a more preferred probe molecule comprises the β-ketoacyl synthase domains from the first and second modules of the rifamycin PKS (Schupp et al., FEMS Microbiology Letters 159: 201–207 (1998)). These can be used to probe a gene library of an epothilone-producing microorganism to isolate the PKS genes responsible for epothilone biosynthesis.

Despite the well-known difficulties with PKS gene isolation in general and despite the difficulties expected to be encountered with the isolation of epothilone biosynthesis genes in particular, by using the methods described in the instant specification, biosynthetic genes for epothilones A and B can surprisingly be cloned from a microorganism that produces that polyketide. Using the methods of gene manipulation and recombinant production described in this specification, the cloned PKS genes can be modified and expressed in transgenic host organisms.

The isolated epothilone biosynthetic genes can be expressed in heterologous hosts to enable the production of the polyketide with greater efficiency than might be possible from native hosts. Techniques for these genetic manipulations are specific for the different available hosts and are known in the art. For example, heterologous genes can be expressed in Streptomyces and other actinomycetes using techniques such as those described in McDaniel et al., *Science* 262: 1546–1550 (1993) and Kao et al., *Science* 265: 509–512 (1994), both of which are incorporated herein by reference. See also, Rowe et al., *Gene* 216: 215–223 (1998); Holmes et al., *EMBO Journal* 12(8): 3183–3191 (1993) and Bibb et al., *Gene* 38: 215–226 (1985), all of which are incorporated herein by reference.

Alternately, genes responsible for polyketide biosynthesis, i.e., epothilone biosynthetic genes, can also be expressed in other host organisms such as pseudomonads and *E. coli*. Techniques for these genetic manipulations are specific for the different available hosts and are known in the art. For example, PKS genes have been sucessfully expressed in *E. coli* using the pT7-7 vector, which uses the T7 promoter. See, Tabor et al., *Proc. Natl. Acad. Sci. USA* 82: 1074–1078 (1985), incorporated herein by reference. in addition, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al., in: *Industrial Microorganisms: Basic and Applied Molecular Genetics*, Eds. Baltz et al., American Society for Microbiology, Washington (1993)).

Other expression systems that may be used with the epothilone biosynthetic genes of the invention include yeast and baculovirus expression systems. See, for example, "The Expression of Recombinant Proteins in Yeasts," Sudbery, P. E., *Curr. Opin. Biotechnol.* 7(5): 517–524 (1996); "Methods for Expressing Recombinant Proteins in Yeast," Mackay, et al., Editor(s): Carey, Paul R., *Protein Eng. Des.* 105–153, Publisher: Academic, San Diego, Calif. (1996); "Expression of heterologous gene products in yeast," Pichuantes, et al., Editor(s): Cleland, J. L., Craik, C. S., *Protein Eng.* 129–161, Publisher: Wiley-Liss, New York, N.Y. (1996); WO 98/127203: Kealey et al., *Proc. Natl. Acad. Sci. USA* 95: 505–509 (1998); "Insect Cell Culture: Recent Advances, Bioengineering Challenges And Implications In Protein Production," Palomares, et al., Editor(s): Galindo, Enrique; Ramirez, Octavio T., *Adv. Bioprocess Eng.* Vol. II, Invited Pap. Int. Symp., 2nd (1998) 25–52, Publisher: Kluwer, Dordrecht, Neth; "Baculovirus Expression Vectors," Jarvis, Donald L., Editor(s): Miller, Lois K., *Baculoviruses* 389–431, Publisher: Plenum, New York, N.Y. (1997); "Production Of Heterologous Proteins Using The Baculovirus/ Insect Expression System," Grittiths, et al., *Methods Mol. Biol.* (Totowa, N.J.) 75 (Basic Cell Culture Protocols (2nd Edition)) 427–440 (1997); and "Insect Cell Expression Technology," Luckow, Verne A., *Protein Eng.* 183–218, Publisher: Wiley-Liss, New York, N.Y. (1996); all of which are incorporated herein by reference.

Another consideration for expression of PKS genes in heterologous hosts is the requirement of enzymes for posttranslational modification of PKS enzymes by phosphopantetheinylation before they can synthesize polyketides. However, the enzymes responsible for this modification of type I PKS enzymes, phosphopantetheinyl (P-pant) transferases are not normally present in many hosts such as *E. coli*. This problem can be solved by coexpression of a P-pant transferase with the PKS genes in the heterologous host, as described by Kealey et al., *Proc. Natl. Acad. Sci. USA* 95: 505–509 (1998), incorporated herein by reference.

Therefore, for the purposes of polyketide production, the significant criteria in the choice of host organism are its ease of manipulation, rapidity of growth (ie. fermentation), possession or the proper molecular machinery for processes such as posttranslational modification, and its lack of susceptibility to the polyketide being overproduced. Most preferred host organisms are actinomycetes such as strains of Streptomyces. Other preferred host organisms are pseudomonads and *E. coli*. The above-described methods of polyketide production have significant advantages over the technology currently used in the preparation of the compounds. These advantages include the cheaper cost of production, the ability to produce greater quantities of the compounds, and the ability to produce compounds of a preferred biological enantiomer, as opposed to racemic mixtures inevitably generated by organic synthesis. Compounds produced by heterologous hosts can be used in medical (e.g. cancer treatment in the case of epothilones) as well as agricultural applications.

EXPERIMENTAL

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), *Current Protocols in Molecular Biology*, John Wiley and Sons, Inc. (1994); T. Maniatis, E. F. Fritsch and J. Sambrook, *Molecular Cloning: A Laboratory Manual*, Cold Spring Harbor laboratory, Cold Spring Harbor, N.Y. (1989); and by T. J. Silhavy, M. L. Berman, and L. W. Enquist, *Experiments with Gene Fusions*, Cold Spring Harbor Laboratory, Cold Spring Harbor, N.Y. (1984).

Example 1

Cultivation of an Epothilone-Producing Strain of Sorangium cellulosum

*Sorangium cellulosum* strain 90 (DSM 6773, Deutsche Sammiung von Mikroorganismen und Zellkulturen, Braunschweig) is streaked out and grown (30° C.) on an agar plate of SolE medium (0.35% glucose, 0.05% tryptone, 0.15% $MgSO_4 \times 7H_2O$, 0.05% ammonium sulfate, 0.1% $CaCl_2$, 0.006% $K_2HPO_4$, 0.01% sodium dithionite, 0.0008% Fe-EDTA, 1.2% HEPES, 3.5% [vol/vol] supernatant of sterilized stationary *S. cellulosum* culture) pH ad. 7.4. Cells from about 1 square cm are picked and inoculated into 5 mls of G51t liquid medium (0.2% glucose, 0.5% starch, 0.2% tryptone, 0.1% probion S, 0.05% CaCl$_2$×2H$_2$O , 0.05% MgSO$_4$×7H$_2$O, 1.2% HEPES, pH ad. 7.4) and incubated at 30° C. with shaking at 225 rpm. After 4 days, the culture is transferred into 50 mls of G51t and incubated as above for 5 days. This culture is used to inoculate 500 mls of G51 t and incubated as above for 6 days. The culture is centrifuged for 10 minutes at 4000 rpm and the cell pellet is resuspended in 50 mls of G51t.

Example 2

Generation of a Bacterial Artificial Chromosome (Bac) Library

To generate a Bac library, S. cellulosum cells cultivated as described in Example 1 above are embedded into agarose blocks, lysed, and the liberated genomic DNA is partially digested by the restriction enzyme HindIII. The digested DNA is separated on an agarose gel by pulsed-field electrophoresis. Large (approximately 90–150 kb) DNA fragments are isolated from the agarose gel and ligated into the vector pBelobacII. pBelobacII contains a gene encoding chloramphenicol resistance, a multiple cloning site in the lacZ gene providing for blue/white selection on appropriate medium, as well as the genes required for the replication and maintenance of the plasmid at one or two copies per cell. The ligation mixture is used to transform *Escherichia coli* DH10B electrocompetent cells using standard electroporation techniques. Chloramphenicol-resistant recombinant (white, lacZ mutant) colonies are transferred to a positively charged nylon membrane filter in 384 3×3 grid format. The clones are lysed and the DNA is cross-linked to the filters. The same clones are also preserved as liquid cultures at −80° C.

Example 3

Screening the Bac Library of *Sorangium cellulosum* 90 for the Presence of Type I Polyketide Synthase-Related Sequences The Bac library filters are probed by standard Southern hybridization procedures. The DNA probes used encode β-ketoacyl synthase domains from the first and second modules of the rifamycin polyketide synthase (Schupp et al., *FEMS Microbiology Letters* 159: 201–207 (1998)). The probe DNAs are generated by PCR with primers flanking each ketosynthase domain using the plasmid pNE95 as the template (pNE95 equals cosmid 2 described in Schupp et al. (1998)). 25 ng of PCR-amplified DNA is isolated from a 0.5% agarose gel and labeled with $^{32}$P-dCTP using a random primer labeling kit (Gibco-BRL, Bethesda Md., USA) according to the manufacturer's instructions. Hybridization is at 65° C. for 36 hours and membranes are washed at high stringency (3 times with 0.1×SSC and 0.5% SDS for 20 min at 65° C). The labeled blot is exposed on a phosphorescent screen and the signals are detected on a Phospholmager 445SI (screen and 445SI from Molecular Dynamics). This results in strong hybridization of certain Bac clones to the probes. These clones are selected and cultured overnight in 5 mls of Luria broth (LB) at 37° C. Bac DNA from the Bac clones of interest is isolated by a typical miniprep procedure. The cells are resuspended in 200 µl lysozyme solution (50 mM glucose, 10 mM EDTA, 25 mM Tris-HCl, 5 mg/ml lysozyme), lysed in 400 µl lysis solution (0.2 N NaOH and 2% SDS), the proteins are precipitated (3.0 M potassium acetate, adjusted to pH 5.2 with acetic acid), and the Bac DNA is precipitated with isopropanol. The DNA is resuspended in 20 µl of nuclease-free distilled water, restricted with BamHI (New England Biolabs, Inc.) and separated on a 0.7% agarose gel. The gel is blotted by Southern hybridization as described above and probed under conditions described above, with a 1.2 kb SmaI DNA fragment encoding the ketosynthase domain of the fourth module of the soraphen polyketide synthase as the probe (see, U.S. Pat. No. 5,716,849). Five different hybridization patterns are observed. One clone representing each of the five patterns is selected and named pEPO15, pEPO20, pEPO30, pEPO31, and pEPO33, respectively.

Example 4

Subcloning of BamHI Fragments from pEPO15, pEPO20, pEPO30, pEPO31, and pEPO33

The DNA of the five selected Bac clones is digested with BamHI and random fragments are subcloned into pBluescript II SK+(Stratagene) at the BamHI site. Subclones carrying inserts between 2 and 10 kb in size are selected for sequencing of the flanking ends of the inserts and also probed with the 1.2 SmaI probe as described above. Subclones that show a high degree of sequence homology to known polyketide synthases and/or strong hybridization to the soraphen ketosynthase domain are used for gene disruption experiments.

Example 5

Preparation of Streptomycin-Resistant Spontaneous Mutants of *Sorangium cellulosum* strain So ce90

0.1 ml of a three day old culture of *Sorangium cellulosum* strain So ce90, which is raised in liquid medium G52-H (0.2% yeast extract, 0.2% soyameal defatted, 0.8% potato starch, 0.2% glucose, 0.1% MgSO4×7H2O, 0.1% CaCl2× 2H2O, 0.008% Fe-EDTA, pH ad 7.4 with KOH), is plated out on agar plates with SolE medium supplemented with 100 µg/ml streptomycin. The plates are incubated at 30° C. for 2 weeks. The colonies growing on this medium are streptomycin-resistant mutants, which are streaked out and cultivated once more on the same agar medium with streptomycin for purification. One of these streptomycin-resistant mutants is selected and is called BCE28/2.

Example 6

Gene Disruptions in *Sorangium cellulosum* BCE28/2 Using the Subcloned BamHI Fragments The BamHI inserts of the subclones generated from the five selected Bac clones as described above are isolated and ligated into the unique BamHI site of plasmid pCIB132 (see, U.S. Pat. No. 5,716,849). The pCIB132 derivatives carrying the inserts are transformed into *Escherichia coli* ED8767 containing the helper plasmid pUZ8 (Hedges and Matthew, *Plasmid* 2: 269–278 (1979). The transformants are used as donors in conjugation experiments with *Sorangium cellulosum* BCE28/2 as recipient. For the conjugation, 5–10×10$^9$ cells of *Sorangium cellulosum* BCE28/2 from an early stationary phase culture (reaching about 5×10$^8$ cells/ml) grown at 30° C. in liquid medium G51b (G51b equals medium G51t with tryptone replaced by peptone) are mixed in a 1:1 cellular ratio with a late-log phase culture (in LB liquid medium) of *E. coli* ED8767 containing pCIB132 derivatives carrying the subcloned BamHI fragments and the helper plasmid pUZ8. The mixed cells are then centrifuged at 4000 rpm for 10 minutes and resuspended in 0.5 ml G51b medium. This cell suspension is then plated as a drop in the center of a plate with So1E agar containg 50 mg/l kanamycin. The cells obtained after incubation for 24 hours at 30° C. are harvested and resuspended in 0.8 ml of G51b medium, and 0.1 to 0.3 ml of this suspension is plated out on a selective So1E solid medium containing phleomycin (30 mg/l), streptomycin (300 mg/l), and kanamycin (50 mg/l). The counterselection of the donor *Escherichia coi* strain takes place with the aid of streptomycin. The colonies that grow on this selective medium after an incubation time of 8–12 days at a temperature of 30° C. are isolated with a plastic loop and streaked out and cultivated on the same agar medium for a second round of selection and purification. The colony-derived cultures that grow on this selective agar medium after 7 days at a temperature of 30° C. are transconjugants of *Sorangium cellulosum* BCE28/2 that have acquired phleomycin resistance by conjugative transfer of the pCIB132 derivatives carrying the subcloned BamHI fragments.

Integration of the pCIB132-derived plasmids into the chromosome of *Sorangium cellulosum* BCE28/2 by homologous recombination is verified by Southern hybridization. For this experiment, complete DNA from 5–10 tranconjugants per transferred BamHI fragment is isolated (from 10 ml cultures grown in medium G52-H for three days) applying the method described by Pospiech and Neumann, *Trends Genet*. 11: 217 (1995). For the Southern blot, the DNA isolated as described above is cleaved either with the restriction enzymes BglII, ClaI, or NotI, and the respective BamHI inserts or pCIB132 are used as 32P labelled probes.

Example 7

Analysis of the Effect of the Integrated BamHI Fragments on Epothilone Production by *Sorangium cellulosum* After Gene Disruption Transconjugant cells grown on about 1 square cm surface of the selective So1E plates of the second round of selection (see Example 6) are transferred by a sterile plastic loop into 10 ml of medium G52-H in an 50 ml Erlenmeyer flask. After incubation at 30° C. and 180 rpm for 3 days, the culture is transfered into 50 ml of medium G52-H in an 200 ml Erlenmeyer flask. After incubation at 30° C. and 180 rpm for 4–5 days, 10 ml of this culture is transfered into 50 ml of medium 23B3 (0.2% glucose, 2% potato starch, 1.6% soya meal defatted, 0.0008% Fe-EDTA Sodium salt, 0.5% HEPES (4-(2-hydroxyethyl)-piperazine-1-ethane-sulfonic-acid), 2% vol/vol polysterole resin XAD16 (Rohm & Haas), pH adjusted to 7.8 with NaOH) in an 200 ml Erlenmeyer flask.

Quantitative determination of the epothilone produced takes place after incubation of the cultures at 30° C. and 180 rpm for 7 days. The complete culture broth is filtered by suction through a 150 μm nylon filter. The resin remaining on the filter is then resuspended in 10 ml isopropanol and extracted by shaking the suspension at 180 rpm for 1 hour. 1 ml is removed from this suspension and centrifuged at 12,000 rpm in an Eppendorff Microfuge. The amount of epothilones A and B therein is determined by means of an HPLC and detection at 250 nm with a UV_DAD detector (HPLC with Waters—Symetry C18 column and a gradient of 0.02% phosphoric acid 60%–0% and acetonitril 40%–100%).

Transconjugants with three different integrated BamHI fragments subcllonded from pEPO15, namely transconjugants with the BamHI fragment of plasmid pEPO15-21, transconjugants with the BamHI fragment of plasmid pEPO15-4-5, and transconjugants with the BamHI fragment of plasmid pEPO15-4-1, are tested in the manner described above. HPLC analysis reveals that all transconjugants no longer produce epothilone A or B. By contrast, epothilone A and B are detectable in a concentration of 2–4 mg/l in transconjugants with BamHI fragments integrated that are derived from pEPO20, pEPO30, pEPO31, pEPO33, and in the parental strain BCE28/2.

Example 8

Nucleotide Sequence Determination of the Cloned Fragments and Construction of Contigs A. BamHI Insert of Plasmid pEPO15-21

Plasmid DNA is isolated from the strain *Escherichia coli* DH10B [pEPO15-21], and the nucleotide sequence of the 2.3-kb BamHI insert in pEPO15-21 is determined. Automated DNA sequencing is done on the double-stranded DNA template by the dideoxynucleotide chain termination method, using Applied Biosystems model 377 sequencers. The primers used are the universal reverse primer (5' GGA AAC AGC TAT GAC CAT G 3' (SEQ ID NO:24)) and the universal forward primer (5' GTA AAA CGA CGG CCA GT 3' (SEQ ID NO:25)). In subsequent rounds of sequencing reactions, custom-synthesized oligonucleotides, designed for the 3' ends of the previously determined sequences, are used to extend and join contigs. Both strands are entirely sequenced, and every nucleotide is sequenced at least two times. The nucleotide sequence is compiled using the program Sequencher vers. 3.0 (Gene Codes Corporation), and analyzed using the University of Wisconsin Genetics Computer Group programs. The nucleotide sequence of the 2213-bp insert corresponds to nucleotides 20779–22991 of SEQ ID NO:1.

B. BamHI Insert of Plasmid pEPO15-4-1

Plasmid DNA is isolated from the strain *Escherichia coli* DH10B [pEPO15-4-1], and the nucleotide sequence of the 3.9-kb BamHI insert in pEPO15-4-1 is determined as described in (A) above. The nucleotide sequence of the 3909-bp insert corresponds to nucleotides 16876–20784 of SEQ ID NO:1.

C. BamHI Insert of Plasmid pEPO15-4-5

Plasmid DNA is isolated from the strain *Escherichia coli* DH10B [pEPO15-4-5], and the nucleotide sequence of the 2.3-kb BamHI insert in pEPO15-4-5 is determined as described in (A) above. The nucleotide sequence of the 2233-bp insert corresponds to nucleotides 42528–44760 of SEQ ID NO:1.

Example 9

Subcloning and Ordering of DNA Fragments from pEPO15 Containing Epothilone Biosynthesis Genes pEPO15 is digested to completion with the restriction enzyme HindIII and the resulting fragments are subcloned into pBluescript II SK– or pNEB 193 (New England Biolabs) that has been cut with HindIII and dephosphorylated with calf intestinal alkaline phosphatase. Six different clones are generated and named pEPO15-NH1, pEPO15-NH2, pEPO15-NH6, pEPO15-NH24 (all based on pNEB193), and pEPO15-H2.7 and pEPO15-H3.0 (both based on pBluescript II SK–).

The BamHI insert of pEPO15-21 is isolated and DIG-labeled (Non-radioactive DNA labeling and detection system, Boehringer Mannheim), and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signal is detected for pEPO15-NH24, indicating that pEPO15-21 is contained within pEPO15-NH24.

The BamHI insert of pEPO15-4-1 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signals are detected for pEPO15-NH24 and pEPO15-H2.7. Nucleotide sequence data generated from one end each of pEPO15-NH24 and pEPO15-H2.7 are also in complete agreement with the previously determined sequence of the BamHI insert of pEPO15-4-1. These experiments demonstrate that pEPO15-4-1 (which contains one internal HindIII site) overlaps pEPO15-H2.7 and pEPO15-NH24, and that pEPO15-H2.7 and pEPO15-NH24, in this order, are contiguous.

The BamHI insert of pEPO15-4-5 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signal is detected for pEPO15-NH2, indicating that pEPO15-21 is contained within pEPO15-NH2.

Nucleotide sequence data is generated from both ends of pEPO15-NH2 and from the end of pEPO15-NH24 that does not overlap with pEPO15-4-1. PCR primers NH24 end "B": GTGACTGGCGCCTGGMTCTGCATGAGC (SEQ ID NO:26), NH2 end "A": AGCGGGAGCTTGCTAGACATTCTGTTTC (SEQ ID NO:27), and NH2 end "B": GACGCGCCTCGGGCAGCGCCCCAA (SEQ ID NO:28), pointing towards the HindIII sites, are designed based on these sequences and used in amplification reactions with pEPO15 and, in separate experiments, with *Sorangium cellulosum* So ce90 genomic DNA as the templates. Specific amplification is found with primer pair NH24 end "B" and NH2 end "A" with both templates. The amplimers are cloned into pBluescript II SK– and completely sequenced. The sequences of the amplimers are identical, and also agree completely with the end sequences of pEPO15-NH24 and pEPO15-NH2, fused at the HindIII site, establishing that the HindIII fragments of pEPO15-NH2 and pEPO15-NH24 are, in this order, contiguous.

The HindIII insert of pEPO15-H2.7 is isolated and DIG-labeled as above, and used as a probe in a DNA hybridization experiment at high stringency against pEPO15 digested by NotI. A NotI fragment of about 9 kb in size shows a strong a hybridization, and is further subcloned into pBluescript II SK– that has been digested with NotI and dephosphorylated with calf intestinal alkaline phosphatase, to yield pEPO15-N9-16. The NotI insert of pEPO15-N9-16 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signals are detected for pEPO15-NH6, and also for the expected clones pEPO15-H2.7 and pEPO15-NH24. Nucleotide sequence data is generated from both ends of pEPO15-NH6 and from the end of pEPO15-H2.7 that does not overlap with pEPO15-4-1. PCR primers are designed pointing towards the HindIII sites and used in amplification reactions with pEPO15 and, in separate experiments, with *Sorangium cellulosum* So ce90 genomic DNA as the templates. Specific amplification is found with primer pair pEPO15-NH6 end "B": CACCGAAGCGTCGATCTG-GTCCATC (SEQ ID NO:29) and pEPO15-H2.7 end "A": CGGTCAGATCGACGACGGGCTTTCC (SEQ ID NO:30) with both templates. The amplimers are cloned into pBluescript II SK– and completely sequenced. The sequences of the amplimers are identical, and also agree completely with the end sequences of pEPO15-NH6 and pEPO15-H2.7, fused at the HindIII site, establishing that the HindIII fragments of pEPO15-NH6 and pEPO15-H2.7 are, in this order, contiguous.

All of these experiments, taken together, establish a contig of HindIII fragments covering a region of about 55 kb and consisting of the HindIII inserts of pEPO15-NH6, pEPO15-H2.7; pEPO15-NH24, and pEPO15-NH2, in this order. The inserts of the remaining two HindIII subclones, namely pEPO15-NH1 and pEPO15-H3.0, are not found to be parts of this contig.

Example 10

Further Extension of the Subclone Contig Covering the Epothilone Biosynthesis Genes An approximately 2.2 kb BamHI-HindIII fragment derived from the downstream end of the insert of pEPO15-NH2 and thus representing the downstream end of the subclone contig described in Example 9 is isolated, DIG-labeled, and used in Southern hybridization experiments against pEPO15 and pEPO15-NH2 DNAs digested with several enzymes. The strongly hybridizing bands are always found to be the same in size between the two target DNAs indicating that the *Sorangium cellulosum* So ce90 genomic DNA fragment cloned into pEPO15 ends with the HindIII site at the downstream end of pEPO15-NH2.

A cosmid DNA library of *Sorangium cellulosum* So ce90 is generated, using established procedures, in pScosTriplex-II (Ji, et al., *Genomics* 31: 185–192 (1996)). Briefly, high-molecular weight genomic DNA of *Sorangium cellulosum* So ce90 is partially digested with the restriction enzyme Sau3AI to provide fragments with average sizes of about 40 kb, and ligated to BamHI and XbaI digested pScosTriplex-II. The ligation mix is packaged with Gigapack III XL (Stratagene) and used to transfect *E. coli* XL1 Blue MR cells.

The cosmid library is screened with the approximately 2.2 kb BamHI-HindIII fragment, derived from the downstream end of the insert of pEPO15-NH2, used as a probe in colony hybridization. A strongly hybridizing clone, named pEPO4E7 is selected.

pEPO4E7 DNA is isolated, digested with several restriction endonucleases, and probed in Southern hybridization experiments with the 2.2 kb BamHI-HindIII fragment. A strongly hybridizing NotI fragment of approximately 9 kb in size is selected and subcloned into pBluescript II SK– to yield pEPO4E7-N9-8. Further Southern hybridization experiments reveal that the approximately 9 kb NotI insert of pEPO4E7-N9-8 overlaps pEPO15-NH2 over 6 kb in a NotI-HindIII fragment, while the remaining approximately 3 kb HindIII-NotI fragment would extend the subclone contig described in Example 9. End sequencing reveals, however, that the downstream end of the insert of pEPO4E7-N9-8 contains the BamHI-NotI polylinker of pScosTriplex-II, thereby indicating that the genomic DNA insert of pEPO4E7 ends at a Sau3AI site within the extending HindIII-NotI fragment and that the NotI site is derived from pScosTriplex-II.

An approximately 1.6 kb PstI-SalI fragment derived from the approximately 3 kb extending HindIII-NotI subfragment of pEPO4E7-N9-8, containing only *Sorangium cellulosum* So ce90-derived sequences free of vector, is used as a probe against the bacterial artificial chromosome library described in Example 2. Besides the previously-isolated EPO15, a Bac clone, named EPO32, is found to strongly hybridize to the probe. pEPO32 is isolated, digested with several restriction endonucleases, and hybridized with the approximately 1.6 kb PstI-SalI probe. A HindIII-EcoRV fragment of about 13 kb in size is found to strongly hybridize to the probe, and is subcloned into pBluescript II SK– digested with HindIII and HincII to yield pEPO32-HEV15.

Oligonucleotide primers are designed based on the downstream end sequence of pEPO15-NH2 and on the upstream (HindIII) end sequence derived from pEPO32-HEV15, and used in sequencing reactions with pEPO4E7-N9-8 as the template. The sequences reveal the existence of a small HindIII fragment (EPO4E7-H0.02) of 24 bp, undetectable in standard restriction analysis, separating the HindIII site at the downstream end of pEPO15-NH2 from the HindIII site at the upstream end of pEPO32-HEV15.

Thus, the subclone contig described in Example 9 is extended to include the HindIII fragment EPO4E7-H0.02 and the insert of pEPO32-HEV15, and constitutes the inserts of: pEPO15-NH6, pEPO15-H2.7, pEPO15-NH24, pEPO15-NH2, EPO4E7-H0.02 and pEPO32-HEV15, in this order.

Example 11

Nucleotide Sequence Determination of the Subclone Contig Covering the Epothilone Biosynthesis Genes The nucleotide sequence of the subclone contig described in Example 10 is determined as follows.

pEPO15-H2.7. Plasmid DNA is isolated from the strain *Escherichia coli* DH10B [pEPO15-H2.7], and the nucleotide sequence of the 2.7-kb BamHI insert in pEPO15-H2.7 is determined. Automated DNA sequencing is done on the double-stranded DNA template by the dideoxynucleotide chain termination method, using Applied Biosystems model 377 sequencers. The primers used are the universal reverse primer (5' GGA AAC AGC TAT GAC CAT G 3' (SEQ ID NO:24)) and the universal forward primer (5' GTA AAA CGA CGG CCA GT 3' (SEQ ID NO:25)). In subsequent rounds of sequencing reactions, custom-synthesized oligonucleotides, designed for the 3' ends of the previously determined sequences, are used to extend and join contigs.

pEPO15-NH6, pEPO15-NH24 and pEPO15-NH2. The HindIII inserts of these plasmids are isolated, and subjected to random fragmentation using a Hydroshear apparatus (Genomic Instrumentation Services, Inc.) to yield an average fragment size of 1–2 kb. The fragments are end-repaired using T4 DNA Polymerase and Klenow DNA Polymerase enzymes in the presence of desoxynucleotide triphosphates, and phosphorylated with T4 DNA Kinase in the presence of ribo-ATP. Fragments in the size range of 1.5–2.2 kb are isolated from agarose gels, and ligated into pBluescript II SK– that has been cut with EcoRV and de-phosphorylated. Random subolones are sequenced using the universal reverse and the universal forward primers.

pEPO32-HEV15. pEPO32-HEV15 is digested with HindIII and SspI, the approximately 13.3 kb fragment containing the ~13 kb HindIII-EcoRV insert from *So. cellulosum* So ce90 and a 0.3 kb HincII-SspI fragment from pBluescript II SK– is isolated, and partially digested with HaeIII to yield fragments with an average size of 1–2 kb. Fragments in the size range of 1.5–2.2 kb are isolated from agarose gels, and ligated into pBluescript II SK– that has been cut with EcoRV and dephosphorylated. Random subclones are sequenced using the universal reverse and the universal forward primers.

The chromatograms are analyzed and assembled into contigs with the Phred, Phrap and Consed programs (Ewing, et al., *Genome Res.* 8(3): 175–185 (1998); Ewing, et al., *Genome Res.* 8(3): 186–194 (1998); Gordon, et al., *Genome Res.* 8(3): 195–202 (1998) Contig gaps are filled, sequence discrepancies are resolved, and low-quality regions are resequenced using custom-designed oligonucleotide primers for sequencing on either the original subclones or selected clones from the random subclone libraries. Both strands are completely sequenced, and every basepair is covered with at least a minimum aggregated Phred score of 40 (confidence level of 99.99%).

The nucleotide sequence of the 68750 bp contig is shown as SEQ ID NO:1.

Example 12

Nucleotide Sequence Analysis of the Epothilone Biosynthesis Genes

SEQ ID NO:1 is found to contain 22 ORFs as detailed below in Table 1:

TABLE 1

| ORF | Start codon | Stop codon | Homology of deduced protein | Proposed function of deduced protein |
| --- | --- | --- | --- | --- |
| orf1 | outside of sequenced range | 1826 | | |
| orf2* | 3171 | 1900 | Hypothetical protein SP: Q11037; DD-peptidase SP:P15555 | |
| orf3 | 3415 | 5556 | Na/H antiporter PID: D1017724 | Transport |
| orf4* | 5992 | 5612 | | |
| orf5 | 6226 | 6675 | | |
| epoA | 7610 | 11875 | Type I polyketide synthase | Epothilone synthase: Thiazole ring formation |
| epoP | 11872 | 16104 | Non-ribosomal peptide synthetase | Epothilone synthase: Thiazole ring formation |
| epoB | 16251 | 21749 | Type I polyketide synthase | Epothilone synthase: Polyketide backbone formation |
| epoC | 21746 | 43519 | Type I polyketide synthase | Epothilone synthase: Polyketide backbone formation |

TABLE 1-continued

| ORF | Start codon | Stop codon | Homology of deduced protein | Proposed function of deduced protein |
| --- | --- | --- | --- | --- |
| epoD | 43524 | 54920 | Type I polyketide synthase | Epothilone synthase: Polyketide backbone formation |
| epoE | 54935 | 62254 | Type I polyketide synthase | Epothilone synthase: Polyketide backbone formation |
| epoF | 62369 | 63628 | Cytochrome P450 | Epothilone macrolactone oxidase |
| orf6 | 63779 | 64333 | | |
| orf7* | 64290 | 63853 | | |
| orf8 | 64363 | 64920 | | |
| orf9* | 64727 | 64287 | | |
| orf10 | 65063 | 65767 | | |
| orf11* | 65874 | 65008 | | |
| orf12* | 66338 | 65871 | | |
| orf13 | 66667 | 67137 | | |
| orf14 | 67334 | 68251 | Hypothetical protein GI:3293544; Cation efflux system protein GI:2623026 | Transport |
| orf15 | 68346 | outside of sequenced range | | |

*On the reverse complementer strand. Numbering according to SEQ ID NO:1.

epoA (nucleotides 7610–11875 of SEQ ID NO:1) codes for EPOS A (SEQ ID NO:2), a type I polyketide synthase consisting of a single module, and harboring the following domains: β-ketoacyl-synthase (KS) (nucleotides 7643–8920 of SEQ ID NO:1, amino acids 11–437 of SEQ ID NO:2); acyltransferase (AT) (nucleotides 9236–10201 of SEQ ID NO:1, amino acids 543–864 of SEQ ID NO:2); enoyl reductase (ER) (nucleotides 10529–11428 of SEQ ID NO:1, amino acids 974–1273 of SEQ ID NO:2); and acyl carrier protein homologous domain (ACP) (nucleotides 11549–11764 of SEQ ID NO:1, amino acids 1314–1385 of SEQ ID NO:2). Sequence comparisons and motif analysis (Haydock, et al. *FEBS Lett.* 374: 246–248 (1995); Tang, et al., *Gene* 216: 255–265 (1998)) reveal that the AT encoded by EPOS A is specific for malonyl-CoA. EPOS A should be involved in the initiation of epothilone biosynthesis by loading the acetate unit to the multienzyme complex that will eventually form part of the 2-methylthiazole ring (C26 and C20).

epoP (nucleotides 11872–16104 of SEQ ID NO:1) codes for EPOS P (SEQ ID NO:3), a non-ribosomal peptide synthetase containing one module. EPOS P harbors the following domains:

peptide bond formation domain, as delineated by motif K (amino acids 72–81 [FPLTDIQESY] of SEQ ID NO:3, corresponding to nucleotide positions 12085–12114 of SEQ ID NO:1); motif L (amino acids 118–125 [VVARHDML] of SEQ ID NO:3, corresponding to nucleotide positions 12223–12246 of SEQ ID NO:1); motif M (amino acids 199–212 [SIDLINVDLGSLSI] of SEQ ID NO:3, corresponding to nucleotide positions 12466–12507 of SEQ ID NO:1); and motif O (amino acids 353–363 [GDFTSMVLLDI] of SEQ ID NO:3, corresponding to nucleotide positions 12928–12960 of SEQ ID NO:1);

aminoacyl adenylate formation domain, as delineated by motif A (amino acids 549–565 [LTYEELSRRSRRLGARL] of SEQ ID NO:3, corresponding to nucleotide positions 13516–13566 of SEQ ID NO:1); motif B (amino acids 588–603 [VAVLAVLESGAAYVPI] of SEQ ID NO:3, corresponding to nucleotide positions 13633–13680 of SEQ ID NO:1); motif C (amino acids 669–684 [AYVIYTSGSTGLPKGV] of SEQ ID NO:3, corresponding to nucleotide positions 13876–13923 of SEQ ID NO:1); motif D (amino acids 815–821 [SLGGATE] of SEQ ID NO:3, corresponding to nucleotide positions 14313–14334 of SEQ ID NO:1); motif E (amino acids 868–892 [GQLYIGGVGLALGYWRDEEKTRKSF] of SEQ ID NO:3, corresponding to nucleotide positions 14473–14547 of SEQ ID NO:1); motif F (amino acids 903–912 [YKTGDLGRYL] of SEQ ID NO:3, corresponding to nucleotide positions 14578–14607 of SEQ ID NO:1); motif G (amino acids 918–940 [EFMGREDNQIKLRGYRVELGEIE] of SEQ ID NO:3, corresponding to nucleotide positions 14623–14692 of SEQ ID NO:1); motif H (amino acids 1268–1274 [LPEYMVP] of SEQ ID NO:3, corresponding to nucleotide positions 15673–15693 of SEQ ID NO:1); and motif I (amino acids 1285–1297 [LTSNGKVDRKALR] of SEQ ID NO:3, corresponding to nucleotide positions 15724–5762 of SEQ ID NO:1);

an unknown domain, inserted between motifs G and H of the aminoacyl adenylate formation domain (amino acids 973–1256 of SEQ ID NO:3, corresponding to nucleotide positions 14788–15639 of SEQ ID NO:1); and a peptidyl carrier protein homologous domain (PCP), delineated by motif J (amino acids 1344–1351 [GATSIHIV] of SEQ ID NO:3, corresponding to nucleotide positions 15901–15924 of SEQ ID NO:1).

It is proposed that EPOS P is involved in the activation of a cysteine by adenylation, binding the activated cysteine as an aminoacyl-S-PCP, forming a peptide bond between the enzyme-bound cysteine and the acetyl-S-ACP supplied by EPOS A, and the formation of the initial thiazoline ring by intramolecular heterocyclization. The unknown domain of EPOS P displays very weak homologies to NAD(P)H oxidases and reductases from Bacillus species. Thus, this unknown domain and/or the ER domain of EPOS A may be involved in the oxidation of the initial 2-methylthiazoline ring to a 2-methylthiazole.

epoB (nucleotides 16251–21749 of SEQ ID NO:1) codes for EPOS B (SEQ ID NO:4), a type I polyketide synthase consisting of a single module, and harboring the following domains: KS (nucleotides 16269–17546 of SEQ ID NO:1, amino acids 7–432 of SEQ ID NO:4); AT (nucleotides 17865–18827 of SEQ ID NO:1, amino acids 539–859 of SEQ ID NO:4); dehydratase (DH) (nucleotides 18855–19361 of SEQ ID NO:1, amino acids 869–1037 of SEQ ID NO:4); β-ketoreductase (KR) (nucleotides 20565–21302 of SEQ ID NO:1, amino acids 1439–1684 of SEQ ID NO:4); and ACP (nucleotides 21414–21626 of SEQ ID NO:1, amino acids 1722–1792 of SEQ ID NO:4). Sequence comparisons and motif analysis reveal that the AT encoded by EPOS B is specific for methylmalonyl-CoA. EPOS A should be involved in the first polyketide chain extension by catalysing the Claisen-like condensation of the 2-methyl-4-thiazolecarboxyl-S-PCP starter group with the methylmalonyl-S-ACP, and the concomitant reduction of the b-keto group of C17 to an enoyl.

epoC (nucleotides 21746–43519 of SEQ ID NO:1) codes for EPOS C (SEQ ID NO:5), a type I polyketide synthase consisting of 4 modules. The first module harbors a KS (nucleotides 21860–23116 of SEQ ID NO:1, amino acids 39–457 of SEQ ID NO:5); a malonyl CoA-specific AT (nucleotides 23431–24397 of SEQ ID NO:1, amino acids 563–884 of SEQ ID NO:5); a KR (nucleotides 25184–25942 of SEQ ID NO:1, amino acids 1147–1399 of SEQ ID NO:5); and an ACP (nucleotides 26045–26263 of SEQ ID NO:1, amino acids 1434–1506 of SEQ ID NO:5). This module incorporates an acetate extender unit (C14–C13) and reduces the β-keto group at C15 to the hydroxyl group that takes part in the final lactonization of the epothilone macrolactone ring. The second module of EPOS C harbors a KS (nucleotides 26318–27595 of SEQ ID NO:1, amino acids 1524–1950 of SEQ ID NO:5); a malonyl CoA-specific AT (nucleotides 27911–28876 of SEQ ID NO:1, amino acids 2056–2377 of SEQ ID NO:5); a KR (nucleotides 29678–30429 of SEQ ID NO:1, amino acids 2645–2895 of SEQ.ID NO:5); and an ACP (nucleotides 30539–30759 of SEQ ID NO:1, amino acids 2932–3005 of SEQ ID NO:5). This module incorporates an acetate extender unit (C12–C11) and reduces the β-keto group at C13 to a hydroxyl group. Thus, the nascent polyketide chain of epothilone corresponds to epothilone A, and the incorporation of the methyl side chain at C12 in epothilone B would require a post-PKS C-methyltransferase activity. The formation of the epoxi ring at C13–C12 would also require a post-PKS oxidation step. The third module of EPOS C harbors a KS (nucleotides 30815–32092 of SEQ ID NO:1, amino acids 3024–3449 of SEQ ID NO:5); a malonyl CoA-specific AT (nucleotides 32408–33373 of SEQ ID NO:1, amino acids 3555–3876 of SEQ ID NO:5); a DH (nucleotides 33401–33889 of SEQ ID NO:1, amino acids 3886–4048 of SEQ ID NO:5); an ER (nucleotides 35042–35902 of SEQ ID NO:1, amino acids 4433–4719 of SEQ ID NO:5); a KR (nucleotides 35930–36667 of SEQ ID NO:1, amino acids 4729–4974 of SEQ ID NO:5); and an ACP (nucleotides 36773–36991 of SEQ ID. NO:1, amino acids 5010–5082 of SEQ ID NO:5). This module incorporates an acetate extender unit (C10–C9) and fully reduces the β-keto group at C11. The fourth module of EPOS C harbors a KS (nucleotides 37052–38320 of SEQ ID NO:1, amino acids 5103–5525 of SEQ ID NO:5); a methylmalonyl CoA-specific AT (nucleotides 38636–39598 of SEQ ID NO:1, amino acids 5631–5951 of SEQ ID NO:5); a DH (nucleotides 39635–40141 of SEQ ID NO:1, amino acids 5964–6132 of SEQ ID NO:5); an ER (nucleotides 41369–42256 of SEQ ID NO:1, amino acids 6542–6837 of SEQ ID NO:5); a KR (nucleotides 42314–43048 of SEQ ID NO:1, amino acids 6857–7101 of SEQ ID NO:5); and an ACP (nucleotides 43163–43378 of SEQ ID NO:1, amino acids 7140–7211 of SEQ ID NO:5). This module incorporates a propionate extender unit (C24 and C8–C7) and fully reduces the β-keto group at C9.

epoD (nucleotides 43524–54920 of SEQ ID NO:1) codes for EPOS D (SEQ ID NO:6), a type I polyketide synthase consisting of 2 modules. The first module harbors a KS (nucleotides 43626–44885 of SEQ ID NO:1, amino acids 35–454 of SEQ ID NO:6); a methylmalonyl CoA-specific AT (nucleotides 45204–46166 of SEQ ID NO:1, amino acids 561–881 of SEQ ID NO:6); a KR (nucleotides 46950–47702 of SEQ ID NO:1, amino acids 1143–1393 of SEQ ID NO:6); and an ACP (nucleotides 47811–48032 of SEQ ID NO:1, amino acids 1430–1503 of SEQ ID NO:6). This module incorporates a propionate extender unit (C23 and C6–C5) and reduces the β-keto group at C7 to a hydoxyl group. The second module harbors a KS (nucleotides 48087–49361 of SEQ ID NO:1, amino acids 1522–1946 of SEQ ID NO: 6); a methylmalonyl CoA-specific AT (nucleotides 49680–50642 of SEQ ID NO:1, amino acids 2053–2373 of SEQ ID NO:6); a DH (nucleotides 50670–51176 of SEQ ID NO:1, amino acids 2383–2551 of SEQ ID NO:6); a methyltransferase (MT, nucleotides 51534–52657 of SEQ ID NO:1, amino acids 2671–3045 of SEQ ID NO:6); a KR (nucleotides 53697–54431 of SEQ ID NO:1, amino acids 3392–3636 of SEQ ID NO:6); and an ACP (nucleotides 54540–54758 of SEQ ID NO:1, amino acids 3673–3745 of SEQ ID NO:6). This module incorporates a propionate extender unit (C21 or C22 and C4-C3) and reduces the β-keto group at C5 to a hydoxyl group. This reduction is somewhat unexpected, since epothilones contain a keto group at C5. Discrepancies of this kind between the deduced reductive capabilities of PKS modules and the redox state of the corresponding positions in the final polyketide products have been, however, reported in the literature (see, for example, Schwecke, et al., *Proc. Natl. Acad. Sci. USA* 92: 7839–7843 (1995) and Schupp, et al., *FEMS Microbiology Letters* 159: 201–207 (1998)). An important feature of epothilones is the presence of gem-methyl side groups at C4 (C21 and C22). The second module of EPOS D is predicted to incorporate a propionate unit into the growing polyketide chain, providing one methyl side chain at C4. This module also contains a methyltransferase domain integrated into the PKS between the DH and the KR domains, in an arrangement similar to the one seen in the HMWP1 yersiniabactin synthase (Gehring, A. M., DeMoll, E., Fetherston, J. D., Mori, I., Mayhew, G. F., Blattner, F. R., Walsh, C. T., and Perry, R. D.: Iron acquisition in plague: modular logic in enzymatic biogenesis of yersiniabactin by *Yersinia pestis*. *Chem. Biol.* 5, 573–586, 1998). This MT domain in EPOS D is proposed to be responsible for the incorporation of the second methyl side group (C21 or C22) at C4.

epoE (nucleotides 54935–62254 of SEQ ID NO:1) codes for EPOS E (SEQ ID NO:7), a type I polyketide synthase consisting of one module, harboring a KS (nucleotides 55028–56284 of SEQ ID NO:1, amino acids 32–450 of SEQ ID NO:7); a malonyl CoA-specific AT (nucleotides 56600–57565 of SEQ ID NO:1, amino acids 556–877 of SEQ ID NO:7); a DH (nucleotides 57593–58087 of SEQ ID NO:1, amino acids 887–1051 of SEQ ID NO:7); a probably nonfunctional ER (nucleotides 59366–60304 of SEQ ID NO:1, amino acids 1478–1790 of SEQ ID NO.7); a KR (nucleotides 60362–61099 of SEQ ID NO:1, amino acids 1810–2055 of SEQ ID NO:7); an ACP (nucleotides 61211–61426 of SEQ ID NO:1, amino acids 2093–2164 of SEQ ID NO:7); and a thioesterase (TE) (nucleotides 61427–62254 of SEQ ID NO:1, amino acids 2165–2439 of SEQ ID NO:7). The ER domain in this module harbors an active site motif with some highly unusual amino acid substitutions that probably render this domain inactive. The module incorporates an acetate extender unit (C2–C1), and reduces the β-keto at C3 to an enoyl group. Epothilones contain a hydroxyl group at C3, so this reduction also appears to be excessive as discussed for the second module of EPOS D. The TE domain of EPOS E takes part in the release and cyclization of the grown polyketide chain via lactonization between the carboxyl group of C1 and the hydroxyl group of C15.

Five ORFs are detected upstream of epoA in the sequenced region. The partially sequenced orf1 has no homologues in the sequence databanks. The deduced protein product (Orf 2, SEQ ID NO:10) of orf2 (nucleotides 3171–1900 on the reverse complement strand of SEQ ID NO:1) shows strong similarities to hypothetical ORFs from Mycobacterium and Streptomyces coelicolor, and more distant similarities to carboxypeptidases and DD-peptidases of different bacteria. The deduced protein product of orf3 (nucleotides 3415–5556 of SEQ ID NO:1), Orf 3 (SEQ ID NO:11), shows homologies to Na/H antiporters of different bacteria. Orf 3 might take part in the export of epothilones from the producer strain. orf4 and orf5 have no homologues in the sequence databanks.

Eleven ORFs are found downstream of epoE in the sequenced region. epoF (nucleotides 62369–63628 of SEQ ID NO:1) codes for EPOS F (SEQ ID NO:8), a deduced protein with strong sequence similarities to cytochrome P450 oxygenases. EPOS F may take part in the adjustment of the redox state of the carbons C12, C5, and/or C3. The deduced protein product of orf14 (nucleotides 67334–68251 of SEQ ID NO:1), Orf 14 (SEQ ID NO:22) shows strong similarities to GI:3293544, a hypothetic protein with no proposed function from Streptomyces coelicolor, and also to GI:2654559, the human embrionic lung protein. It is also more distantly related to cation efflux system proteins like GI:2623026 from Methanobacterium thermoautotrophicum, so it might also take part in the export of epothilones from the producing cells. The remaining ORFs (orf6–orf13 and orf15) show no homologies to entries in the sequence databanks.

Example 13

Recombinant Expression of Epothilone Biosynthesis Genes

Epothilone synthase genes according to the present invention are expressed in heterologous organisms for the purposes of epothilone production at greater quantities than can be accomplished by fermentation of Sorangium cellulosum. A preferable host for heterologous expression is Streptomyces, e.g. Streptomyces coelicolor, which natively produces the polyketide actinorhodin. Techniques for recombinant PKS gene expression in this host are described in McDaniel et al., Science 262:1546–1550 (1993) and Kao et al., Science 265: 509–512 (1994). See also, Holmes et al., EMBO Journal 12(8): 3183–3191 (1993) and Bibb et al., Gene 38: 215–226 (1985), as well as U.S. Pat. Nos. 5,521,077, 5,672,491, and 5,712,146, which are incorporated herein by reference.

According to one method, the heterologous host strain is engineered to contain a chromosomal deletion of the actinorhodin (act) gene cluster. Expression plasmids containing the epothilone synthase genes of the invention are constructed by transferring DNA from a temperature-sensitive donor plasmid to a recipient shuttle vector in E. coli (McDaniel et al. (1993) and Kao et al. (1994)), such that the synthase genes are built-up by homologous recombination within the vector. Alternatively, the epothilone synthase gene cluster is introduced into the vector by restriction fragment ligation. Following selection, e.g. as described in Kao et al. (1994), DNA from the vector is introduced into the act-minus Streptomyces coelicolor strain according to protocols set forth in Hopwood et al., Genetic Manipulation of Streptomyces. A Laboratory Manual (John Innes Foundation, Norwich, United Kingdom, 1985), incorporated herein by reference. The recombinant Streptomyces strain is grown on R2YE medium (Hopwood et al. (1985)) and produces epothilones. Alternatively, the epothilone synthase genes according to the present invention are expressed in other host organisms such as pseudomonads, Bacillus, yeast, insect cells and/or E. coli. PKS and NRPS genes are preferably expressed in E. coli using the pT7-7 vector, which uses the T7 promoter. See, Tabor et al., Proc. Natl. Acad. Sci. USA 82:1074–1078 (1985). In another embodiment, the expression vectors pKK223–3 and pKK223–2 are used to express PKS and NRPS genes in E. coli, either in transcriptional or translational fusion, behind the tac or trc promoter. Expression of PKS and NRPS genes in heterologous hosts, which do not naturally have the phosphopantetheinyl (P-pant) transferases needed for post-translational modification of PKS enzymes, requires the coexpression in the host of a P-pant transferase, as described by Kealey et al., Proc. Natl. Acad. Sci. USA 95: 505–509 (1998).

Example 14

Isolation of Epothilones from Producing Strains

Examples of cultivation, fermentation, and extraction procedures for polyketide isolation, which are useful for extracting epothilones from both native and recombinant hosts according to the present invention, are given in WO 93/10121, incorporated herein by reference, in Example 57 of U.S. Pat. No. 5,639,949, in Gerth et al., J. Antibiotics 49: 560–563 (1996), and in Swiss patent application no. 396/98, filed Feb. 19, 1998, and U.S. patent application Ser. no. 09/248,910 (that discloses also preferred mutant strains of Sorangium cellulosum), both of which are incorporated herein by reference. The following are procedures that are useful for isolating epothilones from cultured Sorangium cellulosum strains, e.g., So ce90, and may also be used for the isolation of epothilone from recombinant hosts.

A: Cultivation of Epothilone-producing Strains

Strain: Sorangium cellulosum Soce-90 or a recombinant host strain according to the present invention.

Preservation of the strain: In liquid $N_2$.

Media:

Precultures and intermediate cultures: G52

Main culture: 1B12

| | |
|---|---|
| yeast extract, low in salt (BioSpringer, Maison Alfort, France) | 2 g/l |
| $MgSO_4$ ($7H_2O$) | 1 g/l |
| $CaCl_2$ ($2H_2O$) | 1 g/l |
| soya meal defatted Soyamine 50T (Lucas Meyer, Hamburg, Germany) | 2 g/l |
| potato starch Noredux A-150 (Blattmann, Waedenswil, Switzerland) | 8 g/l |
| glucose anhydrous | 2 g/l |
| EDTA-Fe(III)-Na salt (8 g/l) | 1 ml/l |
| pH 7.4, corrected with KOH | |
| Sterilisation: 20 mins. 120° C. | |

| | |
|---|---|
| potato starch Noredux A-150 (Blattmann, Waedenswil, Switzerland) | 20 g/l |
| soya meal defatted Soyamine 50T (Lucas Meyer, Hamburg, Germany) | 11 g/l |
| EDTA-Fe(III)-Na salt | 8 mg/l |
| pH 7.8, corrected with KOH | |
| Sterilisation: 20 mins. 120° C. | |

Addition of cyclodextrins and cyclodextrin derivatives:
  Cyclodextrins (Fluka, Buchs, Switzerland, or Wacker Chemie, Munich, Germany) in different concentrations are sterilised separately and added to the 1B12 medium prior to seeding.
Cultivation: 1 ml of the suspension of *Sorangium cellulosum* Soce-90 from a liquid $N_2$ ampoule is transferred to 10 ml of G52 medium (in a 50 ml Erlenmeyer flask) and incubated for 3 days at 180 rpm in an agitator at 30° C., 25 mm displacement. 5 ml of this culture is added to 45 ml of G52 medium (in a 200 ml Erlenmeyer flask) and incubated for 3 days at 180 rpm in an agitator at 30° C., 25 mm displacement. 50 ml of this culture is then added to 450 ml of G52 medium (in a 2 liter Erlenmeyer flask) and incubated for 3 days at 180 rpm in an agitator at 30° C., 50 mm displacement.
Maintenance culture: The culture is overseeded every 3–4 days, by adding 50 ml of culture to 450 ml of G52 medium (in a 2 liter Erlenmeyer flask). All experiments and fermentations are carried out by starting with this maintenance culture.
Tests in a flask:
  (I) Preculture in an agitating flask:
    Starting with the 500 ml of maintenance culture, 1×450 ml of G52 medium are seeded with 50 ml of the maintenance culture and incubated for 4 days at 180 rpm in an agitator at 30° C., 50 mm displacement.
  (ii) Main culture in the agitating flask:
    40 ml of 1B12 medium plus 5 g/l 4-morpholine-propane-sulfonic acid (=MOPS) powder (in a 200 ml Erlenmeyer flask) are mixed with 5 ml of a 10× concentrated cyclodextrin solution, seeded with 10 ml of preculture and incubated for 5 days at 180 rpm in an agitator at 30° C., 50 mm displacement.
Fermentation: Fermentations are carried out on a scale of 10 liters, 100 liters and 500 liters. 20 liter and 100 liter fermentations serve as an intermediate culture step. Whereas the pre-cultures and intermediate cultures are seeded as the maintenance culture 10% (v/v), the main cultures are seeded with 20% (v/v) of the intermediate culture. In contrast to the agitating cultures, ingredients of the fermentation media are calculated on the final culture volume including the inoculum. If, for example, 18 liters of medium +2 liters of inoculum are combined, then substances for 20 liters are weighed in, but are only mixed with 18 liters.
Preculture in an agitating flask:
  Starting with the 500 ml maintenance culture, 4×450 ml of G52 medium (in a 2 liter Erlenmeyer flask) are each seeded with 50 ml thereof, and incubated for 4 days at 180 rpm in an agitator at 30° C., 50 mm displacement.
Intermediate culture, 20 liters or 100 liters:
  20 liters: 18 liters of G52 medium in a fermenter having a total volume of 30 liters are seeded with 2 liters of preculture. Cultivation lasts for 3–4 days, and the conditions are: 30° C., 250 rpm, 0.5 liters of air per liter liquid per min, 0.5 bars excess pressure, no pH control.
  100 liters: 90 liters of G52 medium in a fermenter having a total volume of 150 liters are seeded with 10 liters of the 20 liter intermediate culture. Cultivation lasts for 3–4 days, and the conditions are: 30° C., 150 rpm, 0.5 liters of air per liter liquid per min, 0.5 bars excess pressure, no pH control.
Main culture. 10 liters, 100 liters or 500 liters:
  10 liters: The media substances for 10 liters of 1B12 medium are sterilised in 7 liters of water, then 1 liter of a sterile 10% 2-(hydroxypropyl)-β-cyclodextrin solution are added, and seeded with 2 liters of a 20 liter intermediate culture. The duration of the main culture is 6–7 days, and the conditions are: 30° C., 250 rpm, 0.5 liters of air per liter of liquid per min, 0.5 bars excess pressure, pH control with $H_2SO_4$/KOH to pH 7.6+/−0.5 (i.e. no control between pH 7.1 and 8.1).
  100 liters: The media substances for 100 liters of 1B12 medium are sterilised in 70 liters of water, then 10 liters of a sterile 10% 2-(hydroxypropyl)-β-cyclodextrin solution are added, and seeded with 20 liters of a 20 liter intermediate culture. The duration of the main culture is 6–7 days, and the conditions are: 30° C., 200 rpm, 0.5 liters air per liter liquid per min., 0.5 bars excess pressure, pH control with $H_2SO_4$/KOH to pH 7.6+/−0.5. The chain of seeding for a 100 liter fermentation is shown schematically as follows:

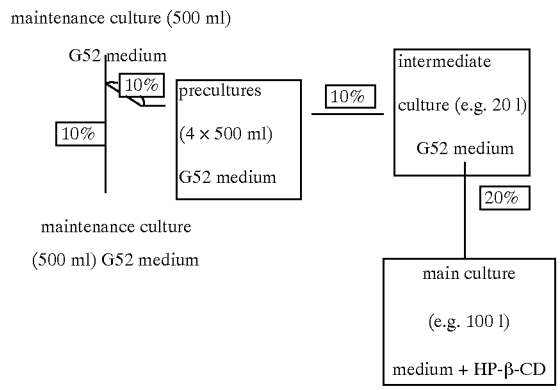

500 liters: The media substances for 500 liters of 1B12 medium are sterilised in 350 liters of water, then 50 liters of a sterile 10% 2-(hydroxypropyl)-β-cyclodextrin solution are added, and seeded with 100 liters of a 100 liter intermediate culture. The duration of the main culture is 6–7 days, and the conditions are: 30° C., 120 rpm, 0.5 liters air per liter liquid per min., 0.5 bars excess pressure, pH control with $H_2SO_4$/KOH to pH 7.6+/−0.5.
Product analysis:
  Preparation of the sample:
    50 ml samples are mixed with 2 ml of polystyrene resin Amberlite XAD16 (Rohm+Haas, Frankfurt, Germany) and shaken at 180 rpm for one hour at 30° C. The resin is subsequently filtered using a 150 μm nylon sieve, washed with a little water and then added together with the filter to a 15 ml Nunc tube.
  Elution of the product from the resin:
    10 ml of isopropanol (>99%) are added to the tube with the filter and the resin. Afterwards, the sealed tube is shaken for 30 minutes at room temperature on a Rota-Mixer (Labinco BV, Netherlands). Then, 2 ml of the liquid are centrifuged off and the supernatant is added using a pipette to HPLC tubes.

HPLC analysis:
Column:
Waters-Symetry C18, 100×4 mm, 3.5 μm
WAT066220+preliminary column 3.9×20 mm
WAT054225
Solvents:
A: 0.02% phosphoric acid
B: Acetonitrile (HPLC-Quality)
Gradient:
41% B from 0 to 7 min.
100% B from 7.2 to 7.8 min.
41% B from 8 to 12 min.
Oven temp.: 30° C.
Detection: 250 nm, UV-DAD detection
Injection vol.: 10 μl
Retention time: Epo A: 4.30 min Epo B: 5.38 min B: Effect of the Addition of Cyclodextrin and Cyclodextrin Derivatives to the Epothilone Concentrations Attained Cyclodextrins are cyclic (α-1,4)-linked oligosaccharides of α-D-glucopyranose with a relatively hydrophobic central cavity and a hydrophilic external surface area.

The following are distinguished in particular (the figures in parenthesis give the number of glucose units per molecule): α-cyclodextrin (6), β-cyclodextrin (7), γ-cyclodextrin (8), δ-cyclodextrin (9), ε-cyclodextrin (10), ζ-cyclodextrin (11), η-cyclodextrin (12), and θ-cyclodextrin (13). Especially preferred are δ-cyclodextrin and in particular α-cyclodextrin, β-cyclodextrin or γ-cyclodextrin, or mixtures thereof.

Cyclodextrin derivatives are primarily derivatives of the above-mentioned cyclodextrins, especially of α-cyclodextrin, β-cyclodextrin or γ-cyclodextrin, primarily those in which one or more up to all of the hydroxy groups (3 per glucose radical) are etherified or esterified. Ethers are primarily alkyl ethers, especially lower alkyl, such as methyl or ethyl ether, also propyl or butyl ether; the aryl-hydroxyalkyl ethers, such as phenyl-hydroxy-lower-alkyl, especially phenyl-hydroxyethyl ether; the hydroxyalkyl ethers, in particular hydroxy-lower-alkyl ethers, especially 2-hydroxyethyl, hydroxypropyl such as 2-hydroxypropyl or hydroxy-butyl such as 2-hydroxybutyl ether; the carboxy-alkyl ethers, in particular carboxy-lower-alkyl ethers, especially carboxymethyl or carboxyethyl ether; derivatised carboxyalkyl ethers, in particular derivatised carboxy-lower-alkyl ether in which the derivatised carboxy is etherified or amidated carboxy (primarily aminocarbonyl, mono- or di-lower-alkyl-aminocarbonyl, morpholino-, piperidino-, pyrrolidino- or piperazino-carbonyl, or alkyloxycarbonyl), in particular lower alkoxycarbonyl-lower-alkyl ether, for example methyloxycarbonylpropyl ether or ethyloxycarbonylpropyl ether; the sulfoalkyl ethers, in particular sulfo-lower-alkyl ethers, especially sulfobutyl ether; cyclodextrins in which one or more OH groups are etherified with a radical of formula —O—[alk-O—]$_n$—H wherein alk is alkyl, especially lower alkyl, and n is a whole number from 2 to 12, especially 2 to 5, in particular 2 or 3; cyclodextrins in which one or more OH groups are etherified with a radical of formula $$\begin{matrix} R' & & O \\ | & & \diagup\diagdown \\ (Alk\text{-}O)_m\text{—}Alk\text{—} & & \\ & & Y \end{matrix}$$

wherein R' is hydrogen, hydroxy, —O-(alk-O)$_z$—H, —O-(alk(-R)—O—)$_p$—H or —O-(alk(-R)—O—)$_q$-alk—CO—Y; alk in all cases is alkyl, especially lower alkyl; m, n, p, q and z are a whole number from 1 to 12, preferably 1 to 5, in particular 1 to 3; and Y is OR$_1$ or NR$_2$R$_3$, wherein R$_1$, R$_2$ and R$_3$ independently of one another, are hydrogen or lower alkyl, or R$_2$ and R$_3$ combined together with the linking nitrogen signify morpholino, piperidino, pyrrolidino or piperazino; or branched cyclodextrins, in which etherifications or acetals with other sugar molecules are present, especially glucosyl-, diglucosyl- (G$_2$-β-cyclodextrin), maltosyl- or di-maltosyl-cyclodextrin, or N-acetylglucosaminyl-, glucosaminyl-, N-acetylgalactosaminyl- or galactosaminyl-cyclodextrin.

Esters are primarily alkanoyl esters, in particular lower alkanoyl esters, such as acetyl esters of cyclodextrins.

It is also possible to have cyclodextrins in which two or more different said ether and ester groups are present at the same time.

Mixtures of two or more of the said cyclodextrins and/or cyclodextrin derivatives may also exist.

Preference is given in particular to α-, β- or γ-cyclodextrins or the lower alkyl ethers thereof, such as methyl-β-cyclodextrin or in particular 2,6-di-O-methyl-β-cyclodextrin, or in particular the hydroxy lower alkyl ethers thereof, such as 2-hydroxypropyl-α-, 2-hydroxypropyl-β- or 2-hydroxypropyl-γ-cyclodextrin.

The cyclodextrins or cyclodextrin derivatives are added to the culture medium preferably in a concentration of 0.02 to 10, preferably 0.05 to 5, especially 0.1 to 4, for example 0.1 to 2 percent by weight (w/v).

Cyclodextrins or cyclodextrin derivatives are known or may be produced by known processes (see for example U.S. Pat. Nos. 3,459,731; 4,383,992; 4,535,152; 4,659,696; EP 0 094 157; EP 0 149 197; EP 0 197 571; EP 0 300 526; EP 0 320 032; EP 0 499 322; EP 0 503 710; EP 0 818 469; WO 90/12035; WO 91/11200; WO 93/19061; WO 95/08993; WO 96/14090; GB 2,189,245; DE 3,118,218; DE 3,317,064 and the references mentioned therein, which also refer to the synthesis of cyclodextrins or cyclodextrin derivatives, or also: T. Loftsson and M. E. Brewster (1996): Pharmaceutical Applications of Cyclodextrins: Drug Solubilization and Stabilisation: Journal of Pharmaceutical Science 85 (10):1017–1025; R. A. Rajewski and V. J. Stella(1996): Pharmaceutical Applications of Cyclodextrins: In Vivo Drug Delivery: Journal of Pharmaceutical Science 85 (11): 1142–1169).

All the cyclodextrin derivatives tested here are obtainable from the company Fluka, Buchs, CH. The tests are carried out in 200 ml agitating flasks with 50 ml culture volume. As controls, flasks with adsorber resin Amberlite XAD-16 (Rohm & Haas, Frankfurt, Germany) and without any adsorber addition are used. After incubation for 5 days, the following epothilone titers can be determined by HPLC:

TABLE 2

| Addition | order No. | Conc [% w/v][1] | Epo A [mg/l] | Epo B [mg/l] |
|---|---|---|---|---|
| Amberlite XAD-16 (v/v) | | 2.0 (% v/v) | 9.2 | 3.8 |
| 2-hydroxypropyl-β-cyclodextrin | 56332 | 0.1 | 2.7 | 1.7 |
| 2-hydroxypropyl-β-cyclodextrin | " | 0.5 | 4.7 | 3.3 |
| 2-hydroxypropyl-β-cyclodextrin | " | 1.0 | 4.7 | 3.4 |
| 2-hydroxypropyl-β-cyclodextrin | " | 2.0 | 4.7 | 4.1 |
| 2-hydroxypropyl-β-cyclodextrin | " | 5.0 | 1.7 | 0.5 |
| 2-hydroxypropyl-α-cyclodextrin | 56330 | 0.5 | 1.2 | 1.2 |
| 2-hydroxypropyl-α-cyclodextrin | " | 1.0 | 1.2 | 1.2 |
| 2-hydroxypropyl-α-cyclodextrin | " | 5.0 | 2.5 | 2.3 |
| β-cyclodextrin | 28707 | 0.1 | 1.6 | 1.3 |
| β-cyclodextrin | " | 0.5 | 3.6 | 2.5 |
| β-cyclodextrin | " | 1.0 | 4.8 | 3.7 |
| β-cyclodextrin | " | 2.0 | 4.8 | 2.9 |
| β-cyclodextrin | " | 5.0 | 1.1 | 0.4 |
| methyl-β-cyclodextrin | 66292 | 0.5 | 0.8 | <0.3 |
| methyl-β-cyclodextrin | " | 1.0 | <0.3 | <0.3 |
| methyl-β-cyclodextrin | " | 2.0 | <0.3 | <0.3 |
| 2,6 di-o-methyl-β-cyclodextrin | 39915 | 1.0 | <0.3 | <0.3 |
| 2-hydroxypropyl-γ-cyclodextrin | 56334 | 0.1 | 0.3 | <0.3 |
| 2-hydroxypropyl-γ-cyclodextrin | " | 0.5 | 0.9 | 0.8 |
| 2-hydroxypropyl-γ-cyclodextrin | " | 1.0 | 1.1 | 0.7 |
| 2-hydroxypropyl-γ-cyclodextrin | " | 2.0 | 2.6 | 0.7 |
| 2-hydroxypropyl-γ-cyclodextrin | " | 5.0 | 5.0 | 1.1 |
| no addition | | | 0.5 | 0.5 |

[1]Apart from Amberlite (% v/v), all percentages are by weight (% w/v).

Few of the cyclodextrins tested (2,6-di-o-methyl-β-cyclodextrin, methyl-β-cyclodextrin) display no effect or a negative effect on epothilone production at the concentrations used. 1–2% 2-hydroxy-propyl-β-cyclodextrin and β-cyclodextrin increase epothilone production in the examples by 6 to 8 times compared with production using no cyclodextrins.

C: 10 Liter Fermentation with 1% 2-(hydroxypropyl)-β-cyclodextrin)

Fermentation is carried out in a 15 liter glass fermenter. The medium contains 10 g/l of 2-(hydroxypropyl)-β-cyclodextrin from Wacker Chemie, Munich, DE. Fermentation progress is illustrated in Table 3. Fermentation is ended after 6 days and working up takes place.

TABLE 3

Progress of a 10 litre fermentation

| duration of culture [d] | Epothilone A [mg/l] | Epothilone B [mg/l] |
|---|---|---|
| 0 | 0 | 0 |
| 1 | 0 | 0 |
| 2 | 0.5 | 0.3 |
| 3 | 1.8 | 2.5 |
| 4 | 3.0 | 5.1 |
| 5 | 3.7 | 5.9 |
| 6 | 3.6 | 5.7 |

D: 100 Liter Fermentation with 1% 2-(hydroxypropyl)-β-cyclodextrin)

Fermentation is carried out in a 150 liter fermenter. The medium contains 10 g/l of 2-(Hydroxypropyl)-β-cyclodextrin. The progress of fermentation is illustrated in Table 4. The frementation is harvested after 7 days and worked up.

TABLE 4

Progress of a 100 litre fermentation

| duration of culture [d] | Epothilone A [mg/l] | Epothilone B [mg/l] |
|---|---|---|
| 0 | 0 | 0 |
| 1 | 0 | 0 |
| 2 | 0.3 | 0 |
| 3 | 0.9 | 1.1 |
| 4 | 1.5 | 2.3 |
| 5 | 1.6 | 3.3 |
| 6 | 1.8 | 3.7 |
| 7 | 1.8 | 3.5 |

E: 500 Liter Fermentation with 1% 2-(hydroxypropyl)-βcyclodextrin)

Fermentation is carried out in a 750 liter fermenter. The medium contains 10 g/l of 2-Hydroxypropyl)-β-cyclodextrin. The progress of fermentation is illustrated in Table 5. The fermentation is harvested after 7 days and worked up.

TABLE 5

Progress of a 500 litre fermentation

| duration of culture [d] | Epothilone A [mg/l] | Epothilone B [mg/l] |
|---|---|---|
| 0 | 0 | 0 |
| 1 | 0 | 0 |
| 2 | 0 | 0 |
| 3 | 0.6 | 0.6 |
| 4 | 1.7 | 2.2 |
| 5 | 3.1 | 4.5 |
| 6 | 3.1 | 5.1 |

F: Comparison Example 10 Liter Fermentation without Adding an Adsorber

Fermentation is carried out in a 15 liter glass fermenter. The medium does not contain any cyclodextrin or other adsorber. The progress of fermentation is illustrated in Table 6. The frementation is not harvested and worked up.

TABLE 6

Progress of a 10 litre fermentation without adsorber.

| duration of culture [d] | Epothilone A [mg/l] | Epothilone B [mg/l] |
|---|---|---|
| 0 | 0 | 0 |
| 1 | 0 | 0 |
| 2 | 0 | 0 |
| 3 | 0 | 0 |
| 4 | 0.7 | 0.7 |
| 5 | 0.7 | 1.0 |
| 6 | 0.8 | 1.3 |

G: Working up of the Epothilones: Isolation from a 500 Liter Main Culture

The volume of harvest from the 500 liter main culture of example 2D is 450 liters and is seperated using a Westfalia clarifying separator Type SA-20–06 (rpm=6500) into the liquid phase (cerntrifugate+rinsing water=650 liters) and solid phase (cells =ca. 15 kg). The main part of the epothilones are found in the centrifugate, The centrifuged cell pulp contains <15% of the determined epothilone portion and is not further processed. The 650 liter centrifugate is then placed in a 4000 liter stirring vessel, mixed with 10 liters of Amberlite XAD-16 (centrifugate:resin volume= 65:1) and stirred. After a period of contact of ca. 2 hours, the resin is centrifuged away in a Heine overflow centrifuge (basket content 40 liters; rpm=2800). The resin is discharged from the centrifuge and washed with 10–15 liters of deionised water. Desorption is effected by stirring the resin twice, each time in portions with 30 liters of isopropanol in 30 liter glass stirring vessels for 30 minutes. Separation of the isopropanol phase from the resin takes place using a suction filter. The isopropanol is then removed from the combined isopropanol phases by adding 15–20 liters of water in a vacuum-operated circulating evaporator (Schmid-Verdampfer) and the resulting water phase of ca. 10 liter is extracted 3× each time with 10 liters of ethyl acetate. Extraction is effected in 30 liter glass stirring vessels. The ethyl acetate extract is concentrated to 3–5 liters in a vacum-operated circulating evaporator (Schmid-Verdampfer) and afterwards concentrated to dryness in a rotary evaporator ((Büchi type) under vacuum. The result is an ethyl acetate extract of 50.2 g. The ethyl acetate extract is dissolved in 500 ml of methanol, the insoluble portions filtered off using a folded filter, and the solution added to a 10 kg Sephadex LH 20 column (Pharmacia, Uppsala, Sweden) (column diameter 20 cm, filling level ca. 1.2 m). Elution is effected with methanol as eluant. Epothilone A and B is present predominantly in fractions 21–23 (at a fraction size of 1 liter). These fractions are concentrated to dryness in a vacuum on a rotary evaporator (total weight 9.0 g). These Sephadex peak fractions (9.0 g) are thereafter dissolved in 92 ml of acetonitrile:-water:-methylene chloride=50:40:2, the solution filtered through a folded filter and added to a RP column (equipment Prepbar 200, Merck; 2.0 kg LiChrospher RP-18 Merck, grain size 12 $\mu$m, column diameter 10 cm, filling level 42 cm; Merck, Darmstadt, Germany). Elution is effected with acetonitrile:water=3:7 (flow rate=500 ml/min.; retention time of epothilone A=ca. 51–59 mins.; retention time of epothilone B=ca. 60–69 mins.). Fractionation is monitored with a UV detector at 250 nm. The fractions are concentrated to dryness under vacuum on a Büchi-Rotavapor rotary evaporator. The weight of the epothilone A peak fraction is 700 mg, and according to HPLC (external standard) it has a content of 75.1%. That of the epothilone B peak fraction is 1980 mg, and the content according to HPLC (external standard) is 86.6%. Finally, the epothilone A fraction (700 mg) is crystallised from 5 ml of ethyl acetate:toluene=2:3, and yields 170 mg of epothilone A pure crystallisate [content according to HLPC (% of area)=94.3%]. Crystallisation of the epothilone B fraction (1980 mg) is effected from 18 ml of methanol and yields 1440 mg of epothilone B pure crystallisate [content according to HPLC (% of area)=99.2%]. m.p. (Epothilone B): e.g. 124–125° C.; $^1$H-NMR data for Epothilone B: 500 MHz-NMR, solvent: DMSO-d6. Chemical displacement $\delta$ in ppm relative to TMS. s=singlet; d=doublet; m=multiplet

| $\delta$ (Multiplicity) | Integral (number of H) |
|---|---|
| 7.34 (s) | 1 |
| 6.50 (s) | 1 |
| 5.28 (d) | 1 |
| 5.08 (d) | 1 |
| 4.46 (d) | 1 |
| 4.08 (m) | 1 |
| 3.47 (m) | 1 |
| 3.11 (m) | 1 |
| 2.83 (dd) | 1 |
| 2.64 (s) | 3 |
| 2.36 (m) | 2 |
| 2.09 (s) | 3 |
| 2.04 (m) | 1 |
| 1.83 (m) | 1 |
| 1.61 (m) | 1 |
| 1.47–1.24 (m) | 4 |
| 1.18 (s) | 6 |
| 1.13 (m) | 2 |
| 1.06 (d) | 3 |
| 0.89 (d + s, overlapping) | 6 |
| | $\rho$ = 41 |

Example 15

Medical Uses of Recombinantly Produced Epothilones

Pharmaceutical preparations or compositions comprising epothilones are used for example in the treatment of cancerous diseases, such as various human solid tumors. Such anticancer formulations comprise, for example, an active amount of an epothilone together with one or more organic or inorganic, liquid or solid, pharmaceutically suitable carrier materials. Such formulations are delivered, for example, enterally, nasally, rectally, orally, or parenterally, particularly intramuscularly or intravenously. The dosage of the active ingredient is dependent upon the weight, age, and physical and pharmacokinetical condition of the patient and is further dependent upon the method of delivery. Because epothilones mimic the biological effects of taxol, epothilones may be substituted for taxol in compositions and methods utilizing taxol in the treatment of cancer. See, for example, U.S. Pat. Nos. 5,496,804, 5,565,478, and 5,641,803, all of which are incorporated herein by reference.

For example, for treatments, epothilone B is supplied in individual 2 ml glass vials formulated as 1 mg/1 ml of clear, colorless intravenous concentrate. The substance is formulated in polyethylene glycol 300 (PEG 300) and diluted with 50 or 100 ml 0.9% Sodium Chloride Injection, USP, to achieve the desired final concentration of the drug for infusion. It is administered as a single 30-minute intravenous infusion every 21 days (treatment three-weekly) for six cycles, or as a single 30-minute intravenous infusion every 7 days (weekly treatment).

Preferably, for weekly treatment, the dose is between about 0.1 and about 6, preferably about 0.1 and about 5 mg/m², more preferably about 0.1 and about 3 mg/m², even more preferably 0.1 and 1.7 mg/m², most preferably about 0.3 and about 1 mg/m²; for three-weekly treatment (treatment every three weeks or every third week) the dose is between about 0.3 and about 18 mg/m², preferably about 0.3 and about 15 mg/m², more preferably about 0.3 and about 12 mg/m², even more preferably about 0.3 and about 7.5 mg/m², still more preferably about 0.3 and about 5 mg/M², most preferably about 1.0 and about 3.0 mg/m². This dose is preferably administered to the human by intravenous (i.v.) administration during 2 to 180 min, preferably 2 to 120 min, more preferably during about 5 to about 30 min, most preferably during about 10 to about 30 min, e.g. during about 30 min.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. An isolated nucleic acid fragment comprising a nucleotide sequence that encodes a non-ribosomal peptide synthetase required for the biosynthesis of epothilone, wherein the complement of said nucleotide sequence hybridizes to nucleotides 11872–16104 of SEQ ID NO:1, under conditions of hybridization at 65° C. for 36 hours and washing 3 times at high stringency with 0.1×SSC and 0.5% SDS for 20 minutes at 65° C.

2. A chimeric gene comprising a heterologous promoter sequence operatively linked to a nucleic acid fragment according to claim 1.

3. A recombinant vector comprising a chimeric gene according to claim 2.

4. A recombinant host cell comprising a chimeric gene according to claim 2.

5. The recombinant host cell of claim 4, which is a bacteria.

6. The recombinant host cell of claim 5, which is an Actinomycete.

7. The recombinant host cell of claim 6, which is Streptomyces.

8. An isolated nucleic acid fragment comprising a nucleotide sequence that encodes a polypeptide comprising the amino acid sequence of SEQ ID NO:3.

9. An isolated nucleic acid fragment according to claim 8, wherein said nucleotide sequence is nucleotides 11872–16104 of SEQ ID NO:1.

10. An isolated non-ribosomal peptide synthetase required for the biosynthesis of epothilone, which comprises an amino acid sequence encoded by a nucleotide sequence whose complement hybridizes to nucleotides 11872–16104 of SEQ ID NO:1, under conditions of hybridization at 65° C. for 36 hours and washing 3 times at high stringency with 0.1×SSC and 0.5% SDS for 20 minutes at 65° C.

11. A recombinant host cell comprising a recombinantly expressed polypeptide according to claim 10.

12. The recombinant host cell of claim 11, which is a bacteria.

13. The recombinant host cell of claim 12, which is an Actinomycete.

14. The recombinant host cell of claim 13, which is Streptomyces.

15. An isolated a non-ribosomal peptide synthetase compising the amino acid sequence of SEQ ID NO:3.

16. A recombinant host cell comprising a recombinantly expressed polypeptide according to claim 15.

17. The recombinant host cell of claim 16, which is a bacteria.

18. The recombinant host cell of claim 17, which is an Actinomycete.

19. The recombinant host cell of claim 18, which is Streptomyces.

20. A chimeric gene comprising a heterologous promoter sequence operatively linked to a nucleic acid fragment according to claim 8.

21. A recombinant vector comprising a chimeric gene according to claim 10.

22. A recombinant host cell comprising a chimeric gene according to claim 20.

23. The recombinant host cell of claim 22, which is a bacteria.

24. The recombinant host cell of claim 23, which is an Actinomycete.

25. The recombinant host cell of claim 24, which is Streptomyces.

* * * * *

UNITED STATES PATENT AND TRADEMARK OFFICE
CERTIFICATE OF CORRECTION

PATENT NO. : 6,383,787 B1  
DATED : May 7, 2002  
INVENTOR(S) : Schupp et al.

It is certified that error appears in the above-identified patent and that said Letters Patent is hereby corrected as shown below:

<u>Column 220,</u>  
Line 5, should read -- according to claim 20. --

Signed and Sealed this

Fifth Day of November, 2002

Attest:

Attesting Officer

JAMES E. ROGAN  
*Director of the United States Patent and Trademark Office*

SEQUENCE LISTING

<160> NUMBER OF SEQ ID NOS: 30

<210> SEQ ID NO 1
<211> LENGTH: 68750
<212> TYPE: DNA
<213> ORGANISM: Sorangium cellulosum

<400> SEQUENCE: 1

```
aagcttcgct cgacgccctc ttcgcccgcg ccacctctgc ccgtgtgctc gatgatggcc      60
acggccgggc cacggagcgg catgtgctcg ccgaggcgcg cgggatcgag gacctccgcg     120
ccctccgaga gcacctccgc atccaggaag ggggccgtc  ctttcactgc atgtgcctcg     180
gcgacctgac ggtggagctc ctcgcgcacg accagcccct cgcgtccatc agcttccacc     240
atgcccgcag cctgaggcac cccgactgga cctcggacgc gatgctcgtc gacggccccg     300
cgctcgtccg gtggctcgcc gcgcgcggcg cgccgggtcc cctccgcgag tacgaagagg     360
agcgcgagcg agcccgaacc gcgcaggagg cgaggcgcct gtggctcgcg gccgcgccgc     420
cctgcttcgc gcccgatctg ccccgcttcg aggacgacgc caacgggctg ccgctcggcc     480
cgatgtcgcc tgaagtcgcc gaggccgagc ggcgcctccg cgcctcgtac gcgactcctg     540
agctcgcctg tgccgcgctg ctcgcctggc tcgggacggg cgcgggtccc tggtccggat     600
atcccgccta cgagatgctg ccagagaatc tgctcctcgg gtttggcctc ccgaccgcga     660
tcgccgcggc ctccgcgccc ggcacatcgg aggccgctct ccgcggcgca gcgcggctgt     720
tcgcctcctg ggaggtcgta tcgagcaaga agagccagct cggcaacatc cccgaagccc     780
tgtgggagcg gctccggacg atcgtccgcg cgatgggcaa tgccgacaac ctctctcgct     840
tcgagcgcgc cgaggcgatc gcggcggagg tgcgccgcct gcgcgcacag ccggcgccct     900
tcgcggcggg cgccggcctg gcggtcgctg gggtctcctc gagcggccgg ctctcgggcc     960
tcgtgaccga cggagacgca ttgtactccg gcgacggcaa cgacatcgtc atgttccaac    1020
ccggccggat ctcgccggtc gtgctgctcg ccggaaccga tcccttcttc gagctcgcac    1080 cgccccctcag ccagatgctc ttcgtcgcgc acgccaacgc gggcaccatc tccaaggtcc    1140
tgacggaagg cagcccctc  atcgtgatgg caagaaacca ggcgcgaccg atgagcctcg    1200
tccacgctcg cgggttcatg gcgtgggtca accaggccat ggtgcccgac cccgagcggg    1260
gcgcgccctt cgtcgtccag cgctcgacca tcatggaatt cgagcacccc acgcctcgtt    1320
gtctccacga gcccgccggc agcgctttct ccctcgcctg cgacgaggag cacctctact    1380
ggtgcgagct ttcggctggc cggctcgagc tatggcgcca cccgcaccac cgccccggcg    1440
ccccgagccg cttcgcgtac ctcggcgagc acccattgc  ggcgacctgg tacccctcgc    1500
tcaccctcaa tgcgacccac gtgctgtggg ccgaccctga tcgcagggcc atcctcgggg    1560
tcgacaagcg caccggcgta gagcccatcg tcctcgcgga gacgcgccat ccccggcgc     1620
```

```
acgtcgtgtc cgaggaccgg gacatcttcg cgcttaccgg acagcccgac tcccgcgact    1680
ggcacgtcga gcacatccgc tccggcgcct ccaccgtcgt ggccgactac cagcgccagc    1740
tatgggaccg ccctgacatg gtgctcaatc ggcgcgcct cttcttcacg acgaacgacc     1800
gcatcctgac gctcgcccgc agctgacatc gctcgacgcc gggccgctca tcgagggcgc    1860
ccggaccgag ctggcgaccc gccgctggcg ggccgcagct catgccgatt cggtggcgac    1920
gtagacgctg cgccagaaac gctcgagagc ccccgagaac aggaagccgg cggattgtgt    1980
catcacgatc ccgatcagct cgcggcccgg atcattgatc caggacgtcc cgaacccgcc    2040
gtcccaccca tagcgcccgg gcacctccga gaccgcgtcc ggcgccgtga ccacggccat    2100
cccataaccc cagccgtgcg tctcgaagaa gcccgggaaa aacgaggacg ccgccttctg    2160
ggccggcgtg aggtgatcgg ccgtcatctc gcgcaccgag gcggcgctca agagccgccg    2220
gccctcgtgc acaccgccgt tcatgagcat gcgcgcgaac aggaggtagt cgtccaccgt    2280
cgacacgagc ccggcggcgc cgaagggaa cgccggcggg ctggcatagg cgctctcggc     2340
cccgtcgcga tccatgcgcg tcttctcccc cgtctgctcg tcggtgaagt aaccgcagcc    2400
cgcgaaccga gcgagcttgt ccgccgggac gtgaaagtcg gtgtcccgca tcccgagcgg    2460
cgcgaggatg cgctcgcgca cgaacgcatc gaagccctgg tcggccgcgc gccccacgag    2520
caccccctgc accaggctcc ccgtgttgta catccactgc gcccccggct gatgcatgag    2580
cggcagcgtc ccgagccgcc ggatccactc gtctggcccg tgcggcgtca tcggcaccgg    2640
ctgcgcgttg acgagcccga gctcgtcgat ggcccgctgg atcggcgacg atgcgtcgaa    2700
cgagattccg aagcccatcg tgaacgtcat caggtcgcgc accgtgatcg gccgctccgc    2760
gggcaccgtc tcgtcgatcg gaccatcgat gcgcgccagc accttccggt tcgcgagctc    2820
cggcaaccat cggtcgacgg gggagtcgag gtcgagcttg ccttcctcga cgagcatcat    2880
caccgccgtc gcggtgaccg ccttcgtcat cgaggcgatc cggaagatcg tgtcccgccg    2940
catgggcgcg ctgccgccga gctcggtcac gcccaccgcg tccacgtgca cgtcgtcgcc    3000
gcgcgcgacc agccagaccg ctcccggcat ctgccccgcc gccacctccg ccgccatcac    3060
ctcgcgcgcg ggcgccagcg cgccggcccc cgcgtcctgc cctggctgcc cctcctcctc    3120
ggccccaccc aacgcgcacc ccggcgccgc cacgctgatc aaagctccca taaactcccg    3180
ccttctcatg accgtcgatg cctctccgag cggggggcgcc tgcccctgcc gagagcactg    3240
actgcccgcg cccgaaaaaa tcatcggtgc cccgtcacga tcgccgccgg gcgtggctcc    3300
gcccggccgc ccgctcgggc gcccgccct ggacgagcaa agctcgcccg cccgcgctca     3360
gcacgccgct tgccatgtcc ggcctgcacc cacaccgagg agccacccac cctgatgcac    3420
ggcctcaccg agcggcaggt cctgctctcg ctcgtcaccc tcgcgctcat cctcgtgacc    3480
gcgcgcgcct ccggcgagct cgcgcggcgg ctgcgccagc ccgaggtgct cggggagctc    3540
ttcggcggcg tcgtgctggg cccctccgtc gtcggcgcgc tcgcgcccgg gttccatcga    3600
gccctcttcc aggagccggc ggtcgggtc gtgctctcgg gcatctcctg gataggcgcg     3660
ctcctcctgc tgctgatggc gggcatcgag gtcgacgtgg gcatcctgcg caaggaggcg    3720
cgccccgggg cgctctcggc gctcggcgcg atcgcgcccc cgctcgcggc gggcgccgcc    3780
ttctcggcgc tcgtgctcga tcggcccctt ccgagcggcc tcttcctcgg gatcgtgctc    3840
tcggtgacgg cggtcagcgt gatcgcgaag gtgctgatcg agcgcgagtc gatgcgccgc    3900
agctatgcgc aggtgacgct cgcggcgggg gtggtcagcg aggtcgctgc ctgggtgctc    3960
```

-continued

| | | | | |
|---|---|---|---|---|
| gtcgcgatga | cgtcgtcgag | ctacggcgcg | tcgcccgcgc | tggcggtcgc | ccggagcgcg | 4020 |
| ctcctggcga | gcggattctt | gctgttcatg | gtgctcgtcg | ggcggcggct | cacccacctc | 4080 |
| gcgatgcgct | gggtggccga | cgcgacgcgc | gtctccaagg | gacaggtgtc | gctcgtcctc | 4140 |
| gtcctcacgt | tcctggccgc | ggcgctgacg | cagcggctcg | gcctgcaccc | gctgctcggc | 4200 |
| gcgttcgcgc | tcggcgtgct | gctcaacagc | gctcctcgca | ccaaccgccc | tctcctcgac | 4260 |
| ggcgtgcaga | cgctcgtggc | gggcctcttc | gcgcctgtgt | tcttcgtcct | cgcgggcatg | 4320 |
| cgcgtcgacg | tgtcgcagct | gcgcacgccg | cggcgtgggg | ggacggtcgc | gttgctgctg | 4380 |
| gcgaccgcga | cggcggcgaa | ggtcgtcccc | gccgcgctcg | gcgcgcggct | cggcgggctc | 4440 |
| agggcagcg | aggcggcgct | cgtggcggtg | ggcctgaaca | tgaagggcgg | cacggacctc | 4500 |
| atcgtcgcga | tcgtcggcgt | cgagctcggg | ctcctctcca | acgaggctta | tacgatgtac | 4560 |
| gccgtcgtcg | cgctggtcac | ggtgaccgcc | tcacccgcgc | tcctcatctg | gctcgagaaa | 4620 |
| agggcgcctc | cgacgcagga | ggagtcggct | cgcctcgagc | gcgaggaggc | cgcgaggcgc | 4680 |
| gcgtacatcc | ccggggtcga | gcggatcctc | gtcccgatcg | tggcgcacgc | cctgcccggg | 4740 |
| ttcgccacgg | acatcgtgga | gagcatcgtc | gcctccaagc | gaaagctcgg | cgagacggtc | 4800 |
| gacatcacgg | agctctccgt | ggagcagcag | gcgcccggcc | catcgcgcgc | gcgcggggag | 4860 |
| gcgagccggg | ggctcgcgag | gctcggcgcg | cgcctccgcg | tcggcatctg | gcggcaaagg | 4920 |
| cgcgagctgc | gcggctcgat | ccaggcgatc | ctgcgcgcct | cgcgggatca | cgatctgctc | 4980 |
| gtgatcggcg | cgcgatcgcc | ggcgcgcgcg | cgcggaatgt | cgttcggtcg | cctgcaggac | 5040 |
| gcgatcgtcc | agcgggccga | gtccaacgtg | ctcgtcgtgg | tgggcgaccc | tccggcggcg | 5100 |
| gagcgcgcct | ccgcgcggcg | gatcctcgtc | ccgatcatcg | gcctcgagta | ctccttcgcc | 5160 |
| gccgccgatc | tcgcggccca | cgtggcgctg | gcgtgggacg | ccgagctcgt | gctgctcagc | 5220 |
| agcgcgcaga | ccgatccggg | cgcggtcgtc | tggcgcgatc | gcgagccatc | ccgggtgcgc | 5280 |
| gcggtggcgc | ggagcgtcgt | cgacgaggcg | gtcttccggg | ggcgccggct | cggcgtgcgc | 5340 |
| gtctcgtcgc | gcgtgcacgt | gggcgcgcac | ccgagcgacg | agataacgcg | ggagctcgcg | 5400 |
| cgcgccccgt | acgatctgct | cgtgctcgga | tgctacgacc | atgggccgct | cggccggctc | 5460 |
| tacctcggca | gcacggtcga | gtcggtggtg | gtccggagcc | gggtgccggt | cgcgttgctc | 5520 |
| gtcgcgcatg | gagggactcg | agagcaggtg | aggtgaggct | tccaccgcgc | tcgcccgtga | 5580 |
| ggaagcgagc | gcccggctct | gccgacgatc | gtcactcccg | gtccgtgtag | gcgatcgtgc | 5640 |
| tgagcagcgc | gttctccgcc | tgacgcgagt | cgagccgggt | atgctgcacg | acgatggggg | 5700 |
| cgtccgattc | gatcacgctg | gcatagtccg | tatcgcgcgg | gatcggctcg | ggttcggtca | 5760 |
| gatcgttgaa | ccggacgtgc | cgggtgcgcc | tcgctggaac | ggtcacccgg | taaggcccgg | 5820 |
| cggggtcgcg | gtcgctgaag | taaacggtga | tggcgacctg | cgcgtcccgg | tccgacgcat | 5880 |
| tcaacaggca | ggccgtctca | tggctcgtca | tctgcggctc | aggtccgttg | ctcccgcctg | 5940 |
| ggatgtagcc | ctctgcgatt | gcacagcgcg | tccgcccgat | cggcttgtcc | atgtgtcctc | 6000 |
| cctcctggct | cctctttggc | agcctccctc | tgctgtccag | gagcgatggc | ctcttcgctc | 6060 |
| gacgcgctcg | gggatccatg | gctgaggatc | ctcgccgagc | gctccctgcc | gaccggcgcg | 6120 |
| ccgagcgccg | acgggctttg | aaagcgcgcg | accggccagc | ccggacgcgg | gcccgagagg | 6180 |
| gacagtgggt | ccgccgtgaa | gcagagaggc | gatcgaggtg | gtgagatgaa | acacgtcgac | 6240 |
| acgggccgac | gattcggccg | ccggataggg | cacacgctcg | gtcttctcgc | gagcatggcg | 6300 |
| ctcgccggct | gcggcggtcc | gagcgagaaa | accgtgcagg | gcacgcggct | cgcgcccggc | 6360 |

-continued

```
gccgatgcgc gcgtcaccgc cgacgtcgac cccgacgccg cgaccacgcg gctggcggtg    6420
gacgtcgttc acctctcgcc gcccgagcgg ctcgaggccg cagcgagcg gttcgtcgtc    6480 tggcagcgtc cgagccccga gtccccgtgg cgacgggtcg gagtgctcga ctacaatgct    6540
gacagccgaa gaggcaagct ggccgagacg accgtgccgt atgccaactt cgagctgctc    6600
atcaccgccg agaagcagag cagccctcag tcgccatcgt ctgccgccgt catcgggccg    6660
acgtctgtcg ggtgacatcg cgctatcagc agcgctgagc ccgccagcag gccccagggc    6720
cctgcctcga tggccttccc catcacccct gcgcactcct ccagcgacgg ccgcgcagcg    6780
acggccgcgt ccaagcaacc gccgtgccgg cgcggctcca cgcgcgcgac aggcgagcgt    6840
cctggcgcgg cctgcgcatc gctggaagga tcggcggagc atggatagag aatcgaggat    6900
cgcgatcttt gttgccatcg cagccaacgt ggcgatcgcg cggtcaagt tcatcgccgc    6960 cgccgtgacc ggcagctcgg cgaggcgttt ccgacttcg gcggcgtccc gcgcgtgctg    7020
ctctacgaca acctcaagag cgccgtcgtc gagcgccacg gcgacgcgat ccggttccac    7080
cccacgctgc tggctctgtc ggcgcattac cgcttcgagc cgcgccccgt cgccgtcgcc    7140
cgcggcaacg agaagggccg cgtccagcgc gccatcacgg cgtggacgac atggcgcgga    7200
aacgtcgtcg taaccgccca gcaatgtcat gggaatggcc ccttgaaatg gcccttgag    7260 ggggctggcc ggggtcgacg atatcgcgcg atctccccgt caattcccga tggtaaaaga    7320
aaaatttgtc atagatcgta agctgtgata gtggtctgtc ttacgttgcg tcttccgcac    7380
ctcgagcgag ttctctcgga taactttcaa ttttttccgag ggggcttgg tctctggttc    7440 ctcaggaagc ctgatcggga cgagctaatt cccatccatt tttttgaggc tctgctcaaa    7500
gggattagat cgagtgagac agttcttttg cagtgcgcga agaacctggg cctcgaccgg    7560
aggacgatcg acgtccgcga gcgggtcagc cgctgaggat gtgcccgtcg tggcggatcg    7620
tcccatcgag cgcgcagccg aagatccgat tgcgatcgtc ggagcgagtt gccgtctgcc    7680
cggtggcgtg atcgatctga gcgggttctg gacgctcctc gagggctcgc gcgacaccgt    7740
cgggcgagtc cccgccgaac gctgggatgc agcagcgtgg tttgatcccg accccgatgc    7800
cccggggaag acgcccgtta cgcgcgcatc tttcctgagc gacgtagcct gcttcgacgc    7860
ctccttcttc ggcatctcgc ctcgcgaagc gctgcggatg gaccctgcac atcgactctt    7920
gctggaggtg tgctgggagg cgctggagaa cgccgcgatc gctccatcgg cgctcgtcgg    7980
tacggaaacg ggagtgttca tcgggatcgg cccgtccgaa tatgaggccg cgctgccgca    8040
agcgacggcg tccgcagaga tcgacgctca tggcgggctg gggacgatgc ccagcgtcgg    8100
agcgggccga atctcgtatg ccctcgggct gcgagggccg tgtgtcgcgg tggatacggc    8160
ctattcgtcc tcgctggtgg ccgttcatct ggcctgtcag agcttgcgct ccggggaatg    8220
ctccacggcc ctggctggtg gggtatcgct gatgttgtcg ccgagcaccc tcgtgtggct    8280
ctcgaagacc cgggcgctgg ccagggacgg tcgctgcaag gcattttcgg cggaggccga    8340
tgggttcgga cgaggcgaag ggtgcgccgt cgtggtcctc aagcggctca gtggagcccg    8400
cgcggacggc gatcggatat tggcggtgat tcgaggatcc gcgatcaatc acgacggtgc    8460
gagcagcggt ctgaccgtgc cgaacgggag ctcccaagaa atcgtgctga acgggccct    8520 ggcggacgca ggctgcgccg cgtcttcggt gggttatgtc gaggcacacg gcacgggcac    8580
gacgcttggt gaccccatcg aaatccaagc tctgaatgcg gtatacggcc tcgggcgaga    8640
tgtcgccacg ccgctgctga tcgggtcggt gaagaccaac cttggccatc ctgagtatgc    8700
```

| | |
|---|---|
| gtcggggatc actgggctgc tgaaggtcgt cttgtcccctt cagcacgggc agattcctgc | 8760 |
| gcacctccac gcgcaggcgc tgaacccccg gatctcatgg ggtgatcttc ggctgaccgt | 8820 |
| cacgcgcgcc cggacaccgt ggccggactg gaatacgccg cgacgggcgg gggtgagctc | 8880 |
| gttcggcatg agcgggacca acgcgcacgt ggtgctggaa gaggcgccgg cggcgacgtg | 8940 |
| cacaccgccg gcgccggagc gaccggcaga gctgctggtg ctgtcggcaa ggaccgcgtc | 9000 |
| agccctggat gcacaggcgg cgcggctgcg cgaccatctg gagacctacc cttcgcagtg | 9060 |
| tctgggcgat gtggcgttca gtctggcgac gacgcgcagc gcgatggagc accggctcgc | 9120 |
| ggtggcggcg acgtcgaggg aggggctgcg ggcagccctg gacgctgcgg cgcagggaca | 9180 |
| gacgtcgccc ggtgcggtgc gcagtatcgc cgattcctca cgcggcaagc tcgcctttct | 9240 |
| cttcaccgga caggggcgc agacgctggg catgggccgt gggctgtacg atgtatggtc | 9300 |
| cgcgttccgc gaggcgttcg acctgtgcgt gaggctgttc aaccaggagc tcgaccggcc | 9360 |
| gctccgcgag gtgatgtggg ccgaaccggc cagcgtcgac gccgcgctgc tcgaccagac | 9420 |
| agccttcacc cagccggcgc tgttcacctt cgaatatgcg ctcgccgcgc tgtggcggtc | 9480 |
| gtggggtgta gagccggagt tggtcgccgg ccatagcatc ggtgagctgg tggctgcctg | 9540 |
| cgtggcgggc gtgttctcgc ttgaggacgc ggtgttcctg gtggctgcgc gcgggcgcct | 9600 |
| gatgcaggcg ctgccggccg gcggggcgat ggtgtcgatc gaggcgccgg aggccgatgt | 9660 |
| ggctgctgcg gtggcgccgc acgcagcgtc ggtgtcgatc gccgcggtca acgctccgga | 9720 |
| ccaggtggtc atcgcgggcg ccgggcaacc cgtgcatgca atcgcggcgg cgatggccgc | 9780 |
| gcgcggggcg cgaaccaagg cgctccacgt ctcgcatgcg ttccactcac cgctcatggc | 9840 |
| cccgatgctg gaggcgttcg ggcgtgtggc cgagtcggtg agctaccggc ggccgtcgat | 9900 |
| cgtcctggtc agcaatctga gcgggaaggc ttgcacagac gaggtgagct cgccgggcta | 9960 |
| ttgggtgcgc cacgcgcgag aggtggtgcg cttcgcggat ggagtgaagg cgctgcacgc | 10020 |
| ggccggtgcg ggcaccttcg tcgaggtcgg tccgaaatcg acgctgctcg gcctggtgcc | 10080 |
| tgcctgcatg ccggacgccc ggccggcgct gctcgcatcg tcgcgcgctg ggcgtgacga | 10140 |
| gccggcgacc gtgctcgagg cgctcggcgg gctctgggcc gtcggtggcc tggtctcctg | 10200 |
| ggccggcctc ttcccctcag gggggcggcg ggtgccgctg cccacgtacc cttggcagcg | 10260 |
| cgagcgctac tggatcgaca cgaaagccga cgacgcggcg cgtggcgacc gccgtgctcc | 10320 |
| gggagcgggt cacgacgagg tcgaggaggg gggcgcggtg cgcggcggcg accggcgcag | 10380 |
| cgctcggctc gaccatccgc cgcccgagag cggacgccgg gagaaggtcg aggccgccgg | 10440 |
| cgaccgtccg ttccggctcg agatcgatga gccaggcgtg cttgatcacc tcgtgcttcg | 10500 |
| ggtcacggag cggcgcgccc ctggtctggg cgaggtcgag atcgccgtcg acgcggcggg | 10560 |
| gctcagcttc aatgatgtcc agctcgcgct gggcatggtg cccgacgacc tgccgggaaa | 10620 |
| gcccaaccct ccgctgctgc tcggaggcga gtgcgccggg cgcatcgtcg ccgtgggcga | 10680 |
| gggcgtgaac ggcctcgtgg tgggccaacc ggtcatcgcc ctttcggcgg gagcgtttgc | 10740 |
| tacccacgtc accacgtcgg ctgcgctggt gctgcctcgg cctcaggcgc tctcggcgat | 10800 |
| cgaggcggcc gccatgcccg tcgcgtacct gacggcatgg tacgcgctcg acagaatagc | 10860 |
| ccgccttcag ccggggagc gggtgctgat ccatgcggcg accggcgggg tcggtctcgc | 10920 |
| cgcggtgcag tgggcgcagc acgtgggagc cgaggtccat cgacggccg gcacgcccga | 10980 |
| gaaacgcgcc tacctggagt cgctgggcgt gcggtatgtg agcgattccc gctcggaccg | 11040 |
| gttcgtcgcc gacgtgcgcg cgtggacggg cggcgaggga gtagacgtcg tgctcaactc | 11100 |

-continued

```
gctctcgggc gagctgatcg acaagagttt caatctcctg cgatcgcacg gccggtttgt    11160
ggagctcggc aagcgcgact gttacgcgga taaccagctc gggctgcggc cgttcctgcg    11220
caatctctcc ttctcgctgg tggatctccg ggggatgatg ctcgagcggc cggcgcgggt    11280
ccgtgcgctc ttggaggagc tcctcggcct gatcgcggca ggcgtgttca cccctccccc    11340
catcgcgacg ctcccgatcg cccgtgtcgc cgatgcgttc cggagcatgg cgcaggcgca    11400
gcatcttggg aagctcgtac tcacgctggg tgacccggag gtccagatcc gtattccaac    11460
ccacgcaggc gccggcccgt ccaccgggga tcgggacctg ctcgacaggc tcgcgtcagc    11520
tgcgccggcc gcgcgcgcgg cggcgctgga ggcgttcctc cgtacgcagg tctcgcaggt    11580
gctgcgcacg cccgaaatca aggtcggcgc ggaggcgctg ttcacccgcc tcggcatgga    11640
ctcgctcatg gccgtggagc tgcgcaatcg tatcgaggcg agcctcaagc tgaagctgtc    11700
gacgacgttc ctgtccacgt cccccaatat cgccttgttg gccaaaaccc tgttggatgc    11760
tctcgccaca gctctctcct tggagcgggt ggcggcggag aacctacggg caggcgtgca    11820
aaacgacttc gtctcatcgg gcgcagatca agactgggaa atcattgccc tatgacgatc    11880
aatcagcttc tgaacgagct cgagcaccag ggtatcaagc tggcggccga tggggagcgc    11940
ctccagatac aggcccccaa gaacgccctg aacccgaacc tgctcgctcg aatctccgag    12000
cacaaaagca cgatcctgac gatgctccgt cagagactcc ccgcagaatc catcgtgccc    12060
gccccagccg agcggcacgc tccgtttcct ctcacagaca tccaagaatc ctactggctg    12120
ggccggacag gagcgtttac ggtccccagc gggatccacg cctatcgcga atacgactgt    12180
acggatctcg acgtgccgag gctgagccgc gcctttcgga aagtcgtcgc gcggcacgac    12240
atgcttcggg cccacacgct gcccgacatg atgcaggtga tcgagcctaa agtcgacgcc    12300
gacatcgaga tcatcgatct gcgcgggctc gaccggagca cacgggaagc gaggctcgtg    12360
tcgttgcgag atgcgatgtc gcaccgcatc tatgacaccg agcgccctcc gctctatcac    12420
gtcgtcgccc ttcggctgga cgagcggcaa acccgtctcg tgctcagtat cgatctcatt    12480
aacgttgacc taggcagcct gtccatcatc ttcaaggact ggctcagctt ctacgaagat    12540
cccgagacct ctctccctgt cctggagctc tcgtaccgcg attatgtact cgcgctggag    12600
tctcgcaaga agtctgaggc gcatcaacga tcgatggatt actggaagcg gcgcatcgcc    12660
gagctcccac ctccgccgac gcttccgatg aaggccgatc catctacccct gaaggagatc    12720 cgcttccggc acacggagca atggctgccg tcggactcct ggggtcgatt gaagcggcgt    12780
gtcggggagc gcgggctgac cccgacgggc gtcatcctgg ctgcattttc cgaggtgatc    12840
gggcgctgga gcgcgagccc ccggtttacg ctcaacataa cgctcttcaa ccggctcccc    12900
gtccatccgc gcgtgaacga tatcaccggg gacttcacgt cgatggtcct cctggacatc    12960
gacaccactc gcgacaagag cttcgaacag cgcgctaagc gtattcaaga gcagctgtgg    13020
gaagcgatgg atcactgcga cgtaagcggt atcgaggtcc agcgagaggc cgcccgggtc    13080
ctggggatcc aacgaggcgc attgttcccc gtggtgctca cgagcgcgct taaccagcaa    13140
gtcgttggtg tcacctcgtt gcagaggctc ggaactccgg tgtacaccag cacgcagact    13200
cctcagctgc tgctggatca tcagctctac gagcacgatg gggacctcgt cctcgcgtgg    13260
gacatcgtcg acggagtgtt cccgcccgac cttctggacg acatgctcga agcgtacgtc    13320 gttttttctcc ggcggctcac tgaggaacca tggggtgaac aggtgcgctg ttcgcttccg    13380
cctgcccagc tagaagcgcg ggcgagcgca aacgcgacca acgcgctgct gagcgagcat    13440
```

```
acgctgcacg gcctgttcgc ggcgcgggtc gagcagctgc ccatgcagct cgccgtggtg   13500
tcggcgcgca agacgctcac gtacgaagag ctttcgcgcc gttcgcggcg acttggcgcg   13560
cggctgcgcg agcaggggc acgcccgaac acattggtcg cggtggtgat ggagaaaggc    13620
tgggagcagg ttgtcgcggt tctcgcggtg ctcgagtcag gcgcggccta cgtgccgatc   13680
gatgccgacc taccggcgga gcgtatccac tacctcctcg atcatggtga ggtaaagctc   13740
gtgctgacgc agccatggct ggatggcaaa ctgtcatggc cgccggggat ccagcggctg   13800
ctcgtgagcg aggccggcgt cgaaggcgac ggcgaccagc ctccgatgat gcccattcag   13860
acaccttcgg atctcgcgta tgtcatctac acctcgggat ccacagggtt gcccaagggg   13920
gtgatgatcg atcatcgggg tgccgtcaac accatcctgg acatcaacga gcgcttcgaa   13980
atagggcccg agacagggt gctggcgctc tcctcgctga gcttcgatct ctcggtctat    14040
gatgtgttcg ggatcctggc ggcgggcggt acgatcgtgg tgccggacgc gtccaagctg   14100
cgcgatccgg cgcattgggc agagttgatc gaacgagaga aggtgacggt gtggaactcg   14160
gtgccggcgc tgatgcggat gctcgtcgag cattttgagg gtcgccccga ttcgctcgct   14220
aggtctctgc ggctttcgct gctgagcggc gactggatcc cggtgggcct gcctggcgag   14280
ctccaggcca tcaggcccgg cgtgtcggtg atcagcctgg gcggggccac cgaagcgtcg   14340
atctggtcca tcgggtaccc cgtgaggaac gtcgacctat cgtgggcgag catcccctac   14400
ggccgtccgc tgcgcaacca gacgttccac gtgctcgatg aggcgctcga accgcgcccg   14460
gtctgggttc cgggcaact ctacattggc ggggtcgggc tggcactggg ctactggcgc    14520
gatgaagaga agacgcgcaa gagcttcctc gtgcaccccg agaccgggga gcgcctctac   14580
aagaccggcg atctgggccg ctacctgccc gatggaaaca tcgagttcat ggggcgtgag   14640
gacaaccaaa tcaagcttcg cggataccgc gttgagctcg gggaaatcga ggaaacgctc   14700
aagtcgcatc cgaacgtacg cgacgcgtg attgtgcccg tcgggaacga cgcggcgaac    14760
aagctccttc tagcctatgt ggtcccggag ggcacacgga gacgcgctgc cgagcaggac   14820
gcgagcctca agaccgagcg gatcgacgcg agagcacacg ccgccgaagc ggacggcttg   14880
agcgacggcg agagggtgca gttcaagctc gctcgacacg gactccggag ggacctggac   14940
ggaaagcccg tcgtcgatct gaccgggcag gatccgcggg aggcggggct ggacgtctac   15000
gcgcgtcgcc gtagcgtccg aacgttcctt gaggccccga ttccgtttgt tgagtttggt   15060
cgattcctga gctgcttgag cagcgtggag cccgacggcg cgacccttcc caaattccgt   15120
tatccatcgg cgggcagcac gtacccggtg caaacctacg cgtatgtcaa atccggccgc   15180
atcgagggcg tggacgaggg cttctattat taccacccgt tcgagcaccg tttgctgaag   15240
ctctccgatc acgggatcga gcgcggagcg cacgttcggc aaaacttcga cgtgttcgat   15300
gaagcggcgt tcaacctcct gttcgtgggc aggatcgacg ccatcgagtc gctgtatgga   15360
tcgtcgtcgc gagaattttg cctgctggag gccggatata tggcgcagct cctgatggag   15420
caggcgcctt cctgcaacat cggcgtctgt ccggtgggc aattcaattt tgaacaggtt    15480
cggccggttc tcgacctgcg acattcggac gtttacgtgc acggcatgct gggcgggcgg   15540
gtagacccgc ggcagttcca ggtctgtacg ctcggtcagg attcctcacc gaggcgcgcc   15600
acgacgcgcg gcgcccctcc cggccgcgag cagcacttcg ccgatatgct tcgcgacttc   15660
ttgaggacca aactacccga gtacatggtg cctacagtct tcgtggagct cgatgcgttg   15720
ccgctgacgt ccaacggcaa ggtcgatcgt aaggccctgc gcgagcggaa ggataccctcg   15780 tcgccgcggc attcggggca cacggcgcca cgggacgcct tggaggagat cctcgtcgcg   15840
```

```
gtcgtacggg aggtgctcgg gctggaggtg gtcgggctcc agcagagctt cgtcgatctt   15900
ggtgcgacat cgattcacat cgttcgcatg aggagcctgt tgcagaagag gctggatagg   15960
gagatcgcca tcaccgagtt gttccagtac ccgaacctcg gctcgctggc gtccggtttg   16020
cgccgagact cgagagatct agatcagcgg ccgaacatgc aggaccgagt ggaggttcgg   16080
cgcaagggca ggagacgtag ctaagagcgc cgaacaaaac caggccgagc gggccgatga   16140
gccgcaagcc cgcctgcgtc accctgggac tcatctgatc tgatcgcggg tacgcgtcgc   16200
gggtgtgcgc gttgagccgt gttgttcgaa cgctgaggaa cggtgagctc atggaagaac   16260
aagagtcctc cgctatcgca gtcatcggca tgtcgggccg ttttccgggg gcgcgggatc   16320
tggacgaatt ctggaggaac cttcgagacg gcacggaggc cgtgcagcgc ttctccgagc   16380
aggagctcgc ggcgtccgga gtcgaccccg cgctggtgct ggacccgagc tacgtccggg   16440
cgggcagcgt gctggaagac gtcgaccggt tcgacgctgc tttcttcggc atcagcccgc   16500
gcgaggcaga gctcatggat ccgcagcacc ggatcttcat ggaatgcgcc tgggaggcgc   16560
tggagaacgc cggatacgac ccgacggctt acgaggctc tatcgcgtg tacgccggcg   16620
```

```
tcgaggatgc ggtggcgatc atctgccggc gcagccggct gctccggcgc atcagcggtc   18240
agggcgagat ggcggtgacc gagctgtcgc tggccgaggc cgaggcggcg ctccgaggct   18300
acgaggatcg ggtgagcgtg gccgtgagca acagcccgcg ctcgacggtg ctctcgggcg   18360
agccggcagc gatcggcgag gtgctgtcgt ccctgaacgc gaagggggtg ttctgccgtc   18420
gggtgaaggt ggatgtcgcc agccacagcc cgcaggtcga cccgctgcgc gaggacctct   18480
tggcagccct gggcgggctc cggccgggtg cggctgcggt gccgatgcgc tcgacggtga   18540
cgggcgccat ggtagcgggc ccggagctcg gagcgaatta ctggatgaac aacctcaggc   18600
agccagtgcg cttcgccgag gtagtccagg cgcagctcca aggcggccac ggtctgttcg   18660
tggagatgag cccgcatccg atcctaacga cttcggtcga ggagatgcgg cgcgcggccc   18720
agcgggcggg cgcagcggtg ggctcgctgc ggcggggca ggacgagcgc ccggcgatgc   18780
tggaggcgct gggcacgctg tgggcgcagg gctaccctgt accctggggg cggctgtttc   18840
ccgcgggggg gcggcgggta ccgctgccga cctatccctg gcagcgcgag cggtactgga   18900
tcgaagcgcc ggccaagagc gccgcgggcg atcgccgcgg cgtgcgtgcg ggcggtcacc   18960
cgctcctcgg tgaaatgcag accctgtcaa cccagacgag cacgcggctg tgggagacga   19020
cgctggatct caagcggctg ccgtggctcg gcgaccaccg ggtgcaggga gcggtcgtgt   19080
ttccgggcgc ggcgtacctg gagatggcga tttcgtcggg ggccgaggct ttgggcgatg   19140 gcccttttgca gataactgac gtggtgctcg ccgaggcgct ggccttcgcg ggcgacgcgg   19200
cggtgttggt ccaggtggtg acgacggagc agccgtcggg gcggctgcag ttccagatcg   19260
cgagccgggc gccgggcgct ggccacgcgt ccttccgggt ccacgctcgc ggcgcgttgc   19320
tccgagtgga gcgcaccgag gtcccggctg ggcttacgct ttccgctgtg cgcgcgcggc   19380
tccaggccag catacccgcc gcggccacct acgcggagct gaccgagatg gggctgcagt   19440
acggccctgc cttccagggg attgctgagc tatgcggggg tgaaggcgag gcgctgggac   19500
gggtacgcct gcccgacgcg gccggctcgg cagcggagta tcggttgcat cctgcgctgc   19560
tggacgcgtg cttccagatc gtcggcagcc tcttcgcccg cagtggcgag gcgacgcgt   19620 gggtgcccgt ggagttgggc tcgctgcggc tcttgcagcg gccttcgggg gagctgtggt   19680
gccatgcgcg cgtcgtgaac catgggcacc aaaccccga tcggcagggc gccgactttt   19740
gggtggtcga cagctcgggt gcagtggtcg ccgaagtttg cgggctcgtg gcgcagcggc   19800
ttccgggagg ggtgcgccgg cgcgaagaag acgattggtt cctggagctc gagtgggaac   19860
ccgcagcggt cggcacagcc aaggtcaacg cgggccggtg gctgctcctc ggcggcggcg   19920
gtgggctcgg cgccgcgttg cgcgcgatgc tggaggccgg cggccatgcc gtcgtgcatg   19980
cggcagagaa caacacgagc gctgccggcg tacgcgcgct cctggcaaag gcctttgacg   20040
gccaggctcc gacggcggtg gtgcacctcg gcagcctcga tggggtggc gagctcgacc   20100 cagggctcgg ggcgcaaggc gcattggacg cgccccggag cgccgacgtc agtcccgatg   20160
ccctcgatcc ggcgctggta cgtggctgcg acagcgtgct ctggaccgtg caggccctgg   20220
ccggcatggg ctttcgagac gccccgcgat tgtggctttt gacccgcggc gcacaggccg   20280
tcggcgccgg cgacgtctcc gtgacacagg caccgctgct ggggctgggc cgcgtcatcg   20340
ccatggagca cgcggatctg cgctgcgctc gggtcgacct cgatccagcc cggcccgagg   20400
gggagctcgc tgccctgctg gccgagctgc tggccgacga cgccgaagcg gaagtcgcgt   20460
tgcgcggtgg cgagcgatgc gtcgctcgga tcgtccgccg gcagcccgag acccggcccc   20520
gggggaggat cgagagctgc gttccgaccg acgtcaccat ccgcgcggac agcacctacc   20580
```

-continued

```
ttgtgaccgg cggtctgggt gggctcggtc tgagcgtggc cggatggctg gccgagcgcg   20640
gcgctggtca cctggtgctg gtgggccgct ccggcgcggc gagcgtggag caacgggcag   20700
ccgtcgcggc gctcgaggcc cgcggcgcgc gcgtcaccgt ggcgaaggcg gatgtcgccg   20760 atcggcgca gctcgagcgg atcctccgcg aggttaccac gtcggggatg ccgctgcggg    20820
gcgtcgtcca tgcggccggc atcttggacg acgggctgct gatgcagcag actcccgcgc   20880
ggtttcgtaa ggtgatggcg cccaaggtca aggggccctt gcacctgcac gcgttgacgc   20940
gcgaagcgcc gctttccttc ttcgtgctgt acgcttcggg agtagggctc ttgggctcgc   21000
cgggccaggg caactacgcc gcggccaaca cgttcctcga cgctctggcg caccaccgga   21060
gggcgcaggg gctgccagcg ttgagcgtcg actggggcct gttcgcggag gtgggcatgg   21120
cggccgcgca ggaagatcgc ggcgcgcggc tggtctcccg cggaatgcgg agcctcaccc   21180
ccgacgaggg gctgtccgct ctggcacggc tgctcgaaag cggccgcgct caggtggggg   21240
tgatgccggt gaacccgcgg ctgtgggtgg agctctaccc cgcggcggcg tcttcgcgaa   21300
tgttgtcgcg cctggtgacg gcgcatcgcg cgagcgccgg cgggccagcc ggggacgggg   21360
acctgctccg ccgcctcgcc gctgccgagc cgagcgcgcg gagcgcgctc ctggagccgc   21420
tcctccgcgc gcagatctcg caggtgctgc gcctccccga gggcaagatc gaggtggacg   21480
ccccgctcac gagcctgggc atgaactcgc tgatgggct cgagctgcgc aaccgcatcg    21540
aggccatgct gggcatcacc gtaccggcaa cgctgttgtg gacctatccc acggtggcgg   21600
cgctgagcgg gcatctggcg cgggaggcat gcgaagccgc tcctgtggag tcaccgcaca   21660
ccaccgccga ctctgccgtc gagatcgagg agatgtcgca ggacgatctg acgcagttga   21720
tcgcagcaaa attcaaggcg cttacatgac tactcgcggt cctacggcac agcagaatcc   21780
gctgaaacaa gcggccatca tcattcagcg gctggaggag cggctcgctg ggctcgcaca   21840
ggcggagctg gaacggaccg agccgatcgc catcgtcggt atcggctgcc gcttccctgg   21900
cggtgcggac gctccggaag cgttttggga gctgctcgac gcggagcgcg acgcggtcca   21960
gccgctcgac atgcgctggg cgctggtggg tgtcgctccc gtcgaggccg tgccgcactg   22020
ggcggggctg ctcaccgagc cgatagattg cttcgatgct gcgttcttcg gcatctcgcc   22080
tcgggaggcg cgatcgctcg acccgcagca tcgtctgttg ctggaggtcg cttgggaggg   22140
gctcgaggac gccggtatcc cgccccggtc catcgacggg agccgcaccg gtgtgttcgt   22200
cggcgctttc acggcggact acgcgcgcac ggtcgctcgg ctgccgcgcg aggagcgaga   22260
cgcgtacagc gccaccggca acatgctcag catcgccgcc ggacggctgt cgtacacgct   22320
ggggttgcag ggaccttgcc tgaccgtcga cacggcgtgc tcgtcatcgc tggtggcgat   22380
tcacctcgcc tgccgcagcc tgcgcgcagg agagagcgat ctcgcgttgg cgggaggggt   22440
cagcgcgctc ctctcccccg acatgatgga agccgcggcg cgcacgcaag cgctgtcgcc   22500
cgatggtcgt tgccggacct tcgatgcttc ggccaacggg ttcgtccgtg gcgagggctg   22560
tggcctggtc gtcctcaaac ggctctccga cgcgcaacgg gatggcgacc gcatctgggc   22620
gctgatccgg ggctcggcca tcaaccatga tggccggtcg accgggttga ccgcgcccaa   22680
cgtgctggct caggagacgg tcttgcgcga ggcgctgcgg agcgcccacg tcgaagctgg   22740
ggccgtcgat tacgtcgaga cccacggaac agggacctcg ctgggcgatc ccatcgaggt   22800
cgaggcgctg cgggcgacgg tggggccggc gcgctccgac ggcacacgct gcgtgctggg   22860
cgcggtgaag accaacatcg gccatctcga ggccgcggca ggcgtagcgg gcctgatcaa   22920
```

```
ggcagcgctt tcgctgacgc acgagcgcat cccgagaaac ctcaacttcc gcacgctcaa    22980
tccgcggatc cggctcgagg gcagcgcgct cgcgttggcg accgagccgg tgccgtggcc    23040
gcgcacggac cgcccgcgct tcgcggggt gagctcgttc gggatgagcg aacgaacgc      23100
gcatgtggtg ctggaagagg cgccggcggt ggagctgtgg cctgccgcgc cggagcgctc    23160
ggcggagctt ttggtgctgt cgggcaagag cgaggggggcg ctcgatgcgc aggcggcgcg   23220
gctgcgcgag cacctggaca tgcacccgga gctcgggctc ggggacgtgg cgttcagcct    23280
ggcgacgacg cgcagcgcga tgagccaccg gctcgcggtg gcggtgacgt cgcgcgaggg    23340
gctgctggcg gcgctctcgg ccgtggcgca ggggcagacg ccggcggggg cggcgcgctg    23400
catcgcgagc tcctcgcgcg gcaagctggc gttcctgttc accggacagg gcgcgcagac    23460
gccgggcatg ggccggggggc tttgcgcggc gtggccagcg ttccgggagg cgttcgaccg   23520
gtgcgtggcg ctgttcgacc gggagctgga ccgcccgctg cgcgaggtga tgtgggcgga    23580
ggcggggagc gccgagtcgt tgttgctcga ccagacggcg ttcacccagc ccgcgctctt    23640
cgcggtggag tacgcgctga cggcgctgtg cggtcgtgg ggcgtagagc cggagctcct     23700
ggttgggcat agcatcgggg agctggtggc ggcgtgcgtg gcggggggtgt tctcgctgga   23760
agatggggtg aggctcgtgg cggcgcgcgg cggctgatg caggggctct cggcgggcgg     23820
cgcgatggtg tcgctcggag cgccggaggc ggaggtggcg gcggcggtgg cgccgcacgc    23880
ggcgtcggtg tcgatcgcgg cggtcaatgg gccggagcag gtggtgatcg gggcgtgga    23940
gcaagcggtg caggcgatcg cggcggggtt cgcggcgcgc ggcgcgcgca ccaagcggct    24000
gcatgtctcg cacgcgttcc actcgccgct gatggaaccg atgctggagg agttcgggcg    24060
ggtggcggcg tcggtgacgt accggcggcc aagcgtttcg ctggtgagca acctgagcgg    24120
gaaggtggtc acggacgagc tgagcgcgcc ggggtactgg gtgcggcacg tgcgggaggc    24180
ggtgcgcttc gcggacgggg tgaaggcgct gcacagaagcc ggcgcgggga cgttcgtcga   24240
agtgggcccg aagccgacgc tgctcgggct gttgccagcc tgcctgccgg aggcggagcc    24300
gacgctgctg gcgtcgttgc gcgccgggcg cgaggaggct gcggggtgc tcgaggcgct    24360
gggcaggctg tgggccgccg gcggctcggt cagctggccg ggcgtcttcc ccacggctgg    24420
gcggcgggtg ccgctgccga cctatccgtg gcagcggcag cggtactgga tcgaggcgcc    24480
ggccgaaggg ctcggagcca cggccgccga tgcgctggcg cagtggttct accgggtgga    24540
ctggcccgag atgcctcgct catccgtgga ttcgcggcga gcccggtccg gcgggtggct    24600
ggtgctggcc gaccggggtg gagtcgggga gcggccgcg gcgcgcttt cgtcgcaggg     24660
atgttcgtgc gccgtgctcc atgcgcccgc cgaggcctcc gcggttgccg agcaggtgac    24720
ccaggccctc ggtggccgca acgactggca ggggtgctg tacctgtggg gtctggacgc     24780
cgtcgtggag gcgggggcat cggccgaaga ggtcgccaaa gtcacccatc ttgccgcggc    24840
gccggtgctc gcgctgattc aggcgctcgg cacggggccg cgctcacccc ggctctggat    24900
cgtgaccccga ggggcctgca cggtgggcgg cgagcctgac gctgccccct gtcaggcggc   24960
gctgtgggt atgggccggg tcgcggcgct agagcatccc ggctcctggg gcgggctcgt     25020
ggacctggat ccggaggaga gcccgacgga ggtcgaggcc ctggtggccg agctgctttc    25080
gccggacgcc gaggatcagc tggcattccg ccaggggcgc cggcgcgcag cgcggcttgt    25140
ggccgcccca ccgagggaa acgcagcgcc ggtgtcgctg tctgcggagg ggagttactt     25200
ggtgacgggt gggctgggcg cccttggcct cctcgttgcg cggtggttgg tggagcgcgg    25260
ggcggggcac cttgtgctga tcagccggca cggattgccc gaccgcgagg aatgggggccg   25320
```

-continued

```
agatcagccg ccagaggtgc gcgcgcgcat tgcggcgatc gaggcgctgg aggcgcaggg   25380
cgcgcgggtc accgtggcgg cggtcgacgt ggccgatgcc gaaggcatgg cggcgctctt   25440
ggcggccgtc gagccgccgc tgcgggggt agtgcacgcc gcgggtctgc tcgacgacgg    25500
gctgctggcc caccaggacg ctggtcggct cgcccgggtg ttgcgcccca aggtggaggg   25560 ggcatggtg ctgcacaccc ttacccgcga gcagccgctg gacctcttcg tactgttttc    25620
ctcggcgtcg ggcgtcttcg gctcgatcgg ccagggcagc tacgcggcag gcaatgcctt   25680
tttggacgcg ctgcggacc tccgccgaac gcagggctc ccgcccctga gcatcgcctg     25740
gggcctgtgg gcggaggggg ggatgggctc gcaggcgcag cgccgggaac acgaggcatc   25800
gggaatctgg gcgatgccga cgagtcgggc cctggcggca tggaatggc tgctcggtac    25860 gcgcgcgacg cagcgcgtgg tcatccagat ggattgggcc catgcgggag cggcgccgcg   25920
cgacgcgagc cgaggccgct tctgggatcg gctggtaact gccacgaaag aggcctcctc   25980
ctcggccgtg ccagctgtgg agcgctggcg caacgcgtct gttgtggaga cccgctcggc   26040
gctctacgag cttgtgcgcg gcgtggtcgc cggggtgatg ggctttaccg accagggcac   26100
gctcgacgtg cgacgaggct tcgccgagca gggcctcgac tccctgatgg ccgtggagat   26160
ccgcaaacgg cttcagggtg agctgggtat gccgctgtcg gcgacgctag cgttcgacca   26220
tccgaccgtg gagcggctgg tggaatactt gctgagccag gcgctggagc tgcaggaccg   26280
caccgacgtg cggagcgttc ggttgccggc gacagaggac ccgatcgcca tcgtgggtgc   26340
cgcctgccgc ttcccgggcg gggtcgagga cctggagtcc tactggcagc tgttgaccga   26400
gggcgtggtg gtcagcaccg aggtgccggc cgaccggtgg aatggggcag acgggcgcgt   26460
ccccggctcg ggagaggcac agagacagac ctacgtgccc aggggtggct ttctgcgcga   26520
ggtggagacg ttcgatgcgg cgttcttcca catctcgcct cgggaggcga tgagcctgga   26580
cccgcaacag cggctgctgc tggaagtgag ctgggaggcg atcgagcgcg cgggccagga   26640
cccgtcggcg ctgcgcgaga gccccacggg cgtgttcgtg ggcgcgggcc caacgaata    26700 tgccgagcgg gtgcaggaac tcgccgatga ggcggcgggg ctctacagcg gcaccggcaa   26760
catgctcagc gttgcggcgg gacggctatc attttttcctg ggcctgcacg ggccgaccct   26820
ggctgtggat acggcgtgct cctcgtcgct ggtggcgctg cacctcggct gccagagctt   26880 gcgacgggc gagtgcgacc aagccctggt tggcggggtc aacatgctgc tctcgccgaa    26940
gaccttcgcg ctgctctcac ggatgcacgc actttcgccc ggcgggcggt gcaagacgtt   27000
ctcggccgac gcggacggct acgcgcgggc cgagggctgc gccgtggtgg tgctcaagcg   27060
gctctccgac gcgcagcgcg accgcgaccc catcctggcc gtgatccggg gtacggcgat   27120
caatcatgat ggcccgagca gcgggctgac agtgccagc ggccctgccc aggaggcgct    27180
gttacgccag gcgctggcgc acgcagggt ggttccggcc gacgtcgatt tcgtggaatg    27240
ccacgggacc gggacggcgc tgggcgaccc gatcgaggtg cgtgcgctga cgacgtgta    27300 cgggcaagcc cgccctgcgg accgaccgct gatcctggga ccgcaaggg ccaaccttgg    27360 gcacatggag cccgcggcgg gcctggccgg cttgctcaag gcggtgctcg cgctggggca   27420
agagcaaata ccagcccagc cggagctggg cgagctcaac ccgctcttgc cgtgggaggc   27480
gctgccggtg gcggtggccc gcgcagcggt gccgtggccg cgcacggacc gcccgcgctt   27540 cgcggggggtg agctcgttcg ggatgagcgg aacgaacgcg catgtggtgc tggaagaggc   27600
gccggcggtg gagctgtggc ctgccgcgcc ggagcgctcg gcggagctt tggtgctgtc    27660
```

-continued

```
gggcaagagc gaggggggcgc tcgatgcgca ggcggcgcgg ctgcgcgagc acctggacat   27720
gcacccggag ctcgggctcg gggacgtggc gttcagcctg gcgacgacgc gcagcgcgat   27780
gaaccaccgg ctcgcggtgg cggtgacgtc gcgcgagggg ctgctggcgg cgctttcggc   27840
cgtggcgcag gggcagacgc cgccgggggc ggcgcgctgc atcgcgagct cgtcgcgcgg   27900
caagctggcg ttcctgttca ccggacaggg cgcgcagacg ccgggcatgg gccgggggct   27960
ttgcgcggcg tggccagcgt tccgggaggc gttcgaccgg tgcgtggcgc tgttcgaccg   28020
ggagctggac cgcccgctgc gcgaggtgat gtgggcggag ccggggagcg ccgagtcgtt   28080
gttgctcgac cagacggcgt tcacccagcc cgcgctcttc acggtggagt acgcgctgac   28140
ggcgctgtgg cggtcgtggg gcgtagagcc ggagctggtg gctgggcata cgccggggga   28200
gctggtggcg gcgtgcgtgg cggggggtgtt ctcgctggaa gatgggtgat ggctcgtggc   28260
ggcgcgcggg cggctgatgc aggggctctc ggcgggcggc gcgatggtgt cgctcggagc   28320
gccggaggcg gaggtggcgg cggcggtggc gccgcacgcg gcgtcggtgt cgatcgcggc   28380
ggtcaatggg ccggagcagg tggtgatcgc gggcgtggag caagcggtgc aggcgatcgc   28440
ggcggggttc gcggcgcgcg cgcgcgcgcac caagcggctg catgtctcgc acgcgtccca   28500
ctcgccgctg atggaaccga tgctggagga gttcgggcgg gtggcggcgt cggtgacgta   28560
ccggcggcca agcgtttcgc tggtgagcaa cctgagcggg aaggtggtcg cggacgagct   28620
gagcgcgccg gggtactggg tgcggcacgt gcgggaggcg gtgcgcttcg cggacggggt   28680
gaaggcgctg cacgaagccg gtgcgggcac gttcgtcgaa gtgggcccga agccgacgct   28740
gctcgggctg ttgccagcct gcctgccgga ggcggagccg acgctgctgg cgtcgttgcg   28800
cgccgggcgc gaggaggctg cggggggtgct cgaggcgctg ggcaggctgt gggccgccgg   28860
cggctcggtc agctggccgg gcgtcttccc cacggctggg cggcgggtgc cgctgccgac   28920
ctatccgtgg cagcggcagc ggtactggcc cgacatcgag cctgacagcc gtcgccacgc   28980
agccgcggat ccgacccaag gctggttcta tcgcgtggac tggccggaga tacctcgcag   29040
cctccagaaa tcagaggagg cgagccgcgg gagctggctg gtattggcgg ataagggtgg   29100
agtcggcgag gcggtcgctg cagcgctgtc gacacgtgga cttccatgcg tcgtgctcca   29160
tgcgccggca gagacatccg cgaccgccga gctggtgacc gaggctgccg gcggtcgaag   29220
cgattggcag gtagtgctct acctgtgggg tctggacgcc gtcgtcggtg cggaggcgtc   29280
gatcgatgag atcggcgacg cgacccgtcg tgctaccgcg ccggtgctcg gcttggctcg   29340
gtttctgagc accgtgtctt gttcgccccg actctgggtc gtgacccggg gggcatgcat   29400
cgttggcgac gagcctgcga tcgccccttg tcaggcggg ttatgggca tgggccgggt   29460 ggcggcgctc gagcatcccg gggcctgggg cgggctcgtg gacctggatc cccgagcgag   29520
cccgccccaa gccagcccga tcgacggcga gatgctcgtc accgagctat tgtcgcagga   29580
gaccgaggat cagctcgcct tccgccatgg gcgccggcac gcggcacggc tggtggccgc   29640
cccgccacag gggcaagcgg caccggtgtc gctgtctgcg gaggcgagct acctggtgac   29700
gggaggcctc ggtgggctgg gcctgatcgt ggcccagtgg ctggtggagc tgggagcgcg   29760
gcacttggtg ctgaccagcc ggcgcggggtt gcccgaccgg caggcgtggt gcgagcagca   29820
gccgcctgag atccgcgcgc ggatcgcagc ggtcgaggcg ctggaggcgc ggggtgcacg   29880
ggtgaccgtg gcagcggtgg acgtggccga cgtcgaaccg atgacagcgc tggtttcgtc   29940
ggtcgagccc ccgctgcgag gggtggtgca cgccgctggc gtcagcgtca tgcgtccact   30000
ggcggagacg gacgagaccc tgctcgagtc ggtgctccgt cccaaggtgg ccgggagctg   30060
```

-continued

```
gctgctgcac cggctgctgc acggccggcc tctcgacctg ttcgtgctgt tctcgtcggg    30120
cgcagcggtg tggggtagcc atagccaggg tgcgtacgcg gcggccaacg ctttcctcga    30180
cgggctcgcg catcttcggc gttcgcaatc gctgcctgcg ttgagcgtcg cgtgggtct    30240 gtgggccgag ggaggcatgg cggacgcgga ggctcatgca cgtctgagcg acatcgggt    30300 tctgcccatg tcgacgtcgg cagcgttgtc ggcgctccag cgcctggtgg agaccggcgc    30360
ggctcagcgc acggtgaccc ggatggactg ggcgcgcttc cgccggtgt acaccgctcg    30420 agggcgtcgc aacctgcttt cggcgctggt cgcagggcgc gacatcatcg cgccttcccc    30480
tccggcggca gcaacccgga actggcgtgg cctgtccgtt gcggaagccc gcgtggctct    30540
gcacgagatc gtccatgggg ccgtcgctcg ggtgctgggc ttcctcgacc cgagcgcgct    30600
cgatcctggg atgggttca atgagcaggg cctcgactcg ttgatggcgg tggagatccg    30660
caacctcctt caggctgagc tggacgtgcg gctttcgacg acgctggcct ttgatcatcc    30720
gacggtacag cggctggtgg agcatctgct cgtcgatgta ctgaagctgg aggatcgcag    30780
cgacacccag catgttcggt cgttggcgtc agacgagccc atcgccatcg tgggagccgc    30840
ctgccgcttc ccgggcgggg tggaggacct ggagtcctac tggcagctat ggccgaggg    30900 cgtggtggtc agcgccgagg tgccggccga ccggtgggat cgggcggact ggtacgaccc    30960
tgatccggag atcccaggcc ggacttacgt gaccaaaggc gccttcctgc gcgatttgca    31020
gagattggat gcgaccttct tccgcatctc gcctcgcgag gcgatgagcc tcgacccgca    31080
gcagcggttg ctcctggagg taagctggga agcgctcgag agcgcgggta tcgctccgga    31140
tacgctgcga gatagcccca ccggggtgtt cgtgggtgcg gggcccaatg agtactacac    31200
gcagcggctg cgaggcttca ccgacggagc ggcagggttg tacggcggca ccgggaacat    31260
gctcagcgtt acggctggac ggctgtcgtt tttcctgggt ctgcacggcc cgacgctggc    31320
catggatacg gcgtgctcgt catccctggt cgcgctgcac ctcgcctgcc agagcctgcg    31380
actgggcgag tgcgatcaag cgctggttgg cggggtcaac gtgctgctcg cgccggagac    31440
cttcgtgctg ctctcacgga tgcgcgcgct ttcgcccgac gggcggtgca agacgttctc    31500
ggccgacgcg gacggctacg cgcggggcga ggggtgcgcc gtggtggtgc tcaagcggct    31560
gcgcgatgcg cagcgcgccg gcgactccat cctggcgctg atccggggaa gcgcggtgaa    31620
ccacgacggc ccgagcagcg ggctgaccgt acccaacgga cccgcccagc aagcattgct    31680
gcgccaggcg ctttcgcaag caggcgtgtc tccggtcgac gttgattttg tggagtgtca    31740
cgggacaggg acggcgctgg gcgacccgat cgaggtgcag gcgctgagcg aggtgtatgg    31800
tccagggcgc tccggggacc gaccgctggt gctggggcc gccaaggcca acgtcgcgca    31860
tctggaggcg gcatctggct tggccagcct gctcaaggcc gtgcttgcgc tgcggcacga    31920
gcagatcccg gccagccgg agctggggga gctcaacccg cacttgccgt ggaacacgct    31980
gccggtggcg gtgccacgta aggcggtgcc gtggggcgc ggcgcacgcc cgcgtcgggc    32040
cggcgtgagc gcgttcgggt tgagcggaac caacgtgcat gtcgtgctgg aggaggcacc    32100
ggaggtggag ccggcgcccg cggcgccggc gcgaccggtg gagctggtcg tgctatcggc    32160
caagagcgcg gcgcgctgg acgccgcggc ggcacggctc tcggcgcacc tgtccgcgca    32220
cccggagctg agcctcggcg acgtggcgtt cagcctggcg acgacgcgca gcccgatgga    32280
gcaccggctc gccatcgcga cgacctcgcg cgaggccctg cgaggcgcgc tggacgccgc    32340
ggcgcagcaa aagacgccgc agggcgcggt gcgcggcaag gccgtgtcct cacgcggtaa    32400
```

-continued

```
gctggctttc ctgttcaccg gacagggcgc gcaaatgccg ggcatgggcc gtgggctgta    32460
cgaaacgtgg cctgcgttcc gggaggcgtt cgaccggtgc gtggcgctct tcgatcggga    32520
gatcgaccag cctctgcgcg aggtgatgtg ggctgcgccg ggcctcgctc aggcggcgcg    32580
gctcgatcag accgcgtacg cgcagccggc tctctttgcg ctggagtacg cgctggctgc    32640
cctgtggcgt tcgtggggcg tggagccgca cgtactgctc ggtcatagca tcggcgagct    32700
ggtcgccgcc tgcgtggcgg gcgtgttctc gctcgaagat gcggtgaggt tggtggccgc    32760
gcgcgggcgg ctgatgcagg cgctacccgc cggcggtgcc atggtagcca tcgcagcgtc    32820
cgaggccgag gtggccgcct ccgtggcgcc ccacgccgcc acggtgtcga tcgccgcggt    32880
caacggtcct gacgccgtcg tgatcgccgg cgccgaggta caggtgctcg ccctcggcgc    32940
gacgttcgcg gcgcgtggga tacgcacgaa gaggctcgcc gtctcccatg cgttccactc    33000
gccgctcatg gatccgatgc tggaagactt ccagcgggtc gctgcgacga tcgcgtaccg    33060
cgcgccagac cgcccggtgg tgtcgaatgt caccggccac gtcgcaggcc ccgagatcgc    33120
cacgcccgag tattgggtcc ggcatgtgcg aagcgccgtg cgcttcggcg acggggcaaa    33180
ggcgttgcat gccgcgggtg ccgccacgtt cgtcgaggtt ggcccgaagc cggtcctgct    33240
cgggctgttg ccagcgtgcc tcggggaagc ggacgcggtc ctcgtgccgt cgctacgcgc    33300
ggaccgctcg gaatgcgagg tggtcctcgc ggcgctcggg gcttggtatg cctgggggg    33360 tgcgctcgac tggaagggcg tgttccccga tggcgcgcgc gcgtggctc tgcccatgta    33420 tccatgcag cgtgagcgcc attggatgga cctcacccccg cgaagcgccg cgcctgcagg    33480
gatcgcaggt cgctggccgc tggctggtgt cgggctctgc atgcccggcg ctgtgttgca    33540
ccacgtgctc tcgatcggac cacgccatca gcccttcctc ggtgatcacc tcgtgttttgg    33600 caaggtggtg gtgcccggcg cctttcatgt cgcggtgatc ctcagcatcg ccgccgagcg    33660
ctggcccgag cgggcgatcg agctgacagg cgtggagttc ctgaaggcca tcgcgatgga    33720
gcccgaccag gaggtcgagc tccacgccgt gctcacccc gaagccgccg gggatggcta    33780
cctgttcgag ctggcgaccc tggcggcgcc ggagaccgaa cgccgatgga cgacccacgc    33840
ccgcggtcgg gtgcagccga cagacggcgc gcccggcgcg ttgccgcgcc tcgaggtgct    33900
ggaggaccgc gcgatccagc ccctcgactt cgccggattc ctcgacaggt tatcggcggt    33960
gcggatcggc tggggtccgc tttggcgatg gctgcaggac gggcgcgtcg gcgacgaggc    34020
ctcgcttgcc accctcgtgc cgacctatcc gaacgcccac gacgtggcgc ccttgcaccc    34080
gatcctgctg gacaacggct ttgcggtgag cctgctgtca acccggagcg agccggagga    34140
cgacgggacg cccccgctgc cgttcgccgt ggaacgggtg cggtggtggc gggcgccggt    34200
tggaagggtg cggtgtggcg gcgtgccgcg gtcgcaggca ttcggtgtct cgagcttcgt    34260
gctggtcgac gaaactggcg aggtggtcgc cgaggtggag ggatttgttt gccgccgggc    34320
gccgcgagag gtgttcctgc ggcaggagtc gggcgcgtcg actgcagcct tgtaccgcct    34380
cgactggccc gaagcgccct tgcccgatgc gcctgcggaa cggatcgagg agagctgggt    34440
cgtggtggca gcacctggct cggagatggc cgcggcgctc gcaacacggc tcaaccgctg    34500
cgtcctcgcc gaacccaaag gcctcgaggc ggccctcgcg ggggtgtctc ccgcaggtgt    34560
gatctgcctc tgggaggctg gagcccacga ggaagctccg gcgcggcgc agcgtgtggc    34620 gaccgagggc ctctcggtgg tgcaggcgct cagggaccgc gcggtgcgcc tgtggtgggt    34680
gaccatgggc gcagtggccg tcgaggccgg tgagcgggtg caggtcgcca cagcgccggt    34740
atggggcctc ggccggacag tgatgcagga gcgcccggag ctcagctgca ctctggtgga    34800
```

-continued

```
tttggagccg gaggccgatg cagcgcgctc agctgacgtt ctgttgcggg agctcggtcg    34860
cgctgacgac gagacacagg tggctttccg ttccggaaag cgccgcgtag cgcggctggt    34920
caaagcgacg accccgaag ggctcctggt ccctgacgca gagtcctatc gactggaggc     34980
tgggcagaag ggcacattgg accagctccg cctcgcgccg gcacagcgcc gggcacctgg    35040
cccgggcgag gtcgagatca aggtaaccgc ctcgggctc aacttccgga ccgtcctcgc     35100
tgtgctggga atgtatccgg gcgacgccgg gccgatgggc ggagattgtg ccggtgtcgc    35160
cacggcggtg ggccaggggg tgcgccacgt cgcggtcggc gatgctgtca tgacgctggg    35220
gacgttgcat cgattcgtca cggtcgacgc gcggctggtg gtccggcagc ctgcagggct    35280
gactcccgcg caggcagcta cggtgccggt cgcgttcctg acggcctggc tcgctctgca    35340
cgacctgggg aatctgcggc gcggcgagcg ggtgctgatc catgctgcgg ccggcggtgt    35400
gggcatggcc gcggtgcaaa tcgcccgatg gataggggcc gaggtgttcg ccacggcgag    35460
cccgtccaag tgggcagcgg ttcaggccat gggcgtgccg cgcacgcaca tcgccagctc    35520
gcggacgctg gagtttgctg agacgttccg gcaggtcacc ggcggccggg gcgtggacgt    35580
ggtgctcaac gcgctggccg gcgagttcgt ggacgcgagc ctgtccctgc tgtcgacggg    35640
cgggcggttc ctcgagatgg gcaagaccga catacgggat cgagccgcgg tcgcggcggc    35700
gcatcccggt gttcgctatc gggtattcga catcctggag ctcgctccgg atcgaactcg    35760
agagatcctc gagcgcgtgg tcgagggctt tgctgcggga catctgcgcg cattgccggt    35820
gcatgcgttc gcgatcacca aggccgaggc agcgtttcgg ttcatggcgc aagcgcggca    35880
tcagggcaag gtcgtgctgc tgccggcgcc ctccgcagcg cccttggcgc cgacgggcac    35940
cgtactgctg accggtgggc tgggagcgtt ggggctccac gtggcccgct ggctcgccca    36000
gcagggcgtg ccgcacatgg tgctcacagg tcggcggggc ctggatacgc cgggcgctgc    36060
caaagccgtc gcggagatcg aagcgctcgg cgctcgggtg acgatcgcgg cgtcggatgt    36120
cgccgatcgg aatgcgctgg aggctgtgct ccaggccatt ccggcggagt ggccgttaca    36180
gggcgtgatc catgcagccg gagcgctcga tgatggtgtg cttgatgagc agaccaccga    36240
ccgcttctcg cgggtgctgg caccgaaggt gactggcgcc tggaatctgc atgagctcac    36300
ggcgggcaac gatctcgctt tcttcgtgct gttctcctcc atgtcggggc tcttgggctc    36360
ggccgggcag tccaactatg cggcggccaa caccttcctc gacgcgctgg ccgcgcatcg    36420
gcgggccgaa ggcctggcgg cgcagagcct cgcgtggggc ccatggtcgg acggaggcat    36480
ggcagcgggg ctcagcgcgg cgctgcaggc gcggctcgct cggcatggga tgggagctct    36540
gtcgccggct cagggcaccg cgctgctcgg gcaggcgctg gctcggccgg aaacgcagct    36600
cggggcgatg tcgctcgacg tgcgtgcggc aagccaagct tcgggagcgg cagtgccgcc    36660
tgtgtggcgc gcgttggtgc gcgcggaggc gcgccatacg gcggctgggg cgcagggggc    36720
attggccgcg cgtcttgggg cgctgcccga ggcgcgtcgc gccgacgagg tgcgcaaggt    36780
cgtgcaggcc gagatcgcgc gcgtgctttc atggagcgcc gcgagcgccg tgcccgtcga    36840
tcggccgctg tcggacttgg gcctcgactc gctcacggcg gtggagctgc gcaacgtgct    36900
cggccagcgc gtgggtgcga cgctgccggc gacgctggca ttcgatcacc cgacggtcga    36960
cgcgctcacg cgctggctgc tcgataaggt cctggccgtg gccgagccga gcgtatcgtc    37020
cgcaaagtcg tcgccgcagg tcgccctcga cgagcccatt gccatcatcg gcatcggctg    37080
ccgtttccca ggcggcgtgg ccgatccgga gtcgttttgg cggctgctcg aagagggcag    37140
```

-continued

```
cgatgccgtc gtcgaggtgc cgcatgagcg atgggacatc gacgcgttct atgatccgga    37200
tccggatgtg cgcggcaaga tgacgacacg ctttggcggc ttcctgtccg atatcgaccg    37260
gttcgatccg gccttcttcg gcatctcgcc gcgcgaagcg acgaccatgg atccgcagca    37320
gcggctgctc ctggagacga gctgggaggc gttcgagcgc gccgggattt tgcccgagcg    37380
gctgatgggc agcgataccg gcgtgttcgt ggggctcttc taccaggagt acgctgcgct    37440
cgccggcggc atcgaggcgt tcgatggcta tctaggcacc ggcaccacgg ccagcgtcgc    37500
ctcgggcagg atctcttatg tgctcgggct aaaggggccg agcctgacgg tggacaccgc    37560
gtgctcctcg tcgctggtcg cggtgcacct ggcctgccag gcgctgcggc ggggcgagtg    37620
ttcggtggcg ctgccggcg gcgtggcgct gatgctcacg ccggcgacgt tcgtggagtt    37680
cagccggctg cgaggcctgg ctcccgacgg acggtgcaag agcttctcgg ccgcagccga    37740
cggcgtgggg tggagcgaag gctgcgccat gctcctgctc aaaccgcttc gcatgcgca    37800 gcgcgatggg gatccgatcc tggcggtgat ccgcggcacc gcggtgaacc aggatgggcg    37860
cagcaacggg ctgacggcgc ccaacgggtc gtcgcagcaa gaggtgatcc gtcgggccct    37920
ggagcaggcg gggctggctc cggcggacgt cagctacgtc gagtgccacg gcaccggcac    37980
gacgttgggc gacccatcg aagtgcaggc cctgggcgcc gtgctggcac aggggcgacc    38040
ctcggaccgg ccgctcgtga tcgggtcggt gaagtccaat atcggacata cgcaggctgc    38100
ggcgggcgtg gccggtgtca tcaaggtggc gctggcgctc gagcgcgggc ttatcccgag    38160
gagcctgcat ttcgacgcgc ccaatccgca cattccgtgg tcggagctcg ccgtgcaggt    38220
ggccgccaaa cccgtcgaat ggacgagaaa cggcgtgccg cgacgagccg gggtgagctc    38280
gtttggcgtc agcgggacca acgcgcacgt ggtgctggag gaggcgccag cggcggcgtt    38340
cgcgcccgcg gcggcgcgtt cagcggagct tttcgtgctg tcggcgaaga gcgccgcggc    38400
gctggacgcg caggcggcgc ggcttcggc gcacgtcgtt gcgcacccgg agctcggcct    38460
cggcgacctg gcgttcagcc tggcgacgac ccgcagcccg atgacgtacc ggctcgcggt    38520
ggcggcgacc tcgcgcgagg cgctgtctgc cgcgctcgac acagcggcgc aggggcaggc    38580
gccgcccgca gcggctcgcg gccacgcttc cacaggcagc gccccaaagg tggtttttcgt    38640 ctttcctggc cagggctccc agtggctggg catgggccaa aagctcctct cggaggagcc    38700
cgtcttccgc gacgcgctct cggcgtgtga ccgagcgatt caggccgaag ccggctggtc    38760
gctgctcgcc gagctcgcgg ccgatgagac cacctcgcag ctcggccgca tcgacgtggt    38820
gcagccggcg ctgttcgcga tcgaggtcgc gctgtcggcg ctgtggcggt cgtggggcgt    38880
cgagccggat gcagtggtag gccacagcat gggcgaagtg gcggccgcgc acgtcgccgg    38940
cgccctgtcg ctcgaggatg ctgtagcgat catctgccgg cgcagcctgc tgctgcggcg    39000
gatcagcggc caaggcgaga tggcggtcgt cgagctttcc ctggccgagg ccgaggcagc    39060
gctcctgggc tacgaagacc ggctcagcgt ggcggtgagc aacagcccgc gctcgacggt    39120
gctggcgggc gagccggcag cgctcgcaga ggtgctggcg atccttgcgg caaaggggt    39180 gttctgccgt cgagtcaagg tggacgtcgc cagccacagc ccacagatcg acccgctgcg    39240
cgacgagcta ttggcagcat tgggcgagct cgagccgcga caagcgaccg tgtcgatgcg    39300
ctcgacggtg acgagcacga tcatggcggg cccggagctc gtggcgagct actgggcgga    39360
caacgttcga cagccggtgc gcttcgccga agcggtgcaa tcgttgatgg aagacggtca    39420
tgggctgttc gtggagatga gccccgcatcc gatcctgacg acatcggtcg aggagatccg    39480
acgggcgacg aagcgggagg gagtcgcggt gggctcgttg cggcgtggac aggacgagcg    39540
```

```
cctgtccatg ttggaggcgc tgggagcgct ctgggtacac ggccaggcgg tgggctggga   39600
gcggctgttc tccgcgggcg gcgcgggcct ccgtcgcgtg ccgctgccga cctatccctg   39660
gcagcgcgag cggtactggg tcgatgcgcc gaccggcggc gcggcgggcg gcagccgctt   39720
tgctcatgcg ggcagtcacc cgctcctggg tgaaatgcag accctgtcga cccagaggag   39780
cacgcgcgtg tgggagacga cgctggatct caaacgctg ccgtggctcg gcgatcaccg    39840
ggtgcagggg gcggtcgtgt tcccgggcgc ggcgtacctg gagatggcgc tttcgtccgg   39900
ggccgaggcc ttgggtgacg gtccgctcca ggtcagcgat gtggtgctcg ccgaggcgct   39960
ggccttcgcg gatgatacgc cggcggcggt gcaggtcatg gcgaccgagg agcgaccagg   40020
ccgcctgcaa ttccacgttg cgagccgggt gccgggccac ggcggtgctg cctttcgaag   40080
ccatgcccgc ggggtgctgc gccagatcga gcgcgccgag gtcccggcga ggctggatct   40140
ggccgcgctt cgtgcccggc ttcaggccag cgcacccgct gcggctacct atgcggcgct   40200
ggccgagatg gggctcgagt acggcccagc gttccagggg cttgtcgagc tgtggcgggg   40260
ggagggcgag gcgctgggac gtgtgcggct cccccgaggcc gccggctccc cagccgcgtg   40320
ccggctccac cccgcgctct tggatgcgtg cttccacgtg agcagcgcct tcgctgaccg   40380
cggcgaggcg acgccatggg tacccgtgga aatcggctcg ctgcggtggt tccagcggcc   40440
gtcgggggag ctgtggtgtc atgcgcggag tgtgagccac ggaaagccaa cacccgaccg   40500
gcggagtacc gacttctggg tggtcgacag cacgggcgcg atcgtcgccg agatctccgg   40560
gctcgtggcg cagcggctcg cgggaggtgt acgccggcgc gaagaagacg actggttcat   40620
ggagccggct tgggaaccga ccgcggtccc cggatccgag gtcatggcgg gccggtggct   40680
gctcatcggc tcgggcggcg ggctcggcgc tgcgctccac tcggcgctga cggaagctgg   40740
ccattccgtc gtccacgcga cagggcgcgg cacgagcgcc gccgggttgc aggcactctt   40800
gacggcgtcc ttcgacggcc aggccccgac gtcggtggtg cacctcggca gcctcgatga   40860
gcgtggcgtg ctcgacgcgg atgccccctt cgacgccgat gcgcttgagg agtcgctggt   40920
gcgcggctgc gacagcgtgc tctggaccgt gcaggccgtg gccggggcgg gcttccgaga   40980
tcctccgcgg ttgtggctcg tgacacgcgg cgctcaggcc atcggcgccg gcgacgtctc   41040
tgtggcgcaa gcgccgctcc tggggctggg ccgcgttatc gccttggagc acgccgagct   41100
gcgctgcgct cggatcgacc tcgatccagc gcggcgcgac ggagaagtcg atgagctgct   41160
tgccgagctg ttggccgacg acgccgagga ggaagtcgcg tttcgcggcg gtgagcggcg   41220
cgtggcccgg ctcgtccgaa ggctgcccga gaccgactgc cgagagaaaa tcgaccccgc   41280
ggaaggccgg ccgttccggc tggagatcga tgggtccggc gtgctcgacg acctggtgct   41340
ccgagccacg gagcggcgcc ctcctggccc gggcgaggtc gagatcgccg tcgaggcggc   41400
ggggctcaac tttctcgacg tgatgagggc catgggatc tacccctgggc ccggggacgg   41460 tccggttgcg ctgggcgccg agtgctccgg ccgaattgtc gcgatgggcg aaggtgtcga   41520
gagccttcgt atcggccagg acgtcgtggc cgtcgcgccc ttcagtttcg gcacccacgt   41580
caccatcgac gcccggatgc tcgcacctcg ccccgcggcg ctgacggccg cgcaggcagc   41640
cgcgctgccc gtcgcattca tgacggcctg gtacggtctc gtccatctgg ggaggctccg   41700
ggccggcgag cgcgtgctca tccactcggc gacggggggc accgggctcg ctgctgtgca   41760
gatcgcccgc cacctcggcg cggagatatt tgcgaccgct ggtacaccgg agaagcgggc   41820
gtggctgcgc gagcagggga tcgcgcacgt gatggactcg cggtcgctgg acttcgccga   41880
```

-continued

```
gcaagtgctg gccgcgacga agggcgaggg ggtcgacgtc gtgttgaact cgctgtctgg    41940
cgccgcgatc gacgcgagcc tttcgaccct cgtgccggac ggccgcttca tcgagctcgg    42000
caagacggac atctatgcag atcgctcgct ggggctcgct cacttcagga agagcctgtc    42060
ctacagcgcc gtcgatcttg cgggcttggc cgtgcgtcgg cccgagcgcg tcgcagcgct    42120
gctggcggag gtggtggacc tgctcgcacg gggagcgctg cagccgcttc cggtagagat    42180
cttccccctc tcgcgggccg cggacgcgtt ccggaaaatg gcgcaagcgc agcatctcgg    42240
gaagctcgtg ctcgcgctgg aggacccgga cgtgcggatc cgcgttccgg gcgaatccgg    42300
cgtcgccatc cgcgcggacg gcgcctacct cgtgaccggc ggtctggggg ggctcggtct    42360
gagcgtggct ggatggctgg ccgagcaggg ggctgggcat ctggtgctgg tgggccgctc    42420
cggcgcggtg agcgcggagc agcagacggc tgtcgccgcg ctcgaggcgc acggcgcgcg    42480
tgtcacggta gcgagggcag acgtcgccga tcgggcgcag atggagcgga tcctccgcga    42540
ggttaccgcg tcgggatgc cgctccgcgg cgtcgttcat gcggccggaa tcctggacga    42600
cgggctgctg atgcagcaaa ccccgcgcg gttccgcgcg gtcatggcgc ccaaggtccg    42660 agggggccttg cacctgcatg cgttgacacg cgaagcgccg ctctccttct tcgtgctgta    42720
cgcttcggga gcagggctct tgggctcgcc gggccagggc aactacgccg cggccaacac    42780
gttcctcgac gcactggcac accaccggag ggcgcagggg ctgccagcat tgagcatcga    42840
ctggggcctg ttcgcggacg tgggtttggc cgccgggcag caaaatcgcg gcgcacggct    42900
ggtcaccccg gggacgcgga gcctcacccc cgacgaaggg ctgtgggcgc tcgagcgcct    42960
gctcgacggc gatcgcaccc aggccggggt catgccgttc gacgtgcggc agtgggtgga    43020
gttctacccg gcgcggcat cttcgcggag gttgtcgcgg ctcatgacgg cacggcgcgt    43080
ggcttccggt cggctcgccg gggatcggga cctgctcgaa cggctcgcca ccgccgaggc    43140
gggcgcgcgg gcagggatgc tgcaggaggt cgtgcgcgcg caggtctcgc aggtgctgcg    43200
cctctccgaa ggcaagctcg acgtggatgc gccgctcacg agcctgggaa tggactcgct    43260 gatgggcta gagctgcgca accgcatcga ggccgtgctc ggcatcacca tgccggcgac    43320
cctgctgtgg acctaccccca cggtggcagc gctgagtgcg catctggctt tcatgtcgt    43380 ctctacgggg gatggggaat ccgcgcgccc gccggataca gggagcgtgg ctccaacgac    43440
ccacgaagtc gcttcgctcg acgaagacgg gttgttcgcg ttgattgatg agtcactcgc    43500
gcgcgcggga aagaggtgat tgcgtgacag accgagaagg ccagctcctg gagcgcttgc    43560
gtgaggttac tctggcccctt cgcaagacgc tgaacgagcg cgatacctg gagctcgaga    43620 agaccgagcc gatcgccatc gtggggatcg gctgccgctt ccccggcgga gcgggcactc    43680
cggaggcgtt ctgggagctg ctcgacgacg ggcgcgacgc gatccggccg ctcgaggagc    43740
gctgggcgct cgtaggtgtc gacccaggcg acgacgtacc cgctgggcg gggctgctca    43800 ccgaggccat cgacggcttc gacgccgcgt tcttcggtat cgccccccgg gaggcacggt    43860
cgctcgaccc gcagcatcgc ctgctgctgg aggtcgcctg ggaggggttc gaagacgccg    43920
gcatcccgcc caggtccctc gtcgggagcc gcaccggcgt gttcgtcggc gtctgcgcca    43980
cggagtacct ccacgccgcc gtcgcgcacc agccgcgcga agagcgggac gcgtacagca    44040
ccaccggcaa catgctcagc atcgccgccg gacggctatc gtacacgctg gggctgcagg    44100
gaccttgcct gaccgtcgat acggcgtgct cgtcatcgct ggtggccatt cacctcgcct    44160
gccgcagcct gcgcgctcga gagagcgatc tcgcgctggg gggagggtc aacatgcttc    44220 tctccccga cacgatgcga gctctggcgc gcacccaggc gctgtcgccc aatggccgtt    44280
```

```
gccagacctt cgacgcgtcg gccaacgggt tcgtccgtgg ggagggctgc ggtctgatcg   44340
tgctcaagcg attgagcgac gcgcggcggg atggggaccg gatctgggcg ctgatccgag   44400
gatcggccat caatcaggac ggccggtcga cggggttgac ggcgcccaac gtgctcgccc   44460 aggggggcgct cttgcgcgag gcgctgcgga acgccggcgt cgaggccgag gccatcggtt   44520
acatcgagac ccacggggcg gcaacctcgc tgggcgaccc catcgagatc gaagcgctgc   44580
gcgctgtggt ggggccggcg cgagccgacg gagcgcgctg cgtgctgggc gcggtgaaga   44640
ccaacctcgg ccacctggag ggcgctgccg gcgtggcggg cctgatcaag gcgacgcttt   44700
cgctacatca cgagcgcatc ccgaggaacc tcaactttcg tacgctcaat ccgcggatcc   44760
ggatcgaggg gaccgcgctc gcgttggcga ccgaaccggt gccctggccg cggacgggcc   44820
ggacgcgctt cgcgggagtg agctcgttcg ggatgagcgg gaccaacgcg catgtggtgt   44880
tggaggaggc gccggcggtg gagcctgagg ccgcggcccc cgagcgcgca gcggagctgt   44940
tcgtcctgtc ggcgaagagc gcggcggcgc tggatgcgca ggcagcccgg ctgcgggacc   45000
acctggagaa gcacgtcgag cttggcctcg gcgatgtggc gttcagcctg gcgacgacgc   45060
gcagcgcgat ggagcaccgg ctggcggtgg ccgcgagctc gcgcgaggcg ctgcgagggg   45120
cgctttcggc cgcagcgcag gggcacacgc cgccgggagc cgtgcgtggg cgggcctcgg   45180
gcggcagcgc gccgaaggtg gtcttcgtgt ttcccggtca gggctcgcag tgggtgggca   45240
tgggccgaaa gctcatggcc gaagagccgg tcttccgggc ggcgctggag ggttgcgacc   45300
gggccatcga ggcggaagcg ggctggtcgc tgctcgggga gctctccgcc gacgaggccg   45360
cctcgcagct cgggcgcatc gacgtggttc agccggtgct cttcgccatg gaagtagcgc   45420
tttctgcgct gtggcggtcg tggggagtgg agccggaagc ggtggtgggc cacagcatgg   45480
gcgaggttgc ggcggcgcac gtggccggcg cgctgtcgct cgaggacgcg gtggcgatca   45540
tctgccggcg cagccggctg ctgcggcgga tcagcggtca gggggagatg cgcctggtcg   45600
agctgtcgct ggaggaggcc gaggcggcgc tgcgtggcca tgagggtcgg ctgagcgtgg   45660
cggtgagcaa cagcccgcgc tcgaccgtgc tcgccggcga gccggcggcg ctctcggagg   45720
tgctggcggc gctgacggcc aaggggggtgt tctggcggca ggtgaaggtg gacgtcgcca   45780
gccatagccc gcaggtcgac ccgctgcgcg aagagctgat cgccggcgctg ggagcgatcc   45840 ggccgcgagc ggctgcggtg ccgatgcgct cgacggtgac gggcggggtg atcgcgggtc   45900
cggagctcgg tgcgagctac tgggcggaca accttcggca gccggtgcgc ttcgctgcgg   45960
cggcgcaagc gctgctggag ggtggccccg cgctgttcat cgagatgagc ccgcacccga   46020
tcctggtgcc gcccctggac gagatccaga cggcggccga gcaaggggc gctgcggtgg   46080 gctcgctgcg gcgagggcag gacgagcgcg cgacgctgct ggaggcgctg gggacgctgt   46140
gggcgtccgg ctatccggtg agctgggctc ggctgttccc cgcgggcggc aggcgggttc   46200
cgctgccgac ctatccctgg cagcacgagc ggtgctggat cgaggtcgag cctgacgccc   46260
gccgcctcgc cgcagccgac cccaccaagg actggttcta ccgaacggac tggcccgagg   46320
tgccccgcgc cgccccgaaa tcggagacag ctcatgggag ctggctgctg ttggccgaca   46380
ggggtggggt cggtgaggcg gtcgctgcag cgctgtcgac gcgcggactt tcctgcaccg   46440
tgcttcatgc gtcggctgac gcctccaccg tcgccgagca ggtatccgaa gctgccagtc   46500
gccgaaacga ctggcaggga gtcctctacc tgtgggggcct cgacgccgtc gtcgatgctg   46560
gggcatcggc cgacgaagtc agcgaggcta cccgccgtgc caccgcaccc gtccttgggc   46620
```

```
tggttcgatt cctgagcgct gcgccccatc ctcctcgctt ctgggtggtg acccgcgggg   46680
catgcacggt gggcggcgag ccagaggcct ctctttgcca agcggcgttg tggggcctcg   46740
cgcgcgtcgc ggcgctggag cacccgctg cctggggtgg cctcgtggac ctggatcctc    46800
agaagagccc gacggagatc gagcccctgg tggccgagct gctttcgccg gacgccgagg   46860
atcaactggc gttccgcagc ggtcgcaggc acgcagcacg ccttgtagcc gccccgccgg   46920
agggcgacgt cgcaccgata tcgctgtccg cggaggggag ctacctggtg acgggcgggc   46980
tgggtggcct tggtctgctc gtggctcggt ggctggtgga gcggggagct cgacatctgg   47040
tgctcaccag ccggcacggg ctgccagagc gacaggcgtc gggcggagag cagccgccgg   47100
aggcccgcgc gcgcatcgca gcggtcgagg ggctggaagc gcagggcgcg cgggtgaccg   47160
tggcagcggt ggatgtcgcc gaggccgatc ccatgacggc gctgctggcc gccatcgagc   47220
ccccgttgcg cggggtggtg cacgccgccg gcgtcttccc cgtgcgtcac ctggcggaga   47280
cggacgaggc cctgctggag tcggtgctcc gtcccaaggt ggccgggagc tggctgctgc   47340
accggctgct gcgcgaccgg cctctcgacc tgttcgtgct gttctcgtcg ggcgcggcgg   47400
tgtggggtgg caaaggccaa ggcgcatacg ccgcggccaa tgcgttcctc gacgggctcg   47460
cgcaccatcg ccgcgcgcac tcgctgccgg cgttgagcct cgcctgggc ttatgggccg    47520 agggaggcat ggttgatgca aaggctcatg cacgtctgag cgacatcggg gtcctgccca   47580
tggccacggg gccggccttg tcggcgctgg agcgcctggt gaacaccagc gctgtccagc   47640
gttcggtcac acgatggac tgggcgcgct tcgcgccgt ctatgccgcg cgagggcggc     47700
gcaacttgct ttcggctctg gtcgcggagg acgagcgcgc tgcgtctccc ccggtgccga   47760
cggcaaaccg gatctggcgc ggcctgtccg ttgcggagac ccgctcagcc ctctacgagc   47820
tcgttcgcgg catcgtcgcc cgggtgctgg gcttctccga cccgggcgcg ctcgacgtcg   47880
gccgaggctt cgccgagcag gggctcgact ccctgatggc tctggagatc cgtaaccgcc   47940
ttcagcgcga gctgggcgaa cggctgtcgg cgactctggc cttcgaccac ccgacggtgg   48000
agcggctggt ggcgcatctc ctcaccgacg tgctgaagct ggaggaccgg agcgacaccc   48060
ggcacatccg gtcggtggcg gcggatgacg acatcgccat cgtcggtgcc gcctgccggt   48120
tcccaggtgg ggatgagggc ctggagacat actggcggca tctggccgag gcatggtgg    48180 tcagcaccga ggtgccagcc gaccggtggc gcgcggcgga ctggtacgac cccgatccgg   48240
aggttccggg ccgacctat gtggccaagg gtgccttcct ccgcgatgtg cgcagcttgg    48300
atgcggcgtt cttcgccatt tcccctcgtg aggcgatgag cctggacccg caacagcggc   48360
tgttgctgga ggtgagctgg gaggcgatcg agcgcgctgg ccaggacccg atggcgctgc   48420
gcgagagcgc cacgggcgtg ttcgtgggca tgatcgggag cgagcacgcc gagcgggtgc   48480
agggcctcga cgacgacgcg gcgttgctgt acggcaccac cggcaacctg ctcagcgtcg   48540
ccgctggacg gctgtcgttc ttcctgggtc tgcacggccc gacgatgacg gtggacaccg   48600
cctgctcgtc gtcgctggtg gcgttgcacc tcgcctgcca gagcctgcga ttgggcgagt   48660
gcgaccaggc cctggccggc gggtccagcg tgcttttgtc gccgcggtca ttcgtcgcgg   48720
cgtcgcgcat gcgtttgctt tcgccagatg ggcggtgcaa gacgttctcg gccgctgcag   48780
acggctttgc gcgggccgag ggctgcgccg tggtggtgct caagcggctc cgtgacgcgc   48840
agcgcgaccg cgaccccatc ctggcggtgg tcaggagcac ggcgatcaac cacgatggcc   48900
cgagcagcgg gctcacggtg cccagcggtc ctgcccagca ggcgttgcta cgccaggcgc   48960
tggcgcaagc gggcgtggcg ccggccgagg tcgatttcgt ggagtgccac gggacgggga   49020
```

```
cagcgctggg tgacccgatc gaggtgcagg cgctgggcgc ggtgtacggg cggggccgcc   49080
ccgcggagcg gccgctctgg ctgggcgctg tcaaggccaa cctcggccac ctggaggccg   49140
cggcgggctt ggccggcgtg ctcaaggtgc tcttggcgct ggagcacgag cagattccgg   49200
ctcaaccgga gctcgacgag ctcaacccgc acatcccgtg gcagagctg ccagtggccg    49260
ttgtccgcag ggcggtcccc tggccgcgcg gcgcgcgccc gcgtcgtgca ggcgtgagcg   49320
ctttcggcct gagcgggacc aacgcgcatg tggtgttgga ggaggcgccg gcggtggagc   49380
ctgtggccgc ggccccgag cgcgcagcgg agctgttcgt cctgtcggcg aagagcgcgg    49440
cggcgctgga tgcgcaggca gcccggctgc gggaccacct ggagaagcat gtcgagcttg   49500
gcctcggcga tgtggcgttc agcctggcga cgacgcgcag cgcgatggag caccggctgg   49560
cggtggccgc gagctcgcgc gaggcgctgc gagggcgct tcggccgca gcgcagggc     49620
acacgccgcc gggagccgtg cgtgggcggg cctcggcgg cagcgcgccg aaggtggtct    49680
tcgtgtttcc cggccagggc tcgcagtggg tgggcatggg ccgaaagctc atggccgaag   49740
agccggtctt ccgggcggcg ctggagggtt gcgaccgggc catcgaggcg gaagcgggct   49800
ggtcgctgct cggggagctc tccgccgacg aggccgcctc gcagctcggg cgcatcgacg   49860
tggttcagcc ggtgctgttc gccatggaag tagcgctttc tgcgctgtgg cggtcgtggg   49920
gagtggagcc ggaagcggtg gtgggccaca gcatgggcga ggttgcggcg gcgcacgtgg   49980
ccggcgcgcg tcgctcgag gacgcggtgg cgatcatctg ccggcgcagc cggctgctgc    50040
ggcggatcag cggtcagggg gagatggcgc tggtcgagct gtcgctggag gaggccgagg   50100
cggcgctgcg tggccatgag ggtcggctga gcgtggcggt gagcaacagc ccgcgctcga   50160
ccgtgctcgc cggcgagccg gcggcgctct cggaggtgct ggcggcgctg acggccaagg   50220
gggtgttctg gcggcaggtg aaggtggacg tcgccagcca tagcccgcag gtcgacccgc   50280
tgcgcgaaga gctgatcgcg gcgctgggag cgatccggcc gcgagcggct gcggtgccga   50340
tgcgctcgac ggtgacgggc ggggtgatcg cgggtccgga gctcggtgcg agctactggg   50400
cggacaacct tcggcagccg gtgcgcttcg ctgcggcggc gcaagcgctg ctggagggtg   50460
gccccgcgct gttcatcgag atgagcccgc acccgatcct ggtgccgccc ctggacgaga   50520
tccagacggc ggccgagcaa gggggcgctg cggtgggctc gctgcggcga gggcaggacg   50580
agcgcgcgac gctgctggag cgctgggga cgctgtgggc gtccggctat ccggtgagct    50640
gggctcggct gttccccgcg ggcggcaggc gggttccgct gccgacctat ccctggcagc   50700
acgagcggta ctggatcgag gacagcgtgc atgggtcgaa gccctcgctg cggcttcggc   50760
agcttcgcaa cggcgccacg gaccatccgc tgctcggggc tccattgctc gtctcggcgc   50820
gacccggagc tcacttgtgg gagcaagcgc tgagcgacga gaggctatcc taccttcgg   50880
aacatagggt ccatggcgaa gccgtgttgc ccagcgcggc gtatgtagag atggcgctcg   50940
ccgccggcgt agatctctat ggcacggcga cgctggtgct ggagcagctg cgctcgagc    51000
gagccctcgc cgtgccctcc gaaggcggac gcatcgtgca agtggccctc agcgaagaag   51060
gtcccggtcg ggcctcattc caggtatcga gtcgtgagga ggcaggtagg agctgggtgc   51120
ggcacgccac ggggcacgtg tgtagcgcc agagctcagc ggtgggagcg ttgaaggaag    51180
ctccgtggga gattcaacgg cgatgtccga gcgtcctgtc gtcggaggcg ctctatccgc   51240
tgctcaacga gcacgccctc gactatggtc cctgcttcca gggcgtggag caggtgtggc   51300
tcggcacggg ggaggtgctc ggccgggtac gcttgccagg agacatggca tcctcaagtg   51360
```

```
gcgcctaccg gattcatccc gccttgttgg atgcatgttt tcaggtgctg acagcgctgc    51420
tcaccacgcc ggaatccatc gagattcgga ggcggctgac ggatctccac gaaccggatc    51480
tcccgcggtc cagggctccg gtgaatcaag cgtgagtga cacctggctg tgggacgccg    51540
cgctggacgg tggacggcgc cagagcgcga gcgtgcccgt cgacctggtg ctcggcagct    51600
tccatgcgaa gtgggaggtc atggagcgcc tcgcgcaggc gtacatcatc ggcactctcc    51660
gcatatggaa cgtcttctgc gctgctggag agcgtcacac gatagacgag ttgctcgtca    51720
ggcttcaaat ctctgtcgtc tacaggaagg tcatcaagcg atggatggaa caccttgtcg    51780
cgatcggcat ccttgtaggg gacggagagc attttgtgag ctctcagccg ctgccggagc    51840
ctgatttggc ggcggtgctc gaggaggccg ggagggtgtt cgccgacctc ccagtcctat    51900
ttgagtggtg caagtttgcc ggggaacggc tcgcggacgt attgaccggt aagacgctcg    51960
cgctcgagat cctcttccct ggtggctcgt tcgatatggc ggagcgaatc tatcgagatt    52020
cgcccatcgc ccgttactcg aacggcatcg tgcgcggtgt cgtcgagtcg gcggcgcggg    52080
tggtagcacc gtcgggaatg ttcagcatct tggagatcgg agcagggacg ggcgcgacca    52140
ccgccgccgt cctcccggtg ttgctgcctg accggacgga gtaccatttc accgatgttt    52200
ctccgctctt ccttgctcgc gcggagcaaa gatttcgaga ttatccattc ctgaagtatg    52260
gcattctgga tgtcgaccag gagccagctg gccaggata cgcacatcag aggtttgacg    52320
tcatcgtcgc ggccaatgtc atccatgcga cccgcgatat aagagccacg gcgaagcgtc    52380
tcctgtcgtt gctcgcgccc ggaggccttc tggtgctggt cgagggcaca gggcatccga    52440
tctggttcga tatcaccacg ggattgattg aggggtggca gaagtacgaa gatgatcttc    52500
gtatcgacca tccgctcctg cctgctcgga cctggtgtga cgtcctgcgc cgggtaggct    52560
ttgcggacgc cgtgagtctg ccaggcgacg gatctccggc ggggatcctc ggacagcacg    52620
tgatcctctc gcgcgcgccg ggcatagcag gagccgcttg tgacagctcc ggtgagtcgg    52680
cgaccgaatc gccggccgcg cgtgcagtac ggcaggaatg ggccgatggc tccgctgacg    52740
tcgtccatcg gatggcgttg gagaggatgt acttccaccg ccggccgggc cggcaggttt    52800
gggtccacgg tcgattgcgt accggtggag gcgcgttcac gaaggcgctc gctggagatc    52860
tgctcctgtt cgaagacacc gggcaggtcg tggcagaggt tcagggctc cgcctgccgc    52920 agctcgaggc ttctgctttc gcgccgcggg acccgcggga agagtggttg tacgctttgg    52980
aatggcagcg caaagaccct ataccagagg ctccggcagc cgcgtcttct tcctccgcgg    53040
gggcttggct cgtgctgatg gaccagggcg ggacaggcgc tgcgctcgta tcgctgctgg    53100
aagggcgagg cgaggcgtgc gtgcgcgtca tcgcgggtac ggcatacgcc tgcctcgcgc    53160
cggggctgta tcaagtcgat ccggcgcagc cagatggctt tcatacccctg ctccgcgatg    53220 cattcggcga ggaccggatt tgtcgcgcgg tagtgcatat gtggagcctt gatgcgacgg    53280
cagcagggga gagggcgaca cgggagtcgc ttcaggccga tcaactcctg gggagcctga    53340
gcgcgctttc tctggtgcag gcgctggtgc gccggaggtg gcgcaacatg ccgcggcttt    53400
ggctcttgac ccgcgccgtg catgcggtgg gcgcggagga cgcagcggcc tcggtggcgc    53460
aggcgccggt gtgggcctc ggtcggacgc tcgcgctcga gcatccagag ctgcggtgca    53520
cgctcgtgga cgtgaacccg gcgccgtctc cagaggacgc agccgcactg gcggtggagc    53580
tcggggcgag cgacagagag gaccaggtcg cattgcgctc ggatggccgc tacgtggcgc    53640
gcctcgtgcg gagctccttt tccggcaagc ctgctacgga ttgcggcatc cggcggacg    53700 gcagctatgt gatcaccgat ggcatgggga gagtgggggct ctcggtcgcg caatggatgg    53760
```

```
tgatgcaggg ggcccgccat gtggtgctcg tggatcgcgg cggcgcttcc gaggcatccc   53820
gggatgccct ccggtccatg gccgaggctg gcgcggaggt gcagatcgtg gaggccgacg   53880
tggctcggcg cgacgatgtc gctcggctcc tctcgaagat cgaaccgtcg atgccgccgc   53940
ttcgggggat cgtgtacgtg gacgggacct ccagggcga ctcctcgatg ctggagctgg   54000
atgcccgtcg cttcaaggag tggatgtatc ccaaggtgct cggagcgtgg aacctgcacg   54060
cgctgaccag ggatagatcg ctggacttct tcgtcctgta ttcctcgggc acctcgcttc   54120
tgggcttgcc aggacagggg agccgcgccg ccggtgacgc cttcttggac gccatcgcgc   54180
atcaccggtg caaggtgggc cttacagcga tgagcatcaa ctggggattg ctctccgaag   54240
catcatcgcc ggcgaccccg aacgacgcg gagcacggct cgaataccgg gggatggaag   54300
gcctcacgct ggagcaggga cggcggcgc tcgggcgctt gctcgcacga cccagggcgc   54360
aggtaggggt gatgcggctg aatctgcgcc agtggttgga gttctatccc aacgcggccc   54420
gattggcgct gtgggcggag ctgctgaagg agcgtgaccg cgccgaccga ggcgcgtcga   54480
acgcgtcgaa cctgcgcgag gcgctgcaga gcgccaggcc cgaagatcgt cagttgattc   54540
tggagaagca cttgagcgag ctgttgggc gggggctgcg ccttccgccg gagaggatcg   54600
agcggcacgt gccgttcagc aatctcggca tggactcgct gataggcctg gagctccgca   54660
accgcatcga ggccgcgctc ggcatcaccg tgccggcgac cctgctatgg acctacccta   54720
acgtagcagc tctgagcggg agcttgctag acattctgtt tccgaatgcc ggcgcgaccc   54780
acgctccggc caccgagcgg gagaagagct tcgagaacga tgccgcagat ctcgaggctc   54840
tgcggggcat gacggacgag cagaaggacg cgttgctcgc cgaaaagctg gcgcagctcg   54900
cgcagatcgt tggtgagtaa gggaccgagg gagtatggcg accacgaatg ccgggaagct   54960
tgagcatgcc cttctgctca tggacaagct tgcgaaaaag aacgcgtctt tggagcaaga   55020
gcggaccgag ccgatcgcca tcgtaggcat tggctgccgc ttccccggcg gagcggacac   55080
tccggaggca ttctgggagc tgctcgactc aggccgagac gcggtccagc cgctcgaccg   55140
gcgctgggcg ctggtcggcg tccatcccag cgaggaggtg ccgcgctggg ccggactgct   55200
caccgaggcg gtggacggct tcgacgccgc gttcttggc acctcgcctc gggaggcgcg   55260
gtcgctcgat cctcagcaac gcctgctgct ggaggtcacc tgggaagggc tcgaggacgc   55320
cggcatcgca ccccagtccc tcgacggcag ccgcaccggg gtgttcctgg gcgcatgcag   55380
cagcgactac tcgcataccg ttgcgcaaca gcggcgcgag gagcaggacg catacgacat   55440
caccggcaat acgctcagcg tcgccgccgg acggttgtct tatacgctag gctgcaggg   55500 accctgcctg accgtcgaca cggcctgctc gtcgtcgctc gtggccatcc accttgcctg   55560
ccgcagcctg cgcgctcgcg agagcgatct cgcgctggcg ggaggcgtca acatgctcct   55620
ttcgtccaag acgatgataa tgctggggcg catccaggcg ctgtcgcccg atggccactg   55680
ccggacattc gacgcctcgg ccaacggggtt cgtccgtggg gagggctgcg gtatggtcgt   55740
gctcaaacgg ctctccgacg cccagcgaca cggcgatccg atctgggctc tgatccgggg   55800
ttcggccatg aatcaggatg gccggtcgac agggttgatg gcacccaatg tgctcgctca   55860
ggaggcgctc ttgcgcgagg cgctgcagag cgctcgcgtc gacgccgggg ccatcggtta   55920
tgtcgagacc cacggaacgg ggacctcgct cggcgacccg atcgaggtcg aggcgctgcg   55980
tgccgtgttg gggccggcgc gggccgatgg gagccgctgc gtgctgggcg cagtgaagac   56040
aaacctcggc cacctggagg gcgctgcagg cgtggcgggt ttgatcaagg cggcgctggc   56100
```

```
tctgcaccac gaactgatcc cgcgaaacct ccatttccac acgctcaatc cgcggatccg    56160
gatcgagggg accgcgctcg cgctggcgac ggagccggtg ccgtggccgc gggcgggccg    56220
accgcgcttc gcggggtga gcgcgttcgg cctcagcggc accaacgtcc atgtcgtgct    56280
ggaggaggcg ccggccacgg tgctcgcacc ggcgacgccg gggcgctcag cggagctttt    56340
ggtgctgtcg gcgaagagcg ccgccgcgct ggacgcacag gcggcgcggc tctcagcgca    56400
catcgccgcg tacccggagc agggtctcgg agacgtcgcg ttcagcctgg tatcgacgcg    56460
tagcccgatg gagcaccggc tcgcggtggc ggcgaccctcg cgcgaggcgc tgcgaagcgc    56520
gctggaggtt gcggcgcagg ggcagacccc ggcaggcgcg gcgcgcggca gggccgcttc    56580
ctcgcccggc aagctcgcct tcctgttcgc cgggcagggc gcgcaggtgc cgggcatggg    56640
ccgtgggttg tgggaggcgt ggccggcgtt ccgcgagacc ttcgaccggt gcgtcacgct    56700
cttcgaccgg gagctccatc agccgctctg cgaggtgatg tgggccgagc cgggcagcag    56760
caggtcgtcg ttgctggacc agacggcgtt cacccagccg gcgctctttg cgctggagta    56820
cgcgctggcc gcgctcttcc ggtcgtgggg cgtggaccg gagctcgtcg ctggccatag    56880
cctcggcgag ctggtggccg cctgcgtggc gggtgtgttc tccctcgagg acgccgtgcg    56940
cttggtggtc gcgcgcggcc ggttgatgca ggcgctgccg gccggcggcg cgatggtatc    57000
gatcgccgcg ccggaggccg acgtggctgc cgcggtggcc ccgcacgcag cgttggtgtc    57060
gatcgcggca gtcaatgggc cggagcaggt ggtgatcgcg ggcgccgaga aattcgtgca    57120
gcagatcgcg gcggcgttcg cggcgcgggg ggcgcgaacc aaaccgctgc atgtctcgca    57180
cgcgttccac tcgccgctca tggatccgat gctggaggcg ttccggcggg tgactgagtc    57240
ggtgacgtac cggcggcctt cgatcgcgct ggtgagcaac ctgagcggga agccctgcac    57300
cgatgaggtg agcgcgccgg gttactgggt gcgtcacgcg cgagaggcgg tgcgcttcgc    57360
ggacggagtg aaggcgctgc acgcggccgg tgcgggcctc ttcgtcgagg tggggccgaa    57420
gccgacgctg ctcggccttg tgccggcctg cctgccggat gccaggccgg tgctgctccc    57480
agcgtcgcgc gccgggcgtg acgaggctgc gagcgcgcta gaggcgctgg gtgggttctg    57540
ggtcgtcggt ggatcggtca cctggtcggg tgtcttccct tcgggcggac ggcgggtacc    57600
gctgccaacc tatccctggc agcgcgagcg ttactggatc gaagcgccgg tcgatcgtga    57660
ggcggacggc accggccgtg ctcgggcggg gggccacccc cttctgggtg aagtcttttc    57720
cgtgtcgacc catgccggtc tgcgcctgtg ggagacgacg ctggaccgaa agcggctgcc    57780
gtggctcggc gagcaccggg cgcaggggga ggtcgtgttt cctggcgccg ggtacctgga    57840
gatggcgctg tcgtcggggg ccgagatctt gggcgatgga ccgatccagg tcacggatgt    57900
ggtgctcatc gagacgctga ccttcgcggg cgatacggcg gtaccggtcc aggtggtgac    57960
gaccgaggag cgaccgggac ggctgcggtt ccaggtagcg agtcgggagc cggggggaacg    58020 tcgcgcgccc ttccggatcc acgcccgcgg cgtgctgcgc cggatcgggc gcgtcgagac    58080
cccggcgagg tcgaacctcg ccgccctgcg cgcccggctt catgccgccg tgcccgctgc    58140
ggctatctat ggtgcgctcg ccgagatggg gcttcaatac ggcccggcgt tgcgggggct    58200
cgccgagctg tggcggggtg agggcgaggc gctgggcagg gtgagactgc ctgaggccgc    58260
cggctccgcg acagcctacc agctgcatcc ggtgctgctg gacgcgtgcg tccaaatgat    58320
tgttggcgcg ttcgccgatc gcgatgaggc gacgccgtgg gcgccggtgg aggtgggctc    58380
ggtgcggctg ttccagcggt ctcctgggga gctatggtgc catgcgcgcg tcgtgagcga    58440
tggtcaacag gcctccagcc ggtggagcgc cgactttgag ttgatggacg gtacgggcgc    58500
```

```
ggtggtcgcc gagatctccc ggctggtggt ggagcggctt cgagcggtg  tacgccggcg   58560 cgacgcagac gactggttcc tggagctgga ttgggagccc gcggcgctcg gtgggcccaa   58620
gatcacagcc ggccggtggc tgctgctcgg cgaggtggt  gggctcgggc gctcgttgtg   58680
ctcggcgctg aaggccgccg gccatgtcgt cgtccacgcc gcggggacg  acacgagcac   58740 tgcaggaatg cgcgcgctcc tggccaacgc gttcgacggc caggcccga  cggccgtggt   58800 gcacctcagc agcctcgacg ggggcggcca gctcggcccg gggctcgggg cgcagggcgc   58860
gctcgacgcg ccccggagcc cagatgtcga tgccgatgcc ctcgaatcgg cgctgatgcg   58920
tggttgcgac agcgtgctct ccctggtgca agcgctggtc ggcatggacc tccgaaacgc   58980
gccgcggctg tggctcttga cccgcggggc tcaggcggcc gccgccggcg atgtctccgt   59040
ggtgcaagcg ccgctgttgg ggctgggccg caccatcgcc ttggagcacg ccgagctgcg   59100
ctgtatcagc gtcgacctcg atccagccga gcctgaaggg gaagccgatg ctttgctggc   59160
cgagctactt gcagatgatg ccgaggagga ggtcgcgctg cgcggtggcg accggctcgt   59220
tgcgcggctc gtccaccggc tgcccgacgc tcagcgccgg gagaaggtcg agcccgccgg   59280
tgacaggccg ttccggctag agatcgatga acccggcgcg ctggaccaac tggtgctccg   59340
agccacgggg cggcgcgctc ctggtccggg cgaggtcgag atctccgtcg aagcggcggg   59400
gctcgactcc atcgacatcc agctggcgtt gggcgttgct cccaatgatc tgcctggaga   59460
agaaatcgag ccgttggtgc tcggaagcga gtgcgccggg cgcatcgtcg ctgtgggcga   59520
gggcgtgaac ggccttgtgg tgggccagcc ggtgatcgcc cttgcggcgg gagtatttgc   59580
tacccatgtc accacgtcgg ccacgctggt gttgcctcgg cctctgggc  tctcggcgac   59640 cgaggcggcc gcgatgcccc tcgcgtattt gacggcctgg tacgccctcg acaaggtcgc   59700
ccacctgcag gcggggagc  gggtgctgat ccatgcggag gccggtggtg tcggtctttg   59760
cgcggtgcga tgggcgcagc gcgtgggcgc cgaggtgtat gcgaccgccg acacgcccga   59820
gaaccgtgcc tacctggagt cgctgggcgt gcggtacgtg agcgattccc gctcgggccg   59880
gttcgtcaca gacgtgcatg catggacgga cggcgagggt gtggacgtcg tgctcgactc   59940
gctttcgggc gagcgcatcg acaagagcct catggtcctg cgcgcctgtg gtcgccttgt   60000
gaagctgggc aggcgcgacg actgcgccga cacgcagcct gggctgccgc cgctcctacg   60060
gaatttttcc ttctcgcagg tggacttgcg gggaatgatg ctcgatcaac cggcgaggat   60120
ccgtgcgctc ctcgacgagc tgttcgggtt ggtcgcagcc ggtgccatca gcccactggg   60180
gtcggggttg cgcgttggcg gatccctcac gccaccgccg gtcgagacct tcccgatctc   60240
tcgcgcagcc gaggcattcc ggaggatggc gcaaggacag catctcggga agctcgtgct   60300
cacgctggac gacccggagg tgcggatccg cgctccggcc gaatccagcg tcgccgtccg   60360
cgcggacggc acctaccttg tgaccggcgg tctgggtggc ctcggtctgc gcgtggccgg   60420
atggctggcc gagcggggcg cggggcaact ggtgctggtg ggccgctccg gtgcggcgag   60480
cgcagagcag cgagccgccg tggcggcgct ggaggcccac ggcgcgcgcg tcacggtggc   60540
gaaagcggac gtcgccgatc ggtcacagat cgagcgggtc ctccgcgagg ttaccgcgtc   60600
ggggatgccg ctgcggggtg tcgtgcatgc ggcaggtctc gtggatgacg ggctgctgat   60660
gcagcagact ccggcgcggt tccgcacggt gatgggacct aaggtccagg gggccttgca   60720
cttgcacacg ctgacacgcg aagcgcctct ttccttcttc gtgctgtacg cttctgcagc   60780
tgggcttttc ggctcgccag gccagggcaa ctatgccgca gccaacgcgt tcctcgacgc   60840
```

```
cctttcgcat caccgaaggg cgcagggcct gccggcgctg agcatcgact ggggcatgtt      60900
cacggaggtg gggatggccg ttgcgcaaga aaccgtggc gcgcggcaga tctctcgcgg       60960
gatgcgggc atcaccccg atgagggtct gtcagctctg gcgcgcttgc tcgagggtga       61020
tcgcgtgcag acggggtga taccgatcac tccgcggcag tgggtggagt tctacccggc      61080
aacagcggcc tcacggaggt tgtcgcggct ggtgaccacg cagcgcgcgg tcgctgatcg      61140
gaccgccggg gatcgggacc tgctcgaaca gcttgcgtcg gctgagccga gcgcgcgggc     61200
ggggctgctg caggacgtcg tgcgcgtgca ggtctcgcat gtgctgcgtc tccctgaaga     61260
caagatcgag gtggatgccc cgctctcgag catgggcatg gactcgctga tgagcctgga     61320
gctgcgcaac cgcatcgagg ctgcgctggg cgtcgccgcg cctgcagcct tggggtggac     61380
gtacccaacg gtagcagcga taacgcgctg gctgctcgac gacgccctcg tcgtccggct     61440
tggcggcggg tcggacacgg acgaatcgac ggcgagcgcc ggttcgttcg tccacgtcct     61500
ccgctttcgt cctgtcgtca agccgcgggc tcgtctcttc tgttttcacg gttctggcgg    61560
ctcgcccgag ggcttccgtt cctggtcgga gaagtctgag tggagcgatc tggaaatcgt     61620
ggccatgtgg cacgatcgca gcctcgcctc cgaggacgcg cctggtaaga agtacgtcca    61680
agaggcggcc tcgctgattc agcactatgc agacgcaccg tttgcgttag tagggttcag     61740
cctgggtgtc cggttcgtca tggggacagc cgtggagctc gccagtcgtt ccggcgcacc    61800
ggctccgctg gccgtcttca cgttgggcgg cagcttgatc tcttcttcag agatcacccc    61860
ggagatggag accgatataa tagccaagct cttcttccga aatgccgcgg gtttcgtgcg    61920
atccacccaa caagtccagg ccgatgctcg cgcagacaag gtcatcacag acaccatggt    61980
ggctccggcc cccggggact cgaaggagcc gcccgtgaag atcgcggtcc ctatcgtcgc    62040
catcgccggc tcggacgatg tgatcgtgcc tccgagcgac gttcaggatc tacaatctcg    62100
caccacggag cgcttctata tgcatctcct tcccggagat cacgaatttc tcgtcgatcg    62160
agggcgcgag atcatgcaca tcgtcgactc gcatctcaat ccgctgctcg ccgcgaggac    62220
gacgtcgtca ggccccgcgt tcgaggcaaa atgatggcag cctccctcgg gcgcgcgaga    62280
tggttgggag cagcgtgggc gctggcggcc ggcggcaggc cgcggaggcg catgagcctt    62340
cctggacgtt tgcagtatag gagatttat gacacaggag caagcgaatc agagtgagac     62400
gaagcctgct ttcgacttca agccgttcgc gcctgggtac gcggaggacc cgttccccgc    62460
gatcgagcgc ctgagagagg caaccccat cttctactgg gatgaaggcc gctcctgggt    62520
cctcacccga taccacgacg tgtcggcggt gttccgcgac gaacgcttcg cggtcagtcg    62580
agaagagtgg gaatcgagcg cggagtactc gtcggccatt cccagctca gcgatatgaa    62640
gaagtacgga ttgttcgggc tgccgccgga ggatcacgct cgggtccgca agctcgtcaa    62700
cccgtcgttt acgtcacgcg ccatcgacct gctgcgcgcc gaaatacagc gcaccgtcga    62760
ccagctgctc gatgctcgct ccggacaaga ggagttcgac gttgtgcggg attacgcgga    62820
gggaatcccg atgcgcgcga tcagcgctct gttgaaggtt ccggccgagt gtgacgaaa    62880
gttccgtcgc ttcggctcgg cgactgcgcg cgcgctcggc gtgggtttgg tgccccaggt    62940
cgatgaggag accaagaccc tggtcgcgtc cgtcaccgag gggctcgcgc tgctccatga    63000
cgtcctcgat gagcggcgca ggaacccgct cgaaaatgac gtcttgacga tgctgcttca    63060
ggccgaggcc gacggcagca ggctgagcac gaaggagctg gtcgcgctcg tgggtgcgat    63120
tatcgctgct ggcaccgata ccacgatcta ccttatcgcg ttcgctgtgc tcaacctgct    63180
gcggtcgccc gaggcgctcg agctggtgaa ggccgagccc gggctcatga ggaacgcgct    63240
```

```
cgatgaggtg ctccgcttcg acaatatcct cagaatagga actgtgcgtt tcgccaggca   63300
ggacctggag tactgcgggg catcgatcaa gaaaggggag atggtctttc tcctgatccc   63360
gagcgccctg agagatggga ctgtattctc caggccagac gtgtttgatg tgcgacggga   63420
cacgggcgcg agcctcgcgt acggtagagg cccccatgtc tgccccgggg tgtcccttgc   63480
tcgcctcgag gcggagatcg ccgtgggcac catcttccgt aggttccccg agatgaagct   63540
gaaagaaact cccgtgtttg gataccaccc cgcgttccgg aacatcgaat cactcaacgt   63600
catcttgaag ccctccaaag ctggatagct cgcggggta tcgcttcccg aacctcattc    63660
cctcatgata cagctcgcgc gcgggtgctg tctgccgcgg gtgcgattcg atccagcgga   63720
caagcccatt gtcagcgcgc gaagatcgaa tccacggccc ggagaagagc ccgtccgggt   63780
gacgtcggaa gaagtgccgg gcgccgccct gggagcgcaa agctcgctcg ttcgcgctca   63840
gcacgccgct cgtcatgtcc ggccctgcac ccgcgccgag gagccgcccg ccctgatgca   63900
cggcctcacc gagcggcagg ttctgctctc gctcgtcgcc ctcgcgctcg tcctcctgac   63960
cgcgcgcgcc ttcggcgagc tcgcgcggcg gctgcgccag cccgaggtgc tcggcgagct   64020
cttcggcggc gtggtgctgg gcccgtccgt cgtcggcgcg ctcgctcctg ggttccatcg   64080
agtcctcttc caggatccgg cggtcggggt cgtgctctcc ggcatctcct ggataggcgc   64140
gctcgtcctg ctgctcatgg cgggtatcga ggtcgatgtg agcatcctgc gcaaggaggc   64200 gcgcccggg gcgctctcgg cgctcggcgc gatcgcgccc ccgctgcgca cgccggggcc   64260
gctggtgcag cgcatgcagg gcgcgttcac gtgggatctc gacgtctcgc cgcgacgctc   64320
tgcgcaagcc tgagcctcgg cgcctgctcg tacacctcgc cggtgctcgc tccgcccgcg   64380
gacatccggc cgcccgccgc ggcccagctc gagccggact cgccggatga cgaggccgac   64440
gaggccgacg aggcgctccg cccgttccgc gacgcgatcg ccgcgtactc ggaggccgtt   64500
cggtgggcgg aggcggcgca gcggccgcgg ctggagagcc tcgtgcggct cgcgatcgtg   64560
cggctgggca aggcgctcga caaggtccct ttcgcgcaca cgacgccgg cgtctcccag   64620 atcgccggca gactccagaa cgatgcggtc tggttcgatg tcgccgcccg gtacgcgagc   64680
ttccgcgcgg cgacggagca cgcgctccgc gacgcggcgt cggccatgga ggcgctcgcg   64740
gccggcccgt accgcggatc gagccgcgtg tccgctgccg tagggagtt tcggggggag   64800 gcggcgcgcc ttcaccccgc ggaccgtgta cccgcgtccg accagcagat cctgaccgcg   64860
ctgcgcgcag ccgagcgggc gctcatcgcg ctctacactg cgttcgcccg tgaggagtga   64920
gcctctctcg ggcgcagccg agcggcggcg tgccggtggt tccctcttcg caaccatgac   64980
cggagccgcg ctcggtccgc gcagcggcta gcgcgcgtcg cggcagagat cgctggagcg   65040
acaggcgacg acccgcccga gggtgtcgaa cggattgccg cagccctcat tgcggatccc   65100
ctccagacac tcgttcagct gcttggcgtc gatgccgcct gggcactcgc cgaaggtcag   65160
ctcgtcgcgc cactcggatc ggatcttgtt cgagcacgcg tccttgctcg aatactcccg   65220
gtcttgtccg atgttgttgc accgcgcctc gcggtcgcac cgcgccgcca cgatgctatc   65280
gacggcgctg ccgactggca ccggcgcctc gccctgcgcg ccacccgggg tttgcgcctc   65340
cccgcctgac cgcttttcgc cgccgcacgc gcgagcagg ctcattcccg acaccgagat    65400
caggcccacg accagcttcc cagcaatctt ttgcatggct tcccctccct cacgacacgt   65460
cacatcagag actctccgct cggctcgtcg gttcgacagc cggcgacggc cacgagcaga   65520
accgtccccg accagaacag ccgcatgcgg gtttctcgca acatgccccg acatccttgc   65580
```

```
gactagcgtg cctccgctcg tgccgagatc ggctgtcctg tgcgacggca atatcctgcg   65640
atcggccggg caggaggtac cgacacgggc gccgggcggg aggtgccgcc acgggctcga   65700
aatgtgctgc ggcaggcgcc tccatgcccg cagccgggaa cgcggcgccc ggccagcctc   65760
ggggtgacgc cgcaaacggg agatgctccc ggagaggcgc cgggcacagc cgagcgccgt   65820
caccaccgtg cgcactcgtg agctccagct cctcggcata aagagaccg tcactcccgg    65880 tccgtgtagg cgatcgtgct gatcagcgcg ttctccgcct gacgcgagtc gagccgggta   65940
tgctgcacga caatgggaac gtccgattcg atcacgctgg catagtccgt atcgcgcggg   66000
atcggctcgg gttcggtcag atcgttgaac cggacgtgcc gggtgcgcct cgctgggacg   66060
gtcacccggt acggcccggc ggggtcgcgg tcgctgaagt agacggtgat ggcgacctgc   66120
gcgtcccggt ccgacgcatt caacaggcag gccgtctcat ggctcgtcat ctgcggctcg   66180
ggtccgttgc tccggcctgg gatgtagccc tctgcgattg cccagcgcgt ccgcccgatc   66240
ggcttctcca tatgtcctcc ctgctggctc ctctttggct gcctccctct gctgtccagg   66300
agcgacggcc tcttctcccg acgcgctcgg ggatccatgg ctgaggatcc tcgccgagcg   66360
ctccttgccg accggcgcgc cgagcgccga cgggctttga agcacgcga ccggacacgt    66420 gatgccggcg cgacgaggcc gccccgcgtc tgatcccgat cgtgacatcg cgacgtccgc   66480
cggcgcctct gcaggccggc ctgagcgttg cgcggtcatg gtcgtcctcg cgtcaccgcc   66540
acccgccgat tcacatccca ccgcggcacg acgcttgctc aaaccgcggc gagacggccg   66600
ggcggctgtg gtaccggcca gcccggacgc gaggcccgag agggacagtg ggtccgccgt   66660
gaagcagtga ggcgatcgag gtggcagatg aaacacgttg acacgggccg acgagtcggc   66720
cgccggatag ggctcacgct cggtctcctc gcgagcatgg cgctcgccgg ctgtggcggc   66780
ccgagcgaga aaatcgtgca gggcacgcgg ctcgcgcccg gcgccgatgc gcacgtcgcc   66840
gccgacgtcg accccgacgc cgcgaccacg cggctggcgg tggacgtcgt tcacctctcg   66900
ccgcccgagc gcatcgaggc cggcagcgag cggttcgtcg tctggcagcg tccgagctcc   66960
gagtccccgt ggcaacgggt cggagtgctc gactacaacg ctgccagccg aagaggcaag   67020
ctggccgaga cgaccgtgcc gcatgccaac ttcgagctgc tcatcaccgt cgagaagcag   67080
agcagccctc agtctccatc ttctgccgcc gtcatcgggc cgacgtccgt cgggtaacat   67140
cgcgctatca gcagcgctga gcccgccagc aggccccaga gccctgcctc gatcgccttc   67200
tccatcatat catccctgcg tactcctcca gcgacggccg cgtcgaagca accgccgtgc   67260
cggcgcggct ctacgtgcgc gacaggagag cgtcctggcg cggcctgcgc atcgctggaa   67320
ggatcggcgg agcatggaga aagaatcgag gatcgcgatc tacggcgcca tcgcagccaa   67380
cgtggcgatc gcggcggtca agttcatcgc cgccgccgtg accggcagct cggcgatgct   67440
ctccgagggc gtgcactccc tcgtcgatac tgcagacggg ctcctcctcc tgctcggcaa   67500
gcaccggagc gcacgcccgc ccgacgccga gcatccgttc ggccacggca aggagctcta   67560
tttctggacg ctgatcgtcg ccatcatgat cttcgccgcg ggcggcggcg tctcgatcta   67620
cgaagggatc ttgcacctct tgcacccgcg ccagatcgag gatccgacgt ggaactacgt   67680
cgtcctcggc gcagcggccg tcttcgaggg gacgtcgctc atcatctcga tccacgagtt   67740
caagaagaag gacggacagg gctacctcgc ggcgatgcgg tccagcaagg acccgacgac   67800
gttcacgatc gtcctggagg actccgcggc gctcgccggg ctcaccatcg ccttcctcgg   67860
cgtctggctc gggcaccgcc tgggaaaccc ctacctcgac ggcgcggcgt cgatcggcat   67920
cggcctcgtg ctcgccgcgg tcgcggtctt cctcgccagc cagagccgtg ggctcctcgt   67980
```

-continued

```
gggggagagc gcggacaggg agctcctcgc cgcgatccgc gcgctcgcca gcgcagatcc    68040
tggcgtgtcg gcggtggggc ggccctgac gatgcacttc ggtccgcacg aagtcctggt    68100
cgtgctgcgc atcgagttcg acgccgcgct cacggcgtcc ggggtcgcgg aggcgatcga    68160
gcgcatcgag acccggatac ggagcgagcg acccgacgtg aagcacatct acgtcgaggc    68220
caggtcgctc accagcgcg cgagggcgtg acgcgccgtg gagagaccgc gcgcggcctc    68280
cgccatcctc cgcggcgccc gggctcaggt ggccctcgca gcagggcgcg cctggcgggc    68340
aaaccgtgca gacgtcgtcc ttcgacgcga ggtacgctgg ttgcaagtcg tcacgccgta    68400
tcgcgaggtc cggcagcgcc ggagcccggg cgggccgggc gcacgaaggc gcggcgagcg    68460
caggcttcga gggggcgac gtcatgagga aggccagggc gcatggggcg atgctcggcg    68520
ggcgagatga cggctggcgt cgcggcctcc ccggcgccgg cgcgcttcgc gccgcgctcc    68580
agcgcggtcg ctcgcgcgat ctcgcccggc gccggctcat cgcctccgtg tccctcgccg    68640
gcggcgccag catggcggtc gtctcgctgt tccagctcgg gatcatcgag cgcctgcccg    68700
atcctccgct tccagggttc gattcggcca aggtgacgag ctccgatatc                 68750
```

<210> SEQ ID NO 2
<211> LENGTH: 1421
<212> TYPE: PRT
<213> ORGANISM: Sorangium cellulosum

<400> SEQUENCE: 2

```
Val Ala Asp Arg Pro Ile Glu Arg Ala Ala Glu Asp Pro Ile Ala Ile
  1               5                  10                  15

Val Gly Ala Ser Cys Arg Leu Pro Gly Gly Val Ile Asp Leu Ser Gly
             20                  25                  30

Phe Trp Thr Leu Leu Glu Gly Ser Arg Asp Thr Val Gly Arg Val Pro
         35                  40                  45

Ala Glu Arg Trp Asp Ala Ala Ala Trp Phe Asp Pro Asp Pro Asp Ala
     50                  55                  60

Pro Gly Lys Thr Pro Val Thr Arg Ala Ser Phe Leu Ser Asp Val Ala
 65                  70                  75                  80

Cys Phe Asp Ala Ser Phe Phe Gly Ile Ser Pro Arg Glu Ala Leu Arg
                 85                  90                  95

Met Asp Pro Ala His Arg Leu Leu Leu Glu Val Cys Trp Glu Ala Leu
            100                 105                 110

Glu Asn Ala Ala Ile Ala Pro Ser Ala Leu Val Gly Thr Glu Thr Gly
        115                 120                 125

Val Phe Ile Gly Ile Gly Pro Ser Glu Tyr Glu Ala Ala Leu Pro Gln
    130                 135                 140

Ala Thr Ala Ser Ala Glu Ile Asp Ala His Gly Gly Leu Gly Thr Met
145                 150                 155                 160

Pro Ser Val Gly Ala Gly Arg Ile Ser Tyr Ala Leu Gly Leu Arg Gly
                165                 170                 175

Pro Cys Val Ala Val Asp Thr Ala Tyr Ser Ser Ser Leu Val Ala Val
            180                 185                 190

His Leu Ala Cys Gln Ser Leu Arg Ser Gly Glu Cys Ser Thr Ala Leu
        195                 200                 205

Ala Gly Gly Val Ser Leu Met Leu Ser Pro Ser Thr Leu Val Trp Leu
    210                 215                 220

Ser Lys Thr Arg Ala Leu Ala Arg Asp Gly Arg Cys Lys Ala Phe Ser
225                 230                 235                 240
```

```
Ala Glu Ala Asp Gly Phe Gly Arg Gly Glu Cys Ala Val Val Val
                245                 250                 255

Leu Lys Arg Leu Ser Gly Ala Arg Ala Asp Gly Asp Arg Ile Leu Ala
                260                 265                 270

Val Ile Arg Gly Ser Ala Ile Asn His Asp Gly Ala Ser Ser Gly Leu
            275                 280                 285

Thr Val Pro Asn Gly Ser Ser Gln Glu Ile Val Leu Lys Arg Ala Leu
            290                 295                 300

Ala Asp Ala Gly Cys Ala Ala Ser Ser Val Gly Tyr Val Glu Ala His
305                 310                 315                 320

Gly Thr Gly Thr Thr Leu Gly Asp Pro Ile Glu Ile Gln Ala Leu Asn
                325                 330                 335

Ala Val Tyr Gly Leu Gly Arg Asp Val Ala Thr Pro Leu Leu Ile Gly
                340                 345                 350

Ser Val Lys Thr Asn Leu Gly His Pro Glu Tyr Ala Ser Gly Ile Thr
                355                 360                 365

Gly Leu Leu Lys Val Val Leu Ser Leu Gln His Gly Gln Ile Pro Ala
            370                 375                 380

His Leu His Ala Gln Ala Leu Asn Pro Arg Ile Ser Trp Gly Asp Leu
385                 390                 395                 400

Arg Leu Thr Val Thr Arg Ala Arg Thr Pro Trp Pro Asp Trp Asn Thr
                405                 410                 415

Pro Arg Arg Ala Gly Val Ser Ser Phe Gly Met Ser Gly Thr Asn Ala
                420                 425                 430

His Val Val Leu Glu Glu Ala Pro Ala Ala Thr Cys Thr Pro Pro Ala
                435                 440                 445

Pro Glu Arg Pro Ala Glu Leu Leu Val Leu Ser Ala Arg Thr Ala Ser
            450                 455                 460

Ala Leu Asp Ala Gln Ala Ala Arg Leu Arg Asp His Leu Glu Thr Tyr
465                 470                 475                 480

Pro Ser Gln Cys Leu Gly Asp Val Ala Phe Ser Leu Ala Thr Thr Arg
                485                 490                 495

Ser Ala Met Glu His Arg Leu Ala Val Ala Ala Thr Ser Arg Glu Gly
                500                 505                 510

Leu Arg Ala Ala Leu Asp Ala Ala Gln Gly Gln Thr Ser Pro Gly
            515                 520                 525

Ala Val Arg Ser Ile Ala Asp Ser Ser Arg Gly Lys Leu Ala Phe Leu
            530                 535                 540

Phe Thr Gly Gln Gly Ala Gln Thr Leu Gly Met Gly Arg Gly Leu Tyr
545                 550                 555                 560

Asp Val Trp Ser Ala Phe Arg Glu Ala Phe Asp Leu Cys Val Arg Leu
                565                 570                 575

Phe Asn Gln Glu Leu Asp Arg Pro Leu Arg Glu Val Met Trp Ala Glu
                580                 585                 590

Pro Ala Ser Val Asp Ala Leu Leu Asp Gln Thr Ala Phe Thr Gln
            595                 600                 605

Pro Ala Leu Phe Thr Phe Glu Tyr Ala Leu Ala Ala Leu Trp Arg Ser
            610                 615                 620

Trp Gly Val Glu Pro Glu Leu Val Ala Gly His Ser Ile Gly Glu Leu
625                 630                 635                 640

Val Ala Ala Cys Val Ala Gly Val Phe Ser Leu Glu Asp Ala Val Phe
                645                 650                 655
```

-continued

```
Leu Val Ala Ala Arg Gly Arg Leu Met Gln Ala Leu Pro Ala Gly Gly
            660                 665                 670

Ala Met Val Ser Ile Glu Ala Pro Glu Ala Asp Val Ala Ala Ala Val
            675                 680                 685

Ala Pro His Ala Ala Ser Val Ser Ile Ala Ala Val Asn Ala Pro Asp
            690                 695                 700

Gln Val Val Ile Ala Gly Ala Gly Gln Pro Val His Ala Ile Ala Ala
705                 710                 715                 720

Ala Met Ala Ala Arg Gly Ala Arg Thr Lys Ala Leu His Val Ser His
            725                 730                 735

Ala Phe His Ser Pro Leu Met Ala Pro Met Leu Glu Ala Phe Gly Arg
            740                 745                 750

Val Ala Glu Ser Val Ser Tyr Arg Arg Pro Ser Ile Val Leu Val Ser
            755                 760                 765

Asn Leu Ser Gly Lys Ala Cys Thr Asp Glu Val Ser Ser Pro Gly Tyr
            770                 775                 780

Trp Val Arg His Ala Arg Glu Val Val Arg Phe Ala Asp Gly Val Lys
785                 790                 795                 800

Ala Leu His Ala Ala Gly Ala Gly Thr Phe Val Glu Val Gly Pro Lys
            805                 810                 815

Ser Thr Leu Leu Gly Leu Val Pro Ala Cys Met Pro Asp Ala Arg Pro
            820                 825                 830

Ala Leu Leu Ala Ser Ser Arg Ala Gly Arg Asp Glu Pro Ala Thr Val
            835                 840                 845

Leu Glu Ala Leu Gly Gly Leu Trp Ala Val Gly Gly Leu Val Ser Trp
            850                 855                 860

Ala Gly Leu Phe Pro Ser Gly Gly Arg Arg Val Pro Leu Pro Thr Tyr
865                 870                 875                 880

Pro Trp Gln Arg Glu Arg Tyr Trp Ile Asp Thr Lys Ala Asp Asp Ala
            885                 890                 895

Ala Arg Gly Asp Arg Arg Ala Pro Gly Ala Gly His Asp Glu Val Glu
            900                 905                 910

Glu Gly Gly Ala Val Arg Gly Gly Asp Arg Arg Ser Ala Arg Leu Asp
            915                 920                 925

His Pro Pro Glu Ser Gly Arg Glu Lys Val Glu Ala Ala Gly
            930                 935                 940

Asp Arg Pro Phe Arg Leu Glu Ile Asp Glu Pro Gly Val Leu Asp His
945                 950                 955                 960

Leu Val Leu Arg Val Thr Glu Arg Arg Ala Pro Gly Leu Gly Glu Val
                965                 970                 975

Glu Ile Ala Val Asp Ala Ala Gly Leu Ser Phe Asn Asp Val Gln Leu
            980                 985                 990

Ala Leu Gly Met Val Pro Asp Asp Leu Pro Gly Lys Pro Asn Pro Pro
            995                 1000                1005

Leu Leu Leu Gly Gly Glu Cys Ala Gly Arg Ile Val Ala Val Gly Glu
    1010                1015                1020

Gly Val Asn Gly Leu Val Val Gly Gln Pro Val Ile Ala Leu Ser Ala
1025                1030                1035                1040

Gly Ala Phe Ala Thr His Val Thr Thr Ser Ala Ala Leu Val Leu Pro
                1045                1050                1055

Arg Pro Gln Ala Leu Ser Ala Ile Glu Ala Ala Met Pro Val Ala
            1060                1065                1070

Tyr Leu Thr Ala Trp Tyr Ala Leu Asp Arg Ile Ala Arg Leu Gln Pro
```

```
                    1075                1080               1085

Gly Glu Arg Val Leu Ile His Ala Ala Thr Gly Gly Val Gly Leu Ala
          1090                1095               1100

Ala Val Gln Trp Ala Gln His Val Gly Ala Glu Val His Ala Thr Ala
1105                1110               1115                1120

Gly Thr Pro Glu Lys Arg Ala Tyr Leu Glu Ser Leu Gly Val Arg Tyr
                1125               1130                1135

Val Ser Asp Ser Arg Ser Asp Arg Phe Val Ala Asp Val Arg Ala Trp
          1140                1145                1150

Thr Gly Gly Glu Gly Val Asp Val Val Leu Asn Ser Leu Ser Gly Glu
          1155                1160               1165

Leu Ile Asp Lys Ser Phe Asn Leu Leu Arg Ser His Gly Arg Phe Val
      1170                1175                1180

Glu Leu Gly Lys Arg Asp Cys Tyr Ala Asp Asn Gln Leu Gly Leu Arg
1185                1190                1195                1200

Pro Phe Leu Arg Asn Leu Ser Phe Ser Leu Val Asp Leu Arg Gly Met
                1205                1210                1215

Met Leu Glu Arg Pro Ala Arg Val Arg Ala Leu Leu Glu Glu Leu Leu
          1220                1225               1230

Gly Leu Ile Ala Ala Gly Val Phe Thr Pro Pro Ile Ala Thr Leu
          1235                1240               1245

Pro Ile Ala Arg Val Ala Asp Ala Phe Arg Ser Met Ala Gln Ala Gln
      1250                1255               1260

His Leu Gly Lys Leu Val Leu Thr Leu Gly Asp Pro Glu Val Gln Ile
1265                1270                1275                1280

Arg Ile Pro Thr His Ala Gly Ala Gly Pro Ser Thr Gly Asp Arg Asp
                1285                1290                1295

Leu Leu Asp Arg Leu Ala Ser Ala Ala Pro Ala Ala Arg Ala Ala Ala
          1300                1305                1310

Leu Glu Ala Phe Leu Arg Thr Gln Val Ser Gln Val Leu Arg Thr Pro
          1315                1320               1325

Glu Ile Lys Val Gly Ala Glu Ala Leu Phe Thr Arg Leu Gly Met Asp
      1330                1335               1340

Ser Leu Met Ala Val Glu Leu Arg Asn Arg Ile Glu Ala Ser Leu Lys
1345                1350                1355                1360

Leu Lys Leu Ser Thr Thr Phe Leu Ser Thr Ser Pro Asn Ile Ala Leu
                1365                1370                1375

Leu Ala Gln Asn Leu Leu Asp Ala Leu Ala Thr Ala Leu Ser Leu Glu
          1380                1385                1390

Arg Val Ala Ala Glu Asn Leu Arg Ala Gly Val Gln Asn Asp Phe Val
          1395                1400               1405

Ser Ser Gly Ala Asp Gln Asp Trp Glu Ile Ile Ala Leu
      1410                1415                1420

<210> SEQ ID NO 3
<211> LENGTH: 1410
<212> TYPE: PRT
<213> ORGANISM: Sorangium cellulosum

<400> SEQUENCE: 3

Met Thr Ile Asn Gln Leu Leu Asn Glu Leu Glu His Gln Gly Ile Lys
1               5                   10                  15

Leu Ala Ala Asp Gly Glu Arg Leu Gln Ile Gln Ala Pro Lys Asn Ala
            20                  25                  30
```

-continued

```
Leu Asn Pro Asn Leu Leu Ala Arg Ile Ser Glu His Lys Ser Thr Ile
         35                  40                  45

Leu Thr Met Leu Arg Gln Arg Leu Pro Ala Glu Ser Ile Val Pro Ala
     50                  55                  60

Pro Ala Glu Arg His Ala Pro Phe Pro Leu Thr Asp Ile Gln Glu Ser
 65                  70                  75                  80

Tyr Trp Leu Gly Arg Thr Gly Ala Phe Thr Val Pro Ser Gly Ile His
                 85                  90                  95

Ala Tyr Arg Glu Tyr Asp Cys Thr Asp Leu Asp Val Pro Arg Leu Ser
                100                 105                 110

Arg Ala Phe Arg Lys Val Val Ala Arg His Asp Met Leu Arg Ala His
             115                 120                 125

Thr Leu Pro Asp Met Met Gln Val Ile Glu Pro Lys Val Asp Ala Asp
     130                 135                 140

Ile Glu Ile Ile Asp Leu Arg Gly Leu Asp Arg Ser Thr Arg Glu Ala
145                 150                 155                 160

Arg Leu Val Ser Leu Arg Asp Ala Met Ser His Arg Ile Tyr Asp Thr
                165                 170                 175

Glu Arg Pro Pro Leu Tyr His Val Val Ala Val Arg Leu Asp Glu Arg
            180                 185                 190

Gln Thr Arg Leu Val Leu Ser Ile Asp Leu Ile Asn Val Asp Leu Gly
        195                 200                 205

Ser Leu Ser Ile Ile Phe Lys Asp Trp Leu Ser Phe Tyr Glu Asp Pro
    210                 215                 220

Glu Thr Ser Leu Pro Val Leu Glu Leu Ser Tyr Arg Asp Tyr Val Leu
225                 230                 235                 240

Ala Leu Glu Ser Arg Lys Lys Ser Glu Ala His Gln Arg Ser Met Asp
                245                 250                 255

Tyr Trp Lys Arg Arg Ile Ala Glu Leu Pro Pro Pro Thr Leu Pro
            260                 265                 270

Met Lys Ala Asp Pro Ser Thr Leu Lys Glu Ile Arg Phe Arg His Thr
        275                 280                 285

Glu Gln Trp Leu Pro Ser Asp Ser Trp Gly Arg Leu Lys Arg Val
    290                 295                 300

Gly Glu Arg Gly Leu Thr Pro Thr Gly Val Ile Leu Ala Ala Phe Ser
305                 310                 315                 320

Glu Val Ile Gly Arg Trp Ser Ala Ser Pro Arg Phe Thr Leu Asn Ile
                325                 330                 335

Thr Leu Phe Asn Arg Leu Pro Val His Pro Arg Val Asn Asp Ile Thr
            340                 345                 350

Gly Asp Phe Thr Ser Met Val Leu Leu Asp Ile Asp Thr Thr Arg Asp
        355                 360                 365

Lys Ser Phe Glu Gln Arg Ala Lys Arg Ile Gln Glu Gln Leu Trp Glu
    370                 375                 380

Ala Met Asp His Cys Asp Val Ser Gly Ile Glu Val Gln Arg Glu Ala
385                 390                 395                 400

Ala Arg Val Leu Gly Ile Gln Arg Gly Ala Leu Phe Pro Val Val Leu
                405                 410                 415

Thr Ser Ala Leu Asn Gln Gln Val Gly Val Thr Ser Leu Gln Arg
            420                 425                 430

Leu Gly Thr Pro Val Tyr Thr Ser Thr Gln Thr Pro Gln Leu Leu Leu
        435                 440                 445

Asp His Gln Leu Tyr Glu His Asp Gly Asp Leu Val Leu Ala Trp Asp
```

-continued

```
              450                 455                 460
Ile Val Asp Gly Val Phe Pro Pro Asp Leu Leu Asp Asp Met Leu Glu
465                 470                 475                 480

Ala Tyr Val Val Phe Leu Arg Arg Leu Thr Glu Glu Pro Trp Gly Glu
                485                 490                 495

Gln Val Arg Cys Ser Leu Pro Pro Ala Gln Leu Glu Ala Arg Ala Ser
                500                 505                 510

Ala Asn Ala Thr Asn Ala Leu Leu Ser Glu His Thr Leu His Gly Leu
                515                 520                 525

Phe Ala Ala Arg Val Glu Gln Leu Pro Met Gln Leu Ala Val Val Ser
                530                 535                 540

Ala Arg Lys Thr Leu Thr Tyr Glu Glu Leu Ser Arg Arg Ser Arg Arg
545                 550                 555                 560

Leu Gly Ala Arg Leu Arg Glu Gln Gly Ala Arg Pro Asn Thr Leu Val
                565                 570                 575

Ala Val Val Met Glu Lys Gly Trp Glu Gln Val Ala Val Leu Ala
                580                 585                 590

Val Leu Glu Ser Gly Ala Ala Tyr Val Pro Ile Asp Ala Asp Leu Pro
                595                 600                 605

Ala Glu Arg Ile His Tyr Leu Leu Asp His Gly Glu Val Lys Leu Val
                610                 615                 620

Leu Thr Gln Pro Trp Leu Asp Gly Lys Leu Ser Trp Pro Pro Gly Ile
625                 630                 635                 640

Gln Arg Leu Leu Val Ser Glu Ala Gly Val Glu Gly Asp Gly Asp Gln
                645                 650                 655

Pro Pro Met Met Pro Ile Gln Thr Pro Ser Asp Leu Ala Tyr Val Ile
                660                 665                 670

Tyr Thr Ser Gly Ser Thr Gly Leu Pro Lys Gly Val Met Ile Asp His
                675                 680                 685

Arg Gly Ala Val Asn Thr Ile Leu Asp Ile Asn Glu Arg Phe Glu Ile
                690                 695                 700

Gly Pro Gly Asp Arg Val Leu Ala Leu Ser Leu Ser Phe Asp Leu
705                 710                 715                 720

Ser Val Tyr Asp Val Phe Gly Ile Leu Ala Ala Gly Gly Thr Ile Val
                725                 730                 735

Val Pro Asp Ala Ser Lys Leu Arg Asp Pro Ala His Trp Ala Glu Leu
                740                 745                 750

Ile Glu Arg Glu Lys Val Thr Val Trp Asn Ser Val Pro Ala Leu Met
                755                 760                 765

Arg Met Leu Val Glu His Phe Glu Gly Arg Pro Asp Ser Leu Ala Arg
770                 775                 780

Ser Leu Arg Leu Ser Leu Leu Ser Gly Asp Trp Ile Pro Val Gly Leu
785                 790                 795                 800

Pro Gly Glu Leu Gln Ala Ile Arg Pro Gly Val Ser Val Ile Ser Leu
                805                 810                 815

Gly Gly Ala Thr Glu Ala Ser Ile Trp Ser Ile Gly Tyr Pro Val Arg
                820                 825                 830

Asn Val Asp Leu Ser Trp Ala Ser Ile Pro Tyr Gly Arg Pro Leu Arg
                835                 840                 845

Asn Gln Thr Phe His Val Leu Asp Glu Ala Leu Glu Pro Arg Pro Val
                850                 855                 860

Trp Val Pro Gly Gln Leu Tyr Ile Gly Gly Val Gly Leu Ala Leu Gly
865                 870                 875                 880
```

```
Tyr Trp Arg Asp Glu Glu Lys Thr Arg Lys Ser Phe Leu Val His Pro
                885                 890                 895
Glu Thr Gly Glu Arg Leu Tyr Lys Thr Gly Asp Leu Gly Arg Tyr Leu
            900                 905                 910
Pro Asp Gly Asn Ile Glu Phe Met Gly Arg Glu Asp Asn Gln Ile Lys
            915                 920                 925
Leu Arg Gly Tyr Arg Val Glu Leu Gly Glu Ile Glu Glu Thr Leu Lys
        930                 935                 940
Ser His Pro Asn Val Arg Asp Ala Val Ile Val Pro Val Gly Asn Asp
945                 950                 955                 960
Ala Ala Asn Lys Leu Leu Leu Ala Tyr Val Val Pro Glu Gly Thr Arg
                965                 970                 975
Arg Arg Ala Ala Glu Gln Asp Ala Ser Leu Lys Thr Glu Arg Ile Asp
            980                 985                 990
Ala Arg Ala His Ala Ala Glu Ala Asp Gly Leu Ser Asp Gly Glu Arg
            995                 1000                1005
Val Gln Phe Lys Leu Ala Arg His Gly Leu Arg Arg Asp Leu Asp Gly
    1010                1015                1020
Lys Pro Val Val Asp Leu Thr Gly Gln Asp Pro Arg Glu Ala Gly Leu
1025                1030                1035                1040
Asp Val Tyr Ala Arg Arg Ser Val Arg Thr Phe Leu Glu Ala Pro
            1045                1050                1055
Ile Pro Phe Val Glu Phe Gly Arg Phe Leu Ser Cys Leu Ser Ser Val
                1060                1065                1070
Glu Pro Asp Gly Ala Thr Leu Pro Lys Phe Arg Tyr Pro Ser Ala Gly
        1075                1080                1085
Ser Thr Tyr Pro Val Gln Thr Tyr Ala Tyr Val Lys Ser Gly Arg Ile
    1090                1095                1100
Glu Gly Val Asp Glu Gly Phe Tyr Tyr His Pro Phe Glu His Arg
1105                1110                1115                1120
Leu Leu Lys Leu Ser Asp His Gly Ile Glu Arg Gly Ala His Val Arg
                1125                1130                1135
Gln Asn Phe Asp Val Phe Asp Glu Ala Ala Phe Asn Leu Leu Phe Val
            1140                1145                1150
Gly Arg Ile Asp Ala Ile Glu Ser Leu Tyr Gly Ser Ser Arg Glu
        1155                1160                1165
Phe Cys Leu Leu Glu Ala Gly Tyr Met Ala Gln Leu Leu Met Glu Gln
    1170                1175                1180
Ala Pro Ser Cys Asn Ile Gly Val Cys Pro Val Gly Gln Phe Asn Phe
1185                1190                1195                1200
Glu Gln Val Arg Pro Val Leu Asp Leu Arg His Ser Asp Val Tyr Val
            1205                1210                1215
His Gly Met Leu Gly Gly Arg Val Asp Pro Arg Gln Phe Gln Val Cys
        1220                1225                1230
Thr Leu Gly Gln Asp Ser Ser Pro Arg Arg Ala Thr Thr Arg Gly Ala
    1235                1240                1245
Pro Pro Gly Arg Glu Gln His Phe Ala Asp Met Leu Arg Asp Phe Leu
1250                1255                1260
Arg Thr Lys Leu Pro Glu Tyr Met Val Pro Thr Val Phe Val Glu Leu
1265                1270                1275                1280
Asp Ala Leu Pro Leu Thr Ser Asn Gly Lys Val Asp Arg Lys Ala Leu
                1285                1290                1295
```

-continued

```
Arg Glu Arg Lys Asp Thr Ser Ser Pro Arg His Ser Gly His Thr Ala
            1300                1305                1310

Pro Arg Asp Ala Leu Glu Glu Ile Leu Val Ala Val Val Arg Glu Val
        1315                1320                1325

Leu Gly Leu Glu Val Val Gly Leu Gln Gln Ser Phe Val Asp Leu Gly
    1330                1335                1340

Ala Thr Ser Ile His Ile Val Arg Met Arg Ser Leu Leu Gln Lys Arg
1345                1350                1355                1360

Leu Asp Arg Glu Ile Ala Ile Thr Glu Leu Phe Gln Tyr Pro Asn Leu
            1365                1370                1375

Gly Ser Leu Ala Ser Gly Leu Arg Arg Asp Ser Arg Asp Leu Asp Gln
        1380                1385                1390

Arg Pro Asn Met Gln Asp Arg Val Glu Val Arg Arg Lys Gly Arg Arg
    1395                1400                1405

Arg Ser
   1410

<210> SEQ ID NO 4
<211> LENGTH: 1832
<212> TYPE: PRT
<213> ORGANISM: Sorangium cellulosum

<400> SEQUENCE: 4

Met Glu Glu Gln Glu Ser Ser Ala Ile Ala Val Ile Gly Met Ser Gly
 1               5                  10                  15

Arg Phe Pro Gly Ala Arg Asp Leu Asp Glu Phe Trp Arg Asn Leu Arg
            20                  25                  30

Asp Gly Thr Glu Ala Val Gln Arg Phe Ser Glu Gln Glu Leu Ala Ala
        35                  40                  45

Ser Gly Val Asp Pro Ala Leu Val Leu Asp Pro Ser Tyr Val Arg Ala
    50                  55                  60

Gly Ser Val Leu Glu Asp Val Asp Arg Phe Asp Ala Ala Phe Phe Gly
65                  70                  75                  80

Ile Ser Pro Arg Glu Ala Glu Leu Met Asp Pro Gln His Arg Ile Phe
                85                  90                  95

Met Glu Cys Ala Trp Glu Ala Leu Glu Asn Ala Gly Tyr Asp Pro Thr
            100                 105                 110

Ala Tyr Glu Gly Ser Ile Gly Val Tyr Ala Gly Ala Asn Met Ser Ser
        115                 120                 125

Tyr Leu Thr Ser Asn Leu His Glu His Pro Ala Met Met Arg Trp Pro
    130                 135                 140

Gly Trp Phe Gln Thr Leu Ile Gly Asn Asp Lys Asp Tyr Leu Ala Thr
145                 150                 155                 160

His Val Ser Tyr Arg Leu Asn Leu Arg Gly Pro Ser Ile Ser Val Gln
                165                 170                 175

Thr Ala Cys Ser Thr Ser Leu Val Ala Val His Leu Ala Cys Met Ser
            180                 185                 190

Leu Leu Asp Arg Glu Cys Asp Met Ala Leu Ala Gly Gly Ile Thr Val
        195                 200                 205

Arg Ile Pro His Arg Ala Gly Tyr Val Tyr Ala Glu Gly Gly Ile Phe
    210                 215                 220

Ser Pro Asp Gly His Cys Arg Ala Phe Asp Ala Lys Ala Asn Gly Thr
225                 230                 235                 240

Ile Met Gly Asn Gly Cys Gly Val Val Leu Leu Lys Pro Leu Asp Arg
                245                 250                 255
```

-continued

```
Ala Leu Ser Asp Gly Asp Pro Val Arg Ala Val Ile Leu Gly Ser Ala
            260                 265                 270

Thr Asn Asn Asp Gly Ala Arg Lys Ile Gly Phe Thr Ala Pro Ser Glu
            275                 280                 285

Val Gly Gln Ala Gln Ala Ile Met Glu Ala Leu Ala Leu Ala Gly Val
            290                 295                 300

Glu Ala Arg Ser Ile Gln Tyr Ile Glu Thr His Gly Thr Gly Thr Leu
305                 310                 315                 320

Leu Gly Asp Ala Ile Glu Thr Ala Ala Leu Arg Arg Val Phe Gly Arg
                    325                 330                 335

Asp Ala Ser Ala Arg Arg Ser Cys Ala Ile Gly Ser Val Lys Thr Gly
            340                 345                 350

Ile Gly His Leu Glu Ser Ala Ala Gly Ile Ala Gly Leu Ile Lys Thr
            355                 360                 365

Val Leu Ala Leu Glu His Arg Gln Leu Pro Pro Ser Leu Asn Phe Glu
            370                 375                 380

Ser Pro Asn Pro Ser Ile Asp Phe Ala Ser Ser Pro Phe Tyr Val Asn
385                 390                 395                 400

Thr Ser Leu Lys Asp Trp Asn Thr Gly Ser Thr Pro Arg Arg Ala Gly
                    405                 410                 415

Val Ser Ser Phe Gly Ile Gly Gly Thr Asn Ala His Val Val Leu Glu
                    420                 425                 430

Glu Ala Pro Ala Ala Lys Leu Pro Ala Ala Pro Ala Arg Ser Ala
            435                 440                 445

Glu Leu Phe Val Val Ser Ala Lys Ser Ala Ala Leu Asp Ala Ala
            450                 455                 460

Ala Ala Arg Leu Arg Asp His Leu Gln Ala His Gln Gly Ile Ser Leu
465                 470                 475                 480

Gly Asp Val Ala Phe Ser Leu Ala Thr Thr Arg Ser Pro Met Glu His
                    485                 490                 495

Arg Leu Ala Met Ala Ala Pro Ser Arg Glu Ala Leu Arg Glu Gly Leu
            500                 505                 510

Asp Ala Ala Ala Arg Gly Gln Thr Pro Pro Gly Ala Val Arg Gly Arg
            515                 520                 525

Cys Ser Pro Gly Asn Val Pro Lys Val Val Phe Val Phe Pro Gly Gln
            530                 535                 540

Gly Ser Gln Trp Val Gly Met Gly Arg Gln Leu Leu Ala Glu Glu Pro
545                 550                 555                 560

Val Phe His Ala Ala Leu Ser Ala Cys Asp Arg Ala Ile Gln Ala Glu
                    565                 570                 575

Ala Gly Trp Ser Leu Leu Ala Glu Leu Ala Ala Asp Glu Gly Ser Ser
                    580                 585                 590

Gln Leu Glu Arg Ile Asp Val Val Gln Pro Val Leu Phe Ala Leu Ala
            595                 600                 605

Val Ala Phe Ala Ala Leu Trp Arg Ser Trp Gly Val Ala Pro Asp Val
            610                 615                 620

Val Ile Gly His Ser Met Gly Glu Val Ala Ala His Val Ala Gly
625                 630                 635                 640

Ala Leu Ser Leu Glu Asp Ala Val Ala Ile Ile Cys Arg Arg Ser Arg
                    645                 650                 655

Leu Leu Arg Arg Ile Ser Gly Gln Gly Glu Met Ala Val Thr Glu Leu
                    660                 665                 670
```

```
Ser Leu Ala Glu Ala Glu Ala Leu Arg Gly Tyr Glu Asp Arg Val
        675                 680                 685

Ser Val Ala Val Ser Asn Ser Pro Arg Ser Thr Val Leu Ser Gly Glu
    690                 695                 700

Pro Ala Ala Ile Gly Glu Val Leu Ser Ser Leu Asn Ala Lys Gly Val
705                 710                 715                 720

Phe Cys Arg Arg Val Lys Val Asp Val Ala Ser His Ser Pro Gln Val
                725                 730                 735

Asp Pro Leu Arg Glu Asp Leu Leu Ala Ala Leu Gly Gly Leu Arg Pro
            740                 745                 750

Gly Ala Ala Val Pro Met Arg Ser Thr Val Thr Gly Ala Met Val
        755                 760                 765

Ala Gly Pro Glu Leu Gly Ala Asn Tyr Trp Met Asn Asn Leu Arg Gln
    770                 775                 780

Pro Val Arg Phe Ala Glu Val Val Gln Ala Gln Leu Gln Gly Gly His
785                 790                 795                 800

Gly Leu Phe Val Glu Met Ser Pro His Pro Ile Leu Thr Thr Ser Val
                805                 810                 815

Glu Glu Met Arg Arg Ala Ala Gln Arg Ala Gly Ala Ala Val Gly Ser
            820                 825                 830

Leu Arg Arg Gly Gln Asp Glu Arg Pro Ala Met Leu Glu Ala Leu Gly
        835                 840                 845

Thr Leu Trp Ala Gln Gly Tyr Pro Val Pro Trp Gly Arg Leu Phe Pro
    850                 855                 860

Ala Gly Gly Arg Arg Val Pro Leu Pro Thr Tyr Pro Trp Gln Arg Glu
865                 870                 875                 880

Arg Tyr Trp Ile Glu Ala Pro Ala Lys Ser Ala Ala Gly Asp Arg Arg
                885                 890                 895

Gly Val Arg Ala Gly Gly His Pro Leu Leu Gly Glu Met Gln Thr Leu
            900                 905                 910

Ser Thr Gln Thr Ser Thr Arg Leu Trp Glu Thr Thr Leu Asp Leu Lys
        915                 920                 925

Arg Leu Pro Trp Leu Gly Asp His Arg Val Gln Gly Ala Val Val Phe
    930                 935                 940

Pro Gly Ala Ala Tyr Leu Glu Met Ala Ile Ser Ser Gly Ala Glu Ala
945                 950                 955                 960

Leu Gly Asp Gly Pro Leu Gln Ile Thr Asp Val Val Leu Ala Glu Ala
                965                 970                 975

Leu Ala Phe Ala Gly Asp Ala Ala Val Leu Val Gln Val Val Thr Thr
            980                 985                 990

Glu Gln Pro Ser Gly Arg Leu Gln Phe Gln Ile Ala Ser Arg Ala Pro
        995                 1000                1005

Gly Ala Gly His Ala Ser Phe Arg Val His Ala Arg Gly Ala Leu Leu
    1010                1015                1020

Arg Val Glu Arg Thr Glu Val Pro Ala Gly Leu Thr Leu Ser Ala Val
1025                1030                1035                1040

Arg Ala Arg Leu Gln Ala Ser Ile Pro Ala Ala Ala Thr Tyr Ala Glu
                1045                1050                1055

Leu Thr Glu Met Gly Leu Gln Tyr Gly Pro Ala Phe Gln Gly Ile Ala
            1060                1065                1070

Glu Leu Trp Arg Gly Glu Gly Glu Ala Leu Gly Arg Val Arg Leu Pro
        1075                1080                1085

Asp Ala Ala Gly Ser Ala Ala Glu Tyr Arg Leu His Pro Ala Leu Leu
```

```
              1090              1095              1100
Asp Ala Cys Phe Gln Ile Val Gly Ser Leu Phe Ala Arg Ser Gly Glu
1105              1110              1115              1120
Ala Thr Pro Trp Val Pro Val Glu Leu Gly Ser Leu Arg Leu Leu Gln
                  1125              1130              1135
Arg Pro Ser Gly Glu Leu Trp Cys His Ala Arg Val Val Asn His Gly
          1140              1145              1150
His Gln Thr Pro Asp Arg Gln Gly Ala Asp Phe Trp Val Val Asp Ser
      1155              1160              1165
Ser Gly Ala Val Val Ala Glu Val Cys Gly Leu Val Ala Gln Arg Leu
1170              1175              1180
Pro Gly Gly Val Arg Arg Arg Glu Glu Asp Asp Trp Phe Leu Glu Leu
1185              1190              1195              1200
Glu Trp Glu Pro Ala Ala Val Gly Thr Ala Lys Val Asn Ala Gly Arg
                  1205              1210              1215
Trp Leu Leu Leu Gly Gly Gly Gly Leu Gly Ala Ala Leu Arg Ala
          1220              1225              1230
Met Leu Glu Ala Gly Gly His Ala Val Val His Ala Ala Glu Asn Asn
      1235              1240              1245
Thr Ser Ala Ala Gly Val Arg Ala Leu Leu Ala Lys Ala Phe Asp Gly
      1250              1255              1260
Gln Ala Pro Thr Ala Val Val His Leu Gly Ser Leu Asp Gly Gly Gly
1265              1270              1275              1280
Glu Leu Asp Pro Gly Leu Gly Ala Gln Gly Ala Leu Asp Ala Pro Arg
                  1285              1290              1295
Ser Ala Asp Val Ser Pro Asp Ala Leu Asp Pro Ala Leu Val Arg Gly
          1300              1305              1310
Cys Asp Ser Val Leu Trp Thr Val Gln Ala Leu Ala Gly Met Gly Phe
      1315              1320              1325
Arg Asp Ala Pro Arg Leu Trp Leu Leu Thr Arg Gly Ala Gln Ala Val
      1330              1335              1340
Gly Ala Gly Asp Val Ser Val Thr Gln Ala Pro Leu Leu Gly Leu Gly
1345              1350              1355              1360
Arg Val Ile Ala Met Glu His Ala Asp Leu Arg Cys Ala Arg Val Asp
                  1365              1370              1375
Leu Asp Pro Ala Arg Pro Glu Gly Glu Leu Ala Ala Leu Leu Ala Glu
          1380              1385              1390
Leu Leu Ala Asp Asp Ala Glu Ala Glu Val Ala Leu Arg Gly Gly Glu
      1395              1400              1405
Arg Cys Val Ala Arg Ile Val Arg Arg Gln Pro Glu Thr Arg Pro Arg
      1410              1415              1420
Gly Arg Ile Glu Ser Cys Val Pro Thr Asp Val Thr Ile Arg Ala Asp
1425              1430              1435              1440
Ser Thr Tyr Leu Val Thr Gly Gly Leu Gly Gly Leu Gly Leu Ser Val
                  1445              1450              1455
Ala Gly Trp Leu Ala Glu Arg Gly Ala Gly His Leu Val Leu Val Gly
          1460              1465              1470
Arg Ser Gly Ala Ala Ser Val Glu Gln Arg Ala Ala Val Ala Ala Leu
      1475              1480              1485
Glu Ala Arg Gly Ala Arg Val Thr Val Ala Lys Ala Asp Val Ala Asp
      1490              1495              1500
Arg Ala Gln Leu Glu Arg Ile Leu Arg Glu Val Thr Thr Ser Gly Met
1505              1510              1515              1520
```

```
Pro Leu Arg Gly Val Val His Ala Ala Gly Ile Leu Asp Asp Gly Leu
            1525                1530                1535

Leu Met Gln Gln Thr Pro Ala Arg Phe Arg Lys Val Met Ala Pro Lys
        1540                1545                1550

Val Gln Gly Ala Leu His Leu His Ala Leu Thr Arg Glu Ala Pro Leu
    1555                1560                1565

Ser Phe Phe Val Leu Tyr Ala Ser Gly Val Gly Leu Leu Gly Ser Pro
1570                1575                1580

Gly Gln Gly Asn Tyr Ala Ala Ala Asn Thr Phe Leu Asp Ala Leu Ala
1585                1590                1595                1600

His His Arg Arg Ala Gln Gly Leu Pro Ala Leu Ser Val Asp Trp Gly
            1605                1610                1615

Leu Phe Ala Glu Val Gly Met Ala Ala Gln Glu Asp Arg Gly Ala
        1620                1625                1630

Arg Leu Val Ser Arg Gly Met Arg Ser Leu Thr Pro Asp Glu Gly Leu
    1635                1640                1645

Ser Ala Leu Ala Arg Leu Leu Glu Ser Gly Arg Ala Gln Val Gly Val
1650                1655                1660

Met Pro Val Asn Pro Arg Leu Trp Val Glu Leu Tyr Pro Ala Ala Ala
1665                1670                1675                1680

Ser Ser Arg Met Leu Ser Arg Leu Val Thr Ala His Arg Ala Ser Ala
            1685                1690                1695

Gly Gly Pro Ala Gly Asp Gly Asp Leu Leu Arg Leu Ala Ala Ala
        1700                1705                1710

Glu Pro Ser Ala Arg Ser Ala Leu Leu Glu Pro Leu Leu Arg Ala Gln
    1715                1720                1725

Ile Ser Gln Val Leu Arg Leu Pro Glu Gly Lys Ile Glu Val Asp Ala
1730                1735                1740

Pro Leu Thr Ser Leu Gly Met Asn Ser Leu Met Gly Leu Glu Leu Arg
1745                1750                1755                1760

Asn Arg Ile Glu Ala Met Leu Gly Ile Thr Val Pro Ala Thr Leu Leu
            1765                1770                1775

Trp Thr Tyr Pro Thr Val Ala Ala Leu Ser Gly His Leu Ala Arg Glu
        1780                1785                1790

Ala Cys Glu Ala Ala Pro Val Glu Ser Pro His Thr Thr Ala Asp Ser
    1795                1800                1805

Ala Val Glu Ile Glu Glu Met Ser Gln Asp Leu Thr Gln Leu Ile
1810                1815                1820

Ala Ala Lys Phe Lys Ala Leu Thr
1825                1830

<210> SEQ ID NO 5
<211> LENGTH: 7257
<212> TYPE: PRT
<213> ORGANISM: Sorangium cellulosum

<400> SEQUENCE: 5

Met Thr Thr Arg Gly Pro Thr Ala Gln Gln Asn Pro Leu Lys Gln Ala
1               5                   10                  15

Ala Ile Ile Ile Gln Arg Leu Glu Glu Arg Leu Ala Gly Leu Ala Gln
            20                  25                  30

Ala Glu Leu Glu Arg Thr Glu Pro Ile Ala Ile Val Gly Ile Gly Cys
        35                  40                  45

Arg Phe Pro Gly Gly Ala Asp Ala Pro Glu Ala Phe Trp Glu Leu Leu
```

-continued

```
            50                      55                      60
Asp Ala Glu Arg Asp Ala Val Gln Pro Leu Asp Met Arg Trp Ala Leu
 65                  70                      75                  80
Val Gly Val Ala Pro Val Glu Ala Val Pro His Trp Ala Gly Leu Leu
                 85                      90                  95
Thr Glu Pro Ile Asp Cys Phe Asp Ala Ala Phe Phe Gly Ile Ser Pro
                100                     105                 110
Arg Glu Ala Arg Ser Leu Asp Pro Gln His Arg Leu Leu Leu Glu Val
                115                     120             125
Ala Trp Glu Gly Leu Glu Asp Ala Gly Ile Pro Pro Arg Ser Ile Asp
130                 135                     140
Gly Ser Arg Thr Gly Val Phe Val Gly Ala Phe Thr Ala Asp Tyr Ala
145                 150                     155                 160
Arg Thr Val Ala Arg Leu Pro Arg Glu Arg Asp Ala Tyr Ser Ala
                165                     170             175
Thr Gly Asn Met Leu Ser Ile Ala Ala Gly Arg Leu Ser Tyr Thr Leu
                180                     185             190
Gly Leu Gln Gly Pro Cys Leu Thr Val Asp Thr Ala Cys Ser Ser Ser
                195                     200             205
Leu Val Ala Ile His Leu Ala Cys Arg Ser Leu Arg Ala Gly Glu Ser
                210                     215             220
Asp Leu Ala Leu Ala Gly Gly Val Ser Ala Leu Leu Ser Pro Asp Met
225                 230                     235                 240
Met Glu Ala Ala Ala Arg Thr Gln Ala Leu Ser Pro Asp Gly Arg Cys
                245                     250             255
Arg Thr Phe Asp Ala Ser Ala Asn Gly Phe Val Arg Gly Glu Gly Cys
                260                     265             270
Gly Leu Val Val Leu Lys Arg Leu Ser Asp Ala Gln Arg Asp Gly Asp
                275                     280             285
Arg Ile Trp Ala Leu Ile Arg Gly Ser Ala Ile Asn His Asp Gly Arg
                290                     295             300
Ser Thr Gly Leu Thr Ala Pro Asn Val Leu Ala Gln Glu Thr Val Leu
305                 310                     315                 320
Arg Glu Ala Leu Arg Ser Ala His Val Glu Ala Gly Ala Val Asp Tyr
                325                     330             335
Val Glu Thr His Gly Thr Gly Thr Ser Leu Gly Asp Pro Ile Glu Val
                340                     345             350
Glu Ala Leu Arg Ala Thr Val Gly Pro Ala Arg Ser Asp Gly Thr Arg
                355                     360             365
Cys Val Leu Gly Ala Val Lys Thr Asn Ile Gly His Leu Glu Ala Ala
370                 375                     380
Ala Gly Val Ala Gly Leu Ile Lys Ala Ala Leu Ser Leu Thr His Glu
385                 390                     395                 400
Arg Ile Pro Arg Asn Leu Asn Phe Arg Thr Leu Asn Pro Arg Ile Arg
                405                     410             415
Leu Glu Gly Ser Ala Leu Ala Leu Ala Thr Glu Pro Val Pro Trp Pro
                420                     425             430
Arg Thr Asp Arg Pro Arg Phe Ala Gly Val Ser Ser Phe Gly Met Ser
                435                     440             445
Gly Thr Asn Ala His Val Val Leu Glu Glu Ala Pro Ala Val Glu Leu
                450                     455             460
Trp Pro Ala Ala Pro Glu Arg Ser Ala Glu Leu Leu Val Leu Ser Gly
465                 470                     475                 480
```

```
Lys Ser Glu Gly Ala Leu Asp Ala Gln Ala Ala Arg Leu Arg Glu His
                485                 490                 495

Leu Asp Met His Pro Glu Leu Gly Leu Gly Asp Val Ala Phe Ser Leu
            500                 505                 510

Ala Thr Thr Arg Ser Ala Met Ser His Arg Leu Ala Val Ala Val Thr
        515                 520                 525

Ser Arg Glu Gly Leu Leu Ala Ala Leu Ser Ala Val Ala Gln Gly Gln
    530                 535                 540

Thr Pro Ala Gly Ala Ala Arg Cys Ile Ala Ser Ser Arg Gly Lys
545                 550                 555                 560

Leu Ala Phe Leu Phe Thr Gly Gln Gly Ala Gln Thr Pro Gly Met Gly
                565                 570                 575

Arg Gly Leu Cys Ala Ala Trp Pro Ala Phe Arg Glu Ala Phe Asp Arg
            580                 585                 590

Cys Val Ala Leu Phe Asp Arg Glu Leu Asp Arg Pro Leu Arg Glu Val
        595                 600                 605

Met Trp Ala Glu Ala Gly Ser Ala Glu Ser Leu Leu Leu Asp Gln Thr
    610                 615                 620

Ala Phe Thr Gln Pro Ala Leu Phe Ala Val Glu Tyr Ala Leu Thr Ala
625                 630                 635                 640

Leu Trp Arg Ser Trp Gly Val Glu Pro Glu Leu Leu Val Gly His Ser
                645                 650                 655

Ile Gly Glu Leu Val Ala Ala Cys Val Ala Gly Val Phe Ser Leu Glu
            660                 665                 670

Asp Gly Val Arg Leu Val Ala Ala Arg Gly Arg Leu Met Gln Gly Leu
        675                 680                 685

Ser Ala Gly Gly Ala Met Val Ser Leu Gly Ala Pro Glu Ala Glu Val
    690                 695                 700

Ala Ala Ala Val Ala Pro His Ala Ser Val Ser Ile Ala Ala Val
705                 710                 715                 720

Asn Gly Pro Glu Gln Val Val Ile Ala Gly Val Glu Gln Ala Val Gln
                725                 730                 735

Ala Ile Ala Ala Gly Phe Ala Ala Arg Gly Ala Arg Thr Lys Arg Leu
            740                 745                 750

His Val Ser His Ala Phe His Ser Pro Leu Met Glu Pro Met Leu Glu
        755                 760                 765

Glu Phe Gly Arg Val Ala Ala Ser Val Thr Tyr Arg Arg Pro Ser Val
    770                 775                 780

Ser Leu Val Ser Asn Leu Ser Gly Lys Val Val Thr Asp Glu Leu Ser
785                 790                 795                 800

Ala Pro Gly Tyr Trp Val Arg His Val Arg Glu Ala Val Arg Phe Ala
                805                 810                 815

Asp Gly Val Lys Ala Leu His Glu Ala Gly Ala Gly Thr Phe Val Glu
            820                 825                 830

Val Gly Pro Lys Pro Thr Leu Leu Gly Leu Leu Pro Ala Cys Leu Pro
        835                 840                 845

Glu Ala Glu Pro Thr Leu Leu Ala Ser Leu Arg Ala Gly Arg Glu Glu
    850                 855                 860

Ala Ala Gly Val Leu Glu Ala Leu Gly Arg Leu Trp Ala Ala Gly Gly
865                 870                 875                 880

Ser Val Ser Trp Pro Gly Val Phe Pro Thr Ala Gly Arg Arg Val Pro
                885                 890                 895
```

-continued

```
Leu Pro Thr Tyr Pro Trp Gln Arg Gln Arg Tyr Trp Ile Glu Ala Pro
            900                 905                 910

Ala Glu Gly Leu Gly Ala Thr Ala Ala Asp Ala Leu Ala Gln Trp Phe
            915                 920                 925

Tyr Arg Val Asp Trp Pro Glu Met Pro Arg Ser Ser Val Asp Ser Arg
            930                 935                 940

Arg Ala Arg Ser Gly Gly Trp Leu Val Leu Ala Asp Arg Gly Gly Val
945                 950                 955                 960

Gly Glu Ala Ala Ala Ala Ala Leu Ser Ser Gln Gly Cys Ser Cys Ala
                965                 970                 975

Val Leu His Ala Pro Ala Glu Ala Ser Ala Val Ala Glu Gln Val Thr
            980                 985                 990

Gln Ala Leu Gly Gly Arg Asn Asp Trp Gln Gly Val Leu Tyr Leu Trp
            995                 1000                1005

Gly Leu Asp Ala Val Glu Ala Gly Ala Ser Ala Glu Glu Val Ala
        1010                1015                1020

Lys Val Thr His Leu Ala Ala Ala Pro Val Leu Ala Leu Ile Gln Ala
1025                1030                1035                1040

Leu Gly Thr Gly Pro Arg Ser Pro Arg Leu Trp Ile Val Thr Arg Gly
                1045                1050                1055

Ala Cys Thr Val Gly Gly Glu Pro Asp Ala Ala Pro Cys Gln Ala Ala
            1060                1065                1070

Leu Trp Gly Met Gly Arg Val Ala Ala Leu Glu His Pro Gly Ser Trp
            1075                1080                1085

Gly Gly Leu Val Asp Leu Asp Pro Glu Glu Ser Pro Thr Glu Val Glu
            1090                1095                1100

Ala Leu Val Ala Glu Leu Leu Ser Pro Asp Ala Glu Asp Gln Leu Ala
1105                1110                1115                1120

Phe Arg Gln Gly Arg Arg Arg Ala Ala Arg Leu Val Ala Ala Pro Pro
            1125                1130                1135

Glu Gly Asn Ala Ala Pro Val Ser Leu Ser Ala Glu Gly Ser Tyr Leu
            1140                1145                1150

Val Thr Gly Gly Leu Gly Ala Leu Gly Leu Leu Val Ala Arg Trp Leu
            1155                1160                1165

Val Glu Arg Gly Ala Gly His Leu Val Leu Ile Ser Arg His Gly Leu
            1170                1175                1180

Pro Asp Arg Glu Glu Trp Gly Arg Asp Gln Pro Pro Glu Val Arg Ala
1185                1190                1195                1200

Arg Ile Ala Ala Ile Glu Ala Leu Glu Ala Gln Gly Ala Arg Val Thr
            1205                1210                1215

Val Ala Ala Val Asp Val Ala Asp Ala Glu Gly Met Ala Ala Leu Leu
            1220                1225                1230

Ala Ala Val Glu Pro Pro Leu Arg Gly Val Val His Ala Ala Gly Leu
            1235                1240                1245

Leu Asp Asp Gly Leu Leu Ala His Gln Asp Ala Gly Arg Leu Ala Arg
            1250                1255                1260

Val Leu Arg Pro Lys Val Glu Gly Ala Trp Val Leu His Thr Leu Thr
1265                1270                1275                1280

Arg Glu Gln Pro Leu Asp Leu Phe Val Leu Phe Ser Ser Ala Ser Gly
            1285                1290                1295

Val Phe Gly Ser Ile Gly Gln Gly Ser Tyr Ala Ala Gly Asn Ala Phe
            1300                1305                1310

Leu Asp Ala Leu Ala Asp Leu Arg Arg Thr Gln Gly Leu Ala Ala Leu
```

-continued

```
        1315                1320                1325
Ser Ile Ala Trp Gly Leu Trp Ala Glu Gly Gly Met Gly Ser Gln Ala
    1330                1335                1340

Gln Arg Arg Glu His Glu Ala Ser Gly Ile Trp Ala Met Pro Thr Ser
1345                1350                1355                1360

Arg Ala Leu Ala Ala Met Glu Trp Leu Leu Gly Thr Arg Ala Thr Gln
        1365                1370                1375

Arg Val Val Ile Gln Met Asp Trp Ala His Ala Gly Ala Ala Pro Arg
    1380                1385                1390

Asp Ala Ser Arg Gly Arg Phe Trp Asp Arg Leu Val Thr Ala Thr Lys
        1395                1400                1405

Glu Ala Ser Ser Ser Ala Val Pro Ala Val Glu Arg Trp Arg Asn Ala
    1410                1415                1420

Ser Val Val Glu Thr Arg Ser Ala Leu Tyr Glu Leu Val Arg Gly Val
1425                1430                1435                1440

Val Ala Gly Val Met Gly Phe Thr Asp Gln Gly Thr Leu Asp Val Arg
        1445                1450                1455

Arg Gly Phe Ala Glu Gln Gly Leu Asp Ser Leu Met Ala Val Glu Ile
        1460                1465                1470

Arg Lys Arg Leu Gln Gly Glu Leu Gly Met Pro Leu Ser Ala Thr Leu
    1475                1480                1485

Ala Phe Asp His Pro Thr Val Glu Arg Leu Val Glu Tyr Leu Leu Ser
    1490                1495                1500

Gln Ala Leu Glu Leu Gln Asp Arg Thr Asp Val Arg Ser Val Arg Leu
1505                1510                1515                1520

Pro Ala Thr Glu Asp Pro Ile Ala Ile Val Gly Ala Ala Cys Arg Phe
        1525                1530                1535

Pro Gly Gly Val Glu Asp Leu Glu Ser Tyr Trp Gln Leu Leu Thr Glu
        1540                1545                1550

Gly Val Val Val Ser Thr Glu Val Pro Ala Asp Arg Trp Asn Gly Ala
    1555                1560                1565

Asp Gly Arg Val Pro Gly Ser Gly Glu Ala Gln Arg Gln Thr Tyr Val
    1570                1575                1580

Pro Arg Gly Gly Phe Leu Arg Glu Val Glu Thr Phe Asp Ala Ala Phe
1585                1590                1595                1600

Phe His Ile Ser Pro Arg Glu Ala Met Ser Leu Asp Pro Gln Gln Arg
        1605                1610                1615

Leu Leu Leu Glu Val Ser Trp Glu Ala Ile Glu Arg Ala Gly Gln Asp
        1620                1625                1630

Pro Ser Ala Leu Arg Glu Ser Pro Thr Gly Val Phe Val Gly Ala Gly
    1635                1640                1645

Pro Asn Glu Tyr Ala Glu Arg Val Gln Glu Leu Ala Asp Glu Ala Ala
    1650                1655                1660

Gly Leu Tyr Ser Gly Thr Gly Asn Met Leu Ser Val Ala Ala Gly Arg
1665                1670                1675                1680

Leu Ser Phe Phe Leu Gly Leu His Gly Pro Thr Leu Ala Val Asp Thr
        1685                1690                1695

Ala Cys Ser Ser Ser Leu Val Ala Leu His Leu Gly Cys Gln Ser Leu
        1700                1705                1710

Arg Arg Gly Glu Cys Asp Gln Ala Leu Val Gly Gly Val Asn Met Leu
    1715                1720                1725

Leu Ser Pro Lys Thr Phe Ala Leu Leu Ser Arg Met His Ala Leu Ser
1730                1735                1740
```

-continued

```
Pro Gly Gly Arg Cys Lys Thr Phe Ser Ala Asp Ala Asp Gly Tyr Ala
1745                1750                1755                1760

Arg Ala Glu Gly Cys Ala Val Val Leu Lys Arg Leu Ser Asp Ala
            1765                1770                1775

Gln Arg Asp Arg Asp Pro Ile Leu Ala Val Ile Arg Gly Thr Ala Ile
        1780                1785                1790

Asn His Asp Gly Pro Ser Ser Gly Leu Thr Val Pro Ser Gly Pro Ala
    1795                1800                1805

Gln Glu Ala Leu Leu Arg Gln Ala Leu Ala His Ala Gly Val Val Pro
    1810                1815                1820

Ala Asp Val Asp Phe Val Glu Cys His Gly Thr Gly Thr Ala Leu Gly
1825                1830                1835                1840

Asp Pro Ile Glu Val Arg Ala Leu Ser Asp Val Tyr Gly Gln Ala Arg
            1845                1850                1855

Pro Ala Asp Arg Pro Leu Ile Leu Gly Ala Ala Lys Ala Asn Leu Gly
            1860                1865                1870

His Met Glu Pro Ala Ala Gly Leu Ala Gly Leu Leu Lys Ala Val Leu
        1875                1880                1885

Ala Leu Gly Gln Glu Gln Ile Pro Ala Gln Pro Glu Leu Gly Glu Leu
    1890                1895                1900

Asn Pro Leu Leu Pro Trp Glu Ala Leu Pro Val Ala Val Ala Arg Ala
1905                1910                1915                1920

Ala Val Pro Trp Pro Arg Thr Asp Arg Pro Arg Phe Ala Gly Val Ser
            1925                1930                1935

Ser Phe Gly Met Ser Gly Thr Asn Ala His Val Val Leu Glu Glu Ala
            1940                1945                1950

Pro Ala Val Glu Leu Trp Pro Ala Ala Pro Glu Arg Ser Ala Glu Leu
        1955                1960                1965

Leu Val Leu Ser Gly Lys Ser Glu Gly Ala Leu Asp Ala Gln Ala Ala
    1970                1975                1980

Arg Leu Arg Glu His Leu Asp Met His Pro Glu Leu Gly Leu Gly Asp
1985                1990                1995                2000

Val Ala Phe Ser Leu Ala Thr Thr Arg Ser Ala Met Asn His Arg Leu
            2005                2010                2015

Ala Val Ala Val Thr Ser Arg Glu Gly Leu Leu Ala Ala Leu Ser Ala
            2020                2025                2030

Val Ala Gln Gly Gln Thr Pro Pro Gly Ala Ala Arg Cys Ile Ala Ser
        2035                2040                2045

Ser Ser Arg Gly Lys Leu Ala Phe Leu Phe Thr Gly Gln Gly Ala Gln
    2050                2055                2060

Thr Pro Gly Met Gly Arg Gly Leu Cys Ala Ala Trp Pro Ala Phe Arg
2065                2070                2075                2080

Glu Ala Phe Asp Arg Cys Val Ala Leu Phe Asp Arg Glu Leu Asp Arg
            2085                2090                2095

Pro Leu Arg Glu Val Met Trp Ala Glu Pro Gly Ser Ala Glu Ser Leu
        2100                2105                2110

Leu Leu Asp Gln Thr Ala Phe Thr Gln Pro Ala Leu Phe Thr Val Glu
    2115                2120                2125

Tyr Ala Leu Thr Ala Leu Trp Arg Ser Trp Gly Val Glu Pro Glu Leu
    2130                2135                2140

Val Ala Gly His Ser Ala Gly Glu Leu Val Ala Ala Cys Val Ala Gly
2145                2150                2155                2160
```

-continued

```
Val Phe Ser Leu Glu Asp Gly Val Arg Leu Val Ala Ala Arg Gly Arg
            2165                2170                2175

Leu Met Gln Gly Leu Ser Ala Gly Ala Met Val Ser Leu Gly Ala
        2180                2185                2190

Pro Glu Ala Glu Val Ala Ala Val Ala Pro His Ala Ala Ser Val
        2195                2200                2205

Ser Ile Ala Ala Val Asn Gly Pro Glu Gln Val Val Ile Ala Gly Val
    2210                2215                2220

Glu Gln Ala Val Gln Ala Ile Ala Ala Gly Phe Ala Ala Arg Gly Ala
2225                2230                2235                2240

Arg Thr Lys Arg Leu His Val Ser His Ala Ser His Ser Pro Leu Met
            2245                2250                2255

Glu Pro Met Leu Glu Glu Phe Gly Arg Val Ala Ala Ser Val Thr Tyr
            2260                2265                2270

Arg Arg Pro Ser Val Ser Leu Val Ser Asn Leu Ser Gly Lys Val Val
            2275                2280                2285

Ala Asp Glu Leu Ser Ala Pro Gly Tyr Trp Val Arg His Val Arg Glu
    2290                2295                2300

Ala Val Arg Phe Ala Asp Gly Val Lys Ala Leu His Glu Ala Gly Ala
2305                2310                2315                2320

Gly Thr Phe Val Glu Val Gly Pro Lys Pro Thr Leu Leu Gly Leu Leu
            2325                2330                2335

Pro Ala Cys Leu Pro Glu Ala Glu Pro Thr Leu Leu Ala Ser Leu Arg
            2340                2345                2350

Ala Gly Arg Glu Glu Ala Ala Gly Val Leu Glu Ala Leu Gly Arg Leu
            2355                2360                2365

Trp Ala Ala Gly Gly Ser Val Ser Trp Pro Gly Val Phe Pro Thr Ala
    2370                2375                2380

Gly Arg Arg Val Pro Leu Pro Thr Tyr Pro Trp Gln Arg Gln Arg Tyr
2385                2390                2395                2400

Trp Pro Asp Ile Glu Pro Asp Ser Arg Arg His Ala Ala Ala Asp Pro
            2405                2410                2415

Thr Gln Gly Trp Phe Tyr Arg Val Asp Trp Pro Glu Ile Pro Arg Ser
            2420                2425                2430

Leu Gln Lys Ser Glu Glu Ala Ser Arg Gly Ser Trp Leu Val Leu Ala
        2435                2440                2445

Asp Lys Gly Gly Val Gly Glu Ala Val Ala Ala Ala Leu Ser Thr Arg
    2450                2455                2460

Gly Leu Pro Cys Val Val Leu His Ala Pro Ala Glu Thr Ser Ala Thr
2465                2470                2475                2480

Ala Glu Leu Val Thr Glu Ala Ala Gly Gly Arg Ser Asp Trp Gln Val
            2485                2490                2495

Val Leu Tyr Leu Trp Gly Leu Asp Ala Val Val Gly Ala Glu Ala Ser
            2500                2505                2510

Ile Asp Glu Ile Gly Asp Ala Thr Arg Arg Ala Thr Ala Pro Val Leu
        2515                2520                2525

Gly Leu Ala Arg Phe Leu Ser Thr Val Ser Cys Ser Pro Arg Leu Trp
    2530                2535                2540

Val Val Thr Arg Gly Ala Cys Ile Val Gly Asp Glu Pro Ala Ile Ala
2545                2550                2555                2560

Pro Cys Gln Ala Ala Leu Trp Gly Met Gly Arg Val Ala Ala Leu Glu
            2565                2570                2575

His Pro Gly Ala Trp Gly Gly Leu Val Asp Leu Asp Pro Arg Ala Ser
```

```
                  2580                2585                2590
Pro Pro Gln Ala Ser Pro Ile Asp Gly Glu Met Leu Val Thr Glu Leu
         2595                2600                2605

Leu Ser Gln Glu Thr Glu Asp Gln Leu Ala Phe Arg His Gly Arg Arg
    2610                2615                2620

His Ala Ala Arg Leu Val Ala Ala Pro Pro Gln Gly Gln Ala Ala Pro
2625                2630                2635                2640

Val Ser Leu Ser Ala Glu Ala Ser Tyr Leu Val Thr Gly Gly Leu Gly
         2645                2650                2655

Gly Leu Gly Leu Ile Val Ala Gln Trp Leu Val Glu Leu Gly Ala Arg
             2660                2665                2670

His Leu Val Leu Thr Ser Arg Arg Gly Leu Pro Asp Arg Gln Ala Trp
    2675                2680                2685

Cys Glu Gln Gln Pro Pro Glu Ile Arg Ala Arg Ile Ala Ala Val Glu
         2690                2695                2700

Ala Leu Glu Ala Arg Gly Ala Arg Val Thr Val Ala Ala Val Asp Val
2705                2710                2715                2720

Ala Asp Val Glu Pro Met Thr Ala Leu Val Ser Ser Val Glu Pro Pro
         2725                2730                2735

Leu Arg Gly Val Val His Ala Ala Gly Val Ser Val Met Arg Pro Leu
         2740                2745                2750

Ala Glu Thr Asp Glu Thr Leu Leu Glu Ser Val Leu Arg Pro Lys Val
         2755                2760                2765

Ala Gly Ser Trp Leu Leu His Arg Leu Leu His Gly Arg Pro Leu Asp
    2770                2775                2780

Leu Phe Val Leu Phe Ser Ser Gly Ala Ala Val Trp Gly Ser His Ser
2785                2790                2795                2800

Gln Gly Ala Tyr Ala Ala Ala Asn Ala Phe Leu Asp Gly Leu Ala His
             2805                2810                2815

Leu Arg Arg Ser Gln Ser Leu Pro Ala Leu Ser Val Ala Trp Gly Leu
         2820                2825                2830

Trp Ala Glu Gly Gly Met Ala Asp Ala Glu Ala His Ala Arg Leu Ser
         2835                2840                2845

Asp Ile Gly Val Leu Pro Met Ser Thr Ser Ala Ala Leu Ser Ala Leu
    2850                2855                2860

Gln Arg Leu Val Glu Thr Gly Ala Ala Gln Arg Thr Val Thr Arg Met
2865                2870                2875                2880

Asp Trp Ala Arg Phe Ala Pro Val Tyr Thr Ala Arg Gly Arg Arg Asn
             2885                2890                2895

Leu Leu Ser Ala Leu Val Ala Gly Arg Asp Ile Ile Ala Pro Ser Pro
         2900                2905                2910

Pro Ala Ala Ala Thr Arg Asn Trp Arg Gly Leu Ser Val Ala Glu Ala
         2915                2920                2925

Arg Val Ala Leu His Glu Ile Val His Gly Ala Val Ala Arg Val Leu
    2930                2935                2940

Gly Phe Leu Asp Pro Ser Ala Leu Asp Pro Gly Met Gly Phe Asn Glu
2945                2950                2955                2960

Gln Gly Leu Asp Ser Leu Met Ala Val Glu Ile Arg Asn Leu Leu Gln
             2965                2970                2975

Ala Glu Leu Asp Val Arg Leu Ser Thr Thr Leu Ala Phe Asp His Pro
             2980                2985                2990

Thr Val Gln Arg Leu Val Glu His Leu Leu Val Asp Val Leu Lys Leu
         2995                3000                3005
```

-continued

```
Glu Asp Arg Ser Asp Thr Gln His Val Arg Ser Leu Ala Ser Asp Glu
    3010                3015                3020
Pro Ile Ala Ile Val Gly Ala Ala Cys Arg Phe Pro Gly Gly Val Glu
3025                3030                3035                3040
Asp Leu Glu Ser Tyr Trp Gln Leu Leu Ala Glu Gly Val Val Ser
            3045                3050                3055
Ala Glu Val Pro Ala Asp Arg Trp Asp Ala Ala Asp Trp Tyr Asp Pro
            3060                3065                3070
Asp Pro Glu Ile Pro Gly Arg Thr Tyr Val Thr Lys Gly Ala Phe Leu
        3075                3080                3085
Arg Asp Leu Gln Arg Leu Asp Ala Thr Phe Phe Arg Ile Ser Pro Arg
    3090                3095                3100
Glu Ala Met Ser Leu Asp Pro Gln Gln Arg Leu Leu Leu Glu Val Ser
3105                3110                3115                3120
Trp Glu Ala Leu Glu Ser Ala Gly Ile Ala Pro Asp Thr Leu Arg Asp
            3125                3130                3135
Ser Pro Thr Gly Val Phe Val Gly Ala Gly Pro Asn Glu Tyr Tyr Thr
            3140                3145                3150
Gln Arg Leu Arg Gly Phe Thr Asp Gly Ala Ala Gly Leu Tyr Gly Gly
        3155                3160                3165
Thr Gly Asn Met Leu Ser Val Thr Ala Gly Arg Leu Ser Phe Phe Leu
    3170                3175                3180
Gly Leu His Gly Pro Thr Leu Ala Met Asp Thr Ala Cys Ser Ser Ser
3185                3190                3195                3200
Leu Val Ala Leu His Leu Ala Cys Gln Ser Leu Arg Leu Gly Glu Cys
            3205                3210                3215
Asp Gln Ala Leu Val Gly Gly Val Asn Val Leu Leu Ala Pro Glu Thr
            3220                3225                3230
Phe Val Leu Leu Ser Arg Met Arg Ala Leu Ser Pro Asp Gly Arg Cys
        3235                3240                3245
Lys Thr Phe Ser Ala Asp Ala Asp Gly Tyr Ala Arg Gly Glu Gly Cys
    3250                3255                3260
Ala Val Val Leu Lys Arg Leu Arg Asp Ala Gln Arg Ala Gly Asp
3265                3270                3275                3280
Ser Ile Leu Ala Leu Ile Arg Gly Ser Ala Val Asn His Asp Gly Pro
            3285                3290                3295
Ser Ser Gly Leu Thr Val Pro Asn Gly Pro Ala Gln Gln Ala Leu Leu
            3300                3305                3310
Arg Gln Ala Leu Ser Gln Ala Gly Val Ser Pro Val Asp Val Asp Phe
        3315                3320                3325
Val Glu Cys His Gly Thr Gly Thr Ala Leu Gly Asp Pro Ile Glu Val
    3330                3335                3340
Gln Ala Leu Ser Glu Val Tyr Gly Pro Gly Arg Ser Gly Asp Arg Pro
3345                3350                3355                3360
Leu Val Leu Gly Ala Ala Lys Ala Asn Val Ala His Leu Glu Ala Ala
            3365                3370                3375
Ser Gly Leu Ala Ser Leu Leu Lys Ala Val Leu Ala Leu Arg His Glu
            3380                3385                3390
Gln Ile Pro Ala Gln Pro Glu Leu Gly Glu Leu Asn Pro His Leu Pro
        3395                3400                3405
Trp Asn Thr Leu Pro Val Ala Val Pro Arg Lys Ala Val Pro Trp Gly
    3410                3415                3420
```

-continued

```
Arg Gly Ala Arg Pro Arg Arg Ala Gly Val Ser Ala Phe Gly Leu Ser
3425                3430                3435                3440

Gly Thr Asn Val His Val Val Leu Glu Glu Ala Pro Glu Val Glu Pro
            3445                3450                3455

Ala Pro Ala Ala Pro Ala Arg Pro Val Glu Leu Val Val Leu Ser Ala
        3460                3465                3470

Lys Ser Ala Ala Ala Leu Asp Ala Ala Ala Arg Leu Ser Ala His
    3475                3480                3485

Leu Ser Ala His Pro Glu Leu Ser Leu Gly Asp Val Ala Phe Ser Leu
3490                3495                3500

Ala Thr Thr Arg Ser Pro Met Glu His Arg Leu Ala Ile Ala Thr Thr
3505                3510                3515                3520

Ser Arg Glu Ala Leu Arg Gly Ala Leu Asp Ala Ala Ala Gln Gln Lys
        3525                3530                3535

Thr Pro Gln Gly Ala Val Arg Gly Lys Ala Val Ser Ser Arg Gly Lys
            3540                3545                3550

Leu Ala Phe Leu Phe Thr Gly Gln Gly Ala Gln Met Pro Gly Met Gly
        3555                3560                3565

Arg Gly Leu Tyr Glu Thr Trp Pro Ala Phe Arg Glu Ala Phe Asp Arg
    3570                3575                3580

Cys Val Ala Leu Phe Asp Arg Glu Ile Asp Gln Pro Leu Arg Glu Val
3585                3590                3595                3600

Met Trp Ala Ala Pro Gly Leu Ala Gln Ala Ala Arg Leu Asp Gln Thr
            3605                3610                3615

Ala Tyr Ala Gln Pro Ala Leu Phe Ala Leu Glu Tyr Ala Leu Ala Ala
        3620                3625                3630

Leu Trp Arg Ser Trp Gly Val Glu Pro His Val Leu Leu Gly His Ser
    3635                3640                3645

Ile Gly Glu Leu Val Ala Ala Cys Val Ala Gly Val Phe Ser Leu Glu
    3650                3655                3660

Asp Ala Val Arg Leu Val Ala Ala Arg Gly Arg Leu Met Gln Ala Leu
3665                3670                3675                3680

Pro Ala Gly Gly Ala Met Val Ala Ile Ala Ala Ser Glu Ala Glu Val
            3685                3690                3695

Ala Ala Ser Val Ala Pro His Ala Ala Thr Val Ser Ile Ala Ala Val
            3700                3705                3710

Asn Gly Pro Asp Ala Val Val Ile Ala Gly Ala Glu Val Gln Val Leu
        3715                3720                3725

Ala Leu Gly Ala Thr Phe Ala Ala Arg Gly Ile Arg Thr Lys Arg Leu
    3730                3735                3740

Ala Val Ser His Ala Phe His Ser Pro Leu Met Asp Pro Met Leu Glu
    3745                3750                3755                3760

Asp Phe Gln Arg Val Ala Ala Thr Ile Ala Tyr Arg Ala Pro Asp Arg
            3765                3770                3775

Pro Val Val Ser Asn Val Thr Gly His Val Ala Gly Pro Glu Ile Ala
            3780                3785                3790

Thr Pro Glu Tyr Trp Val Arg His Val Arg Ser Ala Val Arg Phe Gly
        3795                3800                3805

Asp Gly Ala Lys Ala Leu His Ala Ala Gly Ala Ala Thr Phe Val Glu
    3810                3815                3820

Val Gly Pro Lys Pro Val Leu Leu Gly Leu Leu Pro Ala Cys Leu Gly
3825                3830                3835                3840

Glu Ala Asp Ala Val Leu Val Pro Ser Leu Arg Ala Asp Arg Ser Glu
```

-continued

```
                  3845              3850              3855

Cys Glu Val Val Leu Ala Ala Leu Gly Ala Trp Tyr Ala Trp Gly Gly
                      3860              3865              3870

Ala Leu Asp Trp Lys Gly Val Phe Pro Asp Gly Ala Arg Arg Val Ala
                      3875              3880              3885

Leu Pro Met Tyr Pro Trp Gln Arg Glu Arg His Trp Met Asp Leu Thr
                      3890              3895              3900

Pro Arg Ser Ala Ala Pro Ala Gly Ile Ala Gly Arg Trp Pro Leu Ala
      3905              3910              3915              3920

Gly Val Gly Leu Cys Met Pro Gly Ala Val Leu His His Val Leu Ser
                      3925              3930              3935

Ile Gly Pro Arg His Gln Pro Phe Leu Gly Asp His Leu Val Phe Gly
                      3940              3945              3950

Lys Val Val Pro Gly Ala Phe His Val Ala Val Ile Leu Ser Ile
                      3955              3960              3965

Ala Ala Glu Arg Trp Pro Glu Arg Ala Ile Glu Leu Thr Gly Val Glu
                      3970              3975              3980

Phe Leu Lys Ala Ile Ala Met Glu Pro Asp Gln Glu Val Glu Leu His
      3985              3990              3995              4000

Ala Val Leu Thr Pro Glu Ala Ala Gly Asp Gly Tyr Leu Phe Glu Leu
                      4005              4010              4015

Ala Thr Leu Ala Ala Pro Glu Thr Glu Arg Arg Trp Thr Thr His Ala
                      4020              4025              4030

Arg Gly Arg Val Gln Pro Thr Asp Gly Ala Pro Gly Ala Leu Pro Arg
                      4035              4040              4045

Leu Glu Val Leu Glu Asp Arg Ala Ile Gln Pro Leu Asp Phe Ala Gly
      4050              4055              4060

Phe Leu Asp Arg Leu Ser Ala Val Arg Ile Gly Trp Gly Pro Leu Trp
      4065              4070              4075              4080

Arg Trp Leu Gln Asp Gly Arg Val Gly Asp Glu Ala Ser Leu Ala Thr
                      4085              4090              4095

Leu Val Pro Thr Tyr Pro Asn Ala His Asp Val Ala Pro Leu His Pro
                      4100              4105              4110

Ile Leu Leu Asp Asn Gly Phe Ala Val Ser Leu Leu Ser Thr Arg Ser
                      4115              4120              4125

Glu Pro Glu Asp Asp Gly Thr Pro Pro Leu Pro Phe Ala Val Glu Arg
                      4130              4135              4140

Val Arg Trp Trp Arg Ala Pro Val Gly Arg Val Arg Cys Gly Gly Val
      4145              4150              4155              4160

Pro Arg Ser Gln Ala Phe Gly Val Ser Ser Phe Val Leu Val Asp Glu
                      4165              4170              4175

Thr Gly Glu Val Val Ala Glu Val Glu Gly Phe Val Cys Arg Arg Ala
                      4180              4185              4190

Pro Arg Glu Val Phe Leu Arg Gln Glu Ser Gly Ala Ser Thr Ala Ala
                      4195              4200              4205

Leu Tyr Arg Leu Asp Trp Pro Glu Ala Pro Leu Pro Asp Ala Pro Ala
                      4210              4215              4220

Glu Arg Ile Glu Glu Ser Trp Val Val Ala Ala Pro Gly Ser Glu
      4225              4230              4235              4240

Met Ala Ala Ala Leu Ala Thr Arg Leu Asn Arg Cys Val Leu Ala Glu
                      4245              4250              4255

Pro Lys Gly Leu Glu Ala Ala Leu Ala Gly Val Ser Pro Ala Gly Val
                      4260              4265              4270
```

-continued

```
Ile Cys Leu Trp Glu Ala Gly Ala His Glu Ala Pro Ala Ala Ala
    4275            4280            4285

Gln Arg Val Ala Thr Glu Gly Leu Ser Val Val Gln Ala Leu Arg Asp
    4290            4295            4300

Arg Ala Val Arg Leu Trp Trp Val Thr Met Gly Ala Val Ala Val Glu
4305            4310            4315            4320

Ala Gly Glu Arg Val Gln Val Ala Thr Ala Pro Val Trp Gly Leu Gly
            4325            4330            4335

Arg Thr Val Met Gln Glu Arg Pro Glu Leu Ser Cys Thr Leu Val Asp
            4340            4345            4350

Leu Glu Pro Glu Ala Asp Ala Ala Arg Ser Ala Asp Val Leu Leu Arg
    4355            4360            4365

Glu Leu Gly Arg Ala Asp Asp Glu Thr Gln Val Ala Phe Arg Ser Gly
    4370            4375            4380

Lys Arg Arg Val Ala Arg Leu Val Lys Ala Thr Thr Pro Glu Gly Leu
4385            4390            4395            4400

Leu Val Pro Asp Ala Glu Ser Tyr Arg Leu Glu Ala Gly Gln Lys Gly
            4405            4410            4415

Thr Leu Asp Gln Leu Arg Leu Ala Pro Ala Gln Arg Arg Ala Pro Gly
            4420            4425            4430

Pro Gly Glu Val Glu Ile Lys Val Thr Ala Ser Gly Leu Asn Phe Arg
    4435            4440            4445

Thr Val Leu Ala Val Leu Gly Met Tyr Pro Gly Asp Ala Gly Pro Met
    4450            4455            4460

Gly Gly Asp Cys Ala Gly Val Ala Thr Ala Val Gly Gln Gly Val Arg
4465            4470            4475            4480

His Val Ala Val Gly Asp Ala Val Met Thr Leu Gly Thr Leu His Arg
            4485            4490            4495

Phe Val Thr Val Asp Ala Arg Leu Val Val Arg Gln Pro Ala Gly Leu
            4500            4505            4510

Thr Pro Ala Gln Ala Ala Thr Val Pro Val Ala Phe Leu Thr Ala Trp
    4515            4520            4525

Leu Ala Leu His Asp Leu Gly Asn Leu Arg Arg Gly Glu Arg Val Leu
    4530            4535            4540

Ile His Ala Ala Ala Gly Gly Val Gly Met Ala Ala Val Gln Ile Ala
4545            4550            4555            4560

Arg Trp Ile Gly Ala Glu Val Phe Ala Thr Ala Ser Pro Ser Lys Trp
            4565            4570            4575

Ala Ala Val Gln Ala Met Gly Val Pro Arg Thr His Ile Ala Ser Ser
            4580            4585            4590

Arg Thr Leu Glu Phe Ala Glu Thr Phe Arg Gln Val Thr Gly Gly Arg
    4595            4600            4605

Gly Val Asp Val Val Leu Asn Ala Leu Ala Gly Glu Phe Val Asp Ala
    4610            4615            4620

Ser Leu Ser Leu Leu Ser Thr Gly Gly Arg Phe Leu Glu Met Gly Lys
4625            4630            4635            4640

Thr Asp Ile Arg Asp Arg Ala Ala Val Ala Ala Ala His Pro Gly Val
            4645            4650            4655

Arg Tyr Arg Val Phe Asp Ile Leu Glu Leu Ala Pro Asp Arg Thr Arg
            4660            4665            4670

Glu Ile Leu Glu Arg Val Val Glu Gly Phe Ala Ala Gly His Leu Arg
    4675            4680            4685
```

-continued

```
Ala Leu Pro Val His Ala Phe Ala Ile Thr Lys Ala Glu Ala Ala Phe
    4690                4695                4700

Arg Phe Met Ala Gln Ala Arg His Gln Gly Lys Val Val Leu Leu Pro
4705                4710                4715                4720

Ala Pro Ser Ala Ala Pro Leu Ala Pro Thr Gly Thr Val Leu Leu Thr
                4725                4730                4735

Gly Gly Leu Gly Ala Leu Gly Leu His Val Ala Arg Trp Leu Ala Gln
                4740                4745                4750

Gln Gly Val Pro His Met Val Leu Thr Gly Arg Arg Gly Leu Asp Thr
                4755                4760                4765

Pro Gly Ala Ala Lys Ala Val Ala Glu Ile Glu Ala Leu Gly Ala Arg
                4770                4775                4780

Val Thr Ile Ala Ala Ser Asp Val Ala Asp Arg Asn Ala Leu Glu Ala
4785                4790                4795                4800

Val Leu Gln Ala Ile Pro Ala Glu Trp Pro Leu Gln Gly Val Ile His
                4805                4810                4815

Ala Ala Gly Ala Leu Asp Asp Gly Val Leu Asp Glu Gln Thr Thr Asp
                4820                4825                4830

Arg Phe Ser Arg Val Leu Ala Pro Lys Val Thr Gly Ala Trp Asn Leu
                4835                4840                4845

His Glu Leu Thr Ala Gly Asn Asp Leu Ala Phe Phe Val Leu Phe Ser
                4850                4855                4860

Ser Met Ser Gly Leu Leu Gly Ser Ala Gly Gln Ser Asn Tyr Ala Ala
4865                4870                4875                4880

Ala Asn Thr Phe Leu Asp Ala Leu Ala Ala His Arg Arg Ala Glu Gly
                4885                4890                4895

Leu Ala Ala Gln Ser Leu Ala Trp Gly Pro Trp Ser Asp Gly Gly Met
                4900                4905                4910

Ala Ala Gly Leu Ser Ala Ala Leu Gln Ala Arg Leu Ala Arg His Gly
                4915                4920                4925

Met Gly Ala Leu Ser Pro Ala Gln Gly Thr Ala Leu Leu Gly Gln Ala
                4930                4935                4940

Leu Ala Arg Pro Glu Thr Gln Leu Gly Ala Met Ser Leu Asp Val Arg
4945                4950                4955                4960

Ala Ala Ser Gln Ala Ser Gly Ala Ala Val Pro Pro Val Trp Arg Ala
                4965                4970                4975

Leu Val Arg Ala Glu Ala Arg His Thr Ala Gly Ala Gln Gly Ala
                4980                4985                4990

Leu Ala Ala Arg Leu Gly Ala Leu Pro Glu Ala Arg Arg Ala Asp Glu
                4995                5000                5005

Val Arg Lys Val Val Gln Ala Glu Ile Ala Arg Val Leu Ser Trp Ser
    5010                5015                5020

Ala Ala Ser Ala Val Pro Val Asp Arg Pro Leu Ser Asp Leu Gly Leu
5025                5030                5035                5040

Asp Ser Leu Thr Ala Val Glu Leu Arg Asn Val Leu Gly Gln Arg Val
                5045                5050                5055

Gly Ala Thr Leu Pro Ala Thr Leu Ala Phe Asp His Pro Thr Val Asp
                5060                5065                5070

Ala Leu Thr Arg Trp Leu Leu Asp Lys Val Leu Ala Val Ala Glu Pro
                5075                5080                5085

Ser Val Ser Ser Ala Lys Ser Ser Pro Gln Val Ala Leu Asp Glu Pro
    5090                5095                5100

Ile Ala Ile Ile Gly Ile Gly Cys Arg Phe Pro Gly Gly Val Ala Asp
```

```
                5105                5110                5115                5120
Pro Glu Ser Phe Trp Arg Leu Leu Glu Glu Gly Ser Asp Ala Val Val
                    5125                5130                5135
Glu Val Pro His Glu Arg Trp Asp Ile Asp Ala Phe Tyr Asp Pro Asp
            5140                5145                5150
Pro Asp Val Arg Gly Lys Met Thr Thr Arg Phe Gly Gly Phe Leu Ser
        5155                5160                5165
Asp Ile Asp Arg Phe Asp Pro Ala Phe Phe Gly Ile Ser Pro Arg Glu
    5170                5175                5180
Ala Thr Thr Met Asp Pro Gln Gln Arg Leu Leu Leu Glu Thr Ser Trp
5185                5190                5195                5200
Glu Ala Phe Glu Arg Ala Gly Ile Leu Pro Glu Arg Leu Met Gly Ser
                5205                5210                5215
Asp Thr Gly Val Phe Val Gly Leu Phe Tyr Gln Glu Tyr Ala Ala Leu
            5220                5225                5230
Ala Gly Gly Ile Glu Ala Phe Asp Gly Tyr Leu Gly Thr Gly Thr Thr
        5235                5240                5245
Ala Ser Val Ala Ser Gly Arg Ile Ser Tyr Val Leu Gly Leu Lys Gly
    5250                5255                5260
Pro Ser Leu Thr Val Asp Thr Ala Cys Ser Ser Ser Leu Val Ala Val
5265                5270                5275                5280
His Leu Ala Cys Gln Ala Leu Arg Arg Gly Glu Cys Ser Val Ala Leu
                5285                5290                5295
Ala Gly Gly Val Ala Leu Met Leu Thr Pro Ala Thr Phe Val Glu Phe
            5300                5305                5310
Ser Arg Leu Arg Gly Leu Ala Pro Asp Gly Arg Cys Lys Ser Phe Ser
        5315                5320                5325
Ala Ala Ala Asp Gly Val Gly Trp Ser Glu Gly Cys Ala Met Leu Leu
    5330                5335                5340
Leu Lys Pro Leu Arg Asp Ala Gln Arg Asp Gly Asp Pro Ile Leu Ala
5345                5350                5355                5360
Val Ile Arg Gly Thr Ala Val Asn Gln Asp Gly Arg Ser Asn Gly Leu
                5365                5370                5375
Thr Ala Pro Asn Gly Ser Ser Gln Gln Glu Val Ile Arg Arg Ala Leu
            5380                5385                5390
Glu Gln Ala Gly Leu Ala Pro Ala Asp Val Ser Tyr Val Glu Cys His
        5395                5400                5405
Gly Thr Gly Thr Thr Leu Gly Asp Pro Ile Glu Val Gln Ala Leu Gly
    5410                5415                5420
Ala Val Leu Ala Gln Gly Arg Pro Ser Asp Arg Pro Leu Val Ile Gly
5425                5430                5435                5440
Ser Val Lys Ser Asn Ile Gly His Thr Gln Ala Ala Ala Gly Val Ala
                5445                5450                5455
Gly Val Ile Lys Val Ala Leu Ala Leu Glu Arg Gly Leu Ile Pro Arg
            5460                5465                5470
Ser Leu His Phe Asp Ala Pro Asn Pro His Ile Pro Trp Ser Glu Leu
        5475                5480                5485
Ala Val Gln Val Ala Ala Lys Pro Val Glu Trp Thr Arg Asn Gly Val
    5490                5495                5500
Pro Arg Arg Ala Gly Val Ser Ser Phe Gly Val Ser Gly Thr Asn Ala
5505                5510                5515                5520
His Val Val Leu Glu Glu Ala Pro Ala Ala Ala Phe Ala Pro Ala Ala
                5525                5530                5535
```

-continued

Ala Arg Ser Ala Glu Leu Phe Val Leu Ser Ala Lys Ser Ala Ala Ala
         5540                5545                5550

Leu Asp Ala Gln Ala Ala Arg Leu Ser Ala His Val Val Ala His Pro
         5555                5560                5565

Glu Leu Gly Leu Gly Asp Leu Ala Phe Ser Leu Ala Thr Thr Arg Ser
         5570                5575                5580

Pro Met Thr Tyr Arg Leu Ala Val Ala Ala Thr Ser Arg Glu Ala Leu
5585                5590                5595                5600

Ser Ala Ala Leu Asp Thr Ala Ala Gln Gly Gln Ala Pro Pro Ala Ala
         5605                5610                5615

Ala Arg Gly His Ala Ser Thr Gly Ser Ala Pro Lys Val Val Phe Val
         5620                5625                5630

Phe Pro Gly Gln Gly Ser Gln Trp Leu Gly Met Gly Gln Lys Leu Leu
         5635                5640                5645

Ser Glu Glu Pro Val Phe Arg Asp Ala Leu Ser Ala Cys Asp Arg Ala
         5650                5655                5660

Ile Gln Ala Glu Ala Gly Trp Ser Leu Leu Ala Glu Leu Ala Ala Asp
5665                5670                5675                5680

Glu Thr Thr Ser Gln Leu Gly Arg Ile Asp Val Val Gln Pro Ala Leu
         5685                5690                5695

Phe Ala Ile Glu Val Ala Leu Ser Ala Leu Trp Arg Ser Trp Gly Val
         5700                5705                5710

Glu Pro Asp Ala Val Val Gly His Ser Met Gly Glu Val Ala Ala Ala
         5715                5720                5725

His Val Ala Gly Ala Leu Ser Leu Glu Asp Ala Val Ala Ile Ile Cys
         5730                5735                5740

Arg Arg Ser Leu Leu Leu Arg Arg Ile Ser Gly Gln Gly Glu Met Ala
5745                5750                5755                5760

Val Val Glu Leu Ser Leu Ala Glu Ala Glu Ala Ala Leu Leu Gly Tyr
         5765                5770                5775

Glu Asp Arg Leu Ser Val Ala Val Ser Asn Ser Pro Arg Ser Thr Val
         5780                5785                5790

Leu Ala Gly Glu Pro Ala Ala Leu Ala Glu Val Leu Ala Ile Leu Ala
         5795                5800                5805

Ala Lys Gly Val Phe Cys Arg Arg Val Lys Val Asp Val Ala Ser His
         5810                5815                5820

Ser Pro Gln Ile Asp Pro Leu Arg Asp Glu Leu Leu Ala Ala Leu Gly
5825                5830                5835                5840

Glu Leu Glu Pro Arg Gln Ala Thr Val Ser Met Arg Ser Thr Val Thr
         5845                5850                5855

Ser Thr Ile Met Ala Gly Pro Glu Leu Val Ala Ser Tyr Trp Ala Asp
         5860                5865                5870

Asn Val Arg Gln Pro Val Arg Phe Ala Glu Ala Val Gln Ser Leu Met
         5875                5880                5885

Glu Asp Gly His Gly Leu Phe Val Glu Met Ser Pro His Pro Ile Leu
         5890                5895                5900

Thr Thr Ser Val Glu Glu Ile Arg Arg Ala Thr Lys Arg Glu Gly Val
5905                5910                5915                5920

Ala Val Gly Ser Leu Arg Arg Gly Gln Asp Glu Arg Leu Ser Met Leu
         5925                5930                5935

Glu Ala Leu Gly Ala Leu Trp Val His Gly Gln Ala Val Gly Trp Glu
         5940                5945                5950

-continued

```
Arg Leu Phe Ser Ala Gly Gly Ala Gly Leu Arg Arg Val Pro Leu Pro
    5955                5960                5965

Thr Tyr Pro Trp Gln Arg Glu Arg Tyr Trp Val Asp Ala Pro Thr Gly
    5970                5975                5980

Gly Ala Ala Gly Gly Ser Arg Phe Ala His Ala Gly Ser His Pro Leu
5985                5990                5995                6000

Leu Gly Glu Met Gln Thr Leu Ser Thr Gln Arg Ser Thr Arg Val Trp
    6005                6010                6015

Glu Thr Thr Leu Asp Leu Lys Arg Leu Pro Trp Leu Gly Asp His Arg
    6020                6025                6030

Val Gln Gly Ala Val Val Phe Pro Gly Ala Ala Tyr Leu Glu Met Ala
    6035                6040                6045

Leu Ser Ser Gly Ala Glu Ala Leu Gly Asp Gly Pro Leu Gln Val Ser
    6050                6055                6060

Asp Val Val Leu Ala Glu Ala Leu Ala Phe Ala Asp Asp Thr Pro Ala
6065                6070                6075                6080

Ala Val Gln Val Met Ala Thr Glu Glu Arg Pro Gly Arg Leu Gln Phe
    6085                6090                6095

His Val Ala Ser Arg Val Pro Gly His Gly Gly Ala Ala Phe Arg Ser
    6100                6105                6110

His Ala Arg Gly Val Leu Arg Gln Ile Glu Arg Ala Glu Val Pro Ala
    6115                6120                6125

Arg Leu Asp Leu Ala Ala Leu Arg Ala Arg Leu Gln Ala Ser Ala Pro
    6130                6135                6140

Ala Ala Ala Thr Tyr Ala Ala Leu Ala Glu Met Gly Leu Glu Tyr Gly
6145                6150                6155                6160

Pro Ala Phe Gln Gly Leu Val Glu Leu Trp Arg Gly Glu Gly Glu Ala
    6165                6170                6175

Leu Gly Arg Val Arg Leu Pro Glu Ala Ala Gly Ser Pro Ala Ala Cys
    6180                6185                6190

Arg Leu His Pro Ala Leu Leu Asp Ala Cys Phe His Val Ser Ser Ala
    6195                6200                6205

Phe Ala Asp Arg Gly Glu Ala Thr Pro Trp Val Pro Val Glu Ile Gly
    6210                6215                6220

Ser Leu Arg Trp Phe Gln Arg Pro Ser Gly Glu Leu Trp Cys His Ala
6225                6230                6235                6240

Arg Ser Val Ser His Gly Lys Pro Thr Pro Asp Arg Arg Ser Thr Asp
    6245                6250                6255

Phe Trp Val Val Asp Ser Thr Gly Ala Ile Val Ala Glu Ile Ser Gly
    6260                6265                6270

Leu Val Ala Gln Arg Leu Ala Gly Gly Val Arg Arg Arg Glu Glu Asp
    6275                6280                6285

Asp Trp Phe Met Glu Pro Ala Trp Glu Pro Thr Ala Val Pro Gly Ser
    6290                6295                6300

Glu Val Met Ala Gly Arg Trp Leu Leu Ile Gly Ser Gly Gly Gly Leu
6305                6310                6315                6320

Gly Ala Ala Leu His Ser Ala Leu Thr Glu Ala Gly His Ser Val Val
    6325                6330                6335

His Ala Thr Gly Arg Gly Thr Ser Ala Ala Gly Leu Gln Ala Leu Leu
    6340                6345                6350

Thr Ala Ser Phe Asp Gly Gln Ala Pro Thr Ser Val Val His Leu Gly
    6355                6360                6365

Ser Leu Asp Glu Arg Gly Val Leu Asp Ala Asp Ala Pro Phe Asp Ala
```

-continued

```
          6370               6375               6380
Asp Ala Leu Glu Glu Ser Leu Val Arg Gly Cys Asp Ser Val Leu Trp
6385               6390               6395               6400

Thr Val Gln Ala Val Ala Gly Ala Gly Phe Arg Asp Pro Pro Arg Leu
          6405               6410               6415

Trp Leu Val Thr Arg Gly Ala Gln Ala Ile Gly Ala Gly Asp Val Ser
          6420               6425               6430

Val Ala Gln Ala Pro Leu Leu Gly Leu Gly Arg Val Ile Ala Leu Glu
          6435               6440               6445

His Ala Glu Leu Arg Cys Ala Arg Ile Asp Leu Asp Pro Ala Arg Arg
          6450               6455               6460

Asp Gly Glu Val Asp Glu Leu Leu Ala Glu Leu Leu Ala Asp Asp Ala
6465               6470               6475               6480

Glu Glu Glu Val Ala Phe Arg Gly Gly Glu Arg Arg Val Ala Arg Leu
          6485               6490               6495

Val Arg Arg Leu Pro Glu Thr Asp Cys Arg Glu Lys Ile Glu Pro Ala
          6500               6505               6510

Glu Gly Arg Pro Phe Arg Leu Glu Ile Asp Gly Ser Gly Val Leu Asp
          6515               6520               6525

Asp Leu Val Leu Arg Ala Thr Glu Arg Arg Pro Pro Gly Pro Gly Glu
          6530               6535               6540

Val Glu Ile Ala Val Glu Ala Ala Gly Leu Asn Phe Leu Asp Val Met
6545               6550               6555               6560

Arg Ala Met Gly Ile Tyr Pro Gly Pro Gly Asp Gly Pro Val Ala Leu
          6565               6570               6575

Gly Ala Glu Cys Ser Gly Arg Ile Val Ala Met Gly Glu Gly Val Glu
          6580               6585               6590

Ser Leu Arg Ile Gly Gln Asp Val Val Ala Val Ala Pro Phe Ser Phe
          6595               6600               6605

Gly Thr His Val Thr Ile Asp Ala Arg Met Leu Ala Pro Arg Pro Ala
          6610               6615               6620

Ala Leu Thr Ala Ala Gln Ala Ala Ala Leu Pro Val Ala Phe Met Thr
6625               6630               6635               6640

Ala Trp Tyr Gly Leu Val His Leu Gly Arg Leu Arg Ala Gly Glu Arg
          6645               6650               6655

Val Leu Ile His Ser Ala Thr Gly Gly Thr Gly Leu Ala Ala Val Gln
          6660               6665               6670

Ile Ala Arg His Leu Gly Ala Glu Ile Phe Ala Thr Ala Gly Thr Pro
          6675               6680               6685

Glu Lys Arg Ala Trp Leu Arg Glu Gln Gly Ile Ala His Val Met Asp
          6690               6695               6700

Ser Arg Ser Leu Asp Phe Ala Glu Gln Val Leu Ala Ala Thr Lys Gly
6705               6710               6715               6720

Glu Gly Val Asp Val Val Leu Asn Ser Leu Ser Gly Ala Ala Ile Asp
          6725               6730               6735

Ala Ser Leu Ser Thr Leu Val Pro Asp Gly Arg Phe Ile Glu Leu Gly
          6740               6745               6750

Lys Thr Asp Ile Tyr Ala Asp Arg Ser Leu Gly Leu Ala His Phe Arg
          6755               6760               6765

Lys Ser Leu Ser Tyr Ser Ala Val Asp Leu Ala Gly Leu Ala Val Arg
          6770               6775               6780

Arg Pro Glu Arg Val Ala Ala Leu Leu Ala Glu Val Val Asp Leu Leu
6785               6790               6795               6800
```

-continued

Ala Arg Gly Ala Leu Gln Pro Leu Pro Val Glu Ile Phe Pro Leu Ser
            6805                6810                6815

Arg Ala Ala Asp Ala Phe Arg Lys Met Ala Gln Ala Gln His Leu Gly
            6820                6825                6830

Lys Leu Val Leu Ala Leu Glu Asp Pro Asp Val Arg Ile Arg Val Pro
            6835                6840                6845

Gly Glu Ser Gly Val Ala Ile Arg Ala Asp Gly Ala Tyr Leu Val Thr
            6850                6855                6860

Gly Gly Leu Gly Gly Leu Gly Leu Ser Val Ala Gly Trp Leu Ala Glu
6865                6870                6875                6880

Gln Gly Ala Gly His Leu Val Leu Val Gly Arg Ser Gly Ala Val Ser
            6885                6890                6895

Ala Glu Gln Gln Thr Ala Val Ala Ala Leu Glu Ala His Gly Ala Arg
            6900                6905                6910

Val Thr Val Ala Arg Ala Asp Val Ala Asp Arg Ala Gln Met Glu Arg
            6915                6920                6925

Ile Leu Arg Glu Val Thr Ala Ser Gly Met Pro Leu Arg Gly Val Val
            6930                6935                6940

His Ala Ala Gly Ile Leu Asp Asp Gly Leu Leu Met Gln Gln Thr Pro
6945                6950                6955                6960

Ala Arg Phe Arg Ala Val Met Ala Pro Lys Val Arg Gly Ala Leu His
            6965                6970                6975

Leu His Ala Leu Thr Arg Glu Ala Pro Leu Ser Phe Phe Val Leu Tyr
            6980                6985                6990

Ala Ser Gly Ala Gly Leu Leu Gly Ser Pro Gly Gln Gly Asn Tyr Ala
            6995                7000                7005

Ala Ala Asn Thr Phe Leu Asp Ala Leu Ala His His Arg Arg Ala Gln
            7010                7015                7020

Gly Leu Pro Ala Leu Ser Ile Asp Trp Gly Leu Phe Ala Asp Val Gly
7025                7030                7035                7040

Leu Ala Ala Gly Gln Gln Asn Arg Gly Ala Arg Leu Val Thr Arg Gly
            7045                7050                7055

Thr Arg Ser Leu Thr Pro Asp Glu Gly Leu Trp Ala Leu Glu Arg Leu
            7060                7065                7070

Leu Asp Gly Asp Arg Thr Gln Ala Gly Val Met Pro Phe Asp Val Arg
            7075                7080                7085

Gln Trp Val Glu Phe Tyr Pro Ala Ala Ala Ser Ser Arg Arg Leu Ser
            7090                7095                7100

Arg Leu Met Thr Ala Arg Arg Val Ala Ser Gly Arg Leu Ala Gly Asp
7105                7110                7115                7120

Arg Asp Leu Leu Glu Arg Leu Ala Thr Ala Glu Ala Gly Ala Arg Ala
            7125                7130                7135

Gly Met Leu Gln Glu Val Val Arg Ala Gln Val Ser Gln Val Leu Arg
            7140                7145                7150

Leu Ser Glu Gly Lys Leu Asp Val Asp Ala Pro Leu Thr Ser Leu Gly
            7155                7160                7165

Met Asp Ser Leu Met Gly Leu Glu Leu Arg Asn Arg Ile Glu Ala Val
            7170                7175                7180

Leu Gly Ile Thr Met Pro Ala Thr Leu Leu Trp Thr Tyr Pro Thr Val
7185                7190                7195                7200

Ala Ala Leu Ser Ala His Leu Ala Ser His Val Val Ser Thr Gly Asp
            7205                7210                7215

-continued

```
Gly Glu Ser Ala Arg Pro Pro Asp Thr Gly Ser Val Ala Pro Thr Thr
        7220                7225                7230

His Glu Val Ala Ser Leu Asp Glu Asp Gly Leu Phe Ala Leu Ile Asp
        7235                7240                7245

Glu Ser Leu Ala Arg Ala Gly Lys Arg
        7250                7255
```

<210> SEQ ID NO 6
<211> LENGTH: 3798
<212> TYPE: PRT
<213> ORGANISM: Sorangium cellulosum

<400> SEQUENCE: 6

```
Val Thr Asp Arg Glu Gly Gln Leu Leu Glu Arg Leu Arg Glu Val Thr
  1               5                  10                 15

Leu Ala Leu Arg Lys Thr Leu Asn Glu Arg Asp Thr Leu Glu Leu Glu
             20                 25                 30

Lys Thr Glu Pro Ile Ala Ile Val Gly Ile Gly Cys Arg Phe Pro Gly
         35                 40                 45

Gly Ala Gly Thr Pro Glu Ala Phe Trp Glu Leu Asp Asp Gly Arg
     50                 55                 60

Asp Ala Ile Arg Pro Leu Glu Glu Arg Trp Ala Leu Val Gly Val Asp
 65                 70                 75                 80

Pro Gly Asp Asp Val Pro Arg Trp Ala Gly Leu Leu Thr Glu Ala Ile
                 85                 90                 95

Asp Gly Phe Asp Ala Ala Phe Phe Gly Ile Ala Pro Arg Glu Ala Arg
                100                105                110

Ser Leu Asp Pro Gln His Arg Leu Leu Leu Glu Val Ala Trp Glu Gly
            115                120                125

Phe Glu Asp Ala Gly Ile Pro Pro Arg Ser Leu Val Gly Ser Arg Thr
130                135                140

Gly Val Phe Val Gly Val Cys Ala Thr Glu Tyr Leu His Ala Ala Val
145                150                155                160

Ala His Gln Pro Arg Glu Glu Arg Asp Ala Tyr Ser Thr Thr Gly Asn
            165                170                175

Met Leu Ser Ile Ala Ala Gly Arg Leu Ser Tyr Thr Leu Gly Leu Gln
            180                185                190

Gly Pro Cys Leu Thr Val Asp Thr Ala Cys Ser Ser Ser Leu Val Ala
            195                200                205

Ile His Leu Ala Cys Arg Ser Leu Arg Ala Arg Glu Ser Asp Leu Ala
        210                215                220

Leu Ala Gly Gly Val Asn Met Leu Leu Ser Pro Asp Thr Met Arg Ala
225                230                235                240

Leu Ala Arg Thr Gln Ala Leu Ser Pro Asn Gly Arg Cys Gln Thr Phe
            245                250                255

Asp Ala Ser Ala Asn Gly Phe Val Arg Gly Glu Gly Cys Gly Leu Ile
            260                265                270

Val Leu Lys Arg Leu Ser Asp Ala Arg Asp Gly Asp Arg Ile Trp
        275                280                285

Ala Leu Ile Arg Gly Ser Ala Ile Asn Gln Asp Gly Arg Ser Thr Gly
        290                295                300

Leu Thr Ala Pro Asn Val Leu Ala Gln Gly Ala Leu Leu Arg Glu Ala
305                310                315                320

Leu Arg Asn Ala Gly Val Glu Ala Glu Ala Ile Gly Tyr Ile Glu Thr
            325                330                335
```

-continued

```
His Gly Ala Ala Thr Ser Leu Gly Asp Pro Ile Glu Ile Glu Ala Leu
            340                 345                 350
Arg Ala Val Val Gly Pro Ala Arg Ala Asp Gly Ala Arg Cys Val Leu
            355                 360                 365
Gly Ala Val Lys Thr Asn Leu Gly His Leu Glu Gly Ala Ala Gly Val
            370                 375                 380
Ala Gly Leu Ile Lys Ala Thr Leu Ser Leu His His Glu Arg Ile Pro
385                 390                 395                 400
Arg Asn Leu Asn Phe Arg Thr Leu Asn Pro Arg Ile Arg Ile Glu Gly
            405                 410                 415
Thr Ala Leu Ala Leu Ala Thr Glu Pro Val Pro Trp Pro Arg Thr Gly
            420                 425                 430
Arg Thr Arg Phe Ala Gly Val Ser Ser Phe Gly Met Ser Gly Thr Asn
            435                 440                 445
Ala His Val Val Leu Glu Glu Ala Pro Ala Val Glu Pro Glu Ala Ala
            450                 455                 460
Ala Pro Glu Arg Ala Ala Glu Leu Phe Val Leu Ser Ala Lys Ser Ala
465                 470                 475                 480
Ala Ala Leu Asp Ala Gln Ala Ala Arg Leu Arg Asp His Leu Glu Lys
            485                 490                 495
His Val Glu Leu Gly Leu Gly Asp Val Ala Phe Ser Leu Ala Thr Thr
            500                 505                 510
Arg Ser Ala Met Glu His Arg Leu Ala Val Ala Ala Ser Ser Arg Glu
            515                 520                 525
Ala Leu Arg Gly Ala Leu Ser Ala Ala Ala Gln Gly His Thr Pro Pro
            530                 535                 540
Gly Ala Val Arg Gly Arg Ala Ser Gly Gly Ser Ala Pro Lys Val Val
545                 550                 555                 560
Phe Val Phe Pro Gly Gln Gly Ser Gln Trp Val Gly Met Gly Arg Lys
            565                 570                 575
Leu Met Ala Glu Glu Pro Val Phe Arg Ala Ala Leu Glu Gly Cys Asp
            580                 585                 590
Arg Ala Ile Glu Ala Glu Ala Gly Trp Ser Leu Leu Gly Glu Leu Ser
            595                 600                 605
Ala Asp Glu Ala Ala Ser Gln Leu Gly Arg Ile Asp Val Val Gln Pro
            610                 615                 620
Val Leu Phe Ala Met Glu Val Ala Leu Ser Ala Leu Trp Arg Ser Trp
625                 630                 635                 640
Gly Val Glu Pro Glu Ala Val Val Gly His Ser Met Gly Glu Val Ala
            645                 650                 655
Ala Ala His Val Ala Gly Ala Leu Ser Leu Glu Asp Ala Val Ala Ile
            660                 665                 670
Ile Cys Arg Arg Ser Arg Leu Leu Arg Arg Ile Ser Gly Gln Gly Glu
            675                 680                 685
Met Ala Leu Val Glu Leu Ser Leu Glu Glu Ala Glu Ala Ala Leu Arg
            690                 695                 700
Gly His Glu Gly Arg Leu Ser Val Ala Val Ser Asn Ser Pro Arg Ser
705                 710                 715                 720
Thr Val Leu Ala Gly Glu Pro Ala Ala Leu Ser Glu Val Leu Ala Ala
            725                 730                 735
Leu Thr Ala Lys Gly Val Phe Trp Arg Gln Val Lys Val Asp Val Ala
            740                 745                 750
```

```
Ser His Ser Pro Gln Val Asp Pro Leu Arg Glu Glu Leu Ile Ala Ala
        755                 760                 765

Leu Gly Ala Ile Arg Pro Arg Ala Ala Val Pro Met Arg Ser Thr
770                 775                 780

Val Thr Gly Gly Val Ile Ala Gly Pro Glu Leu Gly Ala Ser Tyr Trp
785                 790                 795                 800

Ala Asp Asn Leu Arg Gln Pro Val Arg Phe Ala Ala Ala Gln Ala
            805                 810                 815

Leu Leu Glu Gly Gly Pro Ala Leu Phe Ile Glu Met Ser Pro His Pro
            820                 825                 830

Ile Leu Val Pro Pro Leu Asp Glu Ile Gln Thr Ala Ala Glu Gln Gly
            835                 840                 845

Gly Ala Ala Val Gly Ser Leu Arg Arg Gly Gln Asp Glu Arg Ala Thr
850                 855                 860

Leu Leu Glu Ala Leu Gly Thr Leu Trp Ala Ser Gly Tyr Pro Val Ser
865                 870                 875                 880

Trp Ala Arg Leu Phe Pro Ala Gly Gly Arg Arg Val Pro Leu Pro Thr
                885                 890                 895

Tyr Pro Trp Gln His Glu Arg Cys Trp Ile Glu Val Glu Pro Asp Ala
            900                 905                 910

Arg Arg Leu Ala Ala Ala Asp Pro Thr Lys Asp Trp Phe Tyr Arg Thr
        915                 920                 925

Asp Trp Pro Glu Val Pro Arg Ala Ala Pro Lys Ser Glu Thr Ala His
930                 935                 940

Gly Ser Trp Leu Leu Leu Ala Asp Arg Gly Val Gly Glu Ala Val
945                 950                 955                 960

Ala Ala Ala Leu Ser Thr Arg Gly Leu Ser Cys Thr Val Leu His Ala
                965                 970                 975

Ser Ala Asp Ala Ser Thr Val Ala Glu Gln Val Ser Glu Ala Ala Ser
            980                 985                 990

Arg Arg Asn Asp Trp Gln Gly Val Leu Tyr Leu Trp Gly Leu Asp Ala
        995                 1000                1005

Val Val Asp Ala Gly Ala Ser Ala Asp Glu Val Ser Glu Ala Thr Arg
    1010                1015                1020

Arg Ala Thr Ala Pro Val Leu Gly Leu Val Arg Phe Leu Ser Ala Ala
1025                1030                1035                1040

Pro His Pro Pro Arg Phe Trp Val Val Thr Arg Gly Ala Cys Thr Val
                1045                1050                1055

Gly Gly Glu Pro Glu Ala Ser Leu Cys Gln Ala Ala Leu Trp Gly Leu
            1060                1065                1070

Ala Arg Val Ala Ala Leu Glu His Pro Ala Ala Trp Gly Gly Leu Val
        1075                1080                1085

Asp Leu Asp Pro Gln Lys Ser Pro Thr Glu Ile Glu Pro Leu Val Ala
        1090                1095                1100

Glu Leu Leu Ser Pro Asp Ala Glu Asp Gln Leu Ala Phe Arg Ser Gly
1105                1110                1115                1120

Arg Arg His Ala Ala Arg Leu Val Ala Ala Pro Pro Glu Gly Asp Val
            1125                1130                1135

Ala Pro Ile Ser Leu Ser Ala Glu Gly Ser Tyr Leu Val Thr Gly Gly
            1140                1145                1150

Leu Gly Gly Leu Gly Leu Leu Val Ala Arg Trp Leu Val Glu Arg Gly
        1155                1160                1165

Ala Arg His Leu Val Leu Thr Ser Arg His Gly Leu Pro Glu Arg Gln
```

-continued

```
              1170                1175                1180
Ala Ser Gly Gly Glu Gln Pro Pro Glu Ala Arg Ala Arg Ile Ala Ala
1185                1190                1195                1200

Val Glu Gly Leu Glu Ala Gln Gly Ala Arg Val Thr Val Ala Ala Val
                1205                1210                1215

Asp Val Ala Glu Ala Asp Pro Met Thr Ala Leu Leu Ala Ala Ile Glu
            1220                1225                1230

Pro Pro Leu Arg Gly Val Val His Ala Ala Gly Val Phe Pro Val Arg
        1235                1240                1245

His Leu Ala Glu Thr Asp Glu Ala Leu Leu Glu Ser Val Leu Arg Pro
1250                1255                1260

Lys Val Ala Gly Ser Trp Leu Leu His Arg Leu Leu Arg Asp Arg Pro
1265                1270                1275                1280

Leu Asp Leu Phe Val Leu Phe Ser Ser Gly Ala Ala Val Trp Gly Gly
                1285                1290                1295

Lys Gly Gln Gly Ala Tyr Ala Ala Ala Asn Ala Phe Leu Asp Gly Leu
            1300                1305                1310

Ala His His Arg Arg Ala His Ser Leu Pro Ala Leu Ser Leu Ala Trp
        1315                1320                1325

Gly Leu Trp Ala Glu Gly Gly Met Val Asp Ala Lys Ala His Ala Arg
    1330                1335                1340

Leu Ser Asp Ile Gly Val Leu Pro Met Ala Thr Gly Pro Ala Leu Ser
1345                1350                1355                1360

Ala Leu Glu Arg Leu Val Asn Thr Ser Ala Val Gln Arg Ser Val Thr
                1365                1370                1375

Arg Met Asp Trp Ala Arg Phe Ala Pro Val Tyr Ala Ala Arg Gly Arg
            1380                1385                1390

Arg Asn Leu Leu Ser Ala Leu Val Ala Glu Asp Glu Arg Ala Ala Ser
        1395                1400                1405

Pro Pro Val Pro Thr Ala Asn Arg Ile Trp Arg Gly Leu Ser Val Ala
    1410                1415                1420

Glu Ser Arg Ser Ala Leu Tyr Glu Leu Val Arg Gly Ile Val Ala Arg
1425                1430                1435                1440

Val Leu Gly Phe Ser Asp Pro Gly Ala Leu Asp Val Gly Arg Gly Phe
                1445                1450                1455

Ala Glu Gln Gly Leu Asp Ser Leu Met Ala Leu Glu Ile Arg Asn Arg
            1460                1465                1470

Leu Gln Arg Glu Leu Gly Glu Arg Leu Ser Ala Thr Leu Ala Phe Asp
        1475                1480                1485

His Pro Thr Val Glu Arg Leu Val Ala His Leu Leu Thr Asp Val Leu
    1490                1495                1500

Lys Leu Glu Asp Arg Ser Asp Thr Arg His Ile Arg Ser Val Ala Ala
1505                1510                1515                1520

Asp Asp Asp Ile Ala Ile Val Gly Ala Ala Cys Arg Phe Pro Gly Gly
                1525                1530                1535

Asp Glu Gly Leu Glu Thr Tyr Trp Arg His Leu Ala Glu Gly Met Val
            1540                1545                1550

Val Ser Thr Glu Val Pro Ala Asp Arg Trp Arg Ala Ala Asp Trp Tyr
        1555                1560                1565

Asp Pro Asp Pro Glu Val Pro Gly Arg Thr Tyr Val Ala Lys Gly Ala
    1570                1575                1580

Phe Leu Arg Asp Val Arg Ser Leu Asp Ala Ala Phe Phe Ala Ile Ser
1585                1590                1595                1600
```

-continued

Pro Arg Glu Ala Met Ser Leu Asp Pro Gln Gln Arg Leu Leu Leu Glu
                1605                1610                1615

Val Ser Trp Glu Ala Ile Glu Arg Ala Gly Gln Asp Pro Met Ala Leu
            1620                1625                1630

Arg Glu Ser Ala Thr Gly Val Phe Val Gly Met Ile Gly Ser Glu His
        1635                1640                1645

Ala Glu Arg Val Gln Gly Leu Asp Asp Ala Ala Leu Leu Tyr Gly
    1650                1655                1660

Thr Thr Gly Asn Leu Leu Ser Val Ala Ala Gly Arg Leu Ser Phe Phe
1665                1670                1675                1680

Leu Gly Leu His Gly Pro Thr Met Thr Val Asp Thr Ala Cys Ser Ser
                1685                1690                1695

Ser Leu Val Ala Leu His Leu Ala Cys Gln Ser Leu Arg Leu Gly Glu
            1700                1705                1710

Cys Asp Gln Ala Leu Ala Gly Gly Ser Ser Val Leu Leu Ser Pro Arg
        1715                1720                1725

Ser Phe Val Ala Ala Ser Arg Met Arg Leu Leu Ser Pro Asp Gly Arg
    1730                1735                1740

Cys Lys Thr Phe Ser Ala Ala Ala Asp Gly Phe Ala Arg Ala Glu Gly
1745                1750                1755                1760

Cys Ala Val Val Val Leu Lys Arg Leu Arg Asp Ala Gln Arg Asp Arg
                1765                1770                1775

Asp Pro Ile Leu Ala Val Val Arg Ser Thr Ala Ile Asn His Asp Gly
            1780                1785                1790

Pro Ser Ser Gly Leu Thr Val Pro Ser Gly Pro Ala Gln Gln Ala Leu
        1795                1800                1805

Leu Arg Gln Ala Leu Ala Gln Ala Gly Val Ala Pro Ala Glu Val Asp
    1810                1815                1820

Phe Val Glu Cys His Gly Thr Gly Thr Ala Leu Gly Asp Pro Ile Glu
1825                1830                1835                1840

Val Gln Ala Leu Gly Ala Val Tyr Gly Arg Gly Arg Pro Ala Glu Arg
                1845                1850                1855

Pro Leu Trp Leu Gly Ala Val Lys Ala Asn Leu Gly His Leu Glu Ala
            1860                1865                1870

Ala Ala Gly Leu Ala Gly Val Leu Lys Val Leu Leu Ala Leu Glu His
        1875                1880                1885

Glu Gln Ile Pro Ala Gln Pro Glu Leu Asp Glu Leu Asn Pro His Ile
    1890                1895                1900

Pro Trp Ala Glu Leu Pro Val Ala Val Val Arg Arg Ala Val Pro Trp
1905                1910                1915                1920

Pro Arg Gly Ala Arg Pro Arg Arg Ala Gly Val Ser Ala Phe Gly Leu
                1925                1930                1935

Ser Gly Thr Asn Ala His Val Val Leu Glu Glu Ala Pro Ala Val Glu
            1940                1945                1950

Pro Val Ala Ala Ala Pro Glu Arg Ala Ala Glu Leu Phe Val Leu Ser
        1955                1960                1965

Ala Lys Ser Ala Ala Ala Leu Asp Ala Gln Ala Ala Arg Leu Arg Asp
    1970                1975                1980

His Leu Glu Lys His Val Glu Leu Gly Leu Gly Asp Val Ala Phe Ser
1985                1990                1995                2000

Leu Ala Thr Thr Arg Ser Ala Met Glu His Arg Leu Ala Val Ala Ala
                2005                2010                2015

```
Ser Ser Arg Glu Ala Leu Arg Gly Ala Leu Ser Ala Ala Gln Gly
        2020                2025                2030
His Thr Pro Pro Gly Ala Val Arg Gly Arg Ala Ser Gly Gly Ser Ala
        2035                2040            2045
Pro Lys Val Val Phe Val Phe Pro Gly Gln Gly Ser Gln Trp Val Gly
    2050                2055                2060
Met Gly Arg Lys Leu Met Ala Glu Glu Pro Val Phe Arg Ala Ala Leu
2065                2070                2075                2080
Glu Gly Cys Asp Arg Ala Ile Glu Ala Glu Ala Gly Trp Ser Leu Leu
            2085                2090                2095
Gly Glu Leu Ser Ala Asp Glu Ala Ala Ser Gln Leu Gly Arg Ile Asp
        2100                2105                2110
Val Val Gln Pro Val Leu Phe Ala Met Glu Val Ala Leu Ser Ala Leu
        2115                2120                2125
Trp Arg Ser Trp Gly Val Glu Pro Glu Ala Val Val Gly His Ser Met
        2130                2135                2140
Gly Glu Val Ala Ala Ala His Val Ala Gly Ala Leu Ser Leu Glu Asp
2145                2150                2155                2160
Ala Val Ala Ile Ile Cys Arg Arg Ser Arg Leu Leu Arg Arg Ile Ser
            2165                2170                2175
Gly Gln Gly Glu Met Ala Leu Val Glu Leu Ser Leu Glu Glu Ala Glu
            2180                2185                2190
Ala Ala Leu Arg Gly His Glu Gly Arg Leu Ser Val Ala Val Ser Asn
        2195                2200                2205
Ser Pro Arg Ser Thr Val Leu Ala Gly Glu Pro Ala Ala Leu Ser Glu
        2210                2215                2220
Val Leu Ala Ala Leu Thr Ala Lys Gly Val Phe Trp Arg Gln Val Lys
2225                2230                2235                2240
Val Asp Val Ala Ser His Ser Pro Gln Val Asp Pro Leu Arg Glu Glu
            2245                2250                2255
Leu Ile Ala Ala Leu Gly Ala Ile Arg Pro Arg Ala Ala Ala Val Pro
            2260                2265                2270
Met Arg Ser Thr Val Thr Gly Gly Val Ile Ala Gly Pro Glu Leu Gly
        2275                2280                2285
Ala Ser Tyr Trp Ala Asp Asn Leu Arg Gln Pro Val Arg Phe Ala Ala
        2290                2295                2300
Ala Ala Gln Ala Leu Leu Glu Gly Gly Pro Ala Leu Phe Ile Glu Met
2305                2310                2315                2320
Ser Pro His Pro Ile Leu Val Pro Pro Leu Asp Glu Ile Gln Thr Ala
            2325                2330                2335
Ala Glu Gln Gly Gly Ala Ala Val Gly Ser Leu Arg Arg Gly Gln Asp
            2340                2345                2350
Glu Arg Ala Thr Leu Leu Glu Ala Leu Gly Thr Leu Trp Ala Ser Gly
        2355                2360                2365
Tyr Pro Val Ser Trp Ala Arg Leu Phe Pro Ala Gly Gly Arg Arg Val
    2370                2375                2380
Pro Leu Pro Thr Tyr Pro Trp Gln His Glu Arg Tyr Trp Ile Glu Asp
2385                2390                2395                2400
Ser Val His Gly Ser Lys Pro Ser Leu Arg Leu Arg Gln Leu Arg Asn
                2405                2410                2415
Gly Ala Thr Asp His Pro Leu Leu Gly Ala Pro Leu Leu Val Ser Ala
            2420                2425                2430
Arg Pro Gly Ala His Leu Trp Glu Gln Ala Leu Ser Asp Glu Arg Leu
```

-continued

```
              2435                2440                2445

Ser Tyr Leu Ser Glu His Arg Val His Gly Glu Ala Val Leu Pro Ser
  2450                2455                2460

Ala Ala Tyr Val Glu Met Ala Leu Ala Ala Gly Val Asp Leu Tyr Gly
2465                2470                2475                2480

Thr Ala Thr Leu Val Leu Glu Gln Leu Ala Leu Glu Arg Ala Leu Ala
              2485                2490                2495

Val Pro Ser Glu Gly Gly Arg Ile Val Gln Val Ala Leu Ser Glu Glu
        2500                2505                2510

Gly Pro Gly Arg Ala Ser Phe Gln Val Ser Ser Arg Glu Glu Ala Gly
        2515                2520                2525

Arg Ser Trp Val Arg His Ala Thr Gly His Val Cys Ser Gly Gln Ser
  2530                2535                2540

Ser Ala Val Gly Ala Leu Lys Glu Ala Pro Trp Glu Ile Gln Arg Arg
2545                2550                2555                2560

Cys Pro Ser Val Leu Ser Ser Glu Ala Leu Tyr Pro Leu Leu Asn Glu
              2565                2570                2575

His Ala Leu Asp Tyr Gly Pro Cys Phe Gln Gly Val Glu Gln Val Trp
        2580                2585                2590

Leu Gly Thr Gly Glu Val Leu Gly Arg Val Arg Leu Pro Gly Asp Met
  2595                2600                2605

Ala Ser Ser Ser Gly Ala Tyr Arg Ile His Pro Ala Leu Leu Asp Ala
  2610                2615                2620

Cys Phe Gln Val Leu Thr Ala Leu Leu Thr Thr Pro Glu Ser Ile Glu
2625                2630                2635                2640

Ile Arg Arg Arg Leu Thr Asp Leu His Glu Pro Asp Leu Pro Arg Ser
              2645                2650                2655

Arg Ala Pro Val Asn Gln Ala Val Ser Asp Thr Trp Leu Trp Asp Ala
              2660                2665                2670

Ala Leu Asp Gly Gly Arg Arg Gln Ser Ala Ser Val Pro Val Asp Leu
        2675                2680                2685

Val Leu Gly Ser Phe His Ala Lys Trp Glu Val Met Glu Arg Leu Ala
  2690                2695                2700

Gln Ala Tyr Ile Ile Gly Thr Leu Arg Ile Trp Asn Val Phe Cys Ala
2705                2710                2715                2720

Ala Gly Glu Arg His Thr Ile Asp Glu Leu Leu Val Arg Leu Gln Ile
        2725                2730                2735

Ser Val Val Tyr Arg Lys Val Ile Lys Arg Trp Met Glu His Leu Val
              2740                2745                2750

Ala Ile Gly Ile Leu Val Gly Asp Gly Glu His Phe Val Ser Ser Gln
        2755                2760                2765

Pro Leu Pro Glu Pro Asp Leu Ala Ala Val Leu Glu Glu Ala Gly Arg
  2770                2775                2780

Val Phe Ala Asp Leu Pro Val Leu Phe Glu Trp Cys Lys Phe Ala Gly
2785                2790                2795                2800

Glu Arg Leu Ala Asp Val Leu Thr Gly Lys Thr Leu Ala Leu Glu Ile
              2805                2810                2815

Leu Phe Pro Gly Gly Ser Phe Asp Met Ala Glu Arg Ile Tyr Arg Asp
        2820                2825                2830

Ser Pro Ile Ala Arg Tyr Ser Asn Gly Ile Val Arg Gly Val Val Glu
        2835                2840                2845

Ser Ala Ala Arg Val Val Ala Pro Ser Gly Met Phe Ser Ile Leu Glu
  2850                2855                2860
```

```
Ile Gly Ala Gly Thr Gly Ala Thr Thr Ala Ala Val Leu Pro Val Leu
2865                2870                2875                2880

Leu Pro Asp Arg Thr Glu Tyr His Phe Thr Asp Val Ser Pro Leu Phe
            2885                2890                2895

Leu Ala Arg Ala Glu Gln Arg Phe Arg Asp Tyr Pro Phe Leu Lys Tyr
            2900                2905                2910

Gly Ile Leu Asp Val Asp Gln Glu Pro Ala Gly Gln Gly Tyr Ala His
        2915                2920                2925

Gln Arg Phe Asp Val Ile Val Ala Ala Asn Val Ile His Ala Thr Arg
    2930                2935                2940

Asp Ile Arg Ala Thr Ala Lys Arg Leu Leu Ser Leu Leu Ala Pro Gly
2945                2950                2955                2960

Gly Leu Leu Val Leu Val Glu Gly Thr Gly His Pro Ile Trp Phe Asp
            2965                2970                2975

Ile Thr Thr Gly Leu Ile Glu Gly Trp Gln Lys Tyr Glu Asp Asp Leu
            2980                2985                2990

Arg Ile Asp His Pro Leu Leu Pro Ala Arg Thr Trp Cys Asp Val Leu
        2995                3000                3005

Arg Arg Val Gly Phe Ala Asp Ala Val Ser Leu Pro Gly Asp Gly Ser
    3010                3015                3020

Pro Ala Gly Ile Leu Gly Gln His Val Ile Leu Ser Arg Ala Pro Gly
3025                3030                3035                3040

Ile Ala Gly Ala Ala Cys Asp Ser Ser Gly Glu Ser Ala Thr Glu Ser
            3045                3050                3055

Pro Ala Ala Arg Ala Val Arg Gln Glu Trp Ala Asp Gly Ser Ala Asp
            3060                3065                3070

Val Val His Arg Met Ala Leu Glu Arg Met Tyr Phe His Arg Arg Pro
        3075                3080                3085

Gly Arg Gln Val Trp Val His Gly Arg Leu Arg Thr Gly Gly Gly Ala
    3090                3095                3100

Phe Thr Lys Ala Leu Ala Gly Asp Leu Leu Leu Phe Glu Asp Thr Gly
3105                3110                3115                3120

Gln Val Val Ala Glu Val Gln Gly Leu Arg Leu Pro Gln Leu Glu Ala
            3125                3130                3135

Ser Ala Phe Ala Pro Arg Asp Pro Arg Glu Glu Trp Leu Tyr Ala Leu
            3140                3145                3150

Glu Trp Gln Arg Lys Asp Pro Ile Pro Glu Ala Pro Ala Ala Ala Ser
        3155                3160                3165

Ser Ser Ser Ala Gly Ala Trp Leu Val Leu Met Asp Gln Gly Gly Thr
    3170                3175                3180

Gly Ala Ala Leu Val Ser Leu Leu Glu Gly Arg Gly Glu Ala Cys Val
3185                3190                3195                3200

Arg Val Ile Ala Gly Thr Ala Tyr Ala Cys Leu Ala Pro Gly Leu Tyr
            3205                3210                3215

Gln Val Asp Pro Ala Gln Pro Asp Gly Phe His Thr Leu Leu Arg Asp
            3220                3225                3230

Ala Phe Gly Glu Asp Arg Ile Cys Arg Ala Val Val His Met Trp Ser
        3235                3240                3245

Leu Asp Ala Thr Ala Ala Gly Glu Arg Ala Thr Ala Glu Ser Leu Gln
    3250                3255                3260

Ala Asp Gln Leu Leu Gly Ser Leu Ser Ala Leu Ser Leu Val Gln Ala
3265                3270                3275                3280
```

-continued

```
Leu Val Arg Arg Arg Trp Arg Asn Met Pro Arg Leu Trp Leu Leu Thr
            3285                3290                3295
Arg Ala Val His Ala Val Gly Ala Glu Asp Ala Ala Ser Val Ala
            3300                3305                3310
Gln Ala Pro Val Trp Gly Leu Gly Arg Thr Leu Ala Leu Glu His Pro
            3315                3320                3325
Glu Leu Arg Cys Thr Leu Val Asp Val Asn Pro Ala Pro Ser Pro Glu
            3330                3335                3340
Asp Ala Ala Leu Ala Val Glu Leu Gly Ala Ser Asp Arg Glu Asp
3345                3350                3355                3360
Gln Val Ala Leu Arg Ser Asp Gly Arg Tyr Val Ala Arg Leu Val Arg
            3365                3370                3375
Ser Ser Phe Ser Gly Lys Pro Ala Thr Asp Cys Gly Ile Arg Ala Asp
            3380                3385                3390
Gly Ser Tyr Val Ile Thr Asp Gly Met Gly Arg Val Gly Leu Ser Val
            3395                3400                3405
Ala Gln Trp Met Val Met Gln Gly Ala Arg His Val Val Leu Val Asp
            3410                3415                3420
Arg Gly Gly Ala Ser Glu Ala Ser Arg Asp Ala Leu Arg Ser Met Ala
3425                3430                3435                3440
Glu Ala Gly Ala Glu Val Gln Ile Val Glu Ala Asp Val Ala Arg Arg
            3445                3450                3455
Asp Asp Val Ala Arg Leu Leu Ser Lys Ile Glu Pro Ser Met Pro Pro
            3460                3465                3470
Leu Arg Gly Ile Val Tyr Val Asp Gly Thr Phe Gln Gly Asp Ser Ser
            3475                3480                3485
Met Leu Glu Leu Asp Ala Arg Arg Phe Lys Glu Trp Met Tyr Pro Lys
            3490                3495                3500
Val Leu Gly Ala Trp Asn Leu His Ala Leu Thr Arg Asp Arg Ser Leu
3505                3510                3515                3520
Asp Phe Phe Val Leu Tyr Ser Ser Gly Thr Ser Leu Leu Gly Leu Pro
            3525                3530                3535
Gly Gln Gly Ser Arg Ala Ala Gly Asp Ala Phe Leu Asp Ala Ile Ala
            3540                3545                3550
His His Arg Cys Lys Val Gly Leu Thr Ala Met Ser Ile Asn Trp Gly
            3555                3560                3565
Leu Leu Ser Glu Ala Ser Ser Pro Ala Thr Pro Asn Asp Gly Gly Ala
            3570                3575                3580
Arg Leu Glu Tyr Arg Gly Met Glu Gly Leu Thr Leu Glu Gln Gly Ala
3585                3590                3595                3600
Ala Ala Leu Gly Arg Leu Leu Ala Arg Pro Arg Ala Gln Val Gly Val
            3605                3610                3615
Met Arg Leu Asn Leu Arg Gln Trp Leu Glu Phe Tyr Pro Asn Ala Ala
            3620                3625                3630
Arg Leu Ala Leu Trp Ala Glu Leu Leu Lys Glu Arg Asp Arg Ala Asp
            3635                3640                3645
Arg Gly Ala Ser Asn Ala Ser Asn Leu Arg Glu Ala Leu Gln Ser Ala
            3650                3655                3660
Arg Pro Glu Asp Arg Gln Leu Ile Leu Glu Lys His Leu Ser Glu Leu
3665                3670                3675                3680
Leu Gly Arg Gly Leu Arg Leu Pro Pro Glu Arg Ile Glu Arg His Val
            3685                3690                3695
Pro Phe Ser Asn Leu Gly Met Asp Ser Leu Ile Gly Leu Glu Leu Arg
```

-continued

Asn Arg Ile Glu Ala Ala Leu Gly Ile Thr Val Pro Ala Thr Leu Leu
           3715                3720                3725

Trp Thr Tyr Pro Asn Val Ala Ala Leu Ser Gly Ser Leu Leu Asp Ile
    3730                3735                3740

Leu Phe Pro Asn Ala Gly Ala Thr His Ala Pro Ala Thr Glu Arg Glu
3745                3750                3755                3760

Lys Ser Phe Glu Asn Asp Ala Ala Asp Leu Glu Ala Leu Arg Gly Met
               3765                3770                3775

Thr Asp Glu Gln Lys Asp Ala Leu Leu Ala Glu Lys Leu Ala Gln Leu
            3780                3785                3790

Ala Gln Ile Val Gly Glu
       3795

<210> SEQ ID NO 7
<211> LENGTH: 2439
<212> TYPE: PRT
<213> ORGANISM: Sorangium cellulosum

<400> SEQUENCE: 7

Met Ala Thr Thr Asn Ala Gly Lys Leu Glu His Ala Leu Leu Leu Met
 1               5                  10                  15

Asp Lys Leu Ala Lys Lys Asn Ala Ser Leu Glu Gln Glu Arg Thr Glu
            20                  25                  30

Pro Ile Ala Ile Val Gly Ile Gly Cys Arg Phe Pro Gly Gly Ala Asp
        35                  40                  45

Thr Pro Glu Ala Phe Trp Glu Leu Leu Asp Ser Gly Arg Asp Ala Val
    50                  55                  60

Gln Pro Leu Asp Arg Arg Trp Ala Leu Val Gly Val His Pro Ser Glu
65                  70                  75                  80

Glu Val Pro Arg Trp Ala Gly Leu Leu Thr Glu Ala Val Asp Gly Phe
                85                  90                  95

Asp Ala Ala Phe Phe Gly Thr Ser Pro Arg Glu Ala Arg Ser Leu Asp
            100                 105                 110

Pro Gln Gln Arg Leu Leu Leu Glu Val Thr Trp Glu Gly Leu Glu Asp
        115                 120                 125

Ala Gly Ile Ala Pro Gln Ser Leu Asp Gly Ser Arg Thr Gly Val Phe
    130                 135                 140

Leu Gly Ala Cys Ser Ser Asp Tyr Ser His Thr Val Ala Gln Gln Arg
145                 150                 155                 160

Arg Glu Glu Gln Asp Ala Tyr Asp Ile Thr Gly Asn Thr Leu Ser Val
                165                 170                 175

Ala Ala Gly Arg Leu Ser Tyr Thr Leu Gly Leu Gln Gly Pro Cys Leu
            180                 185                 190

Thr Val Asp Thr Ala Cys Ser Ser Ser Leu Val Ala Ile His Leu Ala
        195                 200                 205

Cys Arg Ser Leu Arg Ala Arg Glu Ser Asp Leu Ala Leu Ala Gly Gly
    210                 215                 220

Val Asn Met Leu Leu Ser Ser Lys Thr Met Ile Met Leu Gly Arg Ile
225                 230                 235                 240

Gln Ala Leu Ser Pro Asp Gly His Cys Arg Thr Phe Asp Ala Ser Ala
                245                 250                 255

Asn Gly Phe Val Arg Gly Glu Gly Cys Gly Met Val Val Leu Lys Arg
            260                 265                 270

-continued

```
Leu Ser Asp Ala Gln Arg His Gly Asp Arg Ile Trp Ala Leu Ile Arg
        275                 280                 285

Gly Ser Ala Met Asn Gln Asp Gly Arg Ser Thr Gly Leu Met Ala Pro
        290                 295                 300

Asn Val Leu Ala Gln Glu Ala Leu Leu Arg Glu Ala Leu Gln Ser Ala
305                 310                 315                 320

Arg Val Asp Ala Gly Ala Ile Gly Tyr Val Glu Thr His Gly Thr Gly
                325                 330                 335

Thr Ser Leu Gly Asp Pro Ile Glu Val Glu Ala Leu Arg Ala Val Leu
                340                 345                 350

Gly Pro Ala Arg Ala Asp Gly Ser Arg Cys Val Leu Gly Ala Val Lys
                355                 360                 365

Thr Asn Leu Gly His Leu Glu Gly Ala Ala Gly Val Ala Gly Leu Ile
        370                 375                 380

Lys Ala Ala Leu Ala Leu His His Glu Leu Ile Pro Arg Asn Leu His
385                 390                 395                 400

Phe His Thr Leu Asn Pro Arg Ile Arg Ile Glu Gly Thr Ala Leu Ala
                405                 410                 415

Leu Ala Thr Glu Pro Val Pro Trp Pro Arg Ala Gly Arg Pro Arg Phe
                420                 425                 430

Ala Gly Val Ser Ala Phe Gly Leu Ser Gly Thr Asn Val His Val Val
                435                 440                 445

Leu Glu Glu Ala Pro Ala Thr Val Leu Ala Pro Ala Thr Pro Gly Arg
450                 455                 460

Ser Ala Glu Leu Leu Val Leu Ser Ala Lys Ser Ala Ala Leu Asp
465                 470                 475                 480

Ala Gln Ala Ala Arg Leu Ser Ala His Ile Ala Ala Tyr Pro Glu Gln
                485                 490                 495

Gly Leu Gly Asp Val Ala Phe Ser Leu Val Ser Thr Arg Ser Pro Met
                500                 505                 510

Glu His Arg Leu Ala Val Ala Ala Thr Ser Arg Glu Ala Leu Arg Ser
        515                 520                 525

Ala Leu Glu Val Ala Ala Gln Gly Gln Thr Pro Ala Gly Ala Ala Arg
        530                 535                 540

Gly Arg Ala Ala Ser Ser Pro Gly Lys Leu Ala Phe Leu Phe Ala Gly
545                 550                 555                 560

Gln Gly Ala Gln Val Pro Gly Met Gly Arg Gly Leu Trp Glu Ala Trp
                565                 570                 575

Pro Ala Phe Arg Glu Thr Phe Asp Arg Cys Val Thr Leu Phe Asp Arg
                580                 585                 590

Glu Leu His Gln Pro Leu Cys Glu Val Met Trp Ala Glu Pro Gly Ser
        595                 600                 605

Ser Arg Ser Ser Leu Leu Asp Gln Thr Ala Phe Thr Gln Pro Ala Leu
        610                 615                 620

Phe Ala Leu Glu Tyr Ala Leu Ala Ala Leu Phe Arg Ser Trp Gly Val
625                 630                 635                 640

Glu Pro Glu Leu Val Ala Gly His Ser Leu Gly Glu Leu Val Ala Ala
                645                 650                 655

Cys Val Ala Gly Val Phe Ser Leu Glu Asp Ala Val Arg Leu Val Val
                660                 665                 670

Ala Arg Gly Arg Leu Met Gln Ala Leu Pro Ala Gly Gly Ala Met Val
                675                 680                 685

Ser Ile Ala Ala Pro Glu Ala Asp Val Ala Ala Val Ala Pro His
```

-continued

```
            690                 695                 700
Ala Ala Leu Val Ser Ile Ala Ala Val Asn Gly Pro Glu Gln Val Val
705                 710                 715                 720
Ile Ala Gly Ala Glu Lys Phe Val Gln Gln Ile Ala Ala Phe Ala
                725                 730                 735
Ala Arg Gly Ala Arg Thr Lys Pro Leu His Val Ser His Ala Phe His
                740                 745                 750
Ser Pro Leu Met Asp Pro Met Leu Glu Ala Phe Arg Arg Val Thr Glu
                755                 760                 765
Ser Val Thr Tyr Arg Arg Pro Ser Ile Ala Leu Val Ser Asn Leu Ser
        770                 775                 780
Gly Lys Pro Cys Thr Asp Glu Val Ser Ala Pro Gly Tyr Trp Val Arg
785                 790                 795                 800
His Ala Arg Glu Ala Val Arg Phe Ala Asp Gly Val Lys Ala Leu His
                805                 810                 815
Ala Ala Gly Ala Gly Leu Phe Val Glu Val Gly Pro Lys Pro Thr Leu
                820                 825                 830
Leu Gly Leu Val Pro Ala Cys Leu Pro Asp Ala Arg Pro Val Leu Leu
        835                 840                 845
Pro Ala Ser Arg Ala Gly Arg Asp Glu Ala Ala Ser Ala Leu Glu Ala
850                 855                 860
Leu Gly Gly Phe Trp Val Val Gly Gly Ser Val Thr Trp Ser Gly Val
865                 870                 875                 880
Phe Pro Ser Gly Gly Arg Arg Val Pro Leu Pro Thr Tyr Pro Trp Gln
                885                 890                 895
Arg Glu Arg Tyr Trp Ile Glu Ala Pro Val Asp Arg Glu Ala Asp Gly
                900                 905                 910
Thr Gly Arg Ala Arg Ala Gly Gly His Pro Leu Leu Gly Glu Val Phe
                915                 920                 925
Ser Val Ser Thr His Ala Gly Leu Arg Leu Trp Glu Thr Thr Leu Asp
        930                 935                 940
Arg Lys Arg Leu Pro Trp Leu Gly Glu His Arg Ala Gln Gly Glu Val
945                 950                 955                 960
Val Phe Pro Gly Ala Gly Tyr Leu Glu Met Ala Leu Ser Ser Gly Ala
                965                 970                 975
Glu Ile Leu Gly Asp Gly Pro Ile Gln Val Thr Asp Val Val Leu Ile
                980                 985                 990
Glu Thr Leu Thr Phe Ala Gly Asp Thr Ala Val Pro Val Gln Val Val
        995                 1000                1005
Thr Thr Glu Glu Arg Pro Gly Arg Leu Arg Phe Gln Val Ala Ser Arg
        1010                1015                1020
Glu Pro Gly Glu Arg Arg Ala Pro Phe Arg Ile His Ala Arg Gly Val
1025                1030                1035                1040
Leu Arg Arg Ile Gly Arg Val Glu Thr Pro Ala Arg Ser Asn Leu Ala
                1045                1050                1055
Ala Leu Arg Ala Arg Leu His Ala Ala Val Pro Ala Ala Ile Tyr
                1060                1065                1070
Gly Ala Leu Ala Glu Met Gly Leu Gln Tyr Gly Pro Ala Leu Arg Gly
        1075                1080                1085
Leu Ala Glu Leu Trp Arg Gly Glu Gly Glu Ala Leu Gly Arg Val Arg
        1090                1095                1100
Leu Pro Glu Ala Ala Gly Ser Ala Thr Ala Tyr Gln Leu His Pro Val
1105                1110                1115                1120
```

-continued

```
Leu Leu Asp Ala Cys Val Gln Met Ile Val Gly Ala Phe Ala Asp Arg
            1125                1130                1135

Asp Glu Ala Thr Pro Trp Ala Pro Val Glu Val Gly Ser Val Arg Leu
        1140                1145                1150

Phe Gln Arg Ser Pro Gly Glu Leu Trp Cys His Ala Arg Val Val Ser
        1155                1160                1165

Asp Gly Gln Gln Ala Ser Ser Arg Trp Ser Ala Asp Phe Glu Leu Met
    1170                1175                1180

Asp Gly Thr Gly Ala Val Val Ala Glu Ile Ser Arg Leu Val Val Glu
1185                1190                1195                1200

Arg Leu Ala Ser Gly Val Arg Arg Asp Ala Asp Trp Phe Leu
            1205                1210                1215

Glu Leu Asp Trp Glu Pro Ala Ala Leu Gly Gly Pro Lys Ile Thr Ala
            1220                1225                1230

Gly Arg Trp Leu Leu Gly Glu Gly Gly Leu Gly Arg Ser Leu
            1235                1240                1245

Cys Ser Ala Leu Lys Ala Ala Gly His Val Val His Ala Ala Gly
        1250                1255                1260

Asp Asp Thr Ser Thr Ala Gly Met Arg Ala Leu Leu Ala Asn Ala Phe
1265                1270                1275                1280

Asp Gly Gln Ala Pro Thr Ala Val Val His Leu Ser Ser Leu Asp Gly
            1285                1290                1295

Gly Gly Gln Leu Gly Pro Gly Leu Gly Ala Gln Gly Ala Leu Asp Ala
            1300                1305                1310

Pro Arg Ser Pro Asp Val Asp Ala Asp Ala Leu Glu Ser Ala Leu Met
        1315                1320                1325

Arg Gly Cys Asp Ser Val Leu Ser Leu Val Gln Ala Leu Val Gly Met
        1330                1335                1340

Asp Leu Arg Asn Ala Pro Arg Leu Trp Leu Leu Thr Arg Gly Ala Gln
1345                1350                1355                1360

Ala Ala Ala Ala Gly Asp Val Ser Val Val Gln Ala Pro Leu Leu Gly
            1365                1370                1375

Leu Gly Arg Thr Ile Ala Leu Glu His Ala Glu Leu Arg Cys Ile Ser
        1380                1385                1390

Val Asp Leu Asp Pro Ala Glu Pro Glu Gly Glu Ala Asp Ala Leu Leu
        1395                1400                1405

Ala Glu Leu Leu Ala Asp Ala Glu Glu Val Ala Leu Arg Gly
        1410                1415                1420

Gly Asp Arg Leu Val Ala Arg Leu Val His Arg Leu Pro Asp Ala Gln
1425                1430                1435                1440

Arg Arg Glu Lys Val Glu Pro Ala Gly Asp Arg Pro Phe Arg Leu Glu
            1445                1450                1455

Ile Asp Glu Pro Gly Ala Leu Asp Gln Leu Val Leu Arg Ala Thr Gly
            1460                1465                1470

Arg Arg Ala Pro Gly Pro Gly Glu Val Glu Ile Ser Val Glu Ala Ala
        1475                1480                1485

Gly Leu Asp Ser Ile Asp Ile Gln Leu Ala Leu Gly Val Ala Pro Asn
    1490                1495                1500

Asp Leu Pro Gly Glu Glu Ile Glu Pro Leu Val Leu Gly Ser Glu Cys
1505                1510                1515                1520

Ala Gly Arg Ile Val Ala Val Gly Glu Gly Val Asn Gly Leu Val Val
            1525                1530                1535
```

```
Gly Gln Pro Val Ile Ala Leu Ala Ala Gly Val Phe Ala Thr His Val
            1540                1545                1550

Thr Thr Ser Ala Thr Leu Val Leu Pro Arg Pro Leu Gly Leu Ser Ala
        1555                1560                1565

Thr Glu Ala Ala Ala Met Pro Leu Ala Tyr Leu Thr Ala Trp Tyr Ala
    1570                1575                1580

Leu Asp Lys Val Ala His Leu Gln Ala Gly Glu Arg Val Leu Ile His
1585                1590                1595                1600

Ala Glu Ala Gly Gly Val Gly Leu Cys Ala Val Arg Trp Ala Gln Arg
            1605                1610                1615

Val Gly Ala Glu Val Tyr Ala Thr Ala Asp Thr Pro Glu Asn Arg Ala
        1620                1625                1630

Tyr Leu Glu Ser Leu Gly Val Arg Tyr Val Ser Asp Ser Arg Ser Gly
    1635                1640                1645

Arg Phe Val Thr Asp Val His Ala Trp Thr Asp Gly Glu Gly Val Asp
    1650                1655                1660

Val Val Leu Asp Ser Leu Ser Gly Glu Arg Ile Asp Lys Ser Leu Met
1665                1670                1675                1680

Val Leu Arg Ala Cys Gly Arg Leu Val Lys Leu Gly Arg Arg Asp Asp
            1685                1690                1695

Cys Ala Asp Thr Gln Pro Gly Leu Pro Pro Leu Leu Arg Asn Phe Ser
        1700                1705                1710

Phe Ser Gln Val Asp Leu Arg Gly Met Met Leu Asp Gln Pro Ala Arg
    1715                1720                1725

Ile Arg Ala Leu Leu Asp Glu Leu Phe Gly Leu Val Ala Ala Gly Ala
    1730                1735                1740

Ile Ser Pro Leu Gly Ser Gly Leu Arg Val Gly Gly Ser Leu Thr Pro
1745                1750                1755                1760

Pro Pro Val Glu Thr Phe Pro Ile Ser Arg Ala Ala Glu Ala Phe Arg
            1765                1770                1775

Arg Met Ala Gln Gly Gln His Leu Gly Lys Leu Val Leu Thr Leu Asp
        1780                1785                1790

Asp Pro Glu Val Arg Ile Arg Ala Pro Ala Glu Ser Ser Val Ala Val
    1795                1800                1805

Arg Ala Asp Gly Thr Tyr Leu Val Thr Gly Gly Leu Gly Gly Leu Gly
    1810                1815                1820

Leu Arg Val Ala Gly Trp Leu Ala Glu Arg Gly Ala Gly Gln Leu Val
1825                1830                1835                1840

Leu Val Gly Arg Ser Gly Ala Ala Ser Ala Glu Gln Arg Ala Ala Val
            1845                1850                1855

Ala Ala Leu Glu Ala His Gly Ala Arg Val Thr Val Ala Lys Ala Asp
        1860                1865                1870

Val Ala Asp Arg Ser Gln Ile Glu Arg Val Leu Arg Glu Val Thr Ala
    1875                1880                1885

Ser Gly Met Pro Leu Arg Gly Val Val His Ala Ala Gly Leu Val Asp
    1890                1895                1900

Asp Gly Leu Leu Met Gln Gln Thr Pro Ala Arg Phe Arg Thr Val Met
1905                1910                1915                1920

Gly Pro Lys Val Gln Gly Ala Leu His Leu His Thr Leu Thr Arg Glu
            1925                1930                1935

Ala Pro Leu Ser Phe Phe Val Leu Tyr Ala Ser Ala Ala Gly Leu Phe
        1940                1945                1950

Gly Ser Pro Gly Gln Gly Asn Tyr Ala Ala Ala Asn Ala Phe Leu Asp
```

-continued

```
            1955                1960                1965
Ala Leu Ser His His Arg Arg Ala Gln Gly Leu Pro Ala Leu Ser Ile
   1970                1975                1980
Asp Trp Gly Met Phe Thr Glu Val Gly Met Ala Val Ala Gln Glu Asn
1985                1990                1995                2000
Arg Gly Ala Arg Gln Ile Ser Arg Gly Met Arg Gly Ile Thr Pro Asp
            2005                2010                2015
Glu Gly Leu Ser Ala Leu Ala Arg Leu Leu Glu Gly Asp Arg Val Gln
            2020                2025                2030
Thr Gly Val Ile Pro Ile Thr Pro Arg Gln Trp Val Glu Phe Tyr Pro
            2035                2040                2045
Ala Thr Ala Ala Ser Arg Arg Leu Ser Arg Leu Val Thr Thr Gln Arg
   2050                2055                2060
Ala Val Ala Asp Arg Thr Ala Gly Asp Arg Asp Leu Leu Glu Gln Leu
2065                2070                2075                2080
Ala Ser Ala Glu Pro Ser Ala Arg Ala Gly Leu Leu Gln Asp Val Val
            2085                2090                2095
Arg Val Gln Val Ser His Val Leu Arg Leu Pro Glu Asp Lys Ile Glu
            2100                2105                2110
Val Asp Ala Pro Leu Ser Ser Met Gly Met Asp Ser Leu Met Ser Leu
   2115                2120                2125
Glu Leu Arg Asn Arg Ile Glu Ala Ala Leu Gly Val Ala Ala Pro Ala
   2130                2135                2140
Ala Leu Gly Trp Thr Tyr Pro Thr Val Ala Ala Ile Thr Arg Trp Leu
2145                2150                2155                2160
Leu Asp Asp Ala Leu Val Val Arg Leu Gly Gly Gly Ser Asp Thr Asp
            2165                2170                2175
Glu Ser Thr Ala Ser Ala Gly Ser Phe Val His Val Leu Arg Phe Arg
            2180                2185                2190
Pro Val Val Lys Pro Arg Ala Arg Leu Phe Cys Phe His Gly Ser Gly
            2195                2200                2205
Gly Ser Pro Glu Gly Phe Arg Ser Trp Ser Glu Lys Ser Glu Trp Ser
   2210                2215                2220
Asp Leu Glu Ile Val Ala Met Trp His Asp Arg Ser Leu Ala Ser Glu
2225                2230                2235                2240
Asp Ala Pro Gly Lys Lys Tyr Val Gln Glu Ala Ala Ser Leu Ile Gln
            2245                2250                2255
His Tyr Ala Asp Ala Pro Phe Ala Leu Val Gly Phe Ser Leu Gly Val
            2260                2265                2270
Arg Phe Val Met Gly Thr Ala Val Glu Leu Ala Ser Arg Ser Gly Ala
            2275                2280                2285
Pro Ala Pro Leu Ala Val Phe Thr Leu Gly Gly Ser Leu Ile Ser Ser
            2290                2295                2300
Ser Glu Ile Thr Pro Glu Met Glu Thr Asp Ile Ile Ala Lys Leu Phe
2305                2310                2315                2320
Phe Arg Asn Ala Ala Gly Phe Val Arg Ser Thr Gln Gln Val Gln Ala
            2325                2330                2335
Asp Ala Arg Ala Asp Lys Val Ile Thr Asp Thr Met Val Ala Pro Ala
            2340                2345                2350
Pro Gly Asp Ser Lys Glu Pro Pro Val Lys Ile Ala Val Pro Ile Val
            2355                2360                2365
Ala Ile Ala Gly Ser Asp Asp Val Ile Val Pro Pro Ser Asp Val Gln
            2370                2375                2380
```

-continued

```
Asp Leu Gln Ser Arg Thr Thr Glu Arg Phe Tyr Met His Leu Leu Pro
2385                2390                2395                2400

Gly Asp His Glu Phe Leu Val Asp Arg Gly Arg Glu Ile Met His Ile
            2405                2410                2415

Val Asp Ser His Leu Asn Pro Leu Leu Ala Ala Arg Thr Thr Ser Ser
            2420                2425                2430

Gly Pro Ala Phe Glu Ala Lys
        2435

<210> SEQ ID NO 8
<211> LENGTH: 419
<212> TYPE: PRT
<213> ORGANISM: Sorangium cellulosum

<400> SEQUENCE: 8

Met Thr Gln Glu Gln Ala Asn Gln Ser Glu Thr Lys Pro Ala Phe Asp
  1               5                  10                  15

Phe Lys Pro Phe Ala Pro Gly Tyr Ala Glu Asp Pro Phe Pro Ala Ile
                 20                  25                  30

Glu Arg Leu Arg Glu Ala Thr Pro Ile Phe Tyr Trp Asp Glu Gly Arg
             35                  40                  45

Ser Trp Val Leu Thr Arg Tyr His Asp Val Ser Ala Val Phe Arg Asp
 50                  55                  60

Glu Arg Phe Ala Val Ser Arg Glu Glu Trp Glu Ser Ser Ala Glu Tyr
 65                  70                  75                  80

Ser Ser Ala Ile Pro Glu Leu Ser Asp Met Lys Lys Tyr Gly Leu Phe
                 85                  90                  95

Gly Leu Pro Pro Glu Asp His Ala Arg Val Arg Lys Leu Val Asn Pro
            100                 105                 110

Ser Phe Thr Ser Arg Ala Ile Asp Leu Leu Arg Ala Glu Ile Gln Arg
            115                 120                 125

Thr Val Asp Gln Leu Leu Asp Ala Arg Ser Gly Gln Glu Glu Phe Asp
130                 135                 140

Val Val Arg Asp Tyr Ala Glu Gly Ile Pro Met Arg Ala Ile Ser Ala
145                 150                 155                 160

Leu Leu Lys Val Pro Ala Glu Cys Asp Glu Lys Phe Arg Arg Phe Gly
                165                 170                 175

Ser Ala Thr Ala Arg Ala Leu Gly Val Gly Leu Val Pro Gln Val Asp
            180                 185                 190

Glu Glu Thr Lys Thr Leu Val Ala Ser Val Thr Glu Gly Leu Ala Leu
            195                 200                 205

Leu His Asp Val Leu Asp Glu Arg Arg Arg Asn Pro Leu Glu Asn Asp
210                 215                 220

Val Leu Thr Met Leu Leu Gln Ala Glu Ala Asp Gly Ser Arg Leu Ser
225                 230                 235                 240

Thr Lys Glu Leu Val Ala Leu Val Gly Ala Ile Ile Ala Ala Gly Thr
                245                 250                 255

Asp Thr Thr Ile Tyr Leu Ile Ala Phe Ala Val Leu Asn Leu Leu Arg
            260                 265                 270

Ser Pro Glu Ala Leu Glu Leu Val Lys Ala Glu Pro Gly Leu Met Arg
            275                 280                 285

Asn Ala Leu Asp Glu Val Leu Arg Phe Asp Asn Ile Leu Arg Ile Gly
290                 295                 300

Thr Val Arg Phe Ala Arg Gln Asp Leu Glu Tyr Cys Gly Ala Ser Ile
```

```
                305                 310                 315                 320
Lys Lys Gly Glu Met Val Phe Leu Leu Ile Pro Ser Ala Leu Arg Asp
                    325                 330                 335
Gly Thr Val Phe Ser Arg Pro Asp Val Phe Asp Val Arg Arg Asp Thr
                340                 345                 350
Gly Ala Ser Leu Ala Tyr Gly Arg Gly Pro His Val Cys Pro Gly Val
            355                 360                 365
Ser Leu Ala Arg Leu Glu Ala Glu Ile Ala Val Gly Thr Ile Phe Arg
370                 375                 380
Arg Phe Pro Glu Met Lys Leu Lys Glu Thr Pro Val Phe Gly Tyr His
385                 390                 395                 400
Pro Ala Phe Arg Asn Ile Glu Ser Leu Asn Val Ile Leu Lys Pro Ser
                405                 410                 415
Lys Ala Gly

<210> SEQ ID NO 9
<211> LENGTH: 607
<212> TYPE: PRT
<213> ORGANISM: Sorangium cellulosum

<400> SEQUENCE: 9

Ala Ser Leu Asp Ala Leu Phe Arg Ala Thr Ser Ala Arg Val Leu
 1               5                  10                  15
Asp Asp Gly His Gly Arg Ala Thr Glu Arg His Val Leu Ala Glu Ala
                20                  25                  30
Arg Gly Ile Glu Asp Leu Arg Ala Leu Arg Glu His Leu Arg Ile Gln
            35                  40                  45
Glu Gly Gly Pro Ser Phe His Cys Met Cys Leu Gly Asp Leu Thr Val
    50                  55                  60
Glu Leu Leu Ala His Asp Gln Pro Leu Ala Ser Ile Ser Phe His His
65                  70                  75                  80
Ala Arg Ser Leu Arg His Pro Asp Trp Thr Ser Asp Ala Met Leu Val
                85                  90                  95
Asp Gly Pro Ala Leu Val Arg Trp Leu Ala Ala Arg Gly Ala Pro Gly
                100                 105                 110
Pro Leu Arg Glu Tyr Glu Glu Arg Glu Arg Ala Arg Thr Ala Gln
            115                 120                 125
Glu Ala Arg Arg Leu Trp Leu Ala Ala Pro Pro Cys Phe Ala Pro
130                 135                 140
Asp Leu Pro Arg Phe Glu Asp Asp Ala Asn Gly Leu Pro Leu Gly Pro
145                 150                 155                 160
Met Ser Pro Glu Val Ala Glu Ala Glu Arg Arg Leu Arg Ala Ser Tyr
                165                 170                 175
Ala Thr Pro Glu Leu Ala Cys Ala Ala Leu Leu Ala Trp Leu Gly Thr
                180                 185                 190
Gly Ala Gly Pro Trp Ser Gly Tyr Pro Ala Tyr Glu Met Leu Pro Glu
            195                 200                 205
Asn Leu Leu Gly Phe Gly Leu Pro Thr Ala Ile Ala Ala Ser
    210                 215                 220
Ala Pro Gly Thr Ser Glu Ala Ala Leu Arg Gly Ala Ala Arg Leu Phe
225                 230                 235                 240
Ala Ser Trp Glu Val Val Ser Ser Lys Lys Ser Gln Leu Gly Asn Ile
                245                 250                 255
Pro Glu Ala Leu Trp Glu Arg Leu Arg Thr Ile Val Arg Ala Met Gly
```

```
                    260                 265                 270
Asn Ala Asp Asn Leu Ser Arg Phe Glu Arg Ala Glu Ala Ile Ala Ala
            275                 280                 285
Glu Val Arg Arg Leu Arg Ala Gln Pro Ala Pro Phe Ala Ala Gly Ala
        290                 295                 300
Gly Leu Ala Val Ala Gly Val Ser Ser Gly Arg Leu Ser Gly Leu
305                 310                 315                 320
Val Thr Asp Gly Asp Ala Leu Tyr Ser Gly Asp Gly Asn Asp Ile Val
                325                 330                 335
Met Phe Gln Pro Gly Arg Ile Ser Pro Val Val Leu Leu Ala Gly Thr
            340                 345                 350
Asp Pro Phe Phe Glu Leu Ala Pro Pro Leu Ser Gln Met Leu Phe Val
            355                 360                 365
Ala His Ala Asn Ala Gly Thr Ile Ser Lys Val Leu Thr Glu Gly Ser
        370                 375                 380
Pro Leu Ile Val Met Ala Arg Asn Gln Ala Arg Pro Met Ser Leu Val
385                 390                 395                 400
His Ala Arg Gly Phe Met Ala Trp Val Asn Gln Ala Met Val Pro Asp
                405                 410                 415
Pro Glu Arg Gly Ala Pro Phe Val Val Gln Arg Ser Thr Ile Met Glu
            420                 425                 430
Phe Glu His Pro Thr Pro Arg Cys Leu His Glu Pro Ala Gly Ser Ala
            435                 440                 445
Phe Ser Leu Ala Cys Asp Glu Glu His Leu Tyr Trp Cys Glu Leu Ser
        450                 455                 460
Ala Gly Arg Leu Glu Leu Trp Arg His Pro His His Arg Pro Gly Ala
465                 470                 475                 480
Pro Ser Arg Phe Ala Tyr Leu Gly Glu His Pro Ile Ala Ala Thr Trp
                485                 490                 495
Tyr Pro Ser Leu Thr Leu Asn Ala Thr His Val Leu Trp Ala Asp Pro
            500                 505                 510
Asp Arg Arg Ala Ile Leu Gly Val Asp Lys Arg Thr Gly Val Glu Pro
            515                 520                 525
Ile Val Leu Ala Glu Thr Arg His Pro Pro Ala His Val Val Ser Glu
        530                 535                 540
Asp Arg Asp Ile Phe Ala Leu Thr Gly Gln Pro Asp Ser Arg Asp Trp
545                 550                 555                 560
His Val Glu His Ile Arg Ser Gly Ala Ser Thr Val Val Ala Asp Tyr
                565                 570                 575
Gln Arg Gln Leu Trp Asp Arg Pro Asp Met Val Leu Asn Arg Arg Gly
            580                 585                 590
Leu Phe Phe Thr Thr Asn Asp Arg Ile Leu Thr Leu Ala Arg Ser
            595                 600                 605

<210> SEQ ID NO 10
<211> LENGTH: 423
<212> TYPE: PRT
<213> ORGANISM: Sorangium cellulosum

<400> SEQUENCE: 10

Met Gly Ala Leu Ile Ser Val Ala Ala Pro Gly Cys Ala Leu Gly Gly
1               5                   10                  15
Ala Glu Glu Glu Gly Gln Pro Gly Gln Asp Ala Gly Ala Gly Ala Leu
            20                  25                  30
```

```
Ala Pro Ala Arg Glu Val Met Ala Ala Glu Val Ala Ala Gly Gln Met
         35                  40                  45

Pro Gly Ala Val Trp Leu Val Ala Arg Gly Asp Asp Val His Val Asp
     50                  55                  60

Ala Val Gly Val Thr Glu Leu Gly Gly Ser Ala Pro Met Arg Arg Asp
 65                  70                  75                  80

Thr Ile Phe Arg Ile Ala Ser Met Thr Lys Ala Val Thr Ala Thr Ala
                 85                  90                  95

Val Met Met Leu Val Glu Glu Gly Lys Leu Asp Leu Asp Ser Pro Val
             100                 105                 110

Asp Arg Trp Leu Pro Glu Leu Ala Asn Arg Lys Val Leu Ala Arg Ile
             115                 120                 125

Asp Gly Pro Ile Asp Glu Thr Val Pro Ala Glu Arg Pro Ile Thr Val
         130                 135                 140

Arg Asp Leu Met Thr Phe Thr Met Gly Phe Gly Ile Ser Phe Asp Ala
145                 150                 155                 160

Ser Ser Pro Ile Gln Arg Ala Ile Asp Glu Leu Gly Leu Val Asn Ala
                 165                 170                 175

Gln Pro Val Pro Met Thr Pro His Gly Pro Asp Glu Trp Ile Arg Arg
             180                 185                 190

Leu Gly Thr Leu Pro Leu Met His Gln Pro Gly Ala Gln Trp Met Tyr
             195                 200                 205

Asn Thr Gly Ser Leu Val Gln Gly Val Leu Val Gly Arg Ala Ala Asp
         210                 215                 220

Gln Gly Phe Asp Ala Phe Val Arg Glu Arg Ile Leu Ala Pro Leu Gly
225                 230                 235                 240

Met Arg Asp Thr Asp Phe His Val Pro Ala Asp Lys Leu Ala Arg Phe
                 245                 250                 255

Ala Gly Cys Gly Tyr Phe Thr Asp Glu Gln Thr Gly Glu Lys Thr Arg
             260                 265                 270

Met Asp Arg Asp Gly Ala Glu Ser Ala Tyr Ala Ser Pro Pro Ala Phe
             275                 280                 285

Pro Ser Gly Ala Ala Gly Leu Val Ser Thr Val Asp Asp Tyr Leu Leu
         290                 295                 300

Phe Ala Arg Met Leu Met Asn Gly Gly Val His Glu Gly Arg Arg Leu
305                 310                 315                 320

Leu Ser Ala Ala Ser Val Arg Glu Met Thr Ala Asp His Leu Thr Pro
                 325                 330                 335

Ala Gln Lys Ala Ala Ser Ser Phe Phe Pro Gly Phe Phe Glu Thr His
             340                 345                 350

Gly Trp Gly Tyr Gly Met Ala Val Val Thr Ala Pro Asp Ala Val Ser
             355                 360                 365

Glu Val Pro Gly Arg Tyr Gly Trp Asp Gly Gly Phe Gly Thr Ser Trp
         370                 375                 380

Ile Asn Asp Pro Gly Arg Glu Leu Ile Gly Ile Val Met Thr Gln Ser
385                 390                 395                 400

Ala Gly Phe Leu Phe Ser Gly Ala Leu Glu Arg Phe Trp Arg Ser Val
                 405                 410                 415

Tyr Val Ala Thr Glu Ser Ala
             420

<210> SEQ ID NO 11
<211> LENGTH: 713
<212> TYPE: PRT
```

<213> ORGANISM: Sorangium cellulosum

<400> SEQUENCE: 11

```
Met His Gly Leu Thr Glu Arg Gln Val Leu Leu Ser Leu Val Thr Leu
  1               5                  10                  15

Ala Leu Ile Leu Val Thr Ala Arg Ala Ser Gly Glu Leu Ala Arg Arg
             20                  25                  30

Leu Arg Gln Pro Glu Val Leu Gly Glu Leu Phe Gly Gly Val Val Leu
         35                  40                  45

Gly Pro Ser Val Val Gly Ala Leu Ala Pro Gly Phe His Arg Ala Leu
     50                  55                  60

Phe Gln Glu Pro Ala Val Gly Val Val Leu Ser Gly Ile Ser Trp Ile
 65                  70                  75                  80

Gly Ala Leu Leu Leu Leu Met Ala Gly Ile Glu Val Asp Val Gly
                 85                  90                  95

Ile Leu Arg Lys Glu Ala Arg Pro Gly Ala Leu Ser Ala Leu Gly Ala
                100                 105                 110

Ile Ala Pro Pro Leu Ala Ala Gly Ala Ala Phe Ser Ala Leu Val Leu
            115                 120                 125

Asp Arg Pro Leu Pro Ser Gly Leu Phe Leu Gly Ile Val Leu Ser Val
130                 135                 140

Thr Ala Val Ser Val Ile Ala Lys Val Leu Ile Glu Arg Glu Ser Met
145                 150                 155                 160

Arg Arg Ser Tyr Ala Gln Val Thr Leu Ala Ala Gly Val Val Ser Glu
                165                 170                 175

Val Ala Ala Trp Val Leu Val Ala Met Thr Ser Ser Ser Tyr Gly Ala
            180                 185                 190

Ser Pro Ala Leu Ala Val Ala Arg Ser Ala Leu Leu Ala Ser Gly Phe
        195                 200                 205

Leu Leu Phe Met Val Leu Val Gly Arg Arg Leu Thr His Leu Ala Met
    210                 215                 220

Arg Trp Val Ala Asp Ala Thr Arg Val Ser Lys Gly Gln Val Ser Leu
225                 230                 235                 240

Val Leu Val Leu Thr Phe Leu Ala Ala Ala Leu Thr Gln Arg Leu Gly
                245                 250                 255

Leu His Pro Leu Leu Gly Ala Phe Ala Leu Gly Val Leu Leu Asn Ser
            260                 265                 270

Ala Pro Arg Thr Asn Arg Pro Leu Leu Asp Gly Val Gln Thr Leu Val
        275                 280                 285

Ala Gly Leu Phe Ala Pro Val Phe Phe Val Leu Ala Gly Met Arg Val
    290                 295                 300

Asp Val Ser Gln Leu Arg Thr Pro Ala Ala Trp Gly Thr Val Ala Leu
305                 310                 315                 320

Leu Leu Ala Thr Ala Thr Ala Ala Lys Val Val Pro Ala Ala Leu Gly
                325                 330                 335

Ala Arg Leu Gly Gly Leu Arg Ser Glu Ala Ala Leu Val Ala Val
            340                 345                 350

Gly Leu Asn Met Lys Gly Gly Thr Asp Leu Ile Val Ala Ile Val Gly
        355                 360                 365

Val Glu Leu Gly Leu Leu Ser Asn Glu Ala Tyr Thr Met Tyr Ala Val
    370                 375                 380

Val Ala Leu Val Thr Val Thr Ala Ser Pro Ala Leu Leu Ile Trp Leu
385                 390                 395                 400
```

```
Glu Lys Arg Ala Pro Pro Thr Gln Glu Ser Ala Arg Leu Glu Arg
            405                 410                 415

Glu Glu Ala Ala Arg Arg Ala Tyr Ile Pro Gly Val Glu Arg Ile Leu
        420                 425                 430

Val Pro Ile Val Ala His Ala Leu Pro Gly Phe Ala Thr Asp Ile Val
            435                 440                 445

Glu Ser Ile Val Ala Ser Lys Arg Lys Leu Gly Glu Thr Val Asp Ile
    450                 455                 460

Thr Glu Leu Ser Val Glu Gln Gln Ala Pro Gly Pro Ser Arg Ala Ala
465                 470                 475                 480

Gly Glu Ala Ser Arg Gly Leu Ala Arg Leu Gly Ala Arg Leu Arg Val
            485                 490                 495

Gly Ile Trp Arg Gln Arg Arg Glu Leu Arg Gly Ser Ile Gln Ala Ile
            500                 505                 510

Leu Arg Ala Ser Arg Asp His Asp Leu Leu Val Ile Gly Ala Arg Ser
            515                 520                 525

Pro Ala Arg Ala Arg Gly Met Ser Phe Gly Arg Leu Gln Asp Ala Ile
            530                 535                 540

Val Gln Arg Ala Glu Ser Asn Val Leu Val Val Gly Asp Pro Pro
545                 550                 555                 560

Ala Ala Glu Arg Ala Ser Ala Arg Arg Ile Leu Val Pro Ile Ile Gly
                565                 570                 575

Leu Glu Tyr Ser Phe Ala Ala Ala Asp Leu Ala Ala His Val Ala Leu
            580                 585                 590

Ala Trp Asp Ala Glu Leu Val Leu Leu Ser Ser Ala Gln Thr Asp Pro
        595                 600                 605

Gly Ala Val Val Trp Arg Asp Arg Glu Pro Ser Arg Val Arg Ala Val
        610                 615                 620

Ala Arg Ser Val Val Asp Glu Ala Val Phe Arg Gly Arg Arg Leu Gly
625                 630                 635                 640

Val Arg Val Ser Ser Arg Val His Val Gly Ala His Pro Ser Asp Glu
            645                 650                 655

Ile Thr Arg Glu Leu Ala Arg Ala Pro Tyr Asp Leu Leu Val Leu Gly
            660                 665                 670

Cys Tyr Asp His Gly Pro Leu Gly Arg Leu Tyr Leu Gly Ser Thr Val
            675                 680                 685

Glu Ser Val Val Val Arg Ser Arg Val Pro Val Ala Leu Leu Val Ala
    690                 695                 700

His Gly Gly Thr Arg Glu Gln Val Arg
705                 710

<210> SEQ ID NO 12
<211> LENGTH: 126
<212> TYPE: PRT
<213> ORGANISM: Sorangium cellulosum

<400> SEQUENCE: 12

Met Asp Lys Pro Ile Gly Arg Thr Arg Cys Ala Ile Ala Glu Gly Tyr
  1               5                  10                  15

Ile Pro Gly Gly Ser Asn Gly Pro Glu Pro Gln Met Thr Ser His Glu
            20                  25                  30

Thr Ala Cys Leu Leu Asn Ala Ser Asp Arg Asp Ala Gln Val Ala Ile
        35                  40                  45

Thr Val Tyr Phe Ser Asp Arg Asp Pro Ala Gly Pro Tyr Arg Val Thr
    50                  55                  60
```

Val Pro Ala Arg Arg Thr Arg His Val Arg Phe Asn Asp Leu Thr Glu
 65                  70                  75                  80

Pro Glu Pro Ile Pro Arg Asp Thr Asp Tyr Ala Ser Val Ile Glu Ser
             85                  90                  95

Asp Ala Pro Ile Val Val Gln His Thr Arg Leu Asp Ser Arg Gln Ala
            100                 105                 110

Glu Asn Ala Leu Leu Ser Thr Ile Ala Tyr Thr Asp Arg Glu
        115                 120                 125

<210> SEQ ID NO 13
<211> LENGTH: 149
<212> TYPE: PRT
<213> ORGANISM: Sorangium cellulosum

<400> SEQUENCE: 13

Met Lys His Val Asp Thr Gly Arg Arg Phe Gly Arg Ile Gly His
  1               5                  10                  15

Thr Leu Gly Leu Leu Ala Ser Met Ala Leu Ala Gly Cys Gly Gly Pro
             20                  25                  30

Ser Glu Lys Thr Val Gln Gly Thr Arg Leu Ala Pro Gly Ala Asp Ala
         35                  40                  45

Arg Val Thr Ala Asp Val Asp Pro Asp Ala Ala Thr Thr Arg Leu Ala
 50                  55                  60

Val Asp Val Val His Leu Ser Pro Pro Glu Arg Leu Glu Ala Gly Ser
 65                  70                  75                  80

Glu Arg Phe Val Val Trp Gln Arg Pro Ser Pro Glu Ser Pro Trp Arg
             85                  90                  95

Arg Val Gly Val Leu Asp Tyr Asn Ala Asp Ser Arg Arg Gly Lys Leu
            100                 105                 110

Ala Glu Thr Thr Val Pro Tyr Ala Asn Phe Glu Leu Leu Ile Thr Ala
        115                 120                 125

Glu Lys Gln Ser Ser Pro Gln Ser Pro Ser Ser Ala Ala Val Ile Gly
    130                 135                 140

Pro Thr Ser Val Gly
145

<210> SEQ ID NO 14
<211> LENGTH: 184
<212> TYPE: PRT
<213> ORGANISM: Sorangium cellulosum

<400> SEQUENCE: 14

Val Thr Ser Glu Glu Val Pro Gly Ala Ala Leu Gly Ala Gln Ser Ser
  1               5                  10                  15

Leu Val Arg Ala Gln His Ala Ala Arg His Val Arg Pro Cys Thr Arg
             20                  25                  30

Ala Glu Glu Pro Pro Ala Leu Met His Gly Leu Thr Glu Arg Gln Val
         35                  40                  45

Leu Leu Ser Leu Val Ala Leu Ala Leu Val Leu Thr Ala Arg Ala
 50                  55                  60

Phe Gly Glu Leu Ala Arg Arg Leu Arg Gln Pro Glu Val Leu Gly Glu
 65                  70                  75                  80

Leu Phe Gly Gly Val Val Leu Gly Pro Ser Val Val Gly Ala Leu Ala
             85                  90                  95

Pro Gly Phe His Arg Val Leu Phe Gln Asp Pro Ala Val Gly Val Val
            100                 105                 110

```
Leu Ser Gly Ile Ser Trp Ile Gly Ala Leu Val Leu Leu Met Ala
    115                 120                 125
Gly Ile Glu Val Asp Val Ser Ile Leu Arg Lys Glu Ala Arg Pro Gly
    130                 135                 140
Ala Leu Ser Ala Leu Gly Ala Ile Ala Pro Leu Arg Thr Pro Gly
145                 150                 155                 160
Pro Leu Val Gln Arg Met Gln Gly Ala Phe Thr Trp Asp Leu Asp Val
                165                 170                 175
Ser Pro Arg Arg Ser Ala Gln Ala
            180

<210> SEQ ID NO 15
<211> LENGTH: 145
<212> TYPE: PRT
<213> ORGANISM: Sorangium cellulosum

<400> SEQUENCE: 15

Val Asn Ala Pro Cys Met Arg Cys Thr Ser Gly Pro Gly Val Arg Ser
  1               5                  10                  15
Gly Gly Ala Ile Ala Pro Ser Ala Glu Ser Ala Pro Gly Arg Ala Ser
                 20                  25                  30
Leu Arg Arg Met Leu Thr Ser Ser Ile Pro Ala Met Ser Ser Arg
         35                  40                  45
Thr Ser Ala Pro Ile Gln Glu Met Pro Glu Ser Thr Thr Pro Thr Ala
     50                  55                  60
Gly Ser Trp Lys Arg Thr Arg Trp Asn Pro Gly Ala Ser Ala Pro Thr
 65                  70                  75                  80
Thr Asp Gly Pro Ser Thr Thr Pro Pro Lys Ser Ser Pro Ser Thr Ser
                 85                  90                  95
Gly Trp Arg Ser Arg Arg Ala Ser Ser Pro Lys Ala Arg Ala Val Arg
            100                 105                 110
Arg Thr Ser Ala Arg Ala Thr Ser Glu Ser Arg Thr Cys Arg Ser Val
        115                 120                 125
Arg Pro Cys Ile Arg Ala Gly Gly Ser Ser Ala Arg Val Gln Gly Arg
    130                 135                 140
Thr
145

<210> SEQ ID NO 16
<211> LENGTH: 185
<212> TYPE: PRT
<213> ORGANISM: Sorangium cellulosum

<400> SEQUENCE: 16

Val Leu Ala Pro Pro Ala Asp Ile Arg Pro Pro Ala Ala Ala Gln Leu
  1               5                  10                  15
Glu Pro Asp Ser Pro Asp Asp Glu Ala Asp Glu Ala Asp Glu Ala Leu
                 20                  25                  30
Arg Pro Phe Arg Asp Ala Ile Ala Ala Tyr Ser Glu Ala Val Arg Trp
         35                  40                  45
Ala Glu Ala Ala Gln Arg Pro Arg Leu Glu Ser Leu Val Arg Leu Ala
     50                  55                  60
Ile Val Arg Leu Gly Lys Ala Leu Asp Lys Val Pro Phe Ala His Thr
 65                  70                  75                  80
Thr Ala Gly Val Ser Gln Ile Ala Gly Arg Leu Gln Asn Asp Ala Val
                 85                  90                  95
```

```
Trp Phe Asp Val Ala Ala Arg Tyr Ala Ser Phe Arg Ala Ala Thr Glu
                100                 105                 110

His Ala Leu Arg Asp Ala Ser Ala Met Glu Ala Leu Ala Ala Gly
        115                 120                 125

Pro Tyr Arg Gly Ser Ser Arg Val Ser Ala Ala Val Gly Glu Phe Arg
        130                 135                 140

Gly Glu Ala Ala Arg Leu His Pro Ala Asp Arg Val Pro Ala Ser Asp
145                 150                 155                 160

Gln Gln Ile Leu Thr Ala Leu Arg Ala Ala Glu Arg Ala Leu Ile Ala
                165                 170                 175

Leu Tyr Thr Ala Phe Ala Arg Glu Glu
                180                 185

<210> SEQ ID NO 17
<211> LENGTH: 146
<212> TYPE: PRT
<213> ORGANISM: Sorangium cellulosum

<400> SEQUENCE: 17

Met Ala Asp Ala Ala Ser Arg Ser Ala Cys Ser Val Ala Ala Arg Lys
1               5                   10                  15

Leu Ala Tyr Arg Ala Ala Thr Ser Asn Gln Thr Ala Ser Phe Trp Ser
            20                  25                  30

Leu Pro Ala Ile Trp Glu Thr Pro Ala Val Val Cys Ala Lys Gly Thr
        35                  40                  45

Leu Ser Ser Ala Leu Pro Ser Arg Thr Ile Ala Ser Arg Thr Arg Leu
    50                  55                  60

Ser Ser Arg Gly Arg Cys Ala Ala Ser Ala His Arg Thr Ala Ser Glu
65                  70                  75                  80

Tyr Ala Ala Ile Ala Ser Arg Asn Gly Arg Ser Ala Ser Ser Ala Ser
                85                  90                  95

Ser Ala Ser Ser Ser Gly Glu Ser Gly Ser Ser Trp Ala Ala Ala Gly
            100                 105                 110

Gly Arg Met Ser Ala Gly Gly Ala Ser Thr Gly Glu Val Tyr Glu Gln
        115                 120                 125

Ala Pro Arg Leu Arg Leu Ala Gln Ser Val Ala Ala Arg Arg Arg Asp
    130                 135                 140

Pro Thr
145

<210> SEQ ID NO 18
<211> LENGTH: 288
<212> TYPE: PRT
<213> ORGANISM: Sorangium cellulosum

<400> SEQUENCE: 18

Val Thr Val Ser Ser Met Pro Arg Ser Trp Ser Ser Arg Val Arg Thr
1               5                   10                  15

Val Val Thr Ala Leu Gly Cys Ala Arg Arg Leu Ser Gly Ser Ile Ser
            20                  25                  30

Arg Leu Arg Arg His Pro Glu Ala Gly Arg Ala Pro Arg Ser Arg Leu
        35                  40                  45

Arg Ala Trp Arg Arg Leu Pro Gln His Ile Ser Ser Pro Trp Arg His
    50                  55                  60

Leu Pro Pro Gly Ala Arg Val Gly Thr Ser Cys Pro Ala Asp Arg Arg
65                  70                  75                  80
```

```
Ile Leu Pro Ser His Arg Thr Ala Asp Leu Gly Thr Ser Gly Gly Thr
                85                  90                  95

Leu Val Ala Arg Met Ser Gly His Val Ala Arg Asn Pro His Ala Ala
            100                 105                 110

Val Leu Val Gly Asp Gly Ser Ala Arg Gly Arg Arg Leu Ser Asn
        115                 120                 125

Arg Arg Ala Glu Arg Val Ser Asp Val Thr Cys Arg Glu Gly Gly
    130                 135                 140

Glu Ala Met Gln Lys Ile Ala Gly Lys Leu Val Val Gly Leu Ile Ser
145                 150                 155                 160

Val Ser Gly Met Ser Leu Leu Ala Ala Cys Gly Gly Glu Lys Arg Ser
                165                 170                 175

Gly Gly Glu Ala Gln Thr Pro Gly Gly Ala Gln Gly Glu Ala Pro Val
            180                 185                 190

Pro Val Gly Ser Ala Val Asp Ser Ile Val Ala Ala Arg Cys Asp Arg
        195                 200                 205

Glu Ala Arg Cys Asn Asn Ile Gly Gln Asp Arg Glu Tyr Ser Ser Lys
    210                 215                 220

Asp Ala Cys Ser Asn Lys Ile Arg Ser Glu Trp Arg Asp Glu Leu Thr
225                 230                 235                 240

Phe Gly Glu Cys Pro Gly Gly Ile Asp Ala Lys Gln Leu Asn Glu Cys
                245                 250                 255

Leu Glu Gly Ile Arg Asn Glu Gly Cys Gly Asn Pro Phe Asp Thr Leu
            260                 265                 270

Gly Arg Val Val Ala Cys Arg Ser Ser Asp Leu Cys Arg Asp Ala Arg
        275                 280                 285

<210> SEQ ID NO 19
<211> LENGTH: 288
<212> TYPE: PRT
<213> ORGANISM: Sorangium cellulosum

<400> SEQUENCE: 19

Val Thr Val Ser Ser Met Pro Arg Ser Trp Ser Ser Arg Val Arg Thr
 1               5                  10                  15

Val Val Thr Ala Leu Gly Cys Ala Arg Arg Leu Ser Gly Ser Ile Ser
            20                  25                  30

Arg Leu Arg Arg His Pro Glu Ala Gly Arg Ala Pro Arg Ser Arg Leu
        35                  40                  45

Arg Ala Trp Arg Arg Leu Pro Gln His Ile Ser Ser Pro Trp Arg His
    50                  55                  60

Leu Pro Pro Gly Ala Arg Val Gly Thr Ser Cys Pro Ala Asp Arg Arg
65                  70                  75                  80

Ile Leu Pro Ser His Arg Thr Ala Asp Leu Gly Thr Ser Gly Gly Thr
                85                  90                  95

Leu Val Ala Arg Met Ser Gly His Val Ala Arg Asn Pro His Ala Ala
            100                 105                 110

Val Leu Val Gly Asp Gly Ser Ala Arg Gly Arg Arg Leu Ser Asn
        115                 120                 125

Arg Arg Ala Glu Arg Val Ser Asp Val Thr Cys Arg Glu Gly Gly
    130                 135                 140

Glu Ala Met Gln Lys Ile Ala Gly Lys Leu Val Val Gly Leu Ile Ser
145                 150                 155                 160

Val Ser Gly Met Ser Leu Leu Ala Ala Cys Gly Gly Glu Lys Arg Ser
```

-continued

```
                165                 170                 175
Gly Gly Glu Ala Gln Thr Pro Gly Gly Ala Gln Gly Glu Ala Pro Val
            180                 185                 190

Pro Val Gly Ser Ala Val Asp Ser Ile Val Ala Ala Arg Cys Asp Arg
        195                 200                 205

Glu Ala Arg Cys Asn Asn Ile Gly Gln Asp Arg Glu Tyr Ser Ser Lys
    210                 215                 220

Asp Ala Cys Ser Asn Lys Ile Arg Ser Glu Trp Arg Asp Glu Leu Thr
225                 230                 235                 240

Phe Gly Glu Cys Pro Gly Gly Ile Asp Ala Lys Gln Leu Asn Glu Cys
                245                 250                 255

Leu Glu Gly Ile Arg Asn Glu Gly Cys Gly Asn Pro Phe Asp Thr Leu
            260                 265                 270

Gly Arg Val Val Ala Cys Arg Ser Ser Asp Leu Cys Arg Asp Ala Arg
        275                 280                 285

<210> SEQ ID NO 20
<211> LENGTH: 155
<212> TYPE: PRT
<213> ORGANISM: Sorangium cellulosum

<400> SEQUENCE: 20

Met Asp Pro Arg Ala Arg Arg Glu Lys Arg Pro Ser Leu Leu Asp Ser
  1               5                  10                  15

Arg Gly Arg Gln Pro Lys Arg Ser Gln Gln Gly Gly His Met Glu Lys
             20                  25                  30

Pro Ile Gly Arg Thr Arg Trp Ala Ile Ala Glu Gly Tyr Ile Pro Gly
         35                  40                  45

Arg Ser Asn Gly Pro Glu Pro Gln Met Thr Ser His Glu Thr Ala Cys
     50                  55                  60

Leu Leu Asn Ala Ser Asp Arg Asp Ala Gln Val Ala Ile Thr Val Tyr
 65                  70                  75                  80

Phe Ser Asp Arg Asp Pro Ala Gly Pro Tyr Arg Val Thr Val Pro Ala
                 85                  90                  95

Arg Arg Thr Arg His Val Arg Phe Asn Asp Leu Thr Glu Pro Glu Pro
            100                 105                 110

Ile Pro Arg Asp Thr Asp Tyr Ala Ser Val Ile Glu Ser Asp Val Pro
        115                 120                 125

Ile Val Val Gln His Thr Arg Leu Asp Ser Arg Gln Ala Glu Asn Ala
    130                 135                 140

Leu Ile Ser Thr Ile Ala Tyr Thr Asp Arg Glu
145                 150                 155

<210> SEQ ID NO 21
<211> LENGTH: 156
<212> TYPE: PRT
<213> ORGANISM: Sorangium cellulosum

<400> SEQUENCE: 21

Val Arg Arg Ser Arg Trp Gln Met Lys His Val Asp Thr Gly Arg Arg
  1               5                  10                  15

Val Gly Arg Arg Ile Gly Leu Thr Leu Gly Leu Leu Ala Ser Met Ala
             20                  25                  30

Leu Ala Gly Cys Gly Gly Pro Ser Glu Lys Ile Val Gln Gly Thr Arg
         35                  40                  45

Leu Ala Pro Gly Ala Asp Ala His Val Ala Ala Asp Val Asp Pro Asp
```

```
              50                  55                  60
Ala Ala Thr Thr Arg Leu Ala Val Asp Val Val His Leu Ser Pro Pro
 65                  70                  75                  80

Glu Arg Ile Glu Ala Gly Ser Glu Arg Phe Val Val Trp Gln Arg Pro
                 85                  90                  95

Ser Ser Glu Ser Pro Trp Gln Arg Val Gly Val Leu Asp Tyr Asn Ala
                100                 105                 110

Ala Ser Arg Arg Gly Lys Leu Ala Glu Thr Thr Val Pro His Ala Asn
                115                 120                 125

Phe Glu Leu Leu Ile Thr Val Glu Lys Gln Ser Ser Pro Gln Ser Pro
                130                 135                 140

Ser Ser Ala Ala Val Ile Gly Pro Thr Ser Val Gly
145                 150                 155
```

<210> SEQ ID NO 22
<211> LENGTH: 305
<212> TYPE: PRT
<213> ORGANISM: Sorangium cellulosum

<400> SEQUENCE: 22

```
Met Glu Lys Glu Ser Arg Ile Ala Ile Tyr Gly Ala Ile Ala Ala Asn
 1               5                  10                  15

Val Ala Ile Ala Ala Val Lys Phe Ile Ala Ala Val Thr Gly Ser
                 20                  25                  30

Ser Ala Met Leu Ser Glu Gly Val His Ser Leu Val Asp Thr Ala Asp
                 35                  40                  45

Gly Leu Leu Leu Leu Gly Lys His Arg Ser Ala Arg Pro Pro Asp
     50                  55                  60

Ala Glu His Pro Phe Gly His Gly Lys Glu Leu Tyr Phe Trp Thr Leu
 65                  70                  75                  80

Ile Val Ala Ile Met Ile Phe Ala Ala Gly Gly Val Ser Ile Tyr
                 85                  90                  95

Glu Gly Ile Leu His Leu Leu His Pro Arg Gln Ile Glu Asp Pro Thr
                100                 105                 110

Trp Asn Tyr Val Val Leu Gly Ala Ala Val Phe Glu Gly Thr Ser
        115                 120                 125

Leu Ile Ile Ser Ile His Glu Phe Lys Lys Lys Asp Gly Gln Gly Tyr
        130                 135                 140

Leu Ala Ala Met Arg Ser Ser Lys Asp Pro Thr Thr Phe Thr Ile Val
145                 150                 155                 160

Leu Glu Asp Ser Ala Ala Leu Ala Gly Leu Thr Ile Ala Phe Leu Gly
                165                 170                 175

Val Trp Leu Gly His Arg Leu Gly Asn Pro Tyr Leu Asp Gly Ala Ala
                180                 185                 190

Ser Ile Gly Ile Gly Leu Val Leu Ala Ala Val Ala Val Phe Leu Ala
        195                 200                 205

Ser Gln Ser Arg Gly Leu Leu Val Gly Glu Ser Ala Asp Arg Glu Leu
        210                 215                 220

Leu Ala Ala Ile Arg Ala Leu Ala Ser Ala Asp Pro Gly Val Ser Ala
225                 230                 235                 240

Val Gly Arg Pro Leu Thr Met His Phe Gly Pro His Glu Val Leu Val
                245                 250                 255

Val Leu Arg Ile Glu Phe Asp Ala Ala Leu Thr Ala Ser Gly Val Ala
                260                 265                 270
```

```
Glu Ala Ile Glu Arg Ile Glu Thr Arg Ile Arg Ser Glu Arg Pro Asp
            275                 280                 285

Val Lys His Ile Tyr Val Glu Ala Arg Ser Leu His Gln Arg Ala Arg
        290                 295                 300

Ala
305

<210> SEQ ID NO 23
<211> LENGTH: 135
<212> TYPE: PRT
<213> ORGANISM: Sorangium cellulosum

<400> SEQUENCE: 23

Val Gln Thr Ser Ser Phe Asp Ala Arg Tyr Ala Gly Cys Lys Ser Ser
  1               5                  10                  15

Arg Arg Ile Ala Arg Ser Gly Ser Ala Gly Ala Arg Ala Gly Arg Ala
             20                  25                  30

His Glu Gly Ala Ala Ser Ala Gly Phe Glu Gly Gly Asp Val Met Arg
         35                  40                  45

Lys Ala Arg Ala His Gly Ala Met Leu Gly Gly Arg Asp Asp Gly Trp
     50                  55                  60

Arg Arg Gly Leu Pro Gly Ala Gly Ala Leu Arg Ala Ala Leu Gln Arg
 65                  70                  75                  80

Gly Arg Ser Arg Asp Leu Ala Arg Arg Leu Ile Ala Ser Val Ser
                 85                  90                  95

Leu Ala Gly Gly Ala Ser Met Ala Val Val Ser Leu Phe Gln Leu Gly
                100                 105                 110

Ile Ile Glu Arg Leu Pro Asp Pro Leu Pro Gly Phe Asp Ser Ala
            115                 120                 125

Lys Val Thr Ser Ser Asp Ile
        130                 135

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: universal
      reverse primer

<400> SEQUENCE: 24
ggaaacagct atgaccatg                                             19

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: universal
      forward primer

<400> SEQUENCE: 25
gtaaaacgac ggccagt                                               17

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: PCR primer
      NH24 end "B"
```

```
<400> SEQUENCE: 26
gtgactggcg cctggaatct gcatgagc                                              28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: PCR primer
      NH2 end "A"

<400> SEQUENCE: 27
agcgggagct tgctagacat tctgtttc                                              28

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: PCR primer
      NH2 end "B"

<400> SEQUENCE: 28
gacgcgcctc gggcagcgcc ccaa                                                  24

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: PCR primer
      pEPO15-NH6 end "B"

<400> SEQUENCE: 29
caccgaagcg tcgatctggt ccatc                                                 25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: PCR primer
      pEPO15H2.7 end "A"

<400> SEQUENCE: 30
cggtcagatc gacgacgggc tttcc                                                 25
```